US012692508B2

(12) United States Patent
Law et al.

(10) Patent No.: US 12,692,508 B2
(45) Date of Patent: Jul. 28, 2026

(54) ENGINEERING INCREASED SUBERIN LEVELS BY ALTERING GENE EXPRESSION PATTERNS IN A CELL-TYPE SPECIFIC MANNER

(71) Applicant: Salk Institute for Biological Studies, La Jolla, CA (US)

(72) Inventors: Julie Ann Law, La Jolla, CA (US); Mina Rostamza, La Jolla, CA (US); Joseph P. Noel, La Jolla, CA (US); Suzanne Thomas, La Jolla, CA (US); Jeffrey Todd Mindrebo, La Jolla, CA (US); Luke Alden Sarre, London (GB)

(73) Assignee: Salk Institute for Biological Studies, La Jolla, CA (US)

( * ) Notice: Subject to any disclaimer, the term of this patent is extended or adjusted under 35 U.S.C. 154(b) by 112 days.

(21) Appl. No.: 18/032,129

(22) PCT Filed: Oct. 15, 2021

(86) PCT No.: PCT/US2021/055246
§ 371 (c)(1),
(2) Date: Apr. 14, 2023

(87) PCT Pub. No.: WO2022/082020
PCT Pub. Date: Apr. 21, 2022

(65) Prior Publication Data
US 2023/0392159 A1 Dec. 7, 2023

Related U.S. Application Data

(60) Provisional application No. 63/093,205, filed on Oct. 17, 2020.

(51) Int. Cl.
*C12N 15/82* (2006.01)
*A01H 1/00* (2006.01)

(52) U.S. Cl.
CPC ......... *C12N 15/8223* (2013.01); *A01H 1/101* (2021.01)

(58) Field of Classification Search
None
See application file for complete search history.

(56) References Cited

U.S. PATENT DOCUMENTS 11,692,199 B2    7/2023   Medford et al.
2002/0160378 A1 * 10/2002   Harper ............... C12N 15/8273
                                                    435/6.14

(Continued)

FOREIGN PATENT DOCUMENTS

WO          WO 0129074 A1      4/2001
WO      WO-2007149583 A2     12/2007
                (Continued)

OTHER PUBLICATIONS

Höfer, R., Briesen, I., Beck, M., Pinot, F., Schreiber, L., & Franke, R. (2008). The *Arabidopsis* cytochrome P450 CYP86A1 encodes a fatty acid ω-hydroxylase involved in suberin monomer biosynthesis. Journal of experimental botany, 59(9), 2347-2360. (Year: 2008).*

(Continued)

*Primary Examiner* — Amjad Abraham
*Assistant Examiner* — Dequantarius Javon Speed
(74) *Attorney, Agent, or Firm* — Klarquist Sparkman, LLP

(57) ABSTRACT

The present disclosure provides compositions and methods for increasing suberin production in plants.

19 Claims, 20 Drawing Sheets

Specification includes a Sequence Listing.

Expression reporter constructs

GUS assays showing root-specific expression of proHORST

(56) References Cited

U.S. PATENT DOCUMENTS

| | | | |
|---|---|---|---|
| 2007/0180580 | A1 | 8/2007 | Hertzberg |
| 2007/0266457 | A1 | 11/2007 | Hehl et al. |
| 2009/0163729 | A1 | 6/2009 | Li et al. |
| 2014/0123344 | A1 | 5/2014 | Reuzu |
| 2019/0185872 | A1 | 6/2019 | Immanen et al. |
| 2020/0048650 | A1 | 2/2020 | Medford et al. |
| 2020/0102571 | A1 | 4/2020 | Tschaplinski et al. |
| 2023/0002455 | A1* | 1/2023 | Epple ..................... A01H 6/20 |

FOREIGN PATENT DOCUMENTS

| | | |
|---|---|---|
| WO | WO-2008069878 A2 | 6/2008 |
| WO | WO-2008157827 A2 | 12/2008 |
| WO | WO-2017178150 A1 | 10/2017 |
| WO | WO-2018175900 A2 | 9/2018 |
| WO | WO-2021202978 A2 | 10/2021 |
| WO | WO-2021226306 A1 | 11/2021 |
| WO | WO-2022082020 A1 | 4/2022 |

OTHER PUBLICATIONS

GenBank Accession No. AB016885. *Arabidopsis thaliana* genomic DNA, chromosome 5, TAC clone: K19M22. Bethesda (MD): National Library of Medicine (US), National Center for Biotechnology Information. Feb. 14, 2004. Available from: https://www.ncbi.nlm.nih.gov/nuccore/AB016885 (Year: 2004).*

NCBI Reference Sequence: NM_125276.2. *Arabidopsis thaliana* cytochrome P450 86A1 mRNA, complete cds. Bethesda (MD): National Library of Medicine (US), National Center for Biotechnology Information. Jan. 22, 2014. Available from: https://www.ncbi.nlm.nih.gov/nuccore/NM_125276.2 (Year: 2014).*

Cominelli et al., "Over-expression of the *Arabidopsis* AtMYB41 gene alters cell expansion and leaf surface permeability," The Plant Journal 53: 53-64, 2008.

"Q9M0J5-MYB41_Arath," Transcription Factor MYB41, UniProtKB, 2024 (8 pages).

Bowman, "Hypothetical protein BRARA_A01176 [*Brassica. rapa*]," Genbank entry, National Center for Biotechnology Information, Sep. 2018, electronically retrieved at <https://www.ncbi.nlm.nih.gov/protein/RID78335.1> on Jul. 21, 2024.

International Search Report and Written Opinion issued in International Application No. PCT/US2024/025564 by the U.S. Patent and Trademark Office as International Search Authority on Sep. 30, 2024 (11 pages).

"Transcription Factor MYB102 [*Brassica napus*]," Genbank entry, National Center for Biotechnology Information, Jun. 23, 2022, retrieved electronically at <https://www.ncbi.nlm.nih.gov/protein/XP_013669705.1>, on Jul. 21, 2024.

Amelung et al., "Towards a global-scale soil climate mitigation strategy," Nature Communications, 2020 11:5427, 10 pages.

Brady et al., "A high-resolution root spatiotemporal map reveals dominant expression patterns," Science, Nov. 2, 2007, vol. 318, pp. 801-806.

Carrington et al., "Biochemical changes across a carbon saturation gradient: Lignin, cutin, and suberin decomposition and stabilization in fractionated carbon pools," Soil Biology and Biochemistry, 2012, vol. 47, pp. 179-190.

Ejiri et al., "Some Accessions of Amazonian Wild Rice (*Oryza glumaepatula*) Constitutively Form a Barrier to Radial Oxygen Loss along Adventitious Roots under Aerated Conditions," Plants 2020, 9, 880, 13 pages.

Energy Futures Initiative, "From the Ground Up: Cutting-Edge Approaches for Land-Based Carbon Dioxide Removal," Dec. 2020, © 2020 Energy Futures Initiative, 48 pages.

Feng et al., "Molecular-level methods for monitoring soil organic matter responses to global climate change," Journal of Environmental Monitoring, 2011, 13: 1246-1254.

GenBank Accession No. AB005234.1, *Arabidopsis thaliana* genomic DNA, chromosome 5, P1 clone:MBK5, Feb. 14, 2004, 27 pages.

GenBank Accession No. NP _194540. myb domain protein 41 [*Arabidopsis thaliana*], Feb. 14, 2019, 3 pages.

Gou et al., "The MYB107 Transcription Factor Positively Regulates Suberin Biosynthesis," Plant Physiology, Feb. 2017, vol. 173, pp. 1045-1058.

Höfer et al., "The *Arabidopsis* cytochrome P450 CYP86A1 encodes a fatty acid omega-hydroxylase involved in suberin monomer biosynthesis," Journal of Experimental Botany, 2008, vol. 59, No. 9, pp. 2347-2360.

International Preliminary Report on Patentability for International Application No. PCT/US2021/055246 dated Apr. 27, 2023, 9 pages.

International Search Report and Written Opinion for International Application No. PCT/US2021/055246 dated Mar. 9, 2022, 13 pages.

Kosma et al., "Analysis of aliphatic waxes associated with root periderm or exodermis from eleven plant species," Phytochemistry, Sep. 2015, vol. 117, pp. 351-362.

Kosma, et al., "AtMYB41 activates ectopic suberin synthesis and assembly in multiple plant species and cell types,". The Plant Journal, 2014, vol. 80. pp. 216-229.

Kosma et al., "Identification of an *Arabidopsis* Fatty Alcohol: Caffeoyl-Coenzyme A Acyltransferase Required for the Synthesis of Alkyl Hydroxycinnamates in Root Waxes," Plant Physiology, Sep. 2012, vol. 160, pp. 237-248.

Lal, R., "Sequestering Atmospheric Carbon Dioxide," Critical Reviews in Plant Science, 2009, 28:90-96.

Lashbrooke et al., "MYB107 and MYB9 Homologs Regulate Suberin Deposition in Angiosperms," The Plant Cell, Sep. 2016, vol. 28: 2097-2116.

Lippold et al., "AtMyb41 Regulates Transcriptional and Metabolic Responses to Osmotic Stress in *Arabidopsis*," Plant Physiology, Apr. 2009, vol. 149, pp. 1761-1772.

Mahmood et al., "Overexpression of ANAC046 Promotes Suberin Biosynthesis in Roots of *Arabidopsis thaliana*," Int. J. Mol. Sci. 2019, 20, 6117, 18 pages.

Miyawaki et al., "Roles of *Arabidopsis* ATP / ADP isopentenyl transferases and tRNA isopentenyl transferases in cytokinin biosynthesis," PNAS, Oct. 31, 2006, vol. 103, No. 44, pp. 16598-16603.

Molina et al., "Identification of an *Arabidopsis* Feruloyl-Coenzyme A Transferase Required for Suberin Synthesis," Plant Physiology, Nov. 2009, vol. 151, pp. 1317-1328.

Ogura et al., "Root System Depth in *Arabidopsis* Is Shaped by EXOCYST70A3 via the Dynamic Modulation of Auxin Transport," Cell, Jul. 2019, 178, 400-412.

Phililppe et al., "Cutin and suberin: assembly and origins of specialized lipidic cell wall scaffolds," Current Opinion in Plant Biology 2020, 55:11-20.

Preston et al., "13C nuclear magnetic resonance spectroscopy with cross-polarization and magic-angle spinning investigation of the proximate-analysis fractions used to assess litter quality in decomposition studies," Canadian Journal of Botany, 1997, vol. 75, pp. 1601-1613.

Shukla and Barberon, "Building and breaking of a barrier: Suberin plasticity and function in the endodermis," Current Opinion in Plant Biology 2021, 64:102153.

Shukla et al., "Suberin plasticity to developmental and exogenous cues is regulated by a set of MYB transcription factors," bioRxiv, Jan. 27, 2021, 28 pages, preprint doi: https://doi.org/10.1101/2021.01.27.428267.

Takei et al., "AtIPT3 is a Key Determinant of Nitrate-Dependent Cytokinin Biosynthesis in *Arabidopsis*," Plant Cell Physiol. (2004) 45(8): 1053-1062.

Vazquez et al., "Evolution of *Arabidopsis* MIR genes generates novel microRNA classes," Nucleic Acids Research, 2008, vol. 36, No. 20, pp. 6429-6438.

Vishwanath et al., "Suberin: biosynthesis, regulation, and polymer assembly of a protective extracellular barrier," Plant Cell Reports (2015) vol. 34, pp. 573-586.

Wei et al., "MYB41, MYB107, and MYC2 promote ABA-mediated primary fatty alcohol accumulation via activation of AchnFAR in wound suberization in kiwifruit," Horticulture Research (2020) 7:86, 10 pages.

(56) References Cited

OTHER PUBLICATIONS

Wei et al., "Three Transcription Activators of ABA Signaling Positively Regulate Suberin Monomer Synthesis by Activating Cytochrome P450 CYP86A1 in Kiwifruit," Frontiers in Plant Science (2020) 10:1650, 15 pages.

Winkler et al., "Insoluble alkyl carbon components in soils derive mainly from cutin and suberin," Organic Geochemistry, 2005, vol. 36, pp. 519-529.

Wunderling et al., "A molecular framework to study periderm formation in *Arabidopsis*," New Phytologist (2018) 219: 216-229.

Zhang et al., "Drought activates MYB41 orthologs and induces suberization of grapevine fine roots," Plant Direct, Nov. 2020, vol. 4, Issue 11, e00278, 17 pages.

Compagnon, et al., "CYP86B1 is required for very long chain $\omega$-hydroxyacid and $\alpha$, $\omega$-dicarboxylic acid synthesis in root and seed suberin polyester," *Plant Physiology* 150(4): pp. 1831-1843, Aug. 2009.

Domergue, et al., "Three *Arabidopsis* fatty acyl-coenzyme A reductases, FAR1, FAR4, and FAR5, generate primary fatty alcohols associated with suberin deposition," *Plant Physiology* 153(4): pp. 1539-1554, Aug. 2010.

* cited by examiner

Promoter fusion construct proHORST::MYB41

Key:

▨ Exon    ▬ Intron    ▨ 3' UTR    ▨ Intergenic region    ▨ att recombination site Root images showing normal growth in proHORST::MYB41 lines Col-0 proHORST::MYB41
(LS140-LS766) (T3)

proHORST::MYB41
(LS140-LS767) (T3)

proHORST::MYB41
(LS141-LS788) (T3)

Nile Red staining showing more signal in proHORST::MYB41

Expression reporter constructs

FIG. 2A

Graphical summary of results

☐ Strong GUS Activity
☐ Weak GUS Activity
☐ No GUS Activity

Promoter fusion construct proFACT::MYB41 proFACT     MYB41

0     1000     2000     3000

Key:

▨ Exon   ▬ Intron   ▨ 3' UTR   ▨ Intergenic region    att recombination site

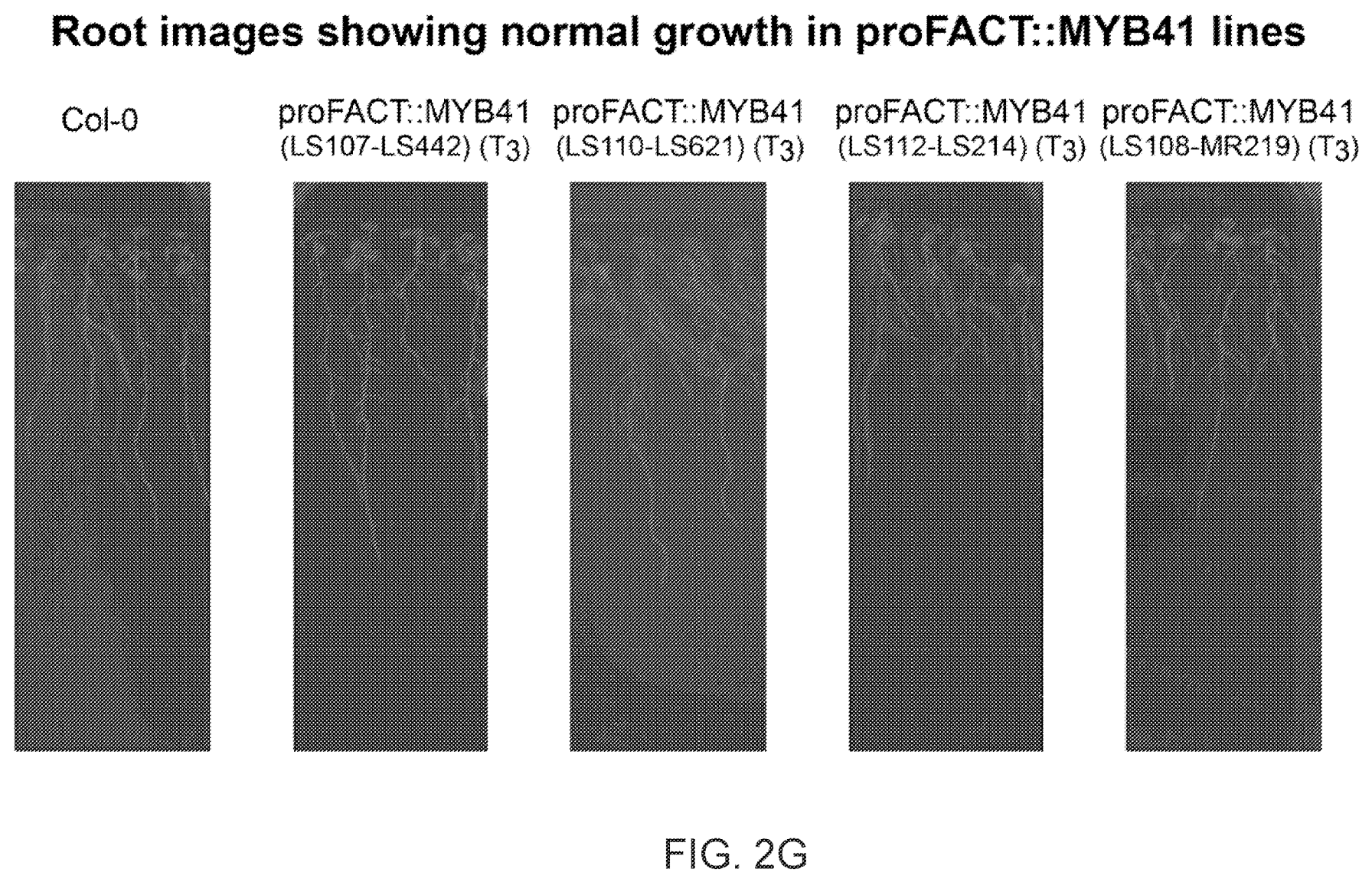

Root images showing normal growth in proFACT::MYB41 lines

Col-0 proFACT::MYB41
(LS107-LS442) (T3)

proFACT::MYB41
(LS110-LS621) (T3)

proFACT::MYB41
(LS112-LS214) (T3)

proFACT::MYB41
(LS108-MR219) (T3)

FIG. 2G

Nile Red staining showing extra periderm in proFACT::MYB41 proFACT:MYB41
(LS107-LS444) (T3)

proFACT:MYB41
(LS108-MRZ19) (T3)

proFACT:MYB41
(LS107-LS442) (T3)

proFACT:MYB41
(LS112-LS214) (T3)

Col-0 proFACT:MYB41
(LS110-LS621) (T3)

ENGINEERING INCREASED SUBERIN LEVELS BY ALTERING GENE EXPRESSION PATTERNS IN A CELL-TYPE SPECIFIC MANNER

FIELD

The present disclosure generally relates to the field of increasing suberin production in plants. More particularly, the present disclosure relates to compositions and methods for generating plants that possess enhanced root cell-type specific expression.

CROSS-REFERENCE TO RELATED APPLICATION

This application is a U.S. national phase application of International PCT Application No. PCT/US2021/055246, filed on Oct. 15, 2021, which claims priority to, and the benefit of U.S. Provisional Patent Application No. 63/093,205, Oct. 17, 2020, each of which is incorporated by reference herein in its entirety for all purposes.

DESCRIPTION OF THE TEXT FILE SUBMITTED ELECTRONICALLY

The Sequence Listing associated with this application is provided in text format in lieu of a paper copy. The contents of the text file submitted electronically herewith are incorporated herein by reference in their entirety. A computer readable format copy of the Sequence Listing (filename: SALK 006 01US.SeqList_ST25.txt, date recorded: Apr. 13, 2023; file size≈144,246 bytes).

BACKGROUND OF THE DISCLOSURE

In plant roots, suberin is deposited in specific locations, including the periderm, where it serves as a barrier between the plant and its environment (Vishwanath et al., 2015). The suberin molecule contains vast amounts of carbon in forms that are thought to persist for long periods of time in the soil (Carrington et al., 2012; Feng and Simpson, 2011; Preston et al., 1997; Winkler et al., 2005). Thus, by increasing suberin levels in roots, more carbon can be sequestered from the atmosphere, through the act of photosynthesis, and stored for long periods of time as a means to mitigate climate change. However, global overexpression of suberin regulators using 35S promoters are known to negatively impact plant health (Mahmood et al., 2019).

Here we describe the generation of transgenic plants that develop additional periderm layers at an earlier stage of root development and/or deposit more suberin in periderm cells without negatively impacting plant health.

SUMMARY OF THE DISCLOSURE

The present disclosure solves the aforementioned goal of increasing suberin production in plants by identifying promoters that express in specific root tissues, such as in the phellogen, pericycle or procambium. Furthermore, the disclosure teaches methodology by which this ability to increase suberin can be imported into any plant genus or species. The importation of this genetic architecture can take many forms, as elaborated upon herein, including: traditional plant breeding, transgenic genetic engineering, next generation plant breeding (CRISPR, base editing, MAS, etc.), and other methods.

In some embodiments as provided herein are isolated nucleic acid molecules comprising a nucleic acid sequence encoding a MYB41 amino acid sequence with at least 80% sequence homology to SEQ ID NO:14 and/or a nucleic acid set forth in SEQ ID NO:13 or SEQ ID NO:15, operably linked to a nucleic acid sequence encoding a heterologous promoter, wherein expression of the isolated nucleic acid molecule in a plant results in increased levels of suberin as compared to wild-type check plants lacking the isolated nucleic acid molecule. In some embodiments of the present invention, the increased levels of suberin occur by generating additional periderm cells and/or depositing more suberin in existing periderm cells.

In some embodiments of the present invention, the isolated nucleic acid molecules have amino acid sequence homologies of at least 85% homology, at least 90% homology, at least 95% homology, at least 96% homology, at least 97% homology, at least 98% homology and at least 99% homology to SEQ ID NO: 14. In some embodiments of the present invention, the isolated nucleic acid molecules have an amino acid sequence homology that is 100% homologous to SEQ ID NO:14. In some embodiments of the present invention, the isolated nucleic acid molecules have nucleic acid sequence homologies of at least 85% homology, at least 90% homology, at least 95% homology, at least 96% homology, at least 97% homology, at least 98% homology or at least 99% homology to SEQ ID NO:13 or SEQ ID NO: 15.

In some embodiments of the present invention, the isolated nucleic acid molecules encoding the heterologous promoter comprises an isolated nucleic acid sequence selected from the group comprising SEQ ID NO:1, SEQ ID NO: 2, SEQ ID NO:3, SEQ ID NO:4, SEQ ID NO:5 and SEQ ID NO:6. In some embodiments, the heterologous promoter is a native promoter of FACT gene. In some embodiments, the heterologous promoter is a native promoter of HORST gene. In some embodiments, the heterologous promoter is a native promoter of ASFT gene. In some embodiments, the heterologous promoter is a native promoter of GPAT5 gene. In some embodiments, the heterologous promoter is a native promoter of RALPH gene. In some embodiments, the heterologous promoter is a native promoter of IYB84 gene.

In some embodiments as provided herein are transformation vectors comprising one or more of the nucleic acid molecules of the present invention.

In some embodiments as provided herein are methods of transforming plant cells comprising introducing the transformation vectors of the present invention into the plant cells, whereby the transformed plant cells produce increased levels of suberin as compared to an untransformed wild-type check plant cell. In some embodiments of the present invention, the methods further comprise producing transformed plant tissues from the transformed plant cells. In some embodiments of the present invention, the methods further comprise producing a transformed plantlet from the transformed plant tissue, wherein the transformed plantlet produces increased levels of suberin as compared to untransformed wild-type check plantlets lacking the isolated nucleic acid molecule.

In some embodiment as provided herein the methods further comprise producing a progeny of the transformed plantlet, wherein the progeny produces increased levels of suberin as compared to untransformed wild-type check plantlets lacking the isolated nucleic acid molecule.

In some embodiments as provided herein, the methods comprise growing the transformed plantlet or the progeny of the transformed plantlet into a mature transformed plant, wherein the mature transformed plant produces increased levels of suberin as compared to mature untransformed wild-type checks lacking the isolated nucleic acid molecule. In some embodiments, the methods provided herein result in increased levels of suberin that occur by generating additional periderm cells and/or depositing more suberin in existing periderm cells. In some embodiments, the methods provided herein result in minimal or no expression of the nucleic acid molecule in cells that are not associated with normal suberin production. In some embodiments, the methods result in minimal or no expression of the nucleic acid molecule in rosette leaves.

In some embodiments as provided herein the methods further comprise using the mature transformed plant or clone of the mature transformed plant in a breeding method. In some embodiments, the breeding methods comprise selfing or crossing the mature transformed plant or clone of the mature transformed plant.

In some embodiments as provided herein the plant breeding methods comprise crossing a first plant comprising a nucleic acid molecule of the present invention with a second plant of the same species and selecting resultant progeny of the cross based on increased levels of suberin as compared to wild-type check plants. In some embodiments, the plant breeding methods further comprise producing clones of the resultant progeny of the cross wherein the clones are selected based on increased levels of suberin as compared to wild-type check plants. In some embodiments, the progeny of the cross that display increased levels of suberin as compared to wild-type check plants are selected using molecular markers that are designed based on the nucleic acid molecule of the present invention. In some embodiments, the methods further comprise using the selected progeny in a breeding method.

In some embodiments of the present invention the methods further comprise growing the mature transformed plant or clone of the mature transformed plant in a greenhouse or outdoors. In some embodiments, the outdoor growing may be in a farm field, a marshland, a plant nursery, rangeland, prairie land, open space, forest land and timber production.

Additional embodiments of the present invention will be readily ascertained by one skilled in the art of molecular genetics, plant breeding, plant husbandry, agricultural production, and other plant-related technologies upon reading the present application.

BRIEF DESCRIPTION OF THE DRAWINGS

FIG. 1A provides a schematic representation of promoter HORST construct. FIG. 1B shows GUS activity assay in Col-0 and one homozygous (MIR13) and two T2 Arabidopsis lines (MR270 and MR276) of proHORST. Plants were grown under ½ MS media for 14 days. The yellow arrow shows GUS expression in periderm (secondary growth) and endodermis cells. FIG. 1C provides a schematic representation of the Arabidopsis primary root longitudinal and cross-section. Arabidopsis root cross-section in the differentiated zone has a simple structure composed of the stele (pericycle and vasculature) surrounded by eight one-cell layer endodermis, and one-cell layer cortex and epidermis. Arabidopsis root cross-section undergoing secondary growth in mature root composed of the vasculature (pheoem and xylem) and periderm cell layer. FIG. 1D provides a graphical summary of GUS result. The dark and/or pale gray color shows where the GUS activities were detected. FIG. 1E provides a schematic representation of proHORST::MYB41 construct. The MYB41 DNA used in the experiments is the full length genomic DNA, including introns and exons. FIG. 1F provides a representative images of Col-0 and homozygous lines of proHORST::MYB41 grown under ½ MS media for 14 days. FIG. 1G shows Nile Staining showing the first (white arrow) layer of periderm is brighter in proHORST::MYB41 homozygous lines than a Col-0 control imaged at the same stage and exposure.

FIGS. 2A-2H illustrate aspects of Examples 1 and 2 with the promoter FACT (proFACT). FIG. 2A provides a schematic representation of the promoter FACT construct. FIG. 2B shows GUS activity assay in Col-0 and 3 different T2 Arabidopsis lines of proFACT. Plants were grown under ½ MS media for 14 days. The yellow arrow shows GUS expression in periderm (secondary growth) and endodermis cells. FIG. 2C provides a schematic representation of the Arabidopsis primary root longitudinal and cross-section. Arabidopsis root cross-section in the differentiated zone has a simple structure composed of the stele (pericycle and vasculature) surrounded by eight one-cell layer endodermis, and one-cell layer cortex and epidermis. Arabidopsis root cross-section undergoing secondary growth in mature root composed of the vasculature (pheoem and xylem) and periderm cell layer. FIG. 2D provides a graphical summary of GUS result. The dark and/or pale gray color shows where the GUS activities were detected. FIG. 2E provides a schematic representation of proFACT::MYB41 construct. The MYB41 DNA used in the experiments is the full length genomic DNA, including introns and exons. FIG. 2F shows expression level of MYB41 in proFACT::MYB41 against two controls; (i) positive control proB-est::MYB41 with β-estradiol treated and (ii) negative control proB-est::MYB41 without β-estradiol treated (Mock). FIG. 2G provides representative images of Col-0 and homozygous lines of proFACT::MYB41 on ½ MS media for 14 days. FIG. 2H Nile Staining showing the first (white arrow) and second layer of periderm (gray arrow) in different proFACT::MYB41 homozygous lines while a Col-0 control imaged at the same stage and exposure only has the first layer of periderm.

FIG. 3A and FIG. 3D provide bar plots showing the levels of suberin biomarkers from dried root tissue from either wild-type, 14 day old Arabidopsis lines or lines expressing either proFACT::MYB41 or proHORST::MYB41 constructs, respectively. Each bar shows the average of three replicate samples where the individual values are represented by the indicated shapes and the error bars represent the standard error of the mean (SEM). In FIG. 3A, data from three independent lines, each harboring the proFACT::MYB41 construct, are represented by the three different shades of gray. In FIG. 3D, data from two independent lines, each harboring the proHORST::MYB41 construct, are shown as indicated by the two shades of dark gray. In this case, three sibling lines (distinguished using symbols) were used for each line. FIG. 3C provides the analysis of the same lines shown in FIG. 3A, but using dried shoot tissue. FIG. 3B and FIG. 3E provide the analysis of the same lines shown in FIG. 3A and FIG. 3D using tissue from 28-day old roots. In all panels, the black arrows denote biomarkers consistently increased compared to the wild-type (WT) control samples.

DETAILED DESCRIPTION OF THE DISCLOSURE

Figure 1A:
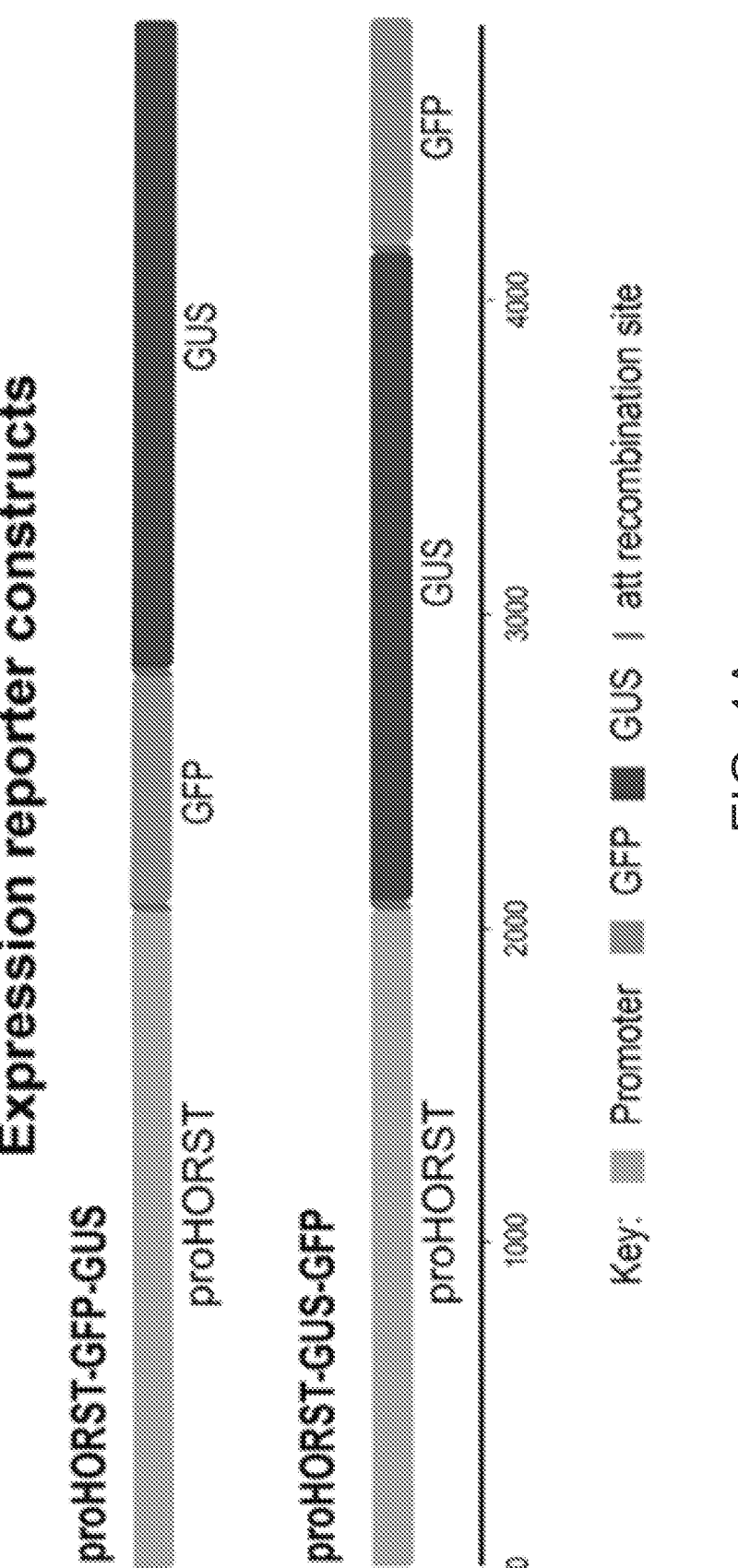
FIGS. 1A-1G illustrate aspects of Examples 1 and 3 with the promoter HORST (proHORST).
Figure 1B:
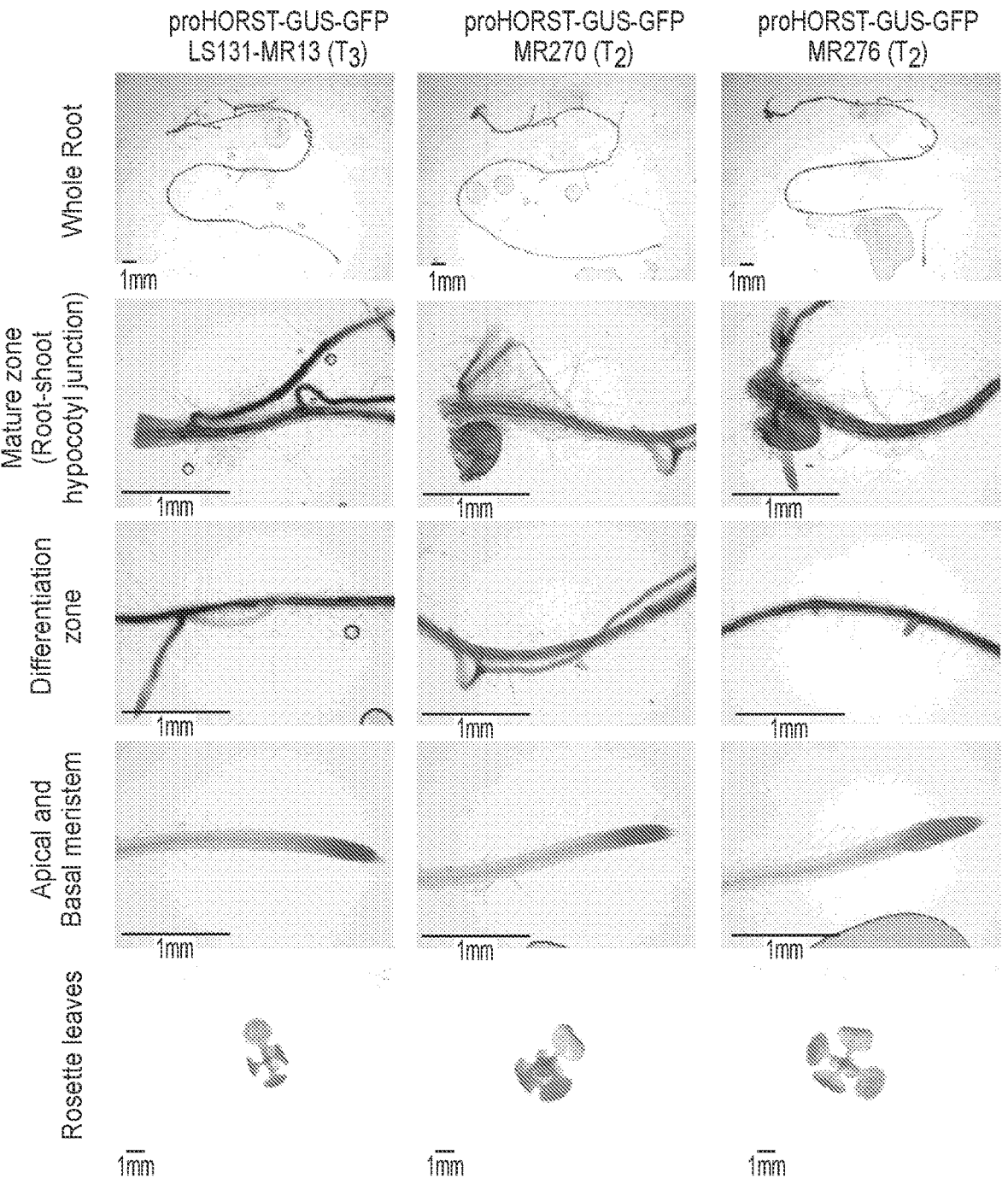
Figure 1C:
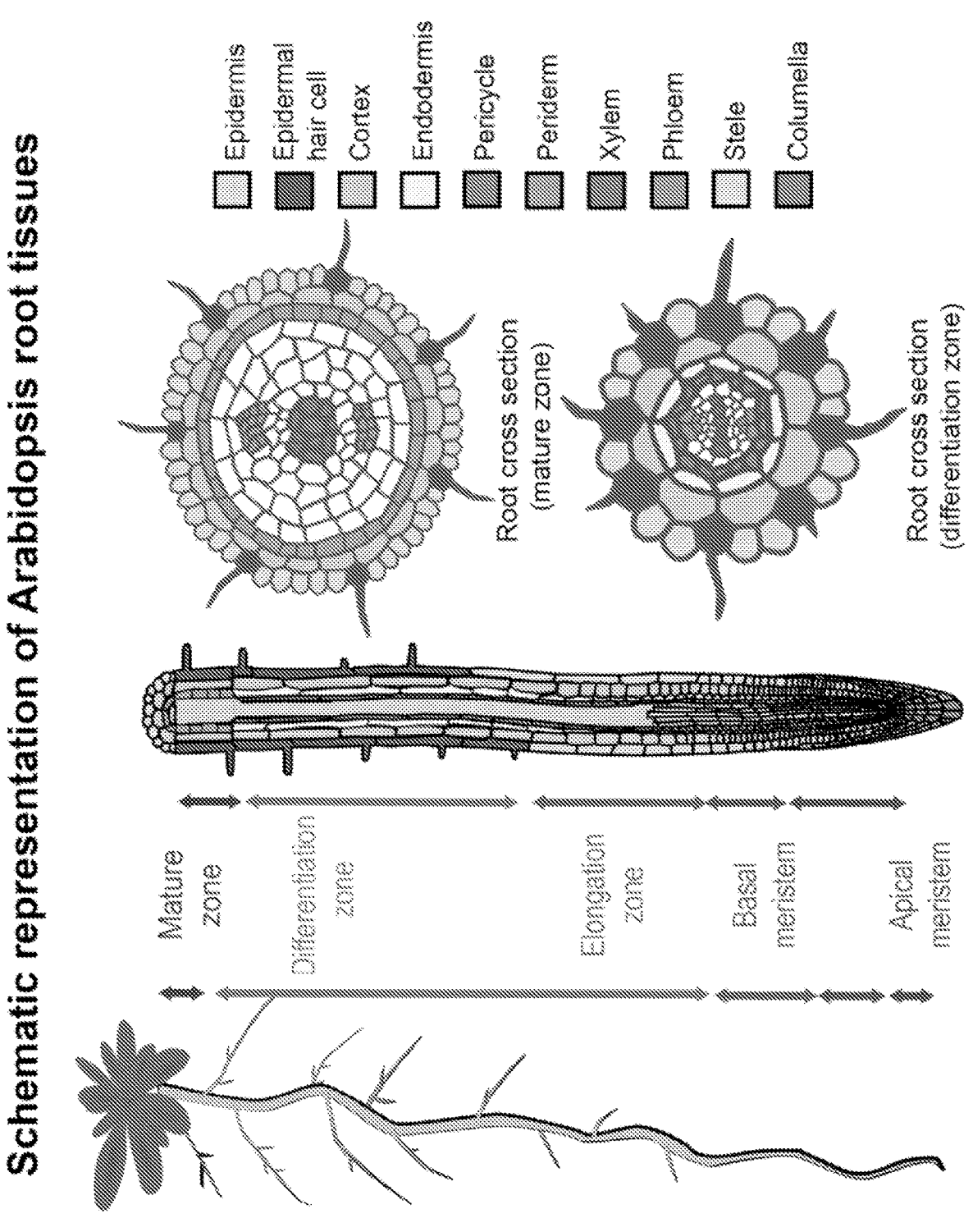
Figure 1D:
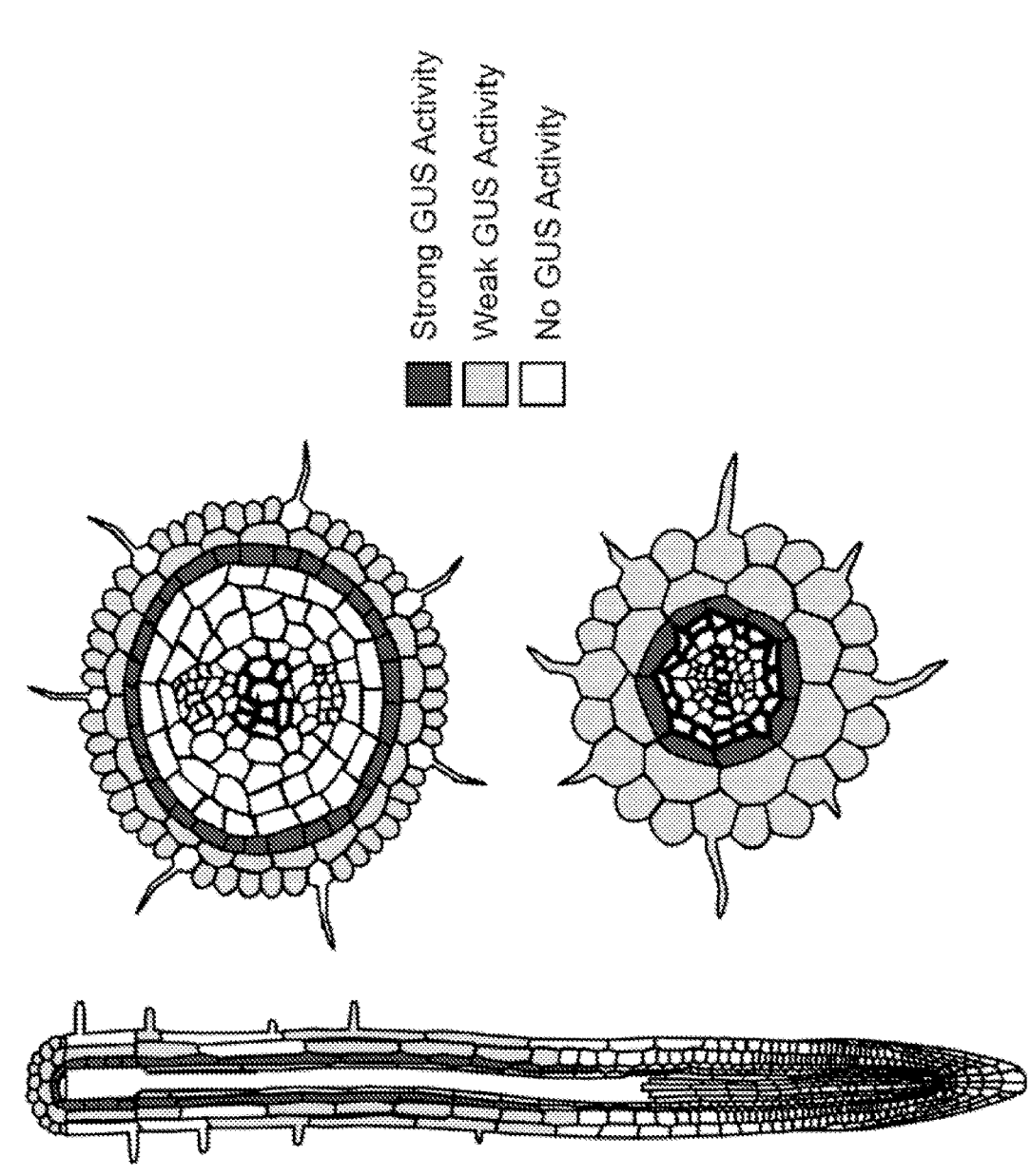

The present disclosure provides a solution for fighting climate change by utilizing improved plants that remove excess carbon from the earth's atmosphere. The present disclosure provides methods of identifying genetic materials that can drive increased carbon sequestration in plant cells, plant tissues, plant parts and whole plants, wherein the carbon is stored in suberin. Also, the present disclosure provides methods of transferring genetic materials to plants in order to give rise to traits that increase suberin content of plant cells, plant tissues, plant parts and whole plants. Furthermore, the present disclosure teaches newly-identified genetic components and methods of generating genetically modified plants, plant cells, tissues, and seeds, having modified carbon sequestration.

I. Definitions

Unless stated otherwise, all technical and scientific terms used herein have the same meaning as commonly understood by those of ordinary skill in the art to which the disclosure belongs. While the following terms are believed to be well understood by one of ordinary skill in the art, the following definitions are set forth to facilitate explanation of the presently disclosed subject matter. Although any methods and materials similar or equivalent to those described herein can be used in the practice or testing of the present disclosure, preferred methods and materials are described. The following terms are defined below. These definitions are for illustrative purposes and are not intended to limit the common meaning in the art of the defined terms.

The term "a" or "an" refers to one or more of that entity, i.e., can refer to a plural referent. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used in this specification, the term "and/or" is used in this disclosure to mean either "and" or "or" unless indicated otherwise.

Throughout this specification, unless the context requires otherwise, the words "comprise", or variations such as "comprises" or "comprising", will be understood to imply the inclusion of a stated element or integer or group of elements or integers but not the exclusion of any other element or integer or group of elements or integers.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the term "at least a portion" or "fragment" of a nucleic acid or polypeptide means a portion having the minimal size characteristics of such sequences, or any larger fragment of the full length molecule, up to and including the full length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids. In some embodiments, a fragment of a polypeptide or polynucleotide comprises at least 10%, 20%, 30%, 40%, 50%, 60%, 70%, 80%, 90%, 95%, 96%, 97%, 98%, or 99% of the entire length of the reference polypeptide or polynucleotide. In some embodiments, a polypeptide or polynucleotide fragment may contain 5, 10, 15, 20, 25, 30, 35, 40, 45, 50, 60, 70, 80, 90, 100, 200, 300, 400, 500, 600, 700, 800, 900, 1000, 2000 or more nucleotides or amino acids.

As used herein, the term "codon optimization" implies that the codon usage of a DNA or RNA is adapted to that of a cell or organism of interest to improve the transcription rate of said recombinant nucleic acid in the cell or organism of interest. The skilled person is well aware of the fact that a target nucleic acid can be modified at one position due to the codon degeneracy, whereas this modification will still lead to the same amino acid sequence at that position after translation, which is achieved by codon optimization to take into consideration the species-specific codon usage of a target cell or organism.

As used herein, the term "endogenous" or "endogenous gene," refers to the naturally occurring gene, in the location in which it is naturally found within the host cell genome. "Endogenous gene" is synonymous with "native gene" as used herein. An endogenous gene as described herein can include alleles of naturally occurring genes that have been mutated according to any of the methods of the present disclosure, i.e. an endogenous gene could have been modified at some point by traditional plant breeding methods and/or next generation plant breeding methods.

As used herein, the term "exogenous" refers to a substance coming from some source other than its native source. For example, the terms "exogenous protein," or "exogenous gene" refer to a protein or gene from a non-native source, and that has been artificially supplied to a biological system. As used herein, the term "exogenous" is used interchangeably with the term "heterologous," and refers to a substance coming from some source other than its native source.

The terms "genetically engineered host cell," "recombinant host cell," and "recombinant strain" are used interchangeably herein and refer to host cells that have been genetically engineered by the methods of the present disclosure. Thus, the terms include a host cell (e.g., bacteria, yeast cell, fungal cell, CHO, human cell, plant cell, protoplast derived from plant, callus, etc.) that has been genetically altered, modified, or engineered, such that it exhibits an altered, modified, or different genotype and/or phenotype (e.g., when the genetic modification affects coding nucleic acid sequences), as compared to the naturally-occurring host cell from which it was derived. It is understood that the terms refer not only to the particular recombinant host cell in question, but also to the progeny or potential progeny of such a host cell.

As used herein, the term "heterologous" refers to a substance coming from some source or location other than its native source or location. In some embodiments, the term "heterologous nucleic acid" refers to a nucleic acid sequence that is not naturally found in the particular organism. For example, the term "heterologous promoter" may refer to a promoter that has been taken from one source organism and utilized in another organism, in which the promoter is not naturally found. However, the term "heterologous promoter" may also refer to a promoter that is from within the same source organism, but has merely been moved to a novel location, in which said promoter is not normally located.

Heterologous gene sequences can be introduced into a target cell by using an "expression vector," which can be a eukaryotic expression vector, for example a plant expression vector. Methods used to construct vectors are well known to a person skilled in the art and described in various publications. In particular, techniques for constructing suitable vectors, including a description of the functional components such as promoters, enhancers, termination and polyadenylation signals, selection markers, origins of replication, and splicing signals, are reviewed in the prior art. Vectors may include but are not limited to plasmid vectors, phagemids, cosmids, artificial/mini-chromosomes (e.g. ACE), or viral vectors such as baculovirus, retrovirus, adenovirus, adeno-associated virus, herpes simplex virus, retroviruses, bacteriophages. The eukaryotic expression vectors will typically contain also prokaryotic sequences that facilitate the propagation of the vector in bacteria such as an origin of replication and antibiotic resistance genes for selection in bacteria. A variety of eukaryotic expression vectors, containing a cloning site into which a polynucleotide can be operatively linked, are well known in the art and some are commercially available from companies such as Stratagene, La Jolla, Calif; Invitrogen, Carlsbad, Calif.; Promega, Madison, Wis. or BD Biosciences Clontech, Palo Alto, Calif. In one embodiment the expression vector comprises at least one nucleic acid sequence which is a regulatory sequence necessary for transcription and translation of nucleotide sequences that encode for a peptide/polypeptide/ protein of interest.

As used herein, the term "naturally occurring" as applied to a nucleic acid, a polypeptide, a cell, or an organism, refers to a nucleic acid, polypeptide, cell, or organism that is found in nature. The term "naturally occurring" may refer to a gene or sequence derived from a naturally occurring source. Thus, for the purposes of this disclosure, a "non-naturally occurring" sequence is a sequence that has been synthesized, mutated, engineered, edited, or otherwise modified to have a different sequence from known natural sequences. In some embodiments, the modification may be at the protein level (e.g., amino acid substitutions). In other embodiments, the modification may be at the DNA level (e.g., nucleotide substitutions).

As used herein, the term "nucleotide change" or "nucleotide modification" refers to, e.g., nucleotide substitution, deletion, and/or insertion, as is well understood in the art. For example, such nucleotide changes/modifications include mutations containing alterations that produce silent substitutions, additions, or deletions, but do not alter the properties or activities of the encoded protein or how the proteins are made. As another example, such nucleotide changes/modifications include mutations containing alterations that produce replacement substitutions, additions, or deletions, that alter the properties or activities of the encoded protein or how the proteins are made.

As used herein, the term "protein modification" refers to, e.g., amino acid substitution, amino acid modification, deletion, and/or insertion, as is well understood in the art.

The term "next generation plant breeding" refers to a host of plant breeding tools and methodologies that are available to today's breeder. A key distinguishing feature of next generation plant breeding is that the breeder is no longer confined to relying upon observed phenotypic variation, in order to infer underlying genetic causes for a given trait. Rather, next generation plant breeding may include the utilization of molecular markers and marker assisted selection (MAS), such that the breeder can directly observe movement of alleles and genetic elements of interest from one plant in the breeding population to another, and is not confined to merely observing phenotype. Further, next generation plant breeding methods are not confined to utilizing natural genetic variation found within a plant population. Rather, the breeder utilizing next generation plant breeding methodology can access a host of modern genetic engineering tools that directly alter/change/edit the plant's underlying genetic architecture in a targeted manner, in order to bring about a phenotypic trait of interest. In aspects, the plants bred with a next generation plant breeding methodology are indistinguishable from a plant that was bred in a traditional manner, as the resulting end product plant could theoretically be developed by either method. In particular aspects, a next generation plant breeding methodology may result in a plant that comprises: a genetic modification that is a deletion or insertion of any size; a genetic modification that is one or more base pair substitution; a genetic modification that is an introduction of nucleic acid sequences from within the plant's natural gene pool (e.g. any plant that could be crossed or bred with a plant of interest) or from editing of nucleic acid sequences in a plant to correspond to a sequence known to occur in the plant's natural gene pool; and offspring of said plants.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA.

The terms "polynucleotide," "nucleic acid," and "nucleotide sequence," used interchangeably herein, refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. This term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. It also includes modified nucleic acids such as methylated and/or capped nucleic acids, nucleic acids containing modified bases, backbone modifications, and the like. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" "nucleic acid," and "nucleotide sequence" should be understood to include, as applicable to the embodiments being described, single-stranded (such as sense or antisense) and double-stranded polynucleotides.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

The term "traditional plant breeding" refers to the utilization of natural variation found within a plant population as a source for alleles and genetic variants that impart a trait of interest to a given plant. Traditional breeding methods make use of crossing procedures that rely largely upon observed phenotypic variation to infer causative allele association. That is, traditional plant breeding relies upon observations of expressed phenotype of a given plant to infer underlying genetic cause. These observations are utilized to inform the breeding procedure in order to move allelic variation into germplasm of interest. Further, traditional plant breeding has also been characterized as comprising random mutagenesis techniques, which can be used to introduce genetic variation into a given germplasm. These random mutagenesis techniques may include chemical and/or radiation-based mutagenesis procedures. Consequently, one key feature of traditional plant breeding, is that the breeder does not utilize a genetic engineering tool that directly alters/changes/edits the plant's underlying genetic architecture in a targeted manner, in order to introduce genetic diversity and bring about a phenotypic trait of interest.

A "CRISPR-associated effector" as used herein can thus be defined as any nuclease, nickase, or recombinase associated with the CRISPR (Clustered Regularly Interspaced Short Palindromic Repeats), having the capacity to introduce a single- or double-strand cleavage into a genomic target site, or having the capacity to introduce a targeted modification, including a point mutation, an insertion, or a deletion, into a genomic target site of interest. At least one CRISPR-associated effector can act on its own, or in combination with other molecules as part of a molecular complex. The CRISPR-associated effector can be present as fusion molecule, or as individual molecules associating by or being associated by at least one of a covalent or non-covalent interaction with gRNA and/or target site so that the components of the CRISPR-associated complex are brought into close physical proximity.

The term "Cas9 nuclease" and "Cas9" can be used interchangeably herein, which refer to a RNA-guided DNA endonuclease enzyme associated with the CRISPR (Clustered Regularly Interspaced Short Palindromic Repeats), including the Cas9 protein or fragments thereof (such as a protein comprising an active DNA cleavage domain of Cas9 and/or a gRNA binding domain of Cas9). Cas9 is a component of the CRISPR/Cas genome editing system, which targets and cleaves a DNA target sequence to form a DNA double strand breaks (DSB) under the guidance of a guide RNA.

The term "CRISPR RNA" or "crRNA" refers to the RNA strand responsible for hybridizing with target DNA sequences, and recruiting CRISPR endonucleases and/or CRISPR-associated effectors. crRNAs may be naturally occurring, or may be synthesized according to any known method of producing RNA.

The term "tracrRNA" refers to a small trans-encoded RNA. TracrRNA is complementary to and base pairs with crRNA to form a crRNA/tracrRNA hybrid, capable of recruiting CRISPR endonucleases and/or CRISPR-associated effectors to target sequences.

The term "Guide RNA" or "gRNA" as used herein refers to an RNA sequence or combination of sequences capable of recruiting a CRISPR endonuclease and/or CRISPR-associated effectors to a target sequence. Typically gRNA is composed of crRNA and tracrRNA molecules forming complexes through partial complement, wherein crRNA comprises a sequence that is sufficiently complementary to a target sequence for hybridization and directs the CRISPR complex (i.e. Cas9-crRNA/tracrRNA hybrid) to specifically bind to the target sequence. Also, single guide RNA (sgRNA) can be designed, which comprises the characteristics of both crRNA and tracrRNA. Therefore, as used herein, a guide RNA can be a natural or synthetic crRNA (e.g., for Cpf1), a natural or synthetic crRNA/tracrRNA hybrid (e.g., for Cas9), or a single-guide RNA (sgRNA).

The term "guide sequence" or "spacer sequence" refers to the portion of a crRNA or guide RNA (gRNA) that is responsible for hybridizing with the target DNA.

The term "protospacer" refers to the DNA sequence targeted by a guide sequence of crRNA or gRNA. In some embodiments, the protospacer sequence hybridizes with the crRNA or gRNA guide (spacer) sequence of a CRISPR complex.

The term "CRISPR landing site" as used herein, refers to a DNA sequence capable of being targeted by a CRISPR-Cas complex. In some embodiments, a CRISPR landing site comprises a proximately placed protospacer/Protopacer Adjacent Motif combination sequence that is capable of being cleaved by a CRISPR complex.

The term "CRISPR complex", "CRISPR endonuclease complex", "CRISPR Cas complex", or "CRISPR-gRNA complex" are used interchangeably herein. "CRISPR complex" refers to a Cas9 nuclease and/or a CRISPR-associated effectors complexed with a guide RNA (gRNA). The term "CRISPR complex" thus refers to a combination of CRISPR endonuclease and guide RNA capable of inducing a double stranded break at a CRISPR landing site. In some embodiments, "CRISPR complex" of the present disclosure refers to a combination of catalytically dead Cas9 protein and guide RNA capable of targeting a target sequence, but not capable of inducing a double stranded break at a CRISPR landing site because it loses a nuclease activity. In other embodiments, "CRISPR complex" of the present disclosure refers to a combination of Cas9 nickase and guide RNA capable of introducing gRNA-targeted single-strand breaks in DNA instead of the double-strand breaks created by wild type Cas enzymes.

As used herein, the term "directing sequence-specific binding" in the context of CRISPR complexes refers to a guide RNA's ability to recruit a CRISPR endonuclease and/or a CRISPR-associated effectors to a CRISPR landing site.

As used herein the term "targeted" refers to the expectation that one item or molecule will interact with another item or molecule with a degree of specificity, so as to exclude non-targeted items or molecules. For example, a first polynucleotide that is targeted to a second polynucleotide, according to the present disclosure has been designed to hybridize with the second polynucleotide in a sequence specific manner (e.g., via Watson-Crick base pairing). In some embodiments, the selected region of hybridization is designed so as to render the hybridization unique to the one, or more targeted regions. A second polynucleotide can cease to be a target of a first targeting polynucleotide, if its targeting sequence (region of hybridization) is mutated, or is otherwise removed/separated from the second polynucle-otide. Furthermore, "targeted" can be interchangeably used with "site-specific" or "site-directed," which refers to an action of molecular biology which uses information on the sequence of a genomic region of interest to be modified, and which further relies on information of the mechanism of action of molecular tools, e.g., nucleases, including CRISPR nucleases and variants thereof, TALENs, ZFNs, meganucle-ases or recombinases, DNA-modifying enzymes, including base modifying enzymes like cytidine deaminase enzymes, histone modifying enzymes and the like, DNA-binding proteins, cr/tracr RNAs, guide RNAs and the like.

The term "seed region" refers to the critical portion of a crRNA's or guide RNA's guide sequence that is most susceptible to mismatches with their targets. In some embodiments, a single mismatch in the seed region of a crRNA/gRNA can render a CRISPR complex inactive at that binding site. In some embodiments, the seed regions for Cas9 endonucleases are located along the last ~12 nts of the 3' portion of the guide sequence, which correspond (hybrid-ize) to the portion of the protospacer target sequence that is adjacent to the PAM. In some embodiments, the seed regions for Cpf1 endonucleases are located along the first ~5 nts of the 5' portion of the guide sequence, which correspond (hybridize) to the portion of the protospacer target sequence adjacent to the PAM.

The term "sequence identity" refers to the percentage of bases or amino acids between two polynucleotide or poly-peptide sequences that are the same, and in the same relative position. As such one polynucleotide or polypeptide sequence has a certain percentage of sequence identity compared to another polynucleotide or polypeptide sequence. For sequence comparison, typically one sequence acts as a reference sequence, to which test sequences are compared. The term "reference sequence" refers to a mol-ecule to which a test sequence is compared. When percent-age of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in con-servative substitutions, the percent sequence identity may be adjusted upwards to correct for the conservative nature of the substitution. Sequences which differ by such conserva-tive substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988).

"Complementary" refers to the capacity for pairing, through base stacking and specific hydrogen bonding, between two sequences comprising naturally or non-natu-rally occurring bases or analogs thereof. For example, if a base at one position of a nucleic acid is capable of hydrogen bonding with a base at the corresponding position of a target, then the bases are considered to be complementary to each other at that position. Nucleic acids can comprise universal bases, or inert abasic spacers that provide no positive or negative contribution to hydrogen bonding. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T. Nichols et al., Nature, 1994; 369:492-493 and Loakes et al., Nucleic Acids Res., 1994; 22:4039-4043. Inosine (I) has also been considered in the art to be a universal base and is considered complementary to any A, C, U, or T. See Watkins and Santa Lucia, Nucl. Acids Research, 2005; 33 (19): 6258-6267.

As referred to herein, a "complementary nucleic acid sequence" is a nucleic acid sequence comprising a sequence of nucleotides that enables it to non-covalently bind to another nucleic acid in a sequence-specific, antiparallel, manner (i.e., a nucleic acid specifically binds to a comple-mentary nucleic acid) under the appropriate in vitro and/or in vivo conditions of temperature and solution ionic strength.

Methods of sequence alignment for comparison and determination of percent sequence identity and percent complementarity are well known in the art. Optimal alignment of sequences for comparison can be conducted, e.g., by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, WI), by manual alignment and visual inspection (see, e.g., Brent et al., (2003) Current Protocols in Molecular Biology), by use of algorithms know in the art including the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, CA). Another alignment program is Sequencher (Gene Codes, Ann Arbor, Michigan), using default parameters, and MUSCLE (Multiple Sequence Comparison by Log-Expection; a computer software licensed as public domain).

Herein, the term "hybridize" refers to pairing between complementary nucleotide bases (e.g., adenine (A) forms a base pair with thymine (T) in a DNA molecule and with uracil (U) in an RNA molecule, and guanine (G) forms a base pair with cytosine (C) in both DNA and RNA molecules) to form a double-stranded nucleic acid molecule. (See, e.g., Wahl and Berger (1987) Methods Enzymol. 152:399; Kimmel, (1987) Methods Enzymol. 152:507). In addition, it is also known in the art that for hybridization between two RNA molecules (e.g., dsRNA), guanine (G) base pairs with uracil (U). For example, G/U base-pairing is partially responsible for the degeneracy (i.e., redundancy) of the genetic code in the context of tRNA anti-codon base-pairing with codons in mRNA. In the context of this disclosure, a guanine (G) of a protein-binding segment (dsRNA duplex) of a guide RNA molecule is considered complementary to a uracil (U), and vice versa. As such, when a G/U base-pair can be made at a given nucleotide position a protein-binding segment (dsRNA duplex) of a guide RNA molecule, the position is not considered to be non-complementary, but is instead considered to be complementary. It is understood in the art that the sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted.

The term "modified" refers to a substance or compound (e.g., a cell, a polynucleotide sequence, and/or a polypeptide sequence) that has been altered or changed as compared to the corresponding unmodified substance or compound.

"Isolated" refers to a material that is free to varying degrees from components which normally accompany it as found in its native state.

The term "gene edited plant, part or cell" as used herein refers to a plant, part or cell that comprises one or more endogenous genes that are edited by a gene editing system. The gene editing system of the present disclosure comprises a targeting element and/or an editing element. The targeting element is capable of recognizing a target genomic sequence. The editing element is capable of modifying the target genomic sequence, e.g., by substitution or insertion of one or more nucleotides in the genomic sequence, deletion of one or more nucleotides in the genomic sequence, alteration of genomic sequences to include regulatory sequences, insertion of transgenes at a safe harbor genomic site or other specific location in the genome, or any combination thereof. The targeting element and the editing element can be on the same nucleic acid molecule or different nucleic acid molecules.

The term "plant part" includes differentiated and undifferentiated tissues including, but not limited to: plant organs, plant tissues, roots, stems, shoots, rootstocks, scions, stipules, petals, leaves, flowers, ovules, pollens, bracts, petioles, internodes, bark, pubescence, tillers, rhizomes, fronds, blades, stamens, fruits, seeds, tumor tissue and plant cells (e.g., single cells, protoplasts, embryos, and callus tissue). Plant cells include, without limitation, cells from seeds, suspension cultures, embryos, meristematic regions, callus tissue, leaves, roots, shoots, gametophytes, sporophytes, pollen and microspores. The plant tissue may be in a plant or in a plant organ, tissue or cell culture.

As used herein when discussing plants, the term "ovule" refers to the female gametophyte, whereas the term "pollen" means the male gametophyte.

As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

As used herein, the term "phenotype" refers to the observable characters of an individual cell, cell culture, organism (e.g., a plant), or group of organisms which results from the interaction between that individual's genetic makeup (i.e., genotype) and the environment.

The terms "transgene" or "transgenic" as used herein refer to at least one nucleic acid sequence that is taken from the genome of one organism, or produced synthetically, and which is then introduced into a host cell or organism or tissue of interest and which is subsequently integrated into the host's genome by means of "stable" transformation or transfection approaches. In contrast, the term "transient" transformation or transfection or introduction refers to a way of introducing molecular tools including at least one nucleic acid (DNA, RNA, single-stranded or double-stranded or a mixture thereof) and/or at least one amino acid sequence, optionally comprising suitable chemical or biological agents, to achieve a transfer into at least one compartment of interest of a cell, including, but not restricted to, the cytoplasm, an organelle, including the nucleus, a mitochondrion, a vacuole, a chloroplast, or into a membrane, resulting in transcription and/or translation and/or association and/or activity of the at least one molecule introduced without achieving a stable integration or incorporation and thus inheritance of the respective at least one molecule introduced into the genome of a cell. The terms "transgene-free" refers to a condition that transgene is not present or found in the genome of a host cell or tissue or organism of interest.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, leaves, stems, roots, root tips, anthers, pistils, meristematic cells, axillary buds, ovaries, seed coat, endosperm, hypocotyls, cotyledons and the like. The term "plant organ" refers to plant tissue or a group of tissues that constitute a morpho-logically and functionally distinct part of a plant. "Progeny" comprises any subsequent generation of a plant.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecu-lar Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

By "biologically active portion" is meant a portion of a full-length parent peptide or polypeptide which portion retains an activity of the parent molecule. For example, a biologically active portion of polypeptide of the disclosure will retain the ability to increase and/or enhance suberin levels in plant cells, tissues and whole plants. As used herein, the term "biologically active portion" includes dele-tion mutants and peptides, for example of at least about 8, 9, 10, 11, 12, 13, 14, 15, 16, 17, 18, 19, 20, 21, 22, 23, 24, 25, 30, 40, 50, 60, 70, 80, 90, 100, 120, 150, 300, 400, 500, 600, 700, 800, 900 or 1000 contiguous amino acids, which comprise an activity of a parent molecule. Portions of this type may be obtained through the application of standard recombinant nucleic acid techniques or synthesized using conventional liquid or solid phase synthesis techniques. For example, reference may be made to solution synthesis or solid phase synthesis as described, for example, in Chapter 9 entitled "Peptide Synthesis" by Atherton and Shephard which is included in a publication entitled "Synthetic Vac-cines" edited by Nicholson and published by Blackwell Scientific Publications. Alternatively, peptides can be pro-duced by digestion of a peptide or polypeptide of the disclosure with proteinases such as endoLys-C, endoArg-C, endoGlu-C and *staphylococcus* V8-protease. The digested fragments can be purified by, for example, high performance liquid chromatographic (HPLC) techniques. Recombinant nucleic acid techniques can also be used to produce such portions.

By "corresponds to" or "corresponding to" is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein.

The terms "growing" or "regeneration" as used herein mean growing a whole, differentiated plant from a plant cell, a group of plant cells, a plant part (including seeds), or a plant piece (e.g., from a protoplast, callus, or tissue part).

As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

By "obtained from" is meant that a sample such as, for example, a nucleic acid extract or polypeptide extract is isolated from, or derived from, a particular source. For example, the extract may be isolated directly from plants.

By "variant" polypeptide is intended a polypeptide derived from the native protein by deletion (so-called trun-cation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present disclosure are biologically active, that is they continue to possess the desired biological activity of the native protein, that is, modulating or regulatory activity as described herein. Such variants may result from, for example, genetic polymor-phism or from human manipulation. Biologically active variants of a native R protein of the disclosure will have at least 40%, 50%, 60%, 70%, generally at least 75%, 80%, 85%, preferably about 90% to 95% or more, and more preferably about 98% or more sequence identity to the amino acid sequence for the native protein as determined by sequence alignment programs described elsewhere herein using default parameters. A biologically active variant of a protein of the disclosure may differ from that protein by as few as 1-15 amino acid residues, as few as 1-10, such as 6-10, as few as 5, as few as 4, 3, 2, or even 1 amino acid residue.

The proteins of the disclosure may be altered in various ways including amino acid substitutions, deletions, trunca-tions, and insertions. Methods for such manipulations are generally known in the art. For example, amino acid sequence variants of the R proteins can be prepared by mutations in the DNA. Methods for mutagenesis and nucleotide sequence alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Con-servative substitutions, such as exchanging one amino acid with another having similar properties, may be preferable.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Con-servative substitution tables providing functionally similar amino acids are well known in the art. The following five groups each contain amino acids that are conservative substitutions for one another, Aliphatic: Glycine (G), Ala-nine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine I, Lysine (K), Histidine (H); Acidic: Aspartic acid (D), Glu-tamic acid (E), Asparagine (N), Glutamine (Q). See also, Creighton, 1984. In addition, individual substitutions, deletions or additions which alter, add or delete a single amino acid or a small percentage of amino acids in an encoded sequence are also "conservatively modified variations."

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development in animal and/or plant.

As used herein, the term "vector", "plasmid", or "construct" refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, recombinant plant viruses. Non-limiting examples of plant viruses include, TMV-mediated (transient) transfection into tobacco (Tuipe, T-H et al (1993), J. Virology Meth, 42: 227-239), ssDNA genomes viruses (e.g., family Geminiviridae), reverse transcribing viruses (e.g., families *Caulimoviridae, Pseudoviridae*, and *Metaviridae*), dsNRA viruses (e.g., families *Reoviridae* and *Partitiviridae*), (–) ssRNA viruses (e.g., families *Rhabdoviridae* and *Bunyaviridae*), (+) ssRNA viruses (e.g., families *Bromoviridae, Closteroviridae, Comoviridae, Luteoviridae, Potyviridae, Sequiviridae* and *Tombusviridae*) and viroids (e.g., families *Pospiviroldae* and *Avsunviroidae*). Detailed classification information of plant viruses can be found in Fauquet et al (2008, "Geminivirus strain demarcation and nomenclature". *Archives of Virology* 153:783-821, incorporated herein by reference in its entirety), and Khan et al. (Plant viruses as molecular pathogens; Publisher Routledge, 2002, ISBN 1560228954, 9781560228950). Examples of non-viral vectors include, but are not limited to, liposomes, polyamine derivatives of DNA, and the like.

Also, "vector" is defined to include, inter alia, any plasmid, cosmid, phage or *Agrobacterium* binary vector in double or single stranded linear or circular form which may or may not be self-transmissible or mobilizable, and which can transform prokaryotic or eukaryotic host either by integration into the cellular genome or exist extrachromosomally (e.g. autonomous replicating plasmid with an origin of replication).

Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

As used herein, the term "offspring" refers to any plant resulting as progeny from a vegetative or sexual reproduction from one or more parent plants or descendants thereof. For instance an offspring plant may be obtained by cloning or selfing of a parent plant or by crossing two parents plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

The term "plant" includes reference to whole plants, plant organs, plant tissues, and plant cells and progeny of same, but is not limited to angiosperms and gymnosperms such as *Arabidopsis*, potato, tomato, tobacco, alfalfa, lettuce, carrot, strawberry, sugarbeet, cassava, sweet potato, soybean, lima bean, pea, chick pea, maize (corn), turf grass, wheat, rice, barley, sorghum, oat, oak, *eucalyptus*, walnut, palm and duckweed as well as fern and moss. Thus, a plant may be a monocot, a dicot, a vascular plant reproduced from spores such as fern or a non-vascular plant such as moss, liverwort, hornwort and algae. The word "plant," as used herein, also encompasses plant cells, seed, plant progeny, propagule whether generated sexually or asexually, and descendants of any of these, such as cuttings or seed. Plant cells include suspension cultures, callus, embryos, meristematic regions, callus tissue, leaves, roots, shoots, gametophytes, sporophytes, pollen, seeds and microspores. Plants may be at various stages of maturity and may be grown in liquid or solid culture, or in soil or suitable media in pots, greenhouses or fields. Expression of an introduced leader, trailer or gene sequences in plants may be transient or permanent. A "selected plant species" may be, but is not limited to, a species of any one of these "plants."

In the present disclosure, the plants are intended to comprise without limitation angiosperm and gymnosperm plants such as acacia, alfalfa, amaranth, apple, apricot, artichoke, ash tree, asparagus, avocado, banana, barley, beans, beet, birch, beech, blackberry, black raspberry, blueberry, broccoli, Brussel's sprouts, cabbage, cane berry, canola, cantaloupe, carrot, cassava, cauliflower, cedar, a cereal, celery, chestnut, cherry, Chinese cabbage, citrus, Clementine, clover, coffee, corn, cotton, cowpea, cucumber, cypress, eggplant, elm, endive, *eucalyptus*, fennel, figs, fir, geranium, grape, grapefruit, groundnuts, ground cherry, gum hemlock, hickory, kale, kiwifruit, kohlrabi, larch, lettuce, leek, lemon, lime, locust, pine, maidenhair, maize, mango, maple, melon, millet, mushroom, mustard, nuts, oak, oats, oil palm, okra, onion, orange, an ornamental plant or flower or tree, *papaya*, palm, parsley, parsnip, pea, peach, peanut, pear, peat, pepper, persimmon, pigeon pea, peach, pine, pineapple, plantain, plum, pomegranate, potato, pumpkin, radicchio, radish, rapeseed, raspberry, rice, rye, sorghum, safflower, sallow, soybean, spinach, spruce, squash, strawberry, sugar beet, sugarcane, sunflower, sweet potato, sweet corn, tangerine, tea, tobacco, tomato, trees, triticale, turf grasses, turnips, vine, walnut, watercress, watermelon, wheat, wild strawberry, yams, yew, and zucchini.

Angiosperm is defined as vascular plants having seeds enclosed in an ovary. Angiosperms are seed plants that produce flowers that bear fruits. Angiosperms are divided into dicotyledonous and monocotyledonous plants.

Dicotyledonous plant (Dicot) is defined as a flowering plant whose embryos have two seed halves or cotyledons, branching leaf veins, and flower parts in multiples of four or five. Examples of dicots include but are not limited to, *Eucalyptus, Populus*, Liquidamber, Acacia, teak, mahogany, tobacco, *Arabidopsis*, tomato, potato sugar beet, broccoli, cassava, sweet potato, pepper, poinsettia, bean, rapeseed/canola, alfalfa, radish, crimson clover, field pennycress, soybean, carrot, strawberry, lettuce, oak, maple, walnut, rose, mint, squash, daisy, geranium, avocado, cotton/cottonseed and cactus.

*Thlaspi arvense*, known by the common name field pennycress (aka pennycress), is a flowering plant in the cabbage family Brassicaceae. CoverCress is a new oilseed crop grown over winter between normal full season corn and soybeans. CoverCress was developed from pennycress. Low fiber pennycress lines are provided in U.S. Pat. No. 10,709,151, which is assigned to CoverCress Inc.

Monocotyledonous Plant (Monocot) is defined as a flowering plant having embryos with one cotyledon or seed leaf, parallel leaf veins, and flower parts in multiples of three. Examples of monocots include, but are not limited to turfgrass, corn/maize, rice, oat, annual ryegrass, wheat, barley, *sorghum*, orchid, iris, lily, onion, and palm. Examples of turfgrass include, but are not limited to *Agrostis* spp. (bentgrass species including colonial bentgrass and creeping bentgrasses), *Poa pratensis* (Kentucky bluegrass), *Lolium* spp. (ryegrass species including annual ryegrass and perennial ryegrass), *Festuca arundinacea* (tall fescue) *Festuca rubra commutata* (Chewings fescue), *Cynodon dactylon* (bermudagrass, *Pennisetum clandestinum* (kikuyu grass), *Stenotaphrum secundatum* (St. Augustine grass), *Zoysia japonica* (zoysia grass), and *Dichondra micrantha*.

The methods for targeted gene-editing system as described herein can be used to confer desired traits on essentially any plant. A wide variety of plants and plant cell systems may be engineered for the desired physiological and agronomic characteristics described herein using the nucleic acid constructs of the present disclosure and the various transformation methods. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, grape, peach, pear, plum, raspberry, black raspberry, blackberry, cane berry, cherry, avocado, strawberry, wild strawberry, orange), forage crops (e.g., alfalfa), root vegetable crops (e.g., carrot, potato, sugar beets, yam), leafy vegetable crops (e.g., lettuce, spinach); flowering plants (e.g., *petunia*, rose, *chrysanthemum*), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). In some embodiments, fruit crops such as tomato, apple, peach, pear, plum, raspberry, black raspberry, blackberry, cane berry, cherry, avocado, strawberry, wild strawberry, grape and orange.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, organism (e.g., a plant), or group of organisms.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes. Since the present disclosure relates to QTLs, i.e. genomic regions that may comprise one or more genes or regulatory sequences, it is in some instances more accurate to refer to "haplotype" (i.e. an allele of a chromosomal segment) instead of "allele", however, in those instances, the term "allele" should be understood to comprise the term "haplotype". Alleles are considered identical when they express a similar phenotype. Differences in sequence are possible but not important as long as they do not influence phenotype.

As used herein, the term "locus" (plural: "loci") refers to any site that has been defined genetically. A locus may be a gene, or part of a gene, or a DNA sequence that has some regulatory role, and may be occupied by different sequences.

As used herein, the term "molecular marker" or "genetic marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. Mapping of molecular markers in the vicinity of an allele is a procedure which can be performed quite easily by the average person skilled in molecular-biological techniques which techniques are for instance described in Lefebvre and Chevre, 1995; Lorez and Wenzel, 2007, Srivastava and Narula, 2004, Meksem and Kahl, 2005, Phillips and Vasil, 2001. General information concerning AFLP technology can be found in Vos et al. (1995, AFLP: a new technique for DNA finger-printing, Nucleic Acids Res. 1995 Nov. 11; 23(21): 4407-4414).

As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

As used herein, the term "heterozygote" refers to a diploid or polyploid individual cell or plant having different alleles (forms of a given gene) present at least at one locus.

As used herein, the term "heterozygous" refers to the presence of different alleles (forms of a given gene) at a particular gene locus.

As used herein, the term "homozygote" refers to an individual cell or plant having the same alleles at one or more loci.

As used herein, the term "homozygous" refers to the presence of identical alleles at one or more loci in homologous chromosomal segments.

As used herein, the term "homologous" or "homolog" is known in the art and refers to related sequences that share a common ancestor or family member and are determined based on the degree of sequence identity. The terms "homology", "homologous", "substantially similar" and "corresponding substantially" are used interchangeably herein. Homologs usually control, mediate, or influence the same or similar biochemical pathways, yet particular homologs may give rise to differing phenotypes. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, sub-species, variety, cultivar or strain. For purposes of this disclosure homologous sequences are compared.

The term "homolog" is sometimes used to apply to the relationship between genes separated by the event of spe-ciation (see "ortholog") or to the relationship between genes separated by the event of genetic duplication (see "para-log").

The term "homeolog" refers to a homeologous gene or chromosome, resulting from polyploidy or chromosomal duplication events. This contrasts with the more common 'homolog', which is defined immediately above.

The term "ortholog" refers to genes in different species that evolved from a common ancestral gene by speciation. Normally, orthologs retain the same function in the course of evolution. Identification of orthologs is critical for reliable prediction of gene function in newly sequenced genomes.

The term "paralog" refers to genes related by duplication within a genome. While orthologs generally retain the same function in the course of evolution, paralogs can evolve new functions, even if these are related to the original one.

"Homologous sequences" or "homologs" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodi-ment, is at least 50% (when using standard sequence align-ment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Michigan), AlignX, and Vector NTI (Invitrogen, Carlsbad, CA).

As used herein, the term "hybrid" refers to any individual cell, tissue or plant resulting from a cross between parents that differ in one or more genes.

As used herein, the term "inbred" or "inbred line" refers to a relatively true-breeding strain.

The term "single allele converted plant" as used herein refers to those plants which are developed by a plant breeding technique called backcrossing wherein essentially all of the desired morphological and physiological charac-teristics of an inbred are recovered in addition to the single allele transferred into the inbred via the backcrossing tech-nique.

As used herein, the term "line" is used broadly to include, but is not limited to, a group of plants vegetatively propa-gated from a single parent plant, via tissue culture tech-niques or a group of inbred plants which are genetically very similar due to descent from a common parent(s). A plant is said to "belong" to a particular line if it (a) is a primary transformant (TO) plant regenerated from material of that line; (b) has a pedigree comprised of a TO plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous con-dition, imparts a desired trait to the plant.

As used herein, the terms "wildtype check", "wildtype" or "check" all refer to a first cell, tissue culture, part or organism which is essentially genetically the same as a second cell, tissue culture, part or organism, respectively, except that the corresponding second cell, tissue culture, part or organism comprises a heterologous genetic element not present in the first cell, tissue culture, part or organism. Thus, for example, a first plant would be a wildtype check relative to a second plant where the only meaningful genetic difference between the two is that the second plant com-prises a heterologous gene (e.g., MYB41) not present in the first plant.

As used herein, the terms "introgression", "introgressed" and "introgressing" refer to the process whereby genes of one species, variety or cultivar are moved into the genome of another species, variety or cultivar, by crossing those species. The crossing may be natural or artificial. The process may optionally be completed by backcrossing to the recurrent parent, in which case introgression refers to infil-tration of the genes of one species into the gene pool of another through repeated backcrossing of an interspecific hybrid with one of its parents. An introgression may also be described as a heterologous genetic material stably inte-grated in the genome of a recipient plant.

As used herein, the term "population" means a genetically homogeneous or heterogeneous collection of plants sharing a common genetic derivation.

As used herein, the term "variety" or "cultivar" means a group of similar plants that by structural features and performance can be identified from other varieties within the same species. The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

A variety is deemed to be essentially derived from another variety ('the initial variety') when: (i) it is predominantly derived from the initial variety, or from a variety that is itself predominantly derived from the initial variety, while retaining the expression of the essential characteristics that result from the genotype or combination of genotypes of the initial variety; (ii) it is clearly distinguishable from the initial variety; and, (iii) except for the differences which result from the act of derivation, it conforms to the initial variety in the expression of the essential characteristics that result from the genotype or combination of genotypes of the initial variety. UPOV, Article 14(5)(b).

As used herein, the term "mass selection" refers to a form of selection in which individual plants are selected and the next generation propagated from the aggregate of their seeds. More details of mass selection are described herein in the specification.

As used herein, the term "open pollination" refers to a plant population that is freely exposed to some gene flow, as opposed to a closed one in which there is an effective barrier to gene flow.

As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

As used herein, the term "self-crossing", "self pollinated" or "self-pollination" means the pollen of one flower on one plant is applied (artificially or naturally) to the ovule (stigma) of the same or a different flower on the same plant.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T and G/C content) of primer. A pair of bi-directional primers consists of one forward and one reverse primer as commonly used in the art of DNA amplification such as in PCR amplification.

A probe comprises an identifiable, isolated nucleic acid that recognizes a target nucleic acid sequence. A probe includes a nucleic acid that is attached to an addressable location, a detectable label or other reporter molecule and that hybridizes to a target sequence. Typical labels include radioactive isotopes, enzyme substrates, co-factors, ligands, chemiluminescent or fluorescent agents, haptens, and enzymes. Methods for labelling and guidance in the choice of labels appropriate for various purposes are discussed, for example, in Sambrook et al. (ed.), *Molecular Cloning: A Laboratory Manual, 2^{nd}* ed., vol. 1-3, Cold Spring Harbor Laboratory Press, Cold Spring Harbor, N Y, 1989 and Ausubel et al. *Short Protocols in Molecular Biology, 4^{th}* ed., John Wiley & Sons, Inc., 1999.

Methods for preparing and using nucleic acid probes and primers are described, for example, in Sambrook et al. (ed.), *Molecular Cloning: A Laboratory Manual, 2^{nd}* ed., vol. 1-3, Cold Spring Harbor Laboratory Press, Cold Spring Harbor, N Y, 1989; Ausubel et al. *Short Protocols in Molecular Biology, 4^{th}* ed., John Wiley & Sons, Inc., 1999; and Innis et al. *PCR Protocols, A Guide to Methods and Applications*, Academic Press, Inc., San Diego, C A, 1990. Amplification primer pairs can be derived from a known sequence, for example, by using computer programs intended for that purpose such as PRIMER (Version 0.5, 1991, Whitehead Institute for Biomedical Research, Cambridge, MA). One of ordinary skill in the art will appreciate that the specificity of a particular probe or primer increases with its length. Thus, in order to obtain greater specificity, probes and primers can be selected that comprise at least 20, 25, 30, 35, 40, 45, 50 or more consecutive nucleotides of a target nucleotide sequences.

For PCR amplifications of the polynucleotides disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (2001) Molecular Cloning: A Laboratory Manual (3rd ed., Cold Spring Harbor Laboratory Press, Plainview, New York). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The present disclosure provides an isolated nucleic acid sequence comprising a sequence selected from the group consisting of MYB41, homologs of MYB41, orthologs of MYB41, paralogs of MYB41, and fragments and variations thereof. In one embodiment, the present disclosure provides an isolated polynucleotide encoding a protein produced by the nucleic acid sequence for MYB41 (e.g. SEQ ID NO:13 or SEQ ID NO: 15), comprising a nucleic acid sequence that shares at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to MYB41 (e.g. SEQ ID NO:13 or SEQ ID NO:15).

Methods of alignment of sequences for comparison are well known in the art. Various programs and alignment algorithms are described in: Smith and Waterman (*Adv. Appl. Math.*, 2:482, 1981); Needleman and Wunsch (*J. Mol. Biol.*, 48:443, 1970); Pearson and Lipman (*Proc. Natl. Acad. Sci.*, 85:2444, 1988); Higgins and Sharp (*Gene*, 73:237-44, 1988); Higgins and Sharp (*CABIOS*, 5:151-53, 1989); Corpet et al. (*Nuc. Acids Res.*, 16:10881-90, 1988); Huang et al. (*Comp. Apps Biosci.*, 8:155-65, 1992); and Pearson et al. (*Meth. Mol. Biol.*, 24:307-31, 1994). Altschul et al. (*Nature Genet.*, 6:119-29, 1994) presents a detailed consideration of sequence alignment methods and homology calculations.

The present disclosure also provides a chimeric gene comprising the isolated nucleic acid sequence of any one of the polynucleotides described above operably linked to suitable regulatory sequences. In some embodiments, a chimeric gene comprises the isolated nucleic acid sequence comprising a sequence selected from the group consisting of MYB41, homologs of MYB41, orthologs of MYB41, paralogs of MYB41, and fragments and variations thereof.

In some embodiments, a chimeric gene comprises a nucleic acid sequence set forth in SEQ ID NO: 13 (*Arabidopsis thaliana* MYB41 gene). In some embodiments, a chimeric gene comprises a nucleic acid sequence set forth in SEQ ID NO: 15 (*Arabidopsis thaliana* MB41 coding sequence (MYB41 CDS)). In some embodiments, a chimeric gene comprises a nucleic acid sequence encoding SEQ ID NO: 14 (*Arabidopsis thaliana* MYB41 protein).

In some embodiments, a chimeric gene comprises an isolated nucleic acid sequence described above, which is operably linked to suitable regulatory sequences including, but not limited to native promoters of FACT, HORST, ASFT, GPAT5, RALPH and/or MYB84.

The present disclosure also provides a recombinant construct comprising the chimeric gene as described above. In one embodiment, said recombinant construct is a gene silencing construct, such as used in RNAi gene silencing. In another embodiment, said recombinant construct is a gene editing construct, such as used in CRISPR-Cas gene editing system.

The expression vectors of the present disclosure may include at least one selectable marker. Such markers include dihydrofolate reductase, G418 or neomycin resistance for eukaryotic cell culture and tetracycline, kanamycin or ampicillin resistance genes for culturing in *E. coli* and other bacteria.

The present disclosure also provides a transformed host cell comprising the chimeric gene as described above. In one embodiment, said host cell is selected from the group consisting of bacteria, yeasts, filamentous fungi, algae, animals, and plants.

These sequences allow the design of gene-specific primers and probes for MYB41, homologs of MYB41, orthologs of MYB41, homeologs of MYB41, paralogs of MYB41, and fragments and variations thereof.

New breeding techniques (NBTs) refer to various new technologies developed and/or used to create new characteristics in plants through genetic variation, the aim being targeted mutagenesis, targeted introduction of new genes or gene silencing (RdDM). The following breeding techniques are within the scope of NBTs: targeted sequence changes facilitated through the use of Zinc finger nuclease (ZFN) technology (ZFN-1, ZFN-2 and ZFN-3, see U.S. Pat. No. 9,145,565, incorporated by reference in its entirety), Oligo-nucleotide directed mutagenesis (ODM, a.k.a., site-directed mutagenesis), Cisgenesis and intragenesis, epigenetic approaches such as RNA-dependent DNA methylation (RdDM, which does not necessarily change nucleotide sequence but can change the biological activity of the sequence), Grafting (on GM rootstock), Reverse breeding, Agro-infiltration for transient gene expression (agro-infiltration "sensu stricto", agro-inoculation, floral dip), Transcription Activator-Like Effector Nucleases (TALENs, see U.S. Pat. Nos. 8,586,363 and 9,181,535, incorporated by reference in their entireties), the CRISPR/Cas system (see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641, which are all hereby incorporated by reference), engineered meganuclease, re-engineered homing endonucleases, DNA guided genome editing (Gao et al., Nature Biotechnology (2016), doi: 10.1038/nbt.3547, incorporated by reference in its entirety), and Synthetic genomics. A major part of today's targeted genome editing, another designation for New Breeding Techniques, is the applications to induce a DNA double strand break (DSB) at a selected location in the genome where the modification is intended. Directed repair of the DSB allows for targeted genome editing. Such applications can be utilized to generate mutations (e.g., targeted mutations or precise native gene editing) as well as precise insertion of genes (e.g., cisgenes, intragenes, or transgenes). The applications leading to mutations are often identified as site-directed nuclease (SDN) technology, such as SDN1, SDN2 and SDN3. For SDN1, the outcome is a targeted, non-specific genetic deletion mutation: the position of the DNA DSB is precisely selected, but the DNA repair by the host cell is random and results in small nucleotide deletions, additions or substitutions. For SDN2, a SDN is used to generate a targeted DSB and a DNA repair template (a short DNA sequence identical to the targeted DSB DNA sequence except for one or a few nucleotide changes) is used to repair the DSB: this results in a targeted and predetermined point mutation in the desired gene of interest. As to the SDN3, the SDN is used along with a DNA repair template that contains new DNA sequence (e.g. gene). The outcome of the technology would be the integration of that DNA sequence into the plant genome. The most likely application illustrating the use of SDN3 would be the insertion of cisgenic, intragenic, or transgenic expression cassettes at a selected genome location. A complete description of each of these techniques can be found in the report made by the Joint Research Center (JRC) Institute for Prospective Technological Studies of the European Commission in 2011 and titled "New plant breeding techniques—State-of-the-art and prospects for commercial development", which is incorporated by reference in its entirety.

As used herein, "suberin" refers to a highly hydrophobic and a somewhat 'rubbery' material. In roots, suberin is deposited in the radial and transverse cell walls of the endodermal cells. This structure, known as the Casparian strip or Casparian band, functions to prevent water and nutrients taken up by the root from entering the stele through the apoplast. Instead, water must bypass the endodermis via the symplast. This allows the plant to select the solutes that pass further into the plant. It thus forms an important barrier to harmful solutes. For example, mangroves use suberin to minimize salt intake from their littoral habitat.

Suberin is found in the phellem layer of the periderm (or cork). This is outermost layer of the bark. The cells in this layer are dead and abundant in suberin, preventing water loss from the tissues below. Suberin can also be found in various other plant structures. For example, they are present in the lenticels on the stems of many plants and the net structure in the rind of a netted melon is composed of suberised cells.

II. MYB41

Myb transcription factors are widespread in animals, plants and fungi. They have been implicated in a wide variety of plant-specific responses, including secondary metabolism, cell shape determination, cell differentiation and stress responses. AtMYB41 from *Arabidopsis* (*Arabidopsis thaliana*) has been described as a gene transcriptionally regulated in response to salinity, desiccation, cold and abscisic acid. Lippold et al. (Plant Physiology, April 2009, Plant Physiology, 149:1761-1772) further characterized the gene by subjecting independently AtMYB41-overexpressing lines to detailed transcriptome and metabolome analysis. Their molecular data indicated that the gene is involved in distinct cellular processes, including control of primary metabolism and negative regulation of short-term transcriptional responses to osmotic stress.

Kosma et al. (The Plant Journal, 2014, 80:216-229) showed that overexpression of AtMYB41 can activate the steps necessary for aliphatic suberin synthesis and deposition of cell wall-associated suberin-like lamellae in both epidermal and mesophyll cells of leaves of both *Arabidopsis thaliana* and *Nicotiana benthamiana*. While the exact biological function remained unclear to the authors, their evidence suggested that this transcription factor plays a role in augmenting aliphatic suberization under conditions of abiotic stress.

Fatty acyl-CoA reductase (FAR) is known to catalyze the generation of primary fatty alcohols by the reduction of fatty acids in suberin biosynthesis. Wei et al. (Horticulture Research, 2020, 7:86, 10 pages) isolated FAR from kiwifruit (*Actinidia chinensis*) and transiently overexpressed the isolated AchnFAR in tobacco (*Nicotiana benthamiana*) leaves. Their studies identified the positive role of transcription factors, including AchnMY41, in the regulation of Achn-FAR.

In accordance with the present disclosure, the AtMTB41 gene and its many orthologs when under the control of appropriate promoters will be useful for facilitating the construction of crop plants that have increased or enhanced suberin levels when comparted to appropriate check or control plants. Thus, the heterologous promoter-MYB41 nucleic acid sequences can be used in breeding programs. See, for example, Gentzbittel et al. (1998, Theor. Appl. Genet. 96:519-523). The sequences may also be used to modulate plant development processes, such as metabolic responses to osmotic stress, regulation of FAR, and protecting the plants from other environmental stresses. See, generally, Sambrook et al. (1989) Molecular Cloning: A Laboratory Manual (2nd ed., Cold Spring Harbor Laboratory Press, Plainview, N.Y.). The sequences of the present disclosure can also be used to generate variants (e.g., by 'domain swapping') for the generation of new plant types with increased or enhanced suberin levels, particularly in root cells, structures and tissues.

The disclosure encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified polynucleotide or polypeptide is substantially free of other cellular material, or culture medium when produced by recombinant techniques, or substantially free of chemical precursors or other chemicals when chemically synthesized. Suitably, an "isolated" polynucleotide is free of sequences (especially protein encoding sequences) that naturally flank the polynucleotide (i.e., sequences located at the 5' and 3' ends of the polynucleotide) in the genomic DNA of the organism from which the polynucleotide was derived. For example, in various embodiments, the isolated polynucleotide can contain less than about 5 kb, 4 kb, 3 kb, 2 kb, 1 kb, 0.5 kb, or 0.1 kb of nucleotide sequences that naturally flank the polynucleotide in genomic DNA of the cell from which the polynucleotide was derived. A polypeptide that is substantially free of cellular material includes preparations of protein having less than about 30%, 20%, 10%, 5%, (by dry weight) of contaminating protein. When the protein of the disclosure or biologically active portion thereof is recombinantly produced, culture medium suitably represents less than about 30%, 20%, 10%, or 5% (by dry weight) of chemical precursors or non-protein-of-interest chemicals.

The *Arabidopsis thaliana* MYB41 gene (AtMTB41) is 1,497 nucleic acid base pairs (bp) long, including the 5' and 3' UTRs (Sequence Name: AT4G28110.1; Tair Accession: 1009098575; GenBank Accession: NM_118951; arabidopsis.org/servlets/TairObject?type=sequence&id=1002502859).

One exemplary MYB41 gene used in the examples of the present invention is that of SEQ ID NO:13, which is 1,216 nucleic acid base pairs (bp) long, including 3 exons and 2 introns and it has no stop codon. The corresponding amino acid sequence is provided in SEQ ID NO: 14. This MYB41 protein sequence is 282 amino acids long (not including stop codon). Also, the complementary DNA (cDNA) of AtMYB41 gene, which codes for MYB41 protein, is provided in SEQ ID NO:15 (AtMYB41 CDS). This AtMYB41 CDS can be used as a replacement of SEQ ID NO: 13 (AtMYB41 gene) for MYB41 expression, after the stop codon sequence (TAA) is removed. Depending on the cloning method used, the stop codon sequence can be included.

A portion of a MYB41 nucleotide sequence that encodes a biologically active portion of a MYB41 polypeptide of the disclosure will encode at least about 5, 6, 7, 8, 9, 10, 11, 12, 13, 14, 15, 16, 17, 18, 19, 20, 21, 22, 23, 24, 25, 30, 40, 50, 60, 70, 80, 90, 100, 120, 150, 300, 400, 500, 600, 700, 800, 900 or 1000 contiguous amino acid residues, or almost up to the total number of amino acids present in a full-length MYB41 polypeptide of the disclosure (for example, 282 amino acid residues for SEQ ID NO: 14). Portions of a MYB41 nucleotide sequence and/or upstream and downstream of the MYB41 gene that are useful as hybridization probes or PCR primers generally need not encode a biologically active portion of a MYB41 polypeptide.

Thus, a portion of a MYB41 nucleotide sequence may encode a biologically active portion of a MYB41 polypeptide, or it may be a fragment that can be used as a hybridization probe or PCR primer using standard methods known in the art. A biologically active portion of a MYB41 polypeptide can be prepared by isolating a portion of one of the MYB41 nucleotide sequences of the disclosure, expressing the encoded portion of the MYB41 polypeptide (e.g., by recombinant expression in vitro), and assessing the activity of the encoded portion of the MYB41 polypeptide. Nucleic acid molecules that are portions of an MYB41 nucleotide sequence comprise at least about 15, 16, 17, 18, 19, 20, 25, 30, 50, 75, 100, 150, 200, 250, 300, 350, 400, 450, 500, 550, 600, 650, 700, 750, 800, 850, 900, 950, 1000, 1050, 1100, 1150, 1200, 1250, or 1300 nucleotides, or almost up to the number of nucleotides present in a full-length MYB41 nucleotide sequence disclosed herein (for example, about from 150 to 1300 nucleotides for SEQ ID NO: 13).

The disclosure also contemplates using variants of the disclosed nucleotide sequences. Nucleic acid variants can be naturally occurring, such as allelic variants (same locus), homologues (different locus), and orthologues (different organism) or can be non-naturally occurring. Naturally occurring variants such as these can be identified with the use of well-known molecular biology techniques, as, for example, with polymerase chain reaction (PCR) and hybridization techniques as known in the art. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product). For nucleotide sequences, conservative variants include those sequences that, because of the degeneracy of the genetic code, encode the amino acid sequence of one of the MYB41 polypeptides of the disclosure. Variant nucleotide sequences also include synthetically derived nucleotide sequences, such as those generated, for example, by using site-directed mutagenesis but which still encode a MYB41 polypeptide of the disclosure. Generally, variants of a particular nucleotide sequence of the disclosure will have at least about 30%, 40% 50%, 55%, 60%, 65%, 70%, generally at least about 75%, 80%, 85%, desirably about 90% to 95% or more, and more suitably about 98% or more sequence identity to that particular nucleotide sequence as determined by sequence alignment programs described elsewhere herein using default parameters.

Variant nucleotide sequences also encompass sequences derived from a mutagenic or recombinant procedures such as 'DNA shuffling' which can be used for swapping domains in a polypeptide of interest with domains of other polypeptides. With DNA shuffling, one or more different MYB41 coding sequences can be manipulated to create a new MYB41 sequence possessing desired properties. In this procedure, libraries of recombinant polynucleotides are generated from a population of related polynucleotides comprising sequence regions that have substantial sequence identity and can be homologously recombined in vitro or in vivo. For example, using this approach, sequence motifs encoding a domain of interest may be shuffled between the MYB41 gene of the disclosure and other known MYB41 genes to obtain a new gene coding for a protein with an improved property of interest, such increasing suberin content of plant cells, plant tissues, plant parts and whole plants. Strategies for DNA shuffling are known in the art. See, for example: Stemmer (1994, Proc. Natl. Acad. Sci. USA 91:10747-10751; 1994, Nature 370:389-391); Crameri et al. (1997, Nature Biotech. 15:436-438); Moore et al. (1997, J. Mol. Biol. 272:336-347); Zlang et al. (1997 Proc. Natl.

Acad. Sci. USA 94:450-44509); Crameri et al. (1998, Nature 391:288-291); and U.S. Pat. Nos. 5,605,793 and 5,837,458.

The present disclosure provides nucleotide sequences comprising at least a portion of the isolated proteins encoded by nucleotide sequences for MYB41, homologs of MYB41, orthologs of MYB41, paralogs of MYB41, and fragments and variations thereof.

In some embodiments, the present disclosure provides a nucleotide sequence encoding MYB41, and/or functional fragments and variations thereof comprising a nucleotide sequence that shares at least about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, about 99.1%, about 99.2%, about 99.3%, about 99.4%, about 99.5%, about 99.6%, about 99.7%, about 99.8%, or about 99.9% sequence identity to SEQ ID NO:13 or SEQ ID NO:15. In some embodiments, a nucleotide sequence encoding MYB41 has the nucleic acid sequence of SEQ ID NO:13 or SEQ ID NO:15.

In some embodiments, the present disclosure provides nucleotide sequences for MYB41, homologs of MYB41, orthologs of MYB41, paralogs of MYB41, and fragments and variations thereof comprising nucleotide sequences that share at least about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, about 99.1%, about 99.2%, about 99.3%, about 99.4%, about 99.5%, about 99.6%, about 99.7%, about 99.8%, or about 99.9% sequence identity to SEQ ID NO:13 or SEQ ID NO:15.

In some embodiments, nucleotide sequences for MYB41, homologs of MYB41, orthologs of MYB41, paralogs of MYB41, and fragments and variations thereof can be used to be expressed in plants. In some embodiments, said nucleotide sequences can be used to be incorporated into an expression cassette, which is capable of directing expression of a nucleotide sequence for MYB41, homologs of MYB41, orthologs of MYB41, paralogs of MYB41, and fragments and variations thereof in a plant cell, plant tissue, plant part or whole plant. This expression cassette comprises a promoter operably linked to the nucleotide sequence of interest (i.e. MYB41, orthologs of MYB41, and fragments and variations thereof) which is operably linked to termination signals. It also typically comprises sequences required for proper translation of the nucleotide sequence. The coding region usually codes for a protein of interest, (i.e. MYB41). In some embodiments, the expression cassette comprising the nucleotide sequence for MYB41, homologs of MYB41, orthologs of MYB41, paralogs of MYB41, and fragments and variations thereof is chimeric so that at least one of its components is heterologous with respect to at least one of its other components.

In other embodiments, the expression cassette is one which is naturally occurring but has been obtained in a recombinant form useful for heterologous expression. The expression of the nucleotide sequence in the expression cassette can be under the control of a constitutive promoter or of an inducible promoter which initiates transcription only when the host cell is exposed to some particular external stimulus. Also, the expression of the nucleotide sequence in the expression cassette can be under the control of a tissue-specific promoter, such as specific root tissues, including, but not limited to, the phellogen, pericycle or procambium. In the case of a multicellular organism, the promoter can also be specific to a particular tissue or organ or stage of development in animal and/or plant.

The present disclosure provides polypeptides and amino acid sequences comprising at least a portion of the proteins encoded by nucleotide sequences for MYB41, homologs of MYB41, orthologs of MYB41, homeologs of MYB41, paralogs of MYB41, and fragments and variations thereof.

The present disclosure also provides an amino acid sequence encoded by the nucleic acid sequences of MYB41, homologs of MYB41, orthologs of MYB41, paralogs of MYB41, and/or fragments and variations thereof. In some embodiments, the present disclosure provides an isolated polypeptide comprising an amino acid sequence that shares at least about 70%, about 75%, about 80%, about 85%, at least about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to an amino acid sequence encoded by the nucleic acid sequences of MYB41, homologs of MYB41, orthologs of MYB41, paralogs of MYB41, and/or fragments and variations thereof. In one embodiment, the present disclosure provides an isolated polypeptide comprising an amino acid sequence which encodes an amino acid sequence that shares at least about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to an amino acid sequence encoded by the nucleic acid sequences of MYB41, homologs of MYB41, orthologs of MYB41, paralogs of MYB41, and/or fragments and variations thereof.

The disclosure also encompasses variants and fragments of proteins of an amino acid sequence encoded by the nucleic acid sequences of MYB41, homologs of MYB41, orthologs of MYB41 and/or paralogs of MYB41. The variants may contain alterations in the amino acid sequences of the constituent proteins. The term "variant" with respect to a polypeptide refers to an amino acid sequence that is altered by one or more amino acids with respect to a reference sequence. The variant can have "conservative" changes, or "nonconservative" changes, e.g., analogous minor variations can also include amino acid deletions or insertions, or both.

Functional fragments and variants of a polypeptide include those fragments and variants that maintain one or more functions of the parent polypeptide. It is recognized that the gene or cDNA encoding a polypeptide can be considerably mutated without materially altering one or more of the polypeptide's functions. First, the genetic code is well-known to be degenerate, and thus different codons encode the same amino acids. Second, even where an amino acid substitution is introduced, the mutation can be conservative and have no material impact on the essential function (s) of a protein. See, e.g., Stryer Biochemistry 3rd Ed., 1988. Third, part of a polypeptide chain can be deleted without impairing or eliminating all of its functions. Fourth, insertions or additions can be made in the polypeptide chain for example, adding epitope tags, without impairing or eliminating its functions (Ausubel et al. J. Immunol. 159(5): 2502-12, 1997). Other modifications that can be made without materially impairing one or more functions of a polypeptide can include, for example, in vivo or in vitro chemical and biochemical modifications or the incorporation of unusual amino acids. Such modifications include, but are not limited to, for example, acetylation, carboxylation, phosphorylation, glycosylation, ubiquination, labelling, e.g., with radionucleotides, and various enzymatic modifications, as will be readily appreciated by those well skilled in the art. A variety of methods for labelling polypeptides, and labels useful for such purposes, are well known in the art, and include radioactive isotopes such as 32P, ligands which bind to or are bound by labelled specific binding partners (e.g., antibodies), fluorophores, chemiluminescent agents, enzymes, and anti-ligands. Functional fragments and variants can be of varying length. For example, some fragments have at least 10, 25, 50, 75, 100, 200, or even more amino acid residues. These mutations can be natural or purposely changed. In some embodiments, mutations containing alterations that produce silent substitutions, additions, or deletions, but do not alter the properties or activities of the proteins or how the proteins are made are an embodiment of the disclosure.

Conservative amino acid substitutions are those substitutions that, when made, least interfere with the properties of the original protein, that is, the structure and especially the function of the protein is conserved and not significantly changed by such substitutions. Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain. Further information about conservative substitutions can be found, for instance, in Ben Bassat et al. (J. Bacteriol., 169:751 757, 1987), O'Regan et al. (Gene, 77:237 251, 1989), Sahin Toth et al. (Protein Sci., 3:240 247, 1994), Hochuli et al. (Bio/Technology, 6:1321 1325, 1988) and in widely used textbooks of genetics and molecular biology. The Blosum matrices are commonly used for determining the relatedness of polypeptide sequences. The Blosum matrices were created using a large database of trusted alignments (the BLOCKS database), in which pairwise sequence alignments related by less than some threshold percentage identity were counted (Henikoff et al., Proc. Natl. Acad. Sci. USA, 89:10915-10919, 1992). A threshold of 90% identity was used for the highly conserved target frequencies of the BLOSUM90 matrix. A threshold of 65% identity was used for the BLOSUM65 matrix. Scores of zero and above in the Blosum matrices are considered "conservative substitutions" at the percentage identity selected. The following table shows exemplary conservative amino acid substitutions.

TABLE 1

| | Exemplary conservative amino acid substitutions listed | | |
|---|---|---|---|
| Original Residue | Very Highly - Conserved Substitutions | Highly Conserved Substitutions (from the Blosum90 Matrix) | Conserved Substitutions (from the Blosum65 Matrix) |
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |

TABLE 1-continued

| | Exemplary conservative amino acid substitutions listed | | |
|---|---|---|---|
| Original Residue | Very Highly - Conserved Substitutions | Highly Conserved Substitutions (from the Blosum90 Matrix) | Conserved Substitutions (from the Blosum65 Matrix) |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

In some examples, variants can have no more than 3, 5, 10, 15, 20, 25, 30, 40, 50, or 100 conservative amino acid changes (such as very highly conserved or highly conserved amino acid substitutions). In other examples, one or several hydrophobic residues (such as Leu, le, Val, Met, Phe, or Trp) in a variant sequence can be replaced with a different hydrophobic residue (such as Leu, le, Val, Met, Phe, or Trp) to create a variant functionally similar to the disclosed an amino acid sequences encoded by the nucleic acid sequences of MYB41, homologs of MYB41, orthologs of MYB4l and/or paralogs of MYB41, and/or fragments and variations thereof.

In some embodiments, variants may differ from the disclosed sequences by alteration of the coding region to fit the codon usage bias of the particular organism into which the molecule is to be introduced. In other embodiments, the coding region may be altered by taking advantage of the degeneracy of the genetic code to alter the coding sequence such that, while the nucleotide sequence is substantially altered, it nevertheless encodes a protein having an amino acid sequence substantially similar to the disclosed an amino acid sequences encoded by the nucleic acid sequences of MYB41, homologs of MYB41, orthologs of MYB41 and/or paralogs of MYB41, and/or fragments and variations thereof.

In some embodiments, functional fragments derived from the MYB41 orthologs of the present disclosure are provided. The functional fragments can still confer the ability to increase suberin content in plant cells, plant tissues, plant parts and whole plants when expressed in a plant. In some embodiments, the functional fragments contain at least the conserved region or Bowman-Birk inhibitor domain of a wild type MYB41 orthologs, or functional variants thereof. In some embodiments, the functional fragments contain one or more conserved region shared by two or more MYB41 orthologs, shared by two or more MYB41 orthologs in the same plant genus, shared by two or more dicot MYB41 orthologs, and/or shared by two or more monocot MYB41 orthologs. The conserved regions or Bowman-Birk inhibitor domains can be determined by any suitable computer program, such as NCBI protein BLAST program and NCBI Alignment program, or equivalent programs. In some embodiments, the functional fragments are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acids shorter compared to the MYB41 orthologs of the present disclosure. In some embodiments, the functional fragments are made by deleting one or more amino acid of the MYB41 orthologs of the present disclosure. In some embodiments, the functional fragments share at least 80%, 85%, 90%, 95%, 96%, 97%, 98%, 99%, or more identity to the MYB41 orthologs of the present disclosure.

In some embodiments, functional chimeric or synthetic polypeptides derived from the MYB41 orthologs of the present disclosure are provided. The functional chimeric or synthetic polypeptides can still confer the ability to increase suberin content when expressed in a plant. In some embodiments, the functional chimeric or synthetic polypeptides contain at least the conserved region or Bowman-Birk inhibitor domain of a wild type MYB41 orthologs, or functional variants thereof. In some embodiments, the functional chimeric or synthetic polypeptides contain one or more conserved region shared by two or more MYB41 orthologs, shared by two or more MYB41 orthologs in the same plant genus, shared by two or more monocot MYB41 orthologs, and/or shared by two or more dicot MYB41 orthologs. The conserved regions or Bowman-Birk inhibitor domains can be determined by any suitable computer program, such as NCBI protein BLAST program and NCBI Alignment program, or equivalent programs. In some embodiments, the functional chimeric or synthetic polypeptides share at least 80%, 85%, 90%, 95%, 96%, 97%, 98%, 99%, or more identity to the MYB41 orthologs of the present disclosure.

Sequences of conserved regions unique to FW-sensitive alleles can also be used to knock-down the level of one or more MYB41 orthologs. In some embodiments, sequences of conserved regions can be used to make gene silencing molecules to target one or more MYB41 orthologs. In some embodiments, the gene silencing molecules are selected from the group consisting of double-stranded polynucleotides, single-stranded polynucleotides or Mixed Duplex Oligonucleotides. In some embodiments, the gene silencing molecules comprises a DNA/RNA fragment of about 10 bp, 15 bp, 19 bp, 20 bp, 21 bp, 25 bp, 30 bp, 40 bp, 50 bp, 60 bp, 70 bp, 80 bp, 90 bp, 100 bp, 150 bp, 200 pb, 250 bp, 300 bp, 350 bp, 400 bp, 500 bp, 600 bp, 700 bp, 800 bp, 900 bp, 1000 bp, or more polynucleotides, wherein the DNA/RNA fragment share at least 90%, 95%, 99%, or more identity to a conserved region of the MYB41 orthologs sequences of the present disclosure, or complementary sequences thereof.

III. Promoter Sequences

As set forth herein, the inventors discovered that certain promoters operably-linked to a MYB41 gene and transformed into plant enable those transgenic plants to develop additional periderm layers at an earlier stage of root development and/or deposit more suberin in periderm cells without negatively impacting plant health.

Bevan and Walsh (The *Arabidopsis* genome: A foundation for plant research, 2005, Genome Research, 15:1632-1642) concluded that the sequencing of the *Arabidopsis* and rice genomes provide a strong platform for supporting integrative plant science across model and crop species (page 1639, second column, Perspectives). Promoters isolated fromArabidopsis have been shown to drive gene expression in important crops species. For example, Jiang et al. (Characterization of a strong and constitutive promoter from the *Arabidopsis* serine carboxypeptidase-like gene AtSCPL30 as a potential tool for crop transgenic breeding, 2018, BMC Biotechnology, 18:59, 13 pages) isolated a full-length promoter (PD1) from *Arabidopsis* and demonstrated it conferred strong and constitutive expression of transgenes in almost all tissues and development stages of *Nicotiana benthamiana* transgenic plants. Drought responsive promoters HVA22E and PLDdelta identified and isolated from *Arabidopsis thaliana* drove transgenic gene expression when used to transform corn and soybeans (U.S. Pat. Nos. 7,632,982 and 8,692,071). Two seed-specific promoters isolated from *Arabidopsis* (i.e., AtS1 and AtS3) conferred seed-specific accumulation of GUS activity in both transgenic *Arabidopsis* and transgenic tobacco (U.S. Pat. No. 6,100,450).

Exemplary promoters are provided in the following table. For all of these promoters presented in Table 2, GUS expression was observed in the periderm and endodermis. Weak GUS expression was also observed in some cortex and in some epidermis cells. Except for proMYB84, no GUS expression was detected in the rosette leaves of the promoters. These results demonstrate that these promoters are specifically root-expressed with no detectable expression in rosette levels at day 14.

TABLE 2

Exemplary Promoters Sequences Driving MYB41 Expression

| Promoter | Nucleic Acid Sequence | Origin |
|---|---|---|
| proFACT (aka pFACT) | SEQ ID NO: 1 | *Arabidopsis thaliana* |
| proHORST (aka pHORST) | SEQ ID NO: 2 | *Arabidopsis thaliana* |
| proASFT (aka pASFT) | SEQ ID NO: 3 | *Arabidopsis thaliana* |
| proGPAT5 (aka pGPAT5) | SEQ ID NO: 4 | *Arabidopsis thaliana* |
| proRALPH (aka pRALPH) | SEQ ID NO: 5 | *Arabidopsis thaliana* |
| proMYB84 (aka pMYB84) | SEQ ID NO: 6 | *Arabidopsis thaliana* |

The present disclosure provides an isolated nucleic acid molecule comprising an isolated nucleic acid sequence encoding a protein of interest (such as MYB41), which is operably linked to a nucleic acid sequence encoding a heterologous promoter selected from the group comprising SEQ ID NO:1, SEQ ID NO: 2, SEQ ID NO:3, SEQ ID NO:4, SEQ ID NO:5 and SEQ ID NO:6. In some embodiments, the heterologous promoter is a native promoter of FACT gene. In some embodiments, the heterologous promoter is a native promoter of HORST gene. In some embodiments, the heterologous promoter is a native promoter of ASFT gene. In some embodiments, the heterologous promoter is a native promoter of GPAT5 gene. In some embodiments, the heterologous promoter is a native promoter of RALPH gene. In some embodiments, the heterologous promoter is a native promoter of MYB84 gene.

In further embodiments, the native promoters of FACT gene, HORST gene, ASFT gene, GPAT5 gene, RALPH gene, and/or MYB84 gene can be derived, obtained, isolated from various plants (including monocots, dicots, vascular plants reproduced from spores). In further embodiments, promoters of FACT gene, HORST gene, ASFT gene, GPAT5 gene, RALPH gene, and/or MYB84 derived, obtained, isolated from *Arabidopsis* and other plants taught herein (including monocots, dicots, vascular plants reproduced from spores) are operably linked to a target gene or a transgene of interest (such as wild-type MYB41 gene, homologs of MYB41, orthologs of MYB41 and/or paralogs of MYB41, and/or fragments and variations thereof) for increased suberin levels by altering gene expression patterns in a cell-type specific manner.

IV. Constructs

As set forth herein, the inventors created constructs comprising expression cassettes comprising promoters listed in Table 1 operably-linked to a MYB41 gene. When these constructs are transformed into plants they enables those transgenic plants to develop additional periderm layers at an earlier stage of root development and/or deposit more suberin in periderm cells without negatively impacting plant health. Exemplary constructs are provided in the following table. SEQ ID NOs:7-12 are the DNA sequences of the entire transformation constructs, each of which that includes the expression cassette (SEQ ID NOs:16-21; i.e. MYB41 gene, 3'UTR and Intergenic region operably linked to each promoter set forth in SEQ ID NOs:1-6, respectively).

TABLE 3

Exemplary Transformation Construct and Expression Cassette Sequences Driving MYB41 Expression

| | Nucleic Acid Sequence |
|---|---|
| Transformation Construct | |
| proFACT::MYB41 | SEQ ID NO: 7 |
| proHORST::MYB41 | SEQ ID NO: 8 |
| proASFT::MYB41 | SEQ ID NO: 9 |
| proGPAT5::MYB41 | SEQ ID NO: 10 |
| proRALPH::MYB41 | SEQ ID NO: 11 |
| proMYB84::MYB41 | SEQ ID NO: 12 |
| Expression Cassette | |
| proFACT::MYB41 (FIG. 2E) | SEQ ID NO: 16 |
| proHORST::MYB41 (FIG. 1E) | SEQ ID NO: 17 |
| proASFT::MYB41 | SEQ ID NO: 18 |
| proGPAT5::MYB41 | SEQ ID NO: 19 |
| proRALPH::MYB41 | SEQ ID NO: 20 |
| proMYB84::MYB41 | SEQ ID NO: 21 |

V. Plant Transformation

The present polynucleotides coding for MYB41, homologs of MYB41, orthologs of MYB41 and/or paralogs of MYB41, and/or fragments and variations thereof of the present disclosure can be transformed into plant cells, plant tissues, plant parts and whole plants.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation. See, for example, U.S. Pat. Nos. 5,405,765; 5,472,869; 5,538,877; 5,538,880; 5,550,318; 5,641,664; 5,736,369 and 5,736,369; International Patent Application Publication Nos. WO2002/038779 and WO/2009/117555; Lu et al., (Plant Cell Reports, 2008, 27:273-278); Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and, Raineri et al., Bio/Tech. 8:33-38 (1990)), each of which is expressly incorporated herein by reference in their entirety.

*Agrobacterium tumefaciens* is a naturally occurring bacterium that is capable of inserting its DNA (genetic information) into plants, resulting in a type of injury to the plant known as crown gall. Most species of plants can now be transformed using this method, including cucurbitaceous species.

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E. I. du Pont de Nemours and Company. Most species of plants have been transformed using this method.

The most common method for the introduction of new genetic material into a plant genome involves the use of living cells of the bacterial pathogen *Agrobacterium tumefaciens* to literally inject a piece of DNA, called transfer or T-DNA, into individual plant cells (usually following wounding of the tissue) where it is targeted to the plant nucleus for chromosomal integration. There are numerous patents governing *Agrobacterium* mediated transformation and particular DNA delivery plasmids designed specifically for use with *Agrobacterium*—for example, U.S. Pat. No. 4,536,475, EP0265556, EP0270822, WO8504899, WO8603516, U.S. Pat. No. 5,591,616, EP0604662, EP0672752, WO8603776, WO9209696, WO9419930, WO9967357, U.S. Pat. No. 4,399,216, WO8303259, U.S. Pat. No. 5,731,179, EP068730, WO9516031, U.S. Pat. Nos. 5,693,512, 6,051,757 and EP904362A1. *Agrobacterium*-mediated plant transformation involves as a first step the placement of DNA fragments cloned on plasmids into living *Agrobacterium* cells, which are then subsequently used for transformation into individual plant cells. *Agrobacterium*-mediated plant transformation is thus an indirect plant transformation method. Methods of *Agrobacterium*-mediated plant transformation that involve using vectors with no T-DNA are also well known to those skilled in the art and can have applicability in the present disclosure. See, for example, U.S. Pat. No. 7,250,554, which utilizes P-DNA instead of T-DNA in the transformation vector.

A transgenic plant formed using *Agrobacterium* transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

Direct plant transformation methods using DNA have also been reported. The first of these to be reported historically is electroporation, which utilizes an electrical current applied to a solution containing plant cells (M. E. Fromm et al., Nature, 319, 791 (1986); H. Jones et al., Plant Mol. Biol., 13, 501 (1989) and H. Yang et al., Plant Cell Reports, 7, 421 (1988). Another direct method, called "biolistic bombardment", uses ultrafine particles, usually tungsten or gold, that are coated with DNA and then sprayed onto the surface of a plant tissue with sufficient force to cause the particles to penetrate plant cells, including the thick cell wall, membrane and nuclear envelope, but without killing at least some of them (U.S. Pat. Nos. 5,204,253, 5,015,580). A third direct method uses fibrous forms of metal or ceramic consisting of sharp, porous or hollow needle-like projections that literally impale the cells, and also the nuclear envelope of cells. Both silicon carbide and aluminum borate whiskers have been used for plant transformation (Mizuno et al., 2004; Petolino et al., 2000; U.S. Pat. No. 5,302,523 US Application 20040197909) and also for bacterial and animal transformation (Kaepler et al., 1992; Raloff, 1990; Wang, 1995). There are other methods reported, and undoubtedly, additional methods will be developed. However, the efficiencies of each of these indirect or direct methods in introducing foreign DNA into plant cells are invariably extremely low, making it necessary to use some method for selection of only those cells that have been transformed, and further, allowing growth and regeneration into plants of only those cells that have been transformed.

For efficient plant transformation, a selection method must be employed such that whole plants are regenerated from a single transformed cell and every cell of the transformed plant carries the DNA of interest. These methods can employ positive selection, whereby a foreign gene is supplied to a plant cell that allows it to utilize a substrate present in the medium that it otherwise could not use, such as mannose or xylose (for example, refer U.S. Pat. Nos. 5,767,378; 5,994,629). More typically, however, negative selection is used because it is more efficient, utilizing selective agents such as herbicides or antibiotics that either kill or inhibit the growth of non-transformed plant cells and reducing the possibility of chimeras. Resistance genes that are effective against negative selective agents are provided on the introduced foreign DNA used for the plant transformation. For example, one of the most popular selective agents used is the antibiotic kanamycin, together with the resistance gene neomycin phosphotransferase (nptII), which confers resistance to kanamycin and related antibiotics (see, for example, Messing & Vierra, Gene 19: 259-268 (1982); Bevan et al., Nature 304:184-187 (1983)). However, many different antibiotics and antibiotic resistance genes can be used for transformation purposes (refer U.S. Pat. Nos. 5,034,322, 6,174,724 and 6,255,560). In addition, several herbicides and herbicide resistance genes have been used for transformation purposes, including the bar gene, which confers resistance to the herbicide phosphinothricin (White et al., Nucl Acids Res 18: 1062 (1990), Spencer et al., Theor Appl Genet 79: 625-631(1990), U.S. Pat. Nos. 4,795,855, 5,378,824 and 6,107,549). In addition, the dhfr gene, which confers resistance to the anticancer agent methotrexate, has been used for selection (Bourouis et al., EMBO J. 2(7): 1099-1104 (1983).

The expression control elements used to regulate the expression of a given protein can either be the expression control element that is normally found associated with the coding sequence (homologous expression element) or can be a heterologous expression control element. A variety of homologous and heterologous expression control elements are known in the art and can readily be used to make expression units for use in the present disclosure. Transcription initiation regions, for example, can include any of the various opine initiation regions, such as octopine, mannopine, nopaline and the like that are found in the Ti plasmids of *Agrobacterium tumefaciens*. Alternatively, plant viral promoters can also be used, such as the cauliflower mosaic virus 19S and 35S promoters (CaMV 19S and CaMV 35S promoters, respectively) to control gene expression in a plant (U.S. Pat. Nos. 5,352,605; 5,530,196 and 5,858,742 for example). Enhancer sequences derived from the CaMV can also be utilized (U.S. Pat. Nos. 5,164,316; 5,196,525; 5,322,938; 5,530,196; 5,352,605; 5,359,142; and 5,858,742 for example). Lastly, plant promoters such as prolifera promoter, fruit specific promoters, Ap3 promoter, heat shock promoters, seed specific promoters, etc. can also be used.

Either a gamete-specific promoter, a constitutive promoter (such as the CaMV or Nos promoter), an organ-specific promoter (such as the E8 promoter from tomato), or an inducible promoter is typically ligated to the protein or antisense encoding region using standard techniques known in the art. The expression unit may be further optimized by employing supplemental elements such as transcription terminators and/or enhancer elements.

Thus, for expression in plants, the expression units will typically contain, in addition to the protein sequence, a plant promoter region, a transcription initiation site and a transcription termination sequence. Unique restriction enzyme sites at the 5' and 3' ends of the expression unit are typically included to allow for easy insertion into a pre-existing vector.

In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include, but are not limited to the *Agrobacterium* octopine synthase signal (Gielen et al., EMBO J3:835-846 (1984)) or the nopaline synthase signal (Depicker et al., Mol. and Appl. Genet. 1:561-573 (1982)). The resulting expression unit is ligated into or otherwise constructed to be included in a vector that is appropriate for higher plant transformation. One or more expression units may be included in the same vector. The vector will typically contain a selectable marker gene expression unit by which transformed plant cells can be identified in culture. Usually, the marker gene will encode resistance to an antibiotic, such as G418, hygromycin, bleomycin, kanamycin, or gentamicin or to an herbicide, such as glyphosate (Round-Up) or glufosinate (BASTA) or atrazine. Replication sequences, of bacterial or viral origin, are generally also included to allow the vector to be cloned in a bacterial or phage host; preferably a broad host range for prokaryotic origin of replication is included. A selectable marker for bacteria may also be included to allow selection of bacterial cells bearing the desired construct. Suitable prokaryotic selectable markers include resistance to antibiotics such as ampicillin, kanamycin or tetracycline. Other DNA sequences encoding additional functions may also be present in the vector, as is known in the art. For instance, in the case of *Agrobacterium* transformations, T-DNA sequences will also be included for subsequent transfer to plant chromosomes.

To introduce a desired gene or set of genes by conventional methods requires a sexual cross between two lines, and then repeated back-crossing between hybrid offspring and one of the parents until a plant with the desired characteristics is obtained. This process, however, is restricted to plants that can sexually hybridize, and genes in addition to the desired gene will be transferred.

Recombinant DNA techniques allow plant researchers to circumvent these limitations by enabling plant geneticists to identify and clone specific genes for desirable traits, such as improved fatty acid composition, and to introduce these genes into already useful varieties of plants. Once the foreign genes have been introduced into a plant, that plant can then be used in imp plant breeding schemes (e.g., pedigree breeding, single-seed-descent breeding schemes, reciprocal recurrent selection) to produce progeny which also contain the gene of interest.

Genes can be introduced in a site directed fashion using homologous recombination. Homologous recombination permits site-specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451,513; 5,501,967 and 5,527,695.

While reducing the present invention to practice, the inventor can construct an expression construct which includes nucleotide sequences encoding MYB41, homologs of MYB41, orthologs of MYB41 and/or paralogs of MYB41, and/or fragments and variations thereof. The expression construct of the present invention can be introduced into embryogenic callus of any plant genus or species and the resulting transformed cells can be regenerated into plants. The transgenic plants are expected to have expression of the MYB41 protein.

The phrase "embryogenic callus cell" used herein refers to an embryogenic cell contained in a cell mass produced in vitro.

Several approaches can be utilized to transform and co-express these polynucleotides in plant cells.

Although less preferred, each of the above described polynucleotide sequences can be separately introduced into a plant cell by using three separate nucleic-acid constructs. In some embodiments, the three polynucleotide sequences can be co-introduced and co-expressed in the plant cell using a single nucleic acid construct. Such a construct can be designed with a single promoter sequences co-which can transcribe a polycistronic message including all three polynucleotide sequences. To enable co-translation of the three polypeptides encoded by the polycistronic message, the polynucleotide sequences can be inter-linked via an internal ribosome entry site (IRES) sequence which facilitates translation of polynucleotide sequences positioned downstream of the IRES sequence. In this case, a transcribed polycistronic RNA molecule encoding the three polypeptides described above will be translated from both the capped 5' end and the two internal IRES sequences of the polycistronic RNA molecule to thereby produce in the cell all three polypeptides.

Alternatively, the polynucleotide segments encoding the plurality of polypeptides capable of conferring increased suberin content in plant cells, plant tissues, plant parts and whole plants can be translationally fused via a protease recognition site cleavable by a protease expressed by the cell to be transformed with the nucleic acid construct. In this case, a chimeric polypeptide translated will be cleaved by a cell-expressed protease to thereby generate the plurality of polypeptides.

In other embodiments, the present invention utilizes a nucleic acid construct which includes three promoter sequences each capable of directing transcription of a specific polynucleotide sequence of the polynucleotide sequences described above.

Suitable promoters which can be used with the nucleic acid of the present invention include constitutive, inducible, or tissue-specific promoters.

Suitable constitutive promoters include, for example, CaMV 35S promoter (Odell et al., Nature 313:810-812, 1985); maize Ubi 1 (Christensen et al., Plant Sol. Biol. 18:675-689, 1992); rice actin (McElroy et al., Plant Cell 2:163-171, 1990); pEMU (Last et al., Theor. Appl. Genet. 81:581-588, 1991); and Synthetic Super MAS (Ni et al., The Plant Journal 7: 661-76, 1995). Other constitutive promoters include those in U.S. Pat. Nos. 5,659,026, 5,608,149; 5,608,144; 5,604,121; 5,569,597: 5,466,785; 5,399,680; 5,268,463; and 5,608,142.

Suitable inducible promoters can be pathogen-inducible promoters such as, for example, the alfalfa PR10 promoter (Coutos-Thevenot et al., Journal of Experimental Botany 52: 901-910, 2001 and the promoters described by Marineau et al., Plant Mol. Biol. 9:335-342, 1987; Matton et al. Molecular Plant-Microbe Interactions 2:325-331, 1989; Somsisch et al., Proc. Natl. Acad. Sci. USA 83:2427-2430, 1986: Somsisch et al., Mol. Gen. Genet. 2:93-98, 1988; and Yang, Proc. Natl. Acad. Sci. USA 93:14972-14977, 1996.

Suitable tissue-specific promoters include, but not limited to, leaf-specific promoters such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993.

The nucleic acid construct of the present invention may also include at least one selectable marker such as, for example, nptII. Preferably, the nucleic acid construct is a shuttle vector, which can propagate both in E. coli (wherein the construct comprises an appropriate selectable marker and origin of replication) and be compatible for propagation in cells. The construct according to the present invention can be, for example, a plasmid, a bacmid, a phagemid, a cosmid, a phage, a virus or an artificial chromosome, preferably a plasmid.

The nucleic acid construct of the present invention can be utilized to stably transform plant cells. The principle methods of causing stable integration of exogenous DNA into plant genome include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/ Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/

Technology (1988) 6:559-563; McCabe et al. Bio/ Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. Suitable *Agrobacterium*-mediated procedures for introducing exogenous DNA to plant cells is described by Dougale et al. (Journal of General Virology, 79:2301-2311, 1998) and in U.S. Pat. No. 6,395,962.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Alternatively, the nucleic acid construct of the present invention can be introduced into plant cells by a microprojectiles bombardment. In this technique, tungsten or gold particles coated with exogenous DNA are accelerated toward the target cells. Suitable plant transformation procedures by microprojectiles bombardment are described by Sagi et al. (Biotechnology 13:481-485, 1995) and by Dougale et al. (Journal of General Virology, 79:2301-2311, 1998). Preferably, the nucleic acid construct of the present invention is introduced into plant cells by a microprojectiles bombardment procedure as described in Example 4 herein below.

Following transformation, the transformed cells are micropropagated to provide a rapid, consistent reproduction of the transformed material.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Stable integration of exogenous DNA sequence in the genome of the transformed plants can be determined using standard molecular biology techniques well known in the art such as PCR and Southern blot hybridization.

Although stable transformation is presently preferred, transient transformation of cultured cells, leaf cells, meristematic cells or the whole plant is also envisaged by the present invention.

Transient transformation can be effected by any of the direct DNA transfer methods described above or by viral infection using modified plant viruses.

Viral infection is preferred since is enables circumventing micropropagation and regeneration of a whole plant from cultured cells. Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman et al. (Communications in Molecular Biology: Viral Vectors, Cold Spring Harbor Laboratory, New York, pp. 172-189, 1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson et al. (Virology 172:285-292, 1989; Takamatsu et al. EMBO J. 6:307-311, 1987; French et al. (Science 231:1294-1297, 1986); and Takamatsu et al. (FEBS Letters 269:73-76, 1990).

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA.

If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of the present invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that the sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

In addition to the above, the nucleic acid molecule of the present invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

VI. Breeding Methods

Open-Pollinated Populations. The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, Plant Breeding Methodology, John Wiley & Sons, Inc. (1988). For population improvement methods specific for soybean see, e.g., J. R. Wilcox, editor (1987) SOYBEANS: Improvement, Production, and Uses, Second Edition, American Society of Agronomy, Inc., Crop Science Society of America, Inc., and Soil Science Society of America, Inc., publishers, 888 pages.

Mass Selection. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enters a synthetic varies widely. In practice, numbers of parental lines range from 10 to several hundred, with 100-200 being the average. Broad based synthetics formed from 100 or more clones would be expected to be more stable during seed multiplication than narrow based synthetics.

Hybrids. As discussed above, hybrid is an individual plant resulting from a cross between parents of differing genotypes. Commercial hybrids are now used extensively in many crops, including corn (maize), *sorghum*, sugar beet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In Hybridization of Crop Plants.

Bulk Segregation Analysis (BSA). BSA, a.k.a. bulked segregation analysis, or bulk segregant analysis, is a method described by Michelmore et al. (Michelmore et al., 1991, Identification of markers linked to disease-resistance genes by bulked segregant analysis: a rapid method to detect markers in specific genomic regions by using segregating populations. *Proceedings of the National Academy of Sciences, USA*, 99:9828-9832) and Quarrie et al. (Quarrie et al., Bulk segregant analysis with molecular markers and its use for improving drought resistance in maize, 1999, *Journal of Experimental Botany*, 50(337):1299-1306).

For BSA of a trait of interest, parental lines with certain different phenotypes are chosen and crossed to generate F2, doubled haploid or recombinant inbred populations with QTL analysis. The population is then phenotyped to identify individual plants or lines having high or low expression of the trait. Two DNA bulks are prepared, one from the individuals having one phenotype (e.g., resistant to pathogen), and the other from the individuals having reversed phenotype (e.g., susceptible to pathogen), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs). Markers linked to the phenotype can be identified and used for breeding or QTL mapping.

Gene Pyramiding. The method to combine into a single genotype a series of target genes identified in different parents is usually referred as gene pyramiding. The first part of a gene pyramiding breeding is called a pedigree and is aimed at cumulating one copy of all target genes in a single genotype (called root genotype). The second part is called the fixation steps and is aimed at fixing the target genes into a homozygous state, that is, to derive the ideal genotype (ideotype) from the root genotype. Gene pyramiding can be combined with marker assisted selection (MAS, see Hospital et al., 1992, 1997a, and 1997b, and Moreau et al, 1998) or marker based recurrent selection (MBRS, see Hospital et al., 2000).

VII. Gene Editing

As used herein, the term "gene editing system" refers to a system comprising one or more DNA-binding domains or components and one or more DNA-modifying domains or components, or isolated nucleic acids, e.g., one or more vectors, encoding said DNA-binding and DNA-modifying domains or components. Gene editing systems are used for modifying the nucleic acid of a target gene and/or for modulating the expression of a target gene. In known gene editing systems, for example, the one or more DNA-binding domains or components are associated with the one or more DNA-modifying domains or components, such that the one or more DNA-binding domains target the one or more DNA-modifying domains or components to a specific nucleic acid site. Methods and compositions for enhancing gene editing is well known in the art. See example, U.S. Patent Application Publication No. 2018/0245065, which is incorporated by reference in its entirety.

Certain gene editing systems are known in the art, and include but are not limited to, zinc finger nucleases, transcription activator-like effector nucleases (TALENs); clustered regularly interspaced short palindromic repeats (CRISPR)/Cas systems, meganuclease systems, and viral vector-mediated gene editing.

In some embodiments, the present disclosure teaches methods for gene editing/cloning utilizing DNA nucleases.

CRISPR complexes, transcription activator-like effector nucleases (TALENs), zinc finger nucleases (ZFNs), and FokI restriction enzymes, which are some of the sequence-specific nucleases that have been used as gene editing tools. These enzymes are able to target their nuclease activities to desired target loci through interactions with guide regions engineered to recognize sequences of interest. In some embodiments, the present disclosure teaches CRISPR-based gene editing methods to genetically engineer the genome of plant species of the present disclosure in order to stimulate, enhance, or modulate suberin content of plant cells, plant tissues, plant parts or whole plants.

(i) CRISPR Systems

CRISPR (Clustered Regularly Interspaced Short Palindromic Repeats) and CRISPR-associated (cas) endonucleases were originally discovered as adaptive immunity systems evolved by bacteria and archaea to protect against viral and plasmid invasion. Naturally occurring CRISPR/Cas systems in bacteria are composed of one or more Cas genes and one or more CRISPR arrays consisting of short palindromic repeats of base sequences separated by genome-targeting sequences acquired from previously encountered viruses and plasmids (called spacers). (Wiedenheft, B., et. al. Nature. 2012; 482:331; Bhaya, D., et. al., Annu. Rev. Genet. 2011; 45:231; and Terms, M. P. et. al., Curr. Opin. Microbiol. 2011; 14:321). Bacteria and archaea possessing one or more CRISPR loci respond to viral or plasmid challenge by integrating short fragments of foreign sequence (protospacers) into the host chromosome at the proximal end of the CRISPR array. Transcription of CRISPR loci generates a library of CRISPR-derived RNAs (crRNAs) containing sequences complementary to previously encountered invading nucleic acids (Haurwitz, R. E., et. al., Science. 2012:329; 1355; Gesner, E. M., et. al., Nat. Struct. Mol. Biol. 2001, 18:688; Jinek, M., et. al., Science. 2012:337; 816-21). Target recognition by crRNAs occurs through complementary base pairing with target DNA, which directs cleavage of foreign sequences by means of Cas proteins. (Jinek et. al. 2012 "A Programmable dual-RNA-guided DNA endonuclease in adaptive bacterial immunity." Science. 2012:337; 816-821).

There are at least five main CRISPR system types (Type I, II, III, IV and V) and at least 16 distinct subtypes (Makarova, K. S., et al., Nat Rev Microbiol. 2015. Nat. Rev. Microbiol. 13, 722-736). CRISPR systems are also classified based on their effector proteins. Class 1 systems possess multi-subunit crRNA-effector complexes, whereas in Class 2 systems all functions of the effector complex are carried out by a single protein (e.g., Cas9 or Cpf1). In some embodiments, the present disclosure provides using type II and/or type V single-subunit effector systems.

As these naturally occur in many different types of bacteria, the exact arrangements of the CRISPR and structure, function and number of Cas genes and their product differ somewhat from species to species. Haft et al. (2005) *PLoS Comput. Biol.* 1: e60; Kunin et al. (2007) *Genome Biol.* 8: R61; Mojica et al. (2005) *J. Mol. Evol.* 60: 174-182; Bolotin et al. (2005) *Microbiol.* 151: 2551-2561; Pourcel et al. (2005)*Microbiol.* 151: 653-663; and Stern et al. (2010) *Trends. Genet.* 28: 335-340. For example, the Cse (Cas subtype, *E. coli*) proteins (e.g., CasA) form a functional complex, Cascade, which processes CRISPR RNA transcripts into spacer-repeat units that Cascade retains. Brouns et al. (2008) *Science* 321: 960-964. In other prokaryotes, Cas6 processes the CRISPR transcript. The CRISPR-based phage inactivation in *E. coli* requires Cascade and Cas3, but not Cas1 or Cas2. The Cmr (Cas RAAMP module) proteins in *Pyrococcus furiosus* and other prokaryotes form a functional complex with small CRISPR RNAs that recognizes and cleaves complementary target RNAs. A simpler CRISPR system relies on the protein Cas9, which is a nuclease with two active cutting sites, one for each strand of the double helix. Combining Cas9 and modified CRISPR locus RNA can be used in a system for gene editing. Pennisi (2013) Science 341: 833-836.

(ii) CRISPR Cas9

In some embodiments, the present disclosure provides methods of gene editing using a Type II CRISPR system. Type II systems rely on a i) single endonuclease protein, ii) a transactivating crRNA (tracrRNA), and iii) a crRNA where a ~20-nucleotide (nt) portion of the 5' end of crRNA is complementary to a target nucleic acid. The region of a CRISPR crRNA strand that is complementary to its target DNA protospacer is hereby referred to as "guide sequence."

In some embodiments, the tracrRNA and crRNA components of a Type II system can be replaced by a single guide RNA (sgRNA), also known as a guide RNA (gRNA). The sgRNA can include, for example, a nucleotide sequence that comprises an at least 12-20 nucleotide sequence complementary to the target DNA sequence (guide sequence) and can include a common scaffold RNA sequence at its 3' end. As used herein, "a common scaffold RNA" refers to any RNA sequence that mimics the tracrRNA sequence or any RNA sequences that function as a tracrRNA.

Cas9 endonucleases produce blunt end DNA breaks, and are recruited to target DNA by a combination of a crRNA and a tracrRNA oligos, which tether the endonuclease via complementary hybridization of the RNA CRISPR complex.

In some embodiments, DNA recognition by the crRNA/endonuclease complex requires additional complementary base-pairing with a protospacer adjacent motif (PAM) (e.g., 5'-NGG-3') located in a 3' portion of the target DNA, downstream from the target protospacer. (Jinek, M., et. al., Science. 2012, 337:816-821). In some embodiments, the PAM motif recognized by a Cas9 varies for different Cas9 proteins.

In some embodiments the Cas9 disclosed herein can be any variant derived or isolated from any source. In other embodiments, the Cas9 peptide of the present disclosure can include one or more of the mutations described in the literature, including but not limited to the functional mutations described in: Fonfara et al. Nucleic Acids Res. 2014 February; 42(4):2577-90; Nishimasu H. et al. Cell. 2014 Feb. 27,156(5):935-49; Jinek M. et al. Science. 2012 337: 816-21; and Jinek M. et al. Science. 2014 Mar. 14, 343 (6176); see also U.S. patent application Ser. No. 13/842,859, filed Mar. 15, 2013, which is hereby incorporated by reference; further, see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641, which are all hereby incorporated by reference. Thus, in some embodiments, the systems and methods disclosed herein can be used with the wild type Cas9 protein having double-stranded nuclease activity, Cas9 mutants that act as single stranded nickases, or other mutants with modified nuclease activity.

According to the present disclosure, Cas9 molecules of, derived from, or based on the Cas9 proteins of a variety of species can be used in the methods and compositions described herein. For example, Cas9 molecules of, derived from, or based on, e.g., *S. pyogenes, S. thermophilus, Staphylococcus aureus* and/or *Neisseria meningitidis* Cas9 molecules, can be used in the systems, methods and compositions described herein. Additional Cas9 species include: *Acidovorax avenae, Actinobacillus pleuropneumoniae, Acti-*

*nobacillus succinogenes, Actinobacillus suis, Actinomyces* sp., *cycliphilus denitrificans, Aminomonas paucivorans, Bacillus cereus, Bacillus smithii, Bacillus thuringiensis, Bacteroides* sp., *Blastopirellula marina, Bradyrhiz obium* sp., *Brevibacillus latemsporus, Campylobacter coli, Campylobacter jejuni, Campylobacter lad, Candidatus Puniceispirillum, Clostridiu cellulolyticum, Clostridium perfringens, Corynebacterium accolens, Corynebacterium diphtheria, Corynebacterium matruchotii, Dinoroseobacter sliibae, Eubacterium dolichum, gamma proteobacterium, Gluconacetobacler diazotrophicus, Haemophilus parainfluenzae, Haemophilus sputorum, Helicobacter canadensis, Helicobacter cinaedi, Helicobacter mustelae, Ilyobacler polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica. Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus lugdunensis, Streptococcus* sp., *Subdoligranulum* sp., *Tislrella mobilis, Treponema* sp., or *Verminephrobacter eiseniae.*

In some embodiments, the present disclosure teaches the use of tools for genome editing techniques in plants such as crops and methods of gene editing using CRISPR-associated (cas) endonucleases including SpyCas9, SaCas9, St1Cas9. These powerful tools for genome editing, which can be applied to plant genome editing are well known in the art. See example, Song et al. (2016), CRISPR/Cas9: A powerful tool for crop genome editing, *The Crop Journal* 4:75-82, Mali et al. (2013) RNA-guided human genome engineering via cas9, Science 339: 823-826; Ran et al. (2015) In vivo genome editing using *Staphylococcus aureus* cas9, Nature 520: 186-191; Esvelt et al. (2013) Orthogonal cas9 proteins for rna-guided gene regulation and editing, Nature methods 10(11): 1116-1121, each of which is hereby incorporated by reference in its entirety for all purposes.

(iii) CRISPR Cpf1

In other embodiments, the present disclosure provides methods of gene editing using a Type V CRISPR system. In some embodiments, the present disclosure provides methods of gene editing using CRISPR from *Prevotella, Francisella, Acidaminococcus, Lachnospiraceae*, and *Moraxella* (Cpf1).

The Cpf1 CRISPR systems of the present disclosure comprise i) a single endonuclease protein, and ii) a crRNA, wherein a portion of the 3' end of crRNA contains the guide sequence complementary to a target nucleic acid. In this system, the Cpf1 nuclease is directly recruited to the target DNA by the crRNA. In some embodiments, guide sequences for Cpf1 must be at least 12 nt, 13 nt, 14 nt, 15 nt, or 16 nt in order to achieve detectable DNA cleavage, and a minimum of 14 nt, 15 nt, 16 nt, 17 nt, or 18 nt to achieve efficient DNA cleavage.

The Cpf1 systems of the present disclosure differ from Cas9 in a variety of ways. First, unlike Cas9, Cpf1 does not require a separate tracrRNA for cleavage. In some embodiments, Cpf1 crRNAs can be as short as about 42-44 bases long—of which 23-25 nt is guide sequence and 19 nt is the constitutive direct repeat sequence. In contrast, the combined Cas9 tracrRNA and crRNA synthetic sequences can be about 100 bases long.

Second, certain Cpf1 systems prefer a "TTN" PAM motif that is located 5' upstream of its target. This is in contrast to the "NGG" PAM motifs located on the 3' of the target DNA for common Cas9 systems such as *Streptococcus pyogenes* Cas9. In some embodiments, the uracil base immediately preceding the guide sequence cannot be substituted (Zetsche, B. et al. 2015. "Cpf1 Is a Single RNA-Guided Endonuclease of a Class 2 CRISPR-Cas System" Cell 163, 759-771, which is hereby incorporated by reference in its entirety for all purposes).

Third, the cut sites for Cpf1 are staggered by about 3-5 bases, which create "sticky ends" (Kim et al., 2016. "Genome-wide analysis reveals specificities of Cpf1 endonucleases in human cells" published online Jun. 6, 2016). These sticky ends with 3-5 nt overhangs are thought to facilitate NHEJ-mediated-ligation, and improve gene editing of DNA fragments with matching ends. The cut sites are in the 3' end of the target DNA, distal to the 5' end where the PAM is. The cut positions usually follow the 18th base on the non-hybridized strand and the corresponding 23rd base on the complementary strand hybridized to the crRNA.

Fourth, in Cpf1 complexes, the "seed" region is located within the first 5 nt of the guide sequence. Cpf1 crRNA seed regions are highly sensitive to mutations, and even single base substitutions in this region can drastically reduce cleavage activity (see Zetsche B. et al. 2015 "Cpf1 Is a Single RNA-Guided Endonuclease of a Class 2 CRISPR-Cas System" Cell 163, 759-771). Critically, unlike the Cas9 CRISPR target, the cleavage sites and the seed region of Cpf1 systems do not overlap. Additional guidance on designing Cpf1 crRNA targeting oligos is available on Zetsche B. et al. 2015. ("Cpf1 Is a Single RNA-Guided Endonuclease of a Class 2 CRISPR-Cas System" Cell 163, 759-771).

(iv) Guide RNA (gRNA)

In some embodiments, the guide RNA of the present disclosure comprises two coding regions, encoding for crRNA and tracrRNA, respectively. In other embodiments, the guide RNA is a single guide RNA (sgRNA) synthetic crRNA/tracrRNA hybrid. In other embodiments, the guide RNA is a crRNA for a Cpf1 endonuclease.

Persons having skill in the art will appreciate that, unless otherwise noted, all references to a single guide RNA (sgRNA) in the present disclosure can be read as referring to a guide RNA (gRNA). Therefore, embodiments described in the present disclosure which refer to a single guide RNA (sgRNA) will also be understood to refer to a guide RNA (gRNA).

The guide RNA is designed so as to recruit the CRISPR endonuclease to a target DNA region. In some embodiments, the present disclosure teaches methods of identifying viable target CRISPR landing sites, and designing guide RNAs for targeting the sites. For example, in some embodiments, the present disclosure teaches algorithms designed to facilitate the identification of CRISPR landing sites within target DNA regions.

In some embodiments, the present disclosure teaches use of software programs designed to identify candidate CRISPR target sequences on both strands of an input DNA sequence based on desired guide sequence length and a CRISPR motif sequence (PAM, protospacer adjacent motif) for a specified CRISPR enzyme. For example, target sites for Cpf1 from *Francisella novicida* U112, with PAM sequences TTN, may be identified by searching for 5'-TTN-3' both on the input sequence and on the reverse-complement of the input. The target sites for Cpf1 from Lachnospiraceae bacterium and Acidaminococcus sp., with PAM sequences TTTN, may be identified by searching for 5'-TTTN-3' both on the input sequence and on the reverse complement of the input. Likewise, target sites for Cas9 of *S. thermophilus* CRISPR, with PAM sequence NNAGAAW, may be identified by searching for 5'-Nx-NNAGAAW-3' both on the input sequence and on the reverse-complement of the input. The PAM sequence for Cas9 of *S. pyogenes* is 5'-NGG-3'.

Since multiple occurrences in the genome of the DNA target site may lead to nonspecific genome editing, after identifying all potential sites, sequences may be filtered out based on the number of times they appear in the relevant reference genome or modular CRISPR construct. For those CRISPR enzymes for which sequence specificity is determined by a 'seed' sequence (such as the first 5 bp of the guide sequence for Cpf1-mediated cleavage) the filtering step may also account for any seed sequence limitations.

In some embodiments, algorithmic tools can also identify potential off target sites for a particular guide sequence. For example, in some embodiments Cas-Offinder can be used to identify potential off target sites for Cpf1 (see Kim et al., 2016. "Genome-wide analysis reveals specificities of Cpf1 endonucleases in human cells" Nature Biotechnology 34, 863-868). Any other publicly available CRISPR design/identification tool may also be used, including for example the Zhang lab crispr.mit.edu tool (see Hsu, et al. 2013 "DNA targeting specificity of RNA guided Cas9 nucleases" Nature Biotech 31, 827-832).

In some embodiments, the user may be allowed to choose the length of the seed sequence. The user may also be allowed to specify the number of occurrences of the seed: PAM sequence in a genome for purposes of passing the filter. The default is to screen for unique sequences. Filtration level is altered by changing both the length of the seed sequence and the number of occurrences of the sequence in the genome. The program may in addition or alternatively provide the sequence of a guide sequence complementary to the reported target sequence(s) by providing the reverse complement of the identified target sequence(s).

In the guide RNA, the "spacer/guide sequence" sequence is complementary to the "proto spacer" sequence in the DNA target. The gRNA"scaffold" for a single stranded gRNA structure is recognized by the Cas9 protein.

In some embodiments, the transgenic plant, plant part, plant cell, or plant tissue culture taught in the present disclosure comprise a recombinant construct, which comprises at least one nucleic acid sequence encoding a guide RNA. In some embodiments, the nucleic acid is operably linked to a promoter. In other embodiments, a recombinant construct further comprises a nucleic acid sequence encoding a Clustered regularly interspaced short palindromic repeats (CRISPR) endonuclease. In other embodiments, the guide RNA is capable of forming a complex with said CRISPR endonuclease, and said complex is capable of binding to and creating a double strand break in a genomic target sequence of said plant genome. In other embodiments, the CRISPR endonuclease is Cas9.

In further embodiments, the target sequence is a nucleic acid for MYB41, homologs of MYB41, orthologs of MYB41 and/or paralogs of MYB41, and/or fragments and variations thereof. In some embodiments, the present disclosure teaches the gene editing of MYB41 in plants using genetic engineering techniques described herein.

In some embodiments, the modified plant cells comprise one or more modifications (e.g., insertions, deletions, or mutations of one or more nucleic acids) in the genomic DNA sequence of an endogenous target gene resulting in the altered function the endogenous gene, thereby modulating, stimulating, or enhancing suberin content in plant cells, plant tissues, plant parts and whole plants. In such embodiments, the modified plant cells comprise a "modified endogenous target gene." In some embodiments, the modifications in the genomic DNA sequence cause mutation, thereby altering the function of the MYB41 protein. In some embodiments, the modifications in the genomic DNA sequence results in amino acid substitutions, thereby altering the normal function of the encoded protein. In some embodiments, the modifications in the genomic DNA sequence encode a modified endogenous protein with modulated, altered, stimulated or enhanced function compared to the unmodified version of the endogenous protein.

In some embodiments, the modified plant cells described herein comprise one or more modified endogenous target genes, wherein the one or more modifications result in an altered function of a gene product (i.e., a protein) encoded by the endogenous target gene compared to an unmodified plant cell. For example, in some embodiments, a modified plant cell demonstrates expression of a protein or an upregulated expression of said protein. In some embodiments, the expression of the gene product (such as genetically-engineered MYB41) in a modified plant cell is enhanced by at least 0.5%, 1%, 2%, 3%, 4%, 5% or higher compared to the expression of the gene product (such as MYB41) in an unmodified plant cell. In other embodiments, the expression of the gene product (such as genetically-engineered MYB41) in a modified plant cell is enhanced by at least 10%, 20%, 30%, 40%, 50%, 60%, 70%, 80%, 90%, or more compared to the expression of the gene product (such as MYB41) in an unmodified plant cell. In some embodiments, the modified plant cells described herein demonstrate enhanced expression and/or function of gene products encoded by a plurality (e.g., two or more) of endogenous target genes compared to the expression of the gene products in an unmodified plant cell. For example, in some embodiments, a modified plant cell demonstrates enhanced expression and/or function of gene products from 2, 3, 4, 5, 6, 7, 8, 9, 10, or more endogenous target genes compared to the expression of the gene products in an unmodified plant cell.

In some embodiments, the modified plant cells described herein comprise one or more modified endogenous target genes, wherein the one or more modifications to the target DNA sequence results in expression of a protein with reduced or altered function (e.g., a "modified endogenous protein") compared to the function of the corresponding protein expressed in an unmodified plant cell (e.g., a "unmodified endogenous protein"). In some embodiments, the modified plant cells described herein comprise 2, 3, 4, 5, 6, 7, 8, 9, 10, or more modified endogenous target genes encoding 2, 3, 4, 5, 6, 7, 8, 9, 10, or more modified endogenous proteins. In some embodiments, the modified endogenous protein demonstrates enhanced or altered binding affinity for another protein expressed by the modified plant cell or expressed by another cell; enhanced or altered signaling capacity; enhanced or altered enzymatic activity; enhanced or altered DNA-binding activity; or reduced or altered ability to function as a scaffolding protein.

EXAMPLES

The present invention is further illustrated by the following examples that should not be construed as limiting. The contents of all references, patents, and published patent applications cited throughout this application, as well as the Figures, are incorporated herein by reference in their entirety for all purposes.

Example 1: Selection of Candidate Promoters for Engineering Increases in Suberin Production We undertook an extensive investigation searching for promoters that might drive more suberin production. More specifically, to engineer more suberin in specific plant layers, we searched for promoters with root cell-type specific expression that might drive suberin-related genes resulting in enhanced suberin production in the roots of transformed plants.

Figure 1E:
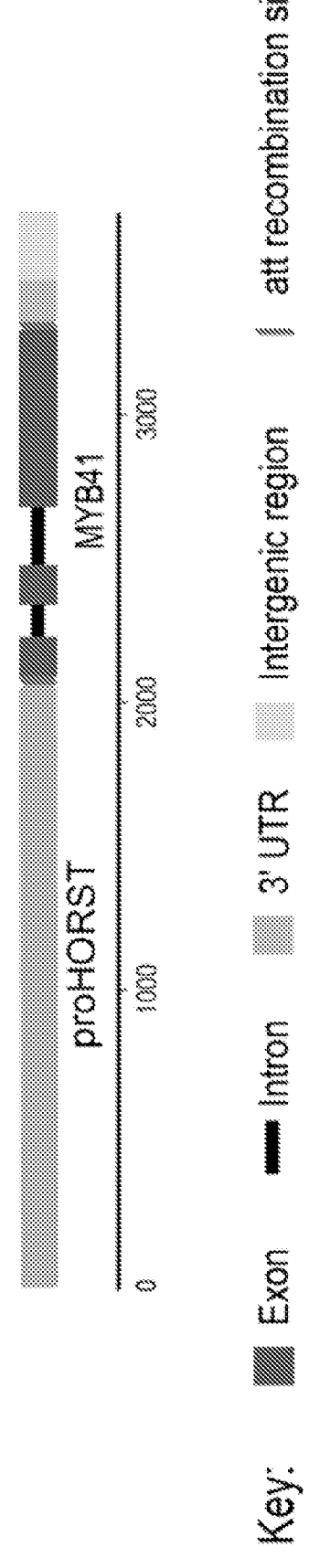
Figure 1E:
Figure 2A:
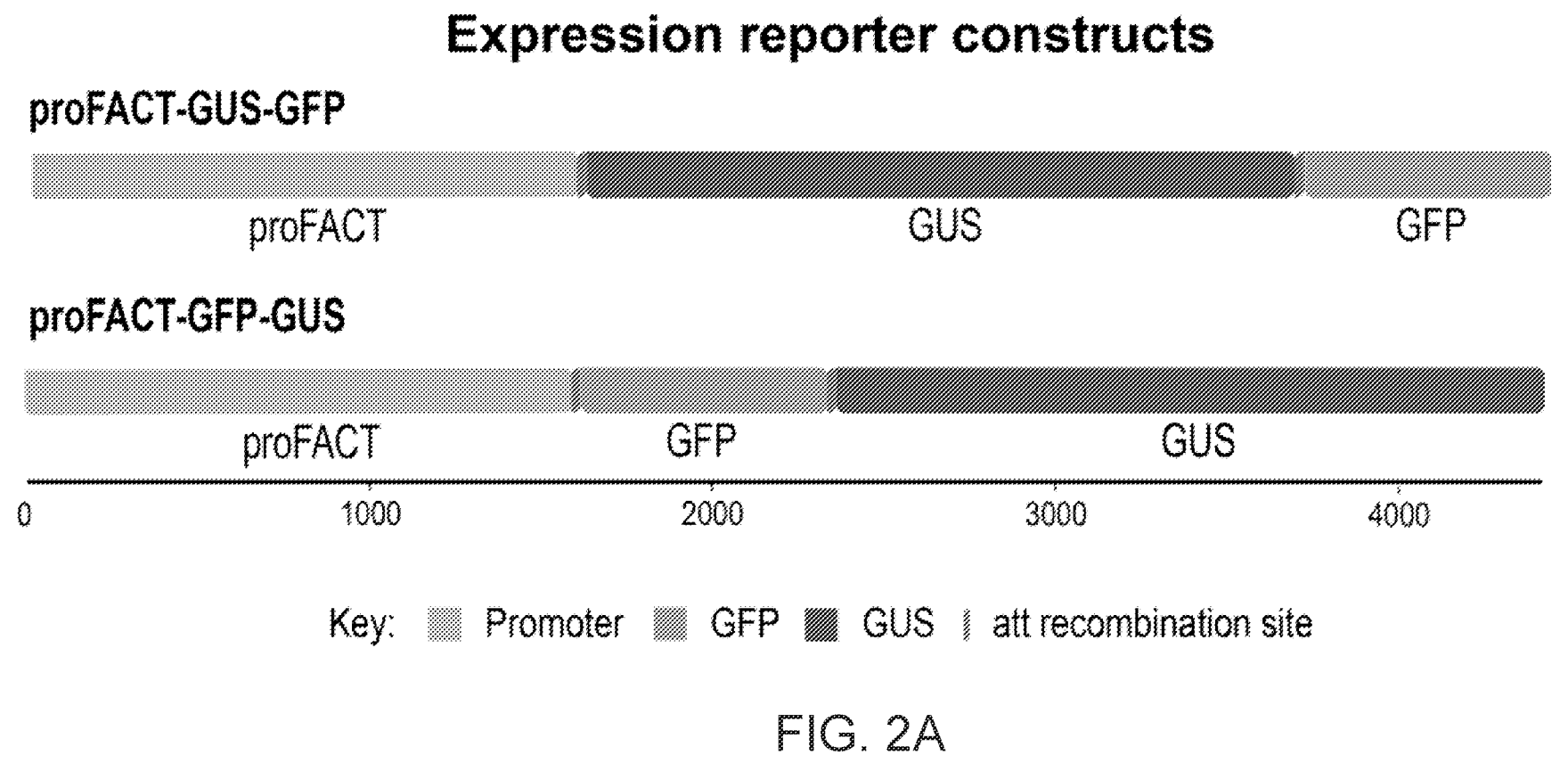
Figure 2B:
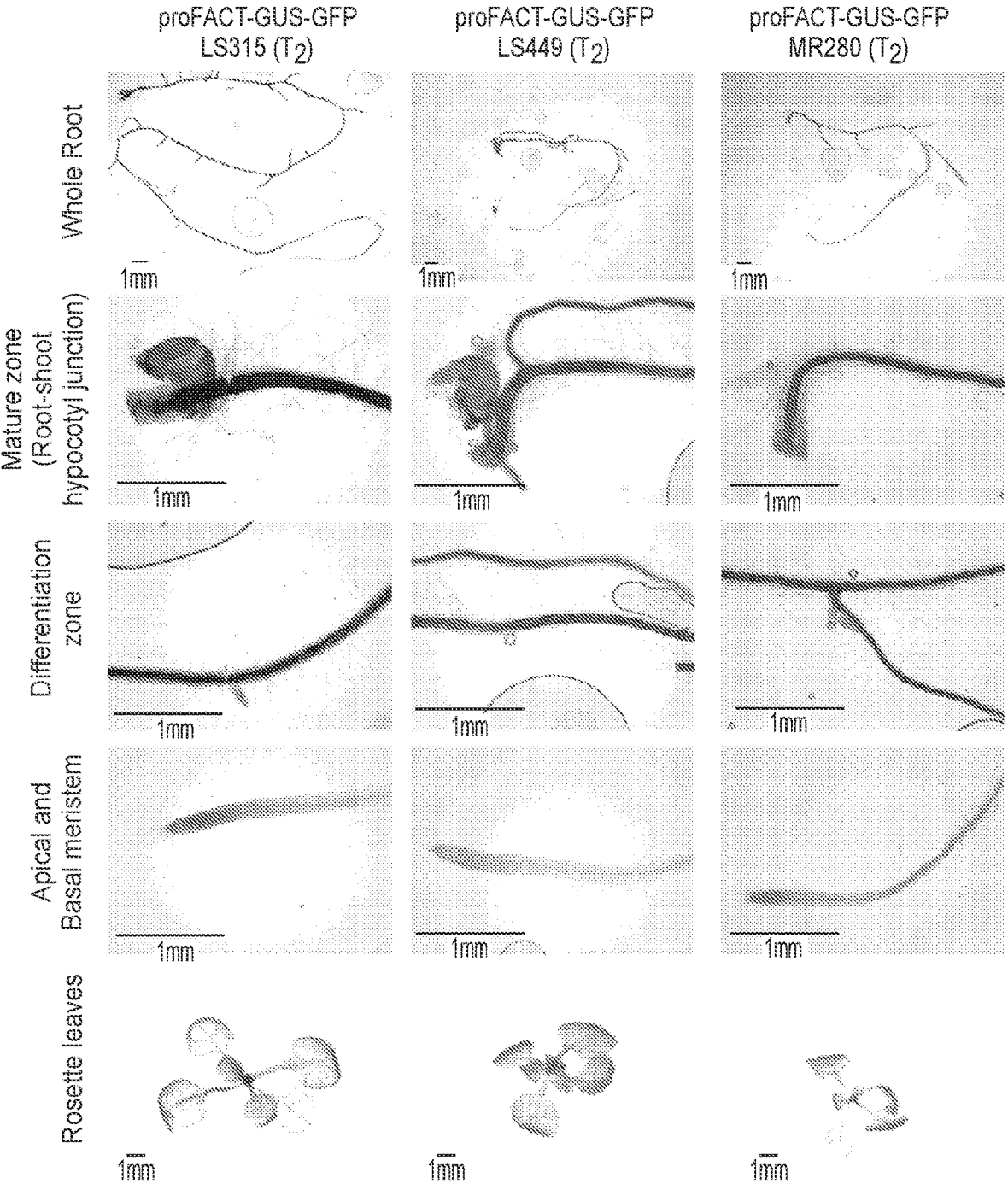
Figure 2C:
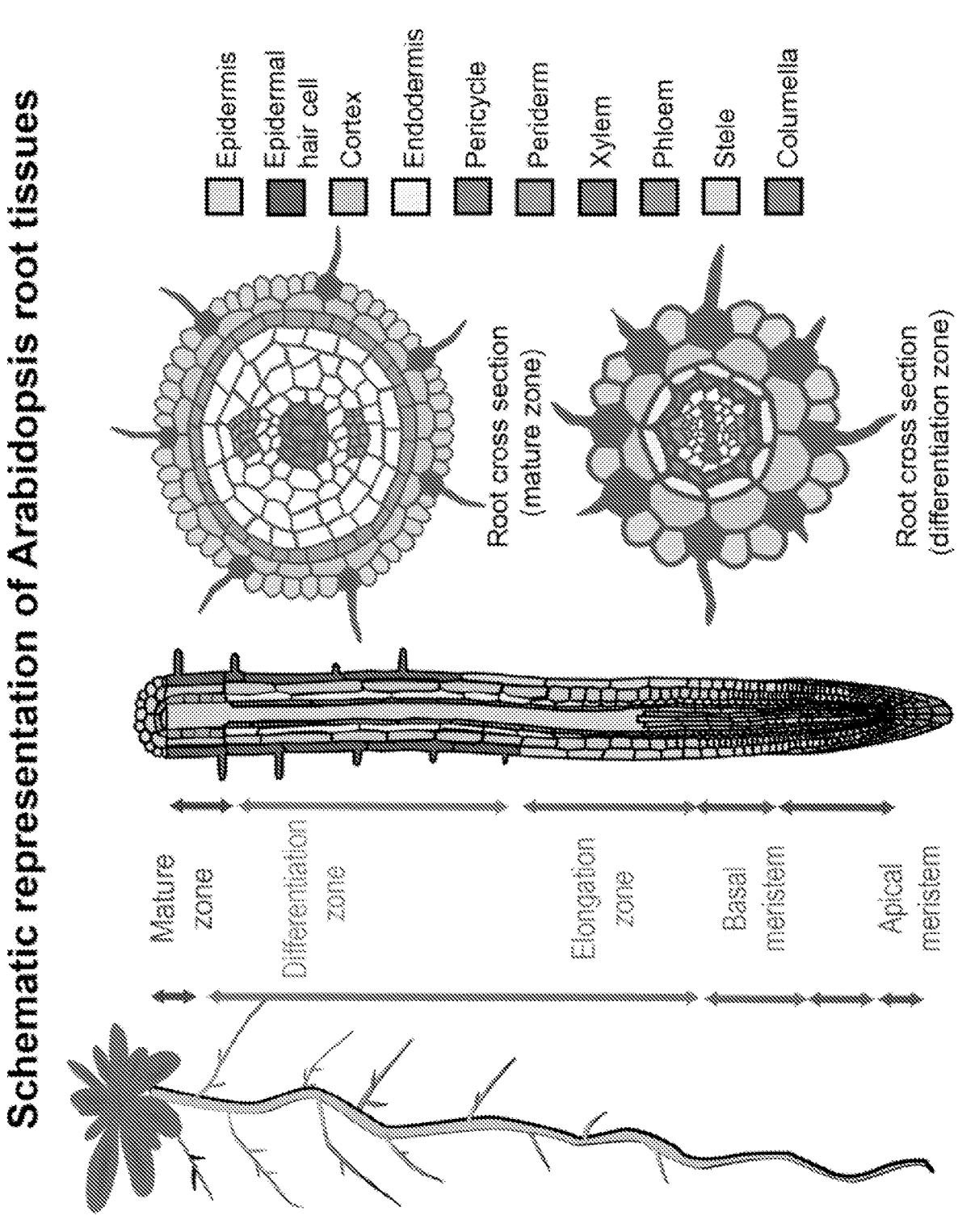
Figure 2D:
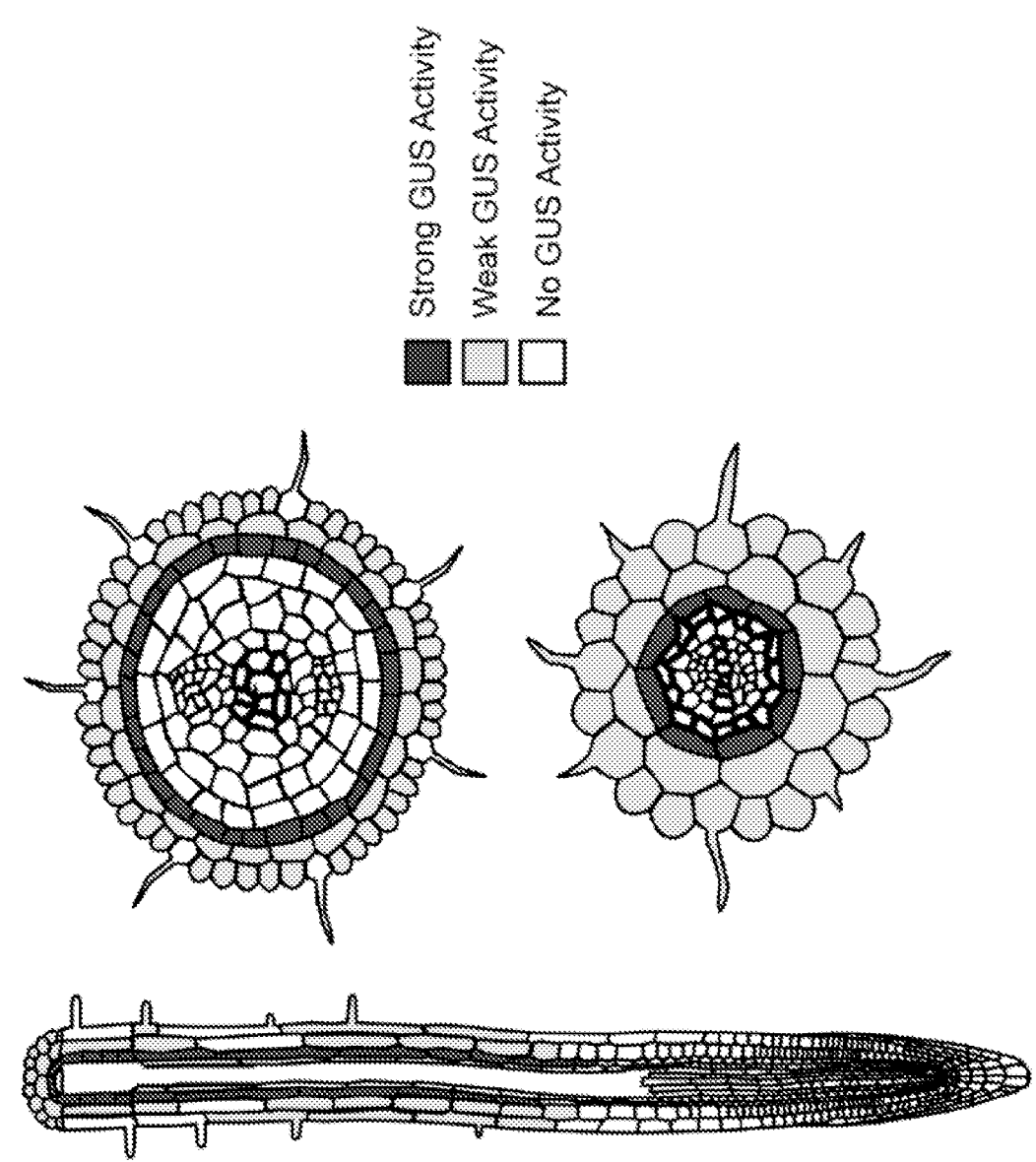
Figure 2E:
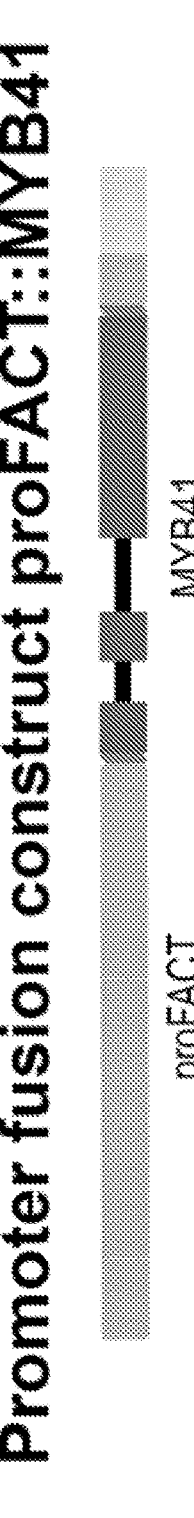
Figure 2E:

As part of this effort, we assessed the expression patterns of two genes believed to be required for the biosynthesis of suberin, HORST (Vishwanath et al., 2015; Hofer et al., 2008; Wei et al., 2020) and FACT (Kosma, 2012; Molina et al., 2009) by generating promoter fusions with dual GUS-GFP reporters (FIGS. 1A and 2A). For each reporter ("proFACT" or "proHORST", respectively) three independently generated *Arabidopsis* lines were characterized and shown to have normal root growth (data not shown) with high GUS expression in the periderm and endodermis of 14-day old roots (FIGS. 1B-D and FIGS. 2B-D). While some weak expression was observed in cortex and epidermis cells, no expression was detected in rosette leaves suggesting that these promoters show minimal expression in cells that are not associated with normal suberin production.

Following similar experimental procedures, five additional promoters were also shown to have GUS expression in the periderm and endodermis (data not shown). These additional promoters are proASFT, proRALPH, proMYB84, proHORST and proGPAT5. ProASFT, proRALPH, proHORST and proGPAT5 had no GUS expression in rosette leaves, while proMYB84 had some rosette leaf expression.

Figure 2F:
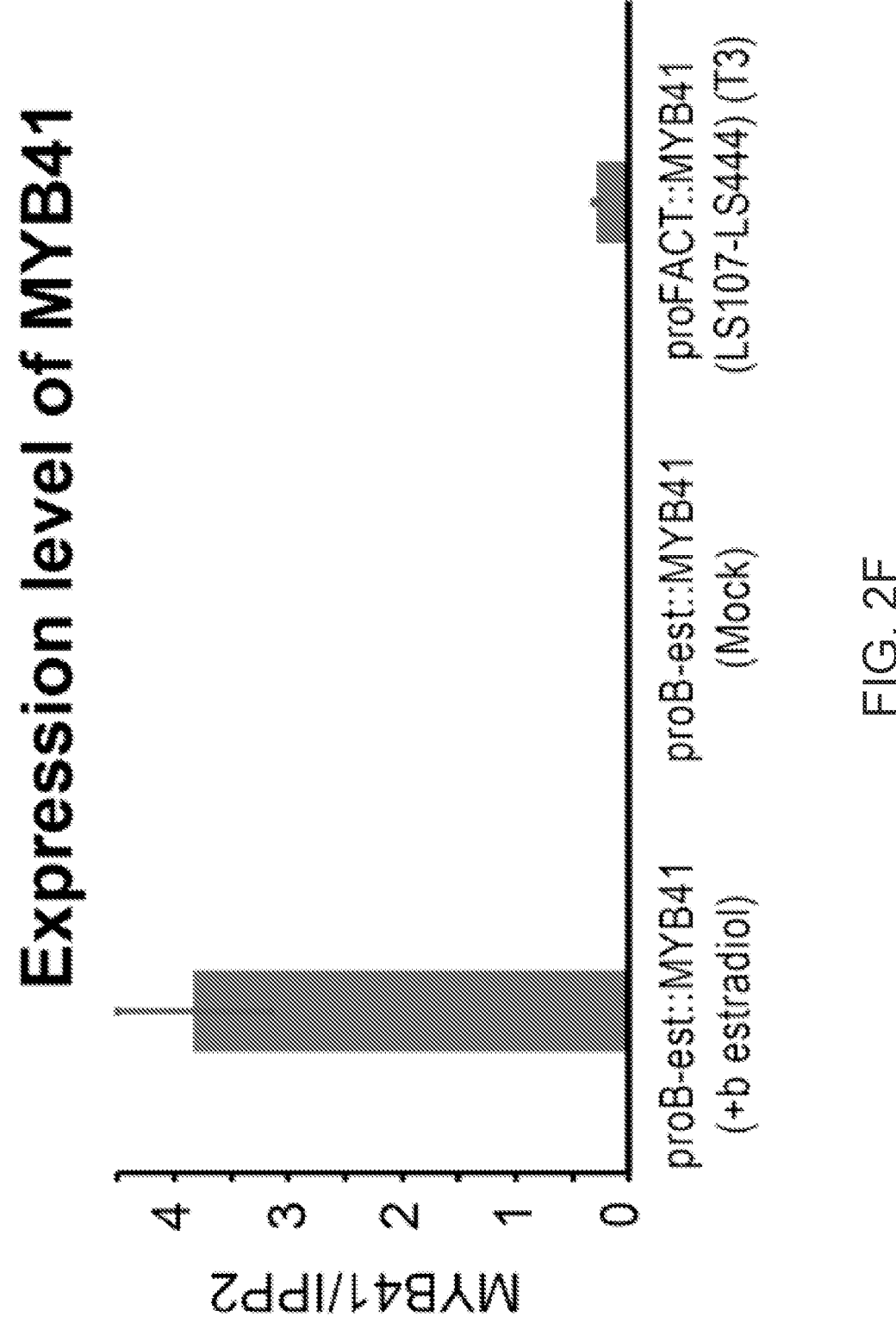

Example 2: Use of ProFACT to Drive Ectopic Expression of MYB41 Transcription Factor The promoter of FACT was used to drive ectopic expression of the MYB41 transcription factor, which was previously shown to induce the production of suberin in tobacco leaves (Kosma et al., 2014), in a root-layer specific manner. Using the proFACT::MYB41 construct (FIG. 2E) (SEQ ID NO:7) and *agrobacterium*-mediated transformation using a floral dip method (S. J. Clough and A. F. Bent, 2008, Foral dip: a simplified method for *Agrobacterium*-mediated transformation of *Arabadopsis thaliana*, The Plant Journal 16(6), 33 pages), four independently generated *Arabidopsis* lines were characterized and shown to express MYB41 (FIG. 2F) and have normal root growth (FIG. 2G).

Figure 2H:
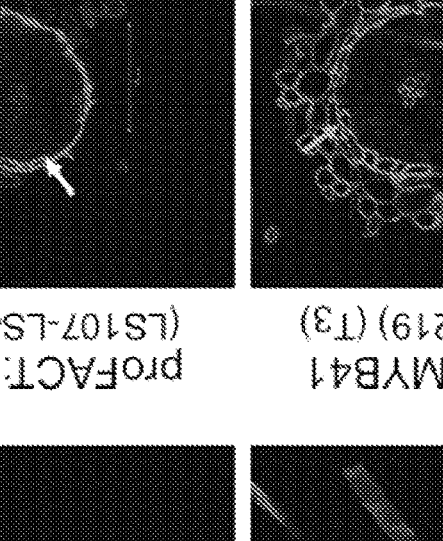
Figure 2H:
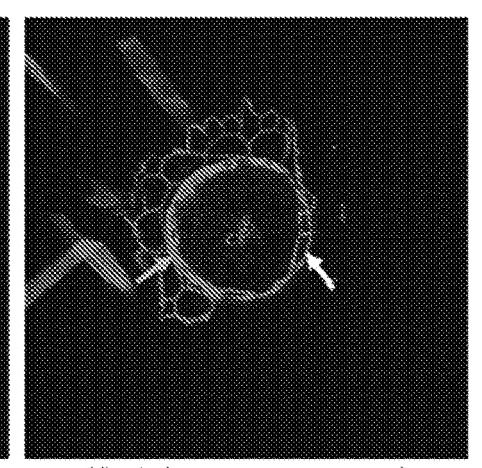
Figure 2H:
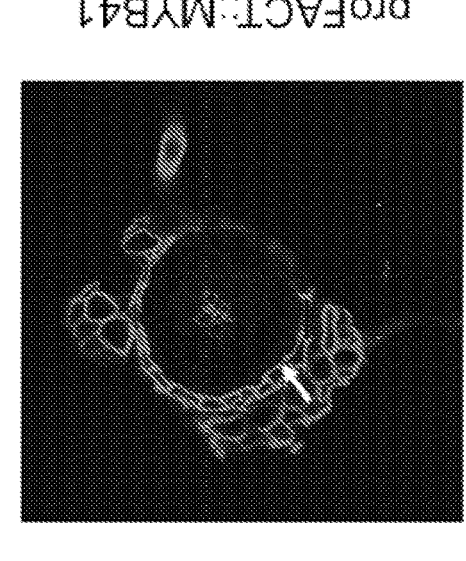
Figure 2H:
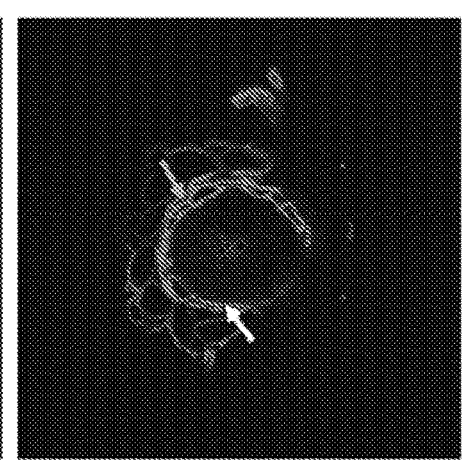

The effects of this construct on suberin deposition were assessed in these lines by Nile Red staining and confocal imaging. These analyses demonstrate that for four independent, homozygous T3 lines (LS 110-LS621, LS 112-LS214, LS108-MR219 and LS107-LS442) and two sibling lines (LS107-LS442 and LS107-LS444) an additional Nile Red stained periderm layer is being formed as compared to a wild-type control (Col-0) (FIG. 2H). Thus, we have identified a highly reproducible means of increasing the levels of suberin by generating additional periderm cells as compared to wild-type plants.

Figure 1F:
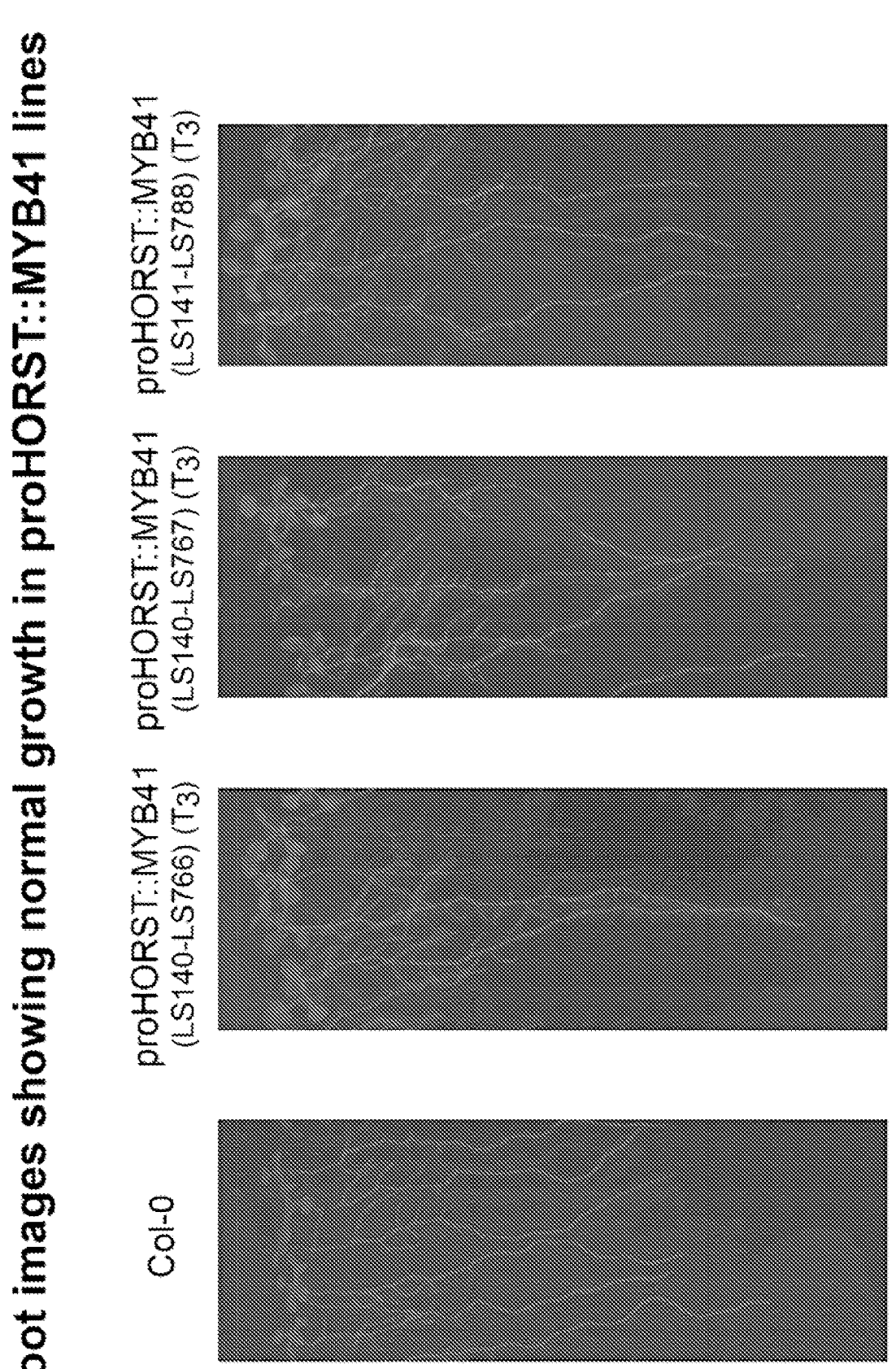

Example 3: Use of ProHORST to Drive Ectopic Expression of MYB41 Transcription Factor The promoter of HORST was used to drive ectopic expression of the MYB41 transcription factor, which was previously shown to induce the production of suberin in tobacco leaves (Kosma et al., 2014), in a root-layer specific manner. Using the proHORST::MYB41 construct (FIG. 1E) (SEQ ID NO:8) and *agrobacterium*-mediated transformation (Clough and Brent, 2008), two independently generated *Arabidopsis* lines were characterized and shown to have normal root growth (FIG. 1F).

Figure 1G:
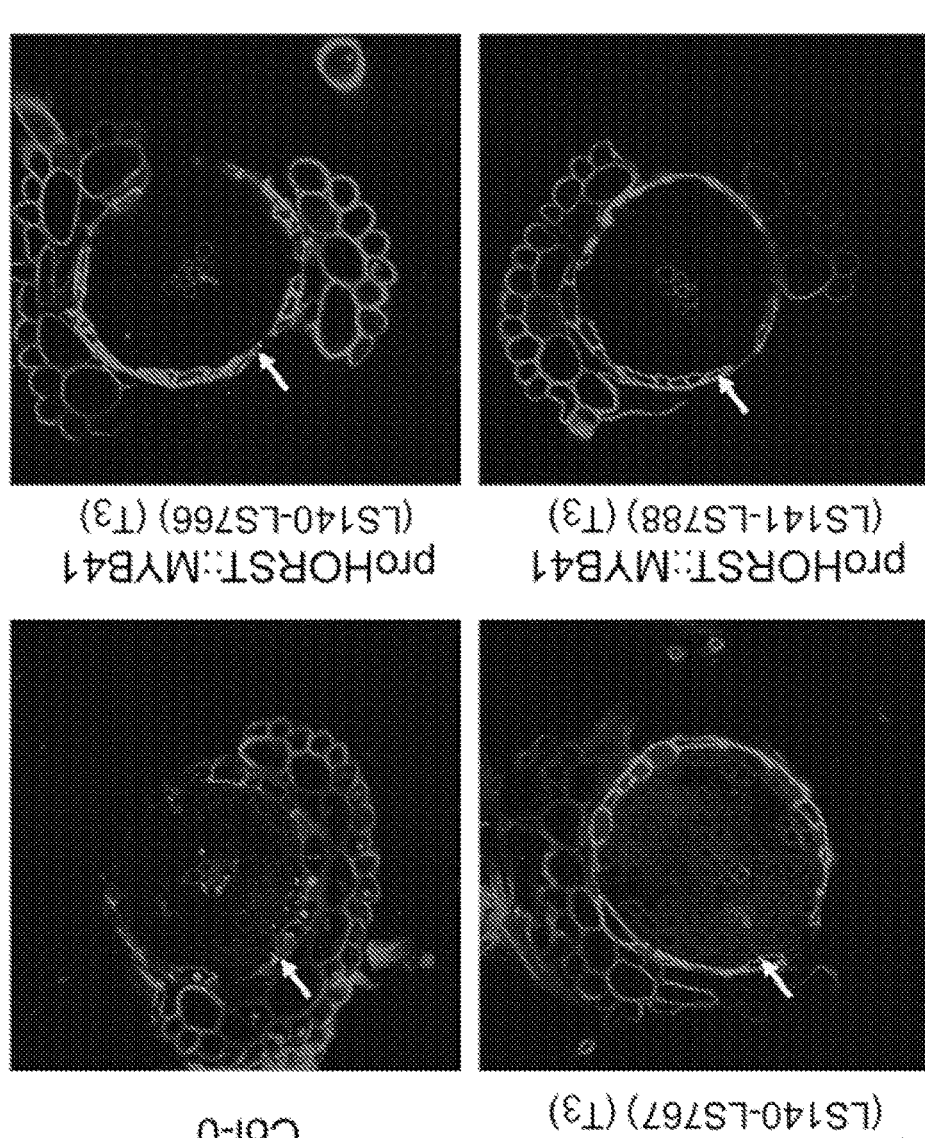

The effects of this construct on suberin deposition were assessed in these lines by Nile Red staining and confocal imaging. In this case we found that in two independent, homozygous T3 lines (LS140-LS766 and LS141-LS788) and two sibling lines (LS140-LS766 and LS140-LS767) more Nile Red signal is observed in the periderm as compared with a wild-type control (Col-0) (FIG. 1G). Thus, we have identified a highly reproducible means of increasing the levels of suberin by depositing more suberin in existing periderm cells as compared to wild-type plants.

Example 4: Quantification of Suberin Biomarkers

To quantify the levels of suberin biomarkers in the pro-FACT::MYB41 and proHORST::MYB41 lines that had more periderm layers and/or increased Nile Red staining, reactive pyrolysis-gas chromatography-mass spectrometry (RxPyGC-MS) experiments were conducted using dried root tissue from either 14 or 28 day old seedlings. For each line, three technical replicates were included, with the average values and the standard error of the mean plotted for the abundances of select fatty acids, $\omega$-hydroxy acids, $\alpha,\omega$-diacids, and phenolics associated with suberin composition (FIGS. 3A-3E).

Figure 3A:
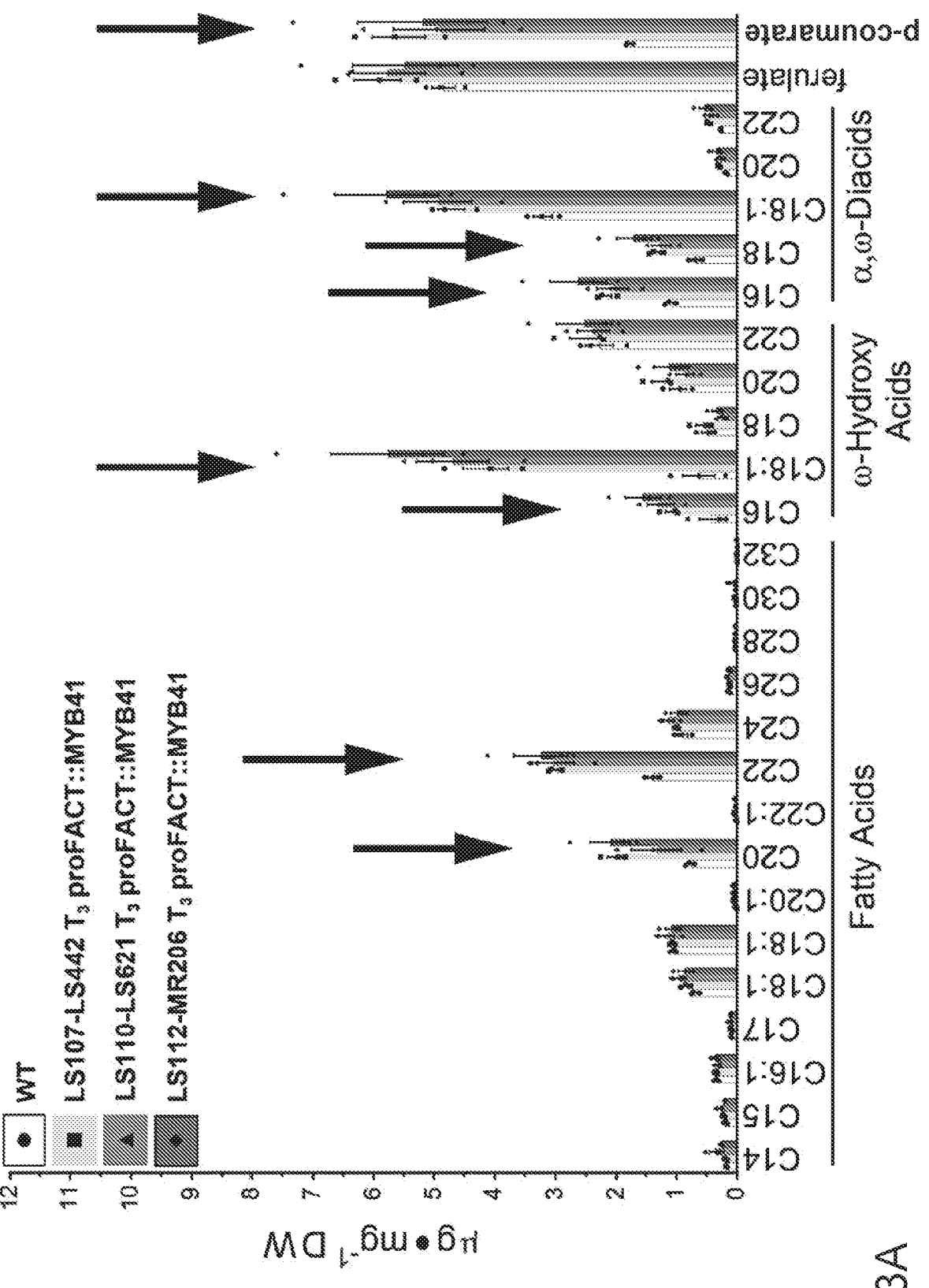
FIGS. 3A-3E illustrate quantification of suberin biomarkers by reactive pyrolysis-gas chromatography-mass spectrometry (pyGCMS).
Figure 3B:
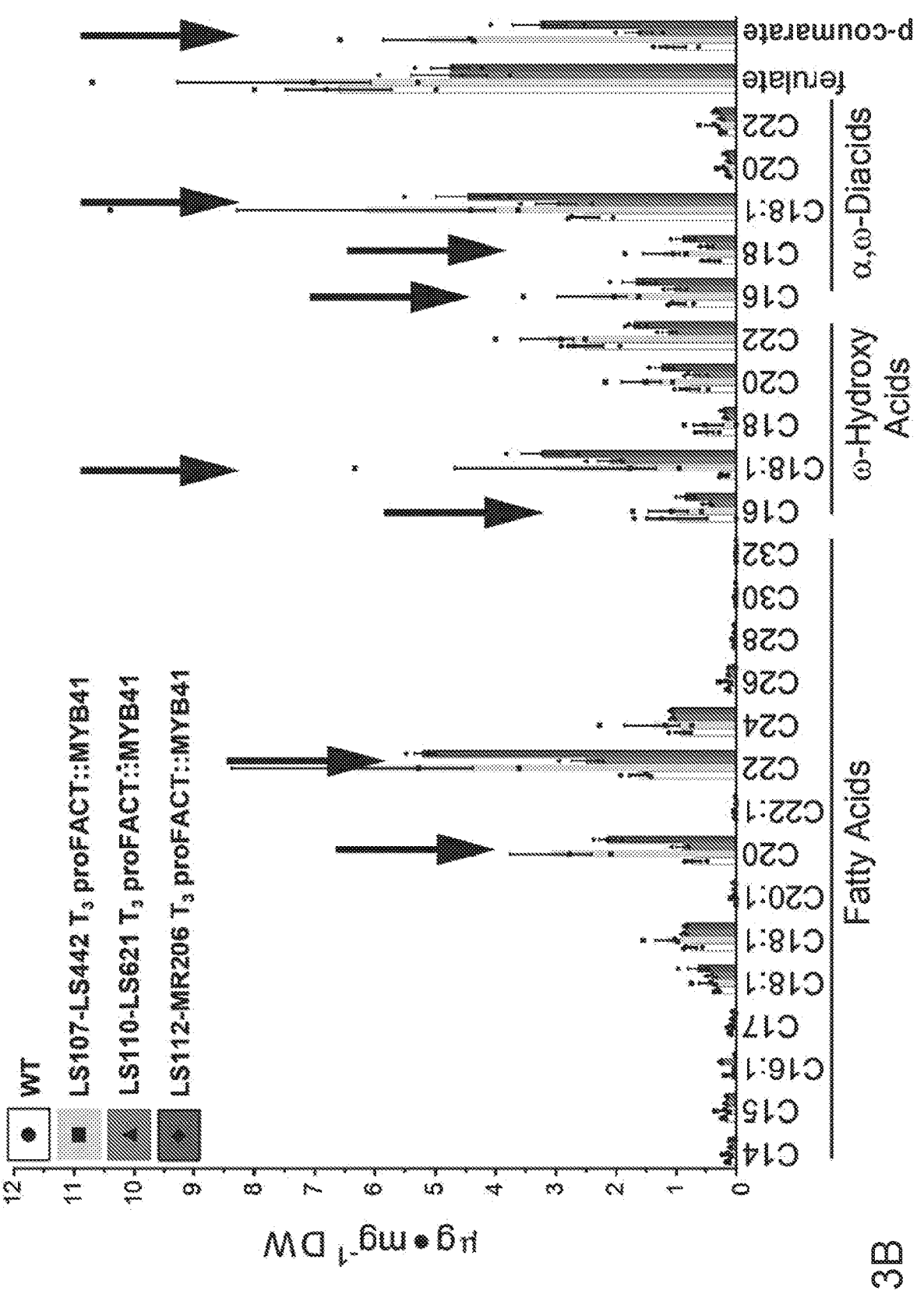
Figure 3C:
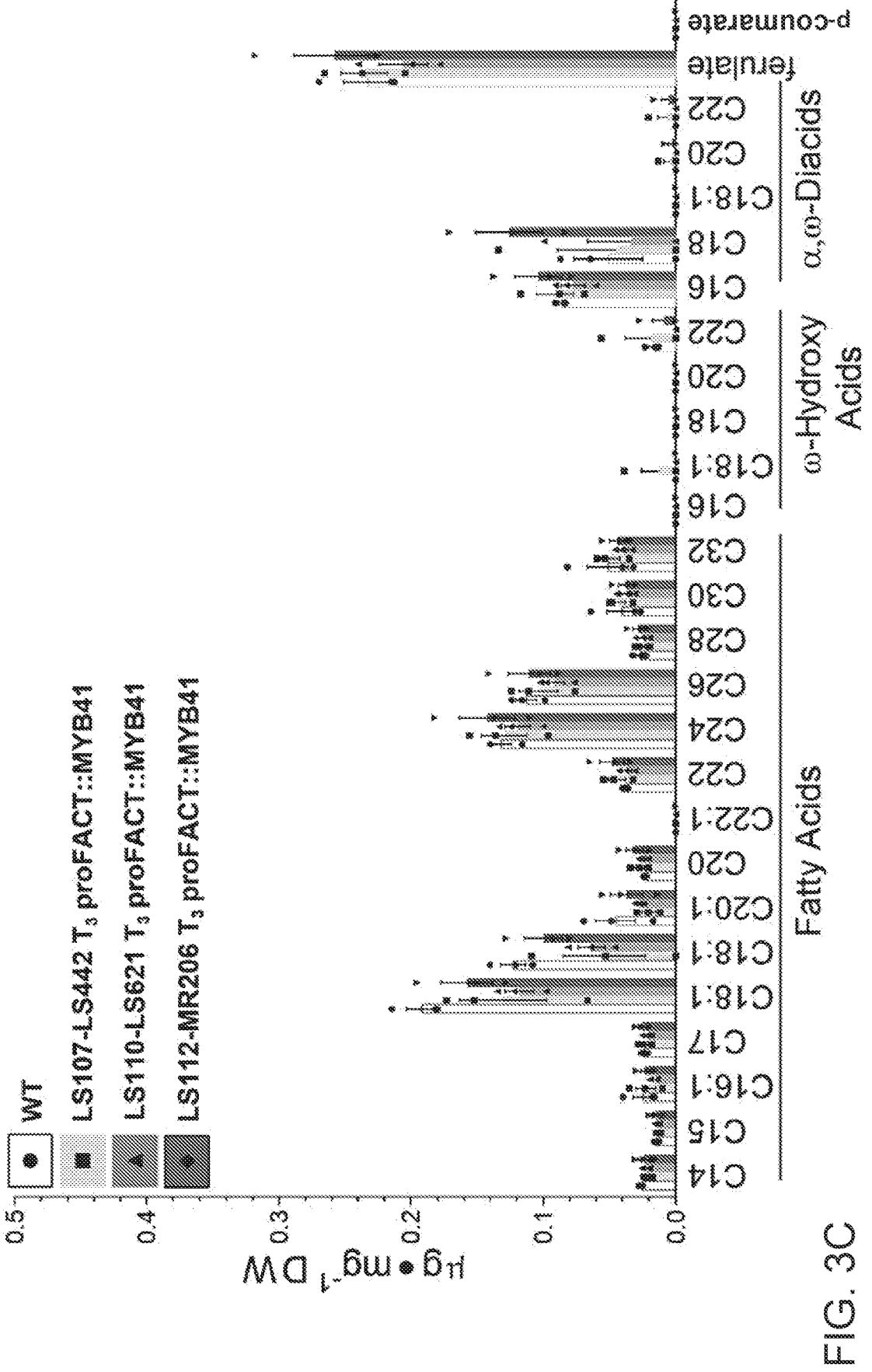
Figure 3D:
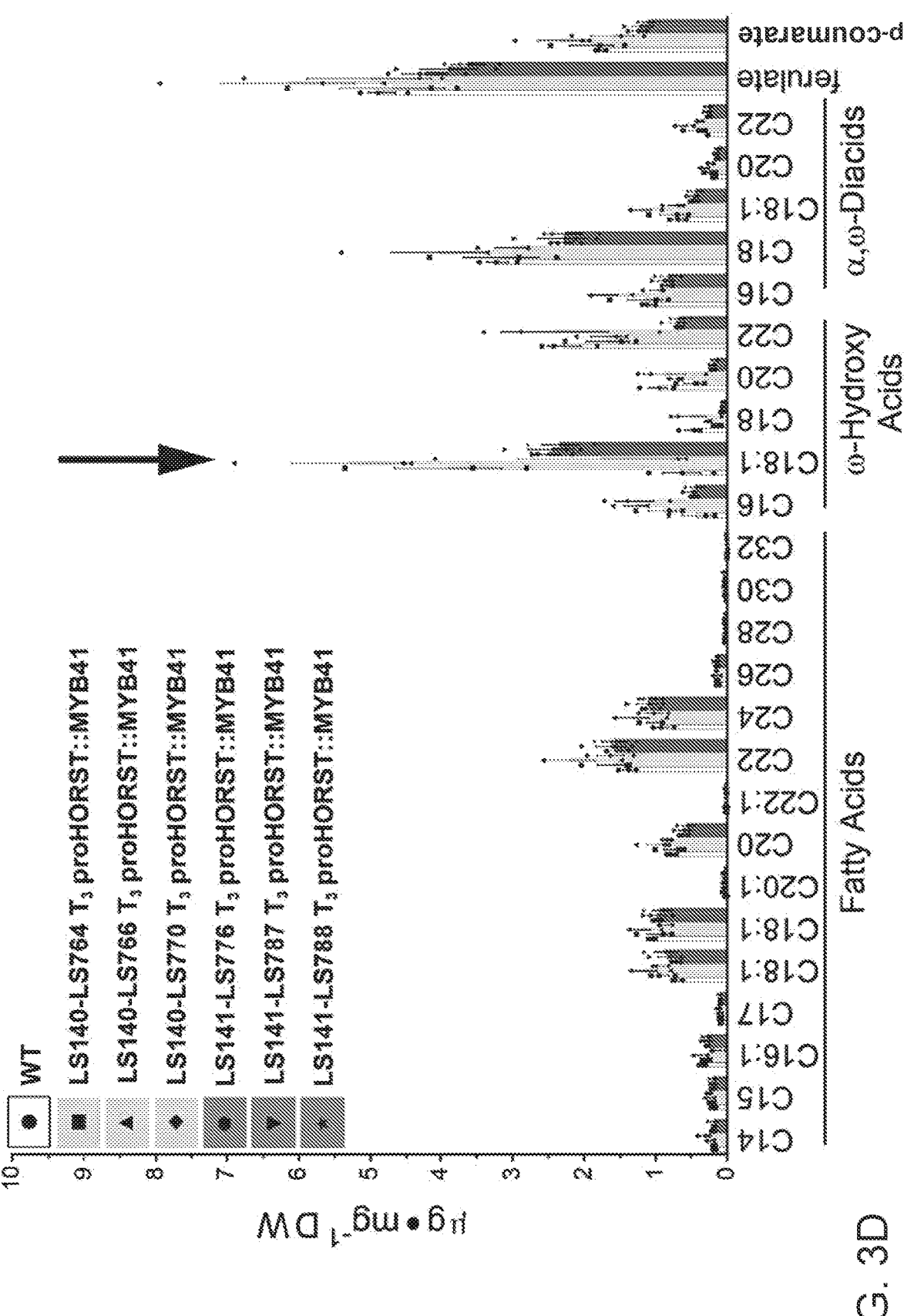
Figure 3E:
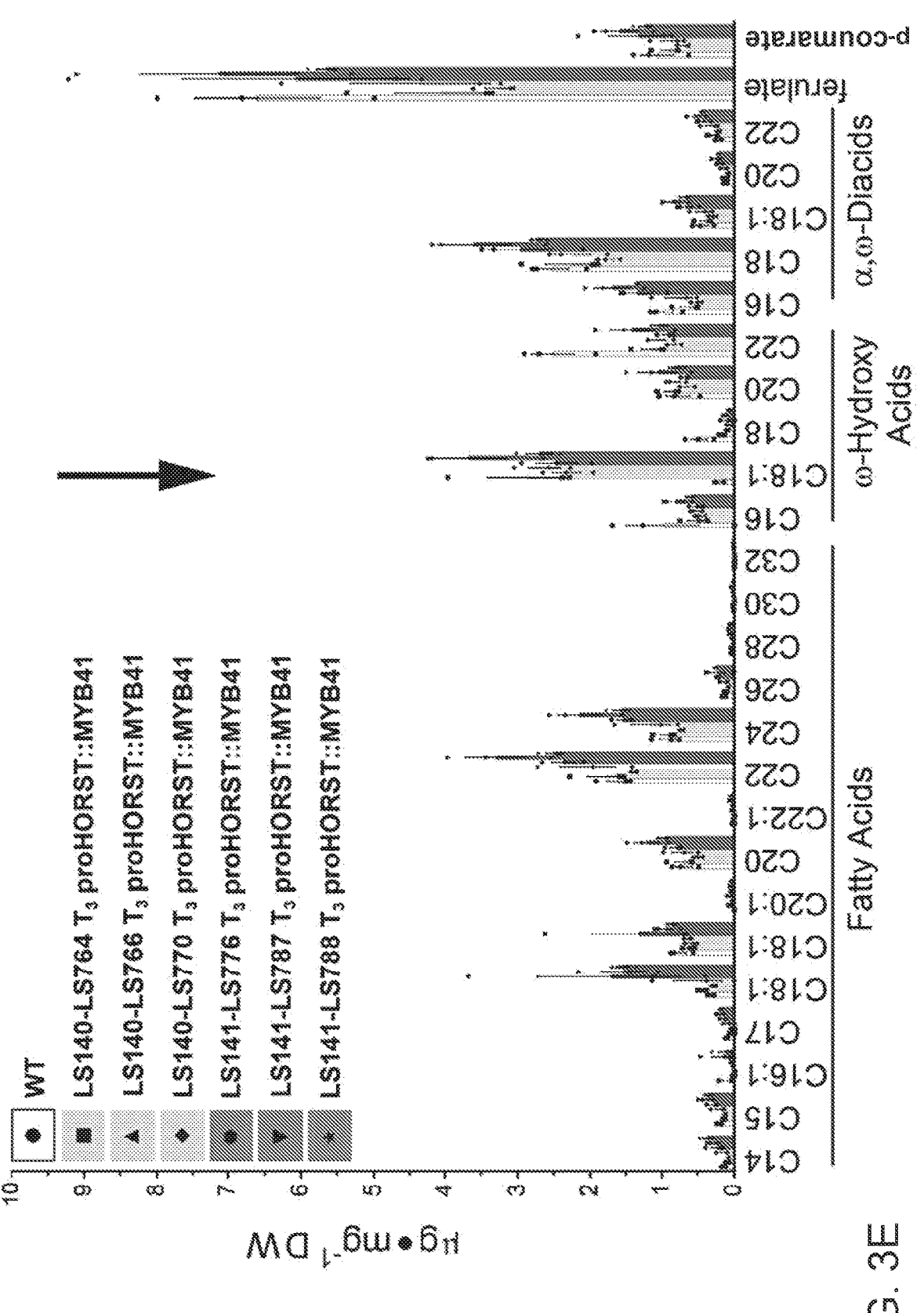

For proFACT::MYB41, three independent T3 homozygous lines were assayed (FIG. 3A and FIG. 3B) and at both the 14 and 28 day time points, these lines consistently showed increased levels of many suberin biomarkers. For these same lines, RxPyGC-MS was also conducted using dried shoot tissue from 14 day old seedlings and no increases in suberin biomarkers were observed (FIG. 3C). These findings are consistent with upregulation of many key steps of suberin biosynthesis specifically in plant roots. Furthermore, the data from the 28 day old root samples indicate that at maturity the engineered lines contain more suberin compared to non-engineered wild-type control lines.

For proHORST::MYB41, three sibling lines from two independent T3 homozygous parents were assayed (FIG. 3D and FIG. 3E) and at both the 14 and 28 day time points, these lines consistently showed increased levels of one suberin biomarker, C18:1 $\omega$-hydroxy acid. Given that these lines show more intense Nile Red staining in periderm tissue, these findings suggest that production of C18:1 $\omega$-hydroxy acids may be partially rate limiting in the suberin biosynthetic pathways. Overall, these analyses of the pFACT::MYB41 and pHORST::MYB41 lines demonstrate that depending on where MYB41 is expressed, different patterns of suberin staining can be generated in vivo and that these changes are associated with different suberin biomarker signatures specifically in root tissue.

Example 5: Use of Additional Promoters to Drive Ectopic Expression of MYB41 Transcription Factor The promoters of ASFT, GPAT5, RALPH and MYB84 can each be used to drive ectopic expression of the MYB41 transcription factor, which was previously shown to induce the production of suberin in tobacco leaves (Kosma et al., 2014), in a root-layer specific manner. Using any one or more of proASFT::MYB41, proGPAT5::MYB41, proRAL-PH::MYB41 and proMYB84:MYB41 constructs (SEQ ID NO:9, SEQ ID NO:10, SEQ ID NO:11 and SEQ ID NO:12, respectively) and *agrobacterium*-mediated transformation, independently generated *Arabidopsis* lines can be characterized and shown to have normal root growth.

The effects of these constructs on suberin deposition can be assessed in these lines by Nile Red staining and confocal imaging. Using this process, one can find independent, homozygous T3 lines and sibling lines in which more Nile Red signal is observed in the periderm as compared with a wild-type control (Col-0). Thus, in this way we provided a highly reproducible means of increasing the levels of suberin by depositing more suberin in existing periderm cells as compared to wild-type plants.

Example 6. Use of Promoters to Drive Ectopic Expression of MYB41 Transcription Factor in Tobacco The promoters of FACT, HORST, ASFT, GPAT5, RALPH and MYB84 derived or isolated from *Arabidopsis*, tobacco or other plant species can each be used to drive ectopic expression of the MYB41 transcription factor, which was previously shown to induce the production of suberin in tobacco leaves (Kosma et al., 2014), in a root-layer specific manner. Using any one or more of proFACT::MYB41, proHORST::MYB41, proASFT::MYB41, proGPAT5::MYB41, proRALPH::MYB41 and proMYB84:MYB41 constructs (SEQ ID NO:7, SEQ ID NO:8, SEQ ID NO:9, SEQ ID NO: 10, SEQ ID NO:11 and SEQ ID NO:12, respectively) and *agrobacterium*-mediated transformation (Kosma et al., 2014), independently generated tobacco (*Nicotiana tabacum*) lines can be characterized and shown to have normal root growth.

The effects of these constructs on suberin deposition can be assessed in these lines by Nile Red staining and confocal imaging. Using this process, one can find independent, homozygous lines and sibling lines in which more Nile Red signal is observed in the periderm as compared with a wild-type control. Thus, in this way we provided a highly reproducible means of increasing the levels of suberin by depositing more suberin in existing periderm cells as compared to wild-type plants.

Example 7: Use of Promoters to Drive Ectopic Expression of MYB41 Transcription Factor in Rice The promoters of FACT, HORST, ASFT, GPAT5, RALPH and MYB84 derived or isolated from *Arabidopsis*, rice or other plant species can each be used to drive ectopic expression of the MYB41 transcription factor in a root-layer specific manner. Using any one or more of proFACT::MYB41, proHORST::MYB41, proASFT::MYB41, proGPAT5::MYB41, proRALPH::MYB41 and proMYB84:MYB41 constructs (SEQ ID NO:7, SEQ ID NO:8, SEQ ID NO:9, SEQ ID NO:10, SEQ ID NO:11 and SEQ ID NO:12, respectively) and *agrobacterium*-mediated transformation (see, e.g., Ratanasut et al., 2017, In planta *Agrobacterium*-Mediated Transormation of Rice, Rice Science 24(3):181-186), independently generated rice (genus *Oryza*) lines can be characterized and shown to have normal root growth.

The effects of these constructs on suberin deposition can be assessed in these lines by Nile Red staining and confocal imaging. Using this process, one can find independent, homozygous lines and sibling lines in which more Nile Red signal is observed in the periderm as compared with a wild-type control. Thus, in this way we provided a highly reproducible means of increasing the levels of suberin by depositing more suberin in existing periderm cells as compared to wild-type plants.

Example 8: Use of Promoters to Drive Ectopic Expression of MYB41 Transcription Factor in Corn The promoters of FACT, HORST, ASFT, GPAT5, RALPH and MYB84 derived or isolated from *Arabidopsis*, corn or other plant species can each be used to drive ectopic expression of the MYB41 transcription factor in a root-layer specific manner. Using any one or more of proFACT:: MYB41, proHORST::MYB41, proASFT::MYB41, proGPAT5::MYB41, proRALPH::MYB41 and proMYB84:: MYB41 constructs (SEQ ID NO:7, SEQ ID NO:8, SEQ ID NO:9, SEQ ID NO:10, SEQ ID NO:11 and SEQ ID NO:12, respectively) and standard corn transformation methods (see, Section V. Plant Transformation), independently generated corn (*Zea mays*, aka maize) lines can be characterized and shown to have normal root growth.

The effects of these constructs on suberin deposition can be assessed in these lines by Nile Red staining and confocal imaging. Using this process, one can find independent, homozygous lines and sibling lines in which more Nile Red signal is observed in the periderm as compared with a wild-type control. Thus, in this way we provided a highly reproducible means of increasing the levels of suberin by depositing more suberin in existing periderm cells as compared to wild-type plants.

Example 9: Use of Promoters to Drive Ectopic Expression of MYB41 Transcription Factor in Soybean The promoters of FACT, HORST, ASFT, GPAT5, RALPH and MYB84 derived or isolated from *Arabidopsis*, soybean or other plant species can each be used to drive ectopic expression of the MYB41 transcription factor in a root-layer specific manner. Using any one or more of proFACT:: MYB41, proHORST::MYB41, proASFT::MYB41, proGPAT5::MYB41, proRALPH::MYB41 and proMYB84:: MYB41 constructs (SEQ ID NO:7, SEQ ID NO:8, SEQ ID NO:9, SEQ ID NO:10, SEQ ID NO:11 and SEQ ID NO:12, respectively) and standard soybean transformation methods (see, Section V. Plant Transformation), independently generated soybean (*Glycine max*, aka soya) lines can be characterized and shown to have normal root growth.

The effects of these constructs on suberin deposition can be assessed in these lines by Nile Red staining and confocal imaging. Using this process, one can find independent, homozygous lines and sibling lines in which more Nile Red signal is observed in the periderm as compared with a wild-type control. Thus, in this way we provided a highly reproducible means of increasing the levels of suberin by depositing more suberin in existing periderm cells as compared to wild-type plants.

Example 10: Use of Promoters to Drive Ectopic Expression of MYB41 Transcription Factor in Wheat The promoters of FACT, HORST, ASFT, GPAT5, RALPH and MYB84 derived or isolated from *Arabidopsis*, wheat or other plant species can each be used to drive ectopic expression of the MYB41 transcription factor in a root-layer specific manner. Using any one or more of proFACT:: MYB41, proHORST::MYB41, proASFT::MYB41, proGPAT5::MYB41, proRALPH::MYB41 and proMYB84:: MYB41 constructs (SEQ ID NO:7, SEQ ID NO:8, SEQ ID NO:9, SEQ ID NO: 10, SEQ ID NO:11 and SEQ ID NO: 12, respectively) and standard wheat transformation methods (see, Section V. Plant Transformation), independently generated wheat (genus *Triticum*) lines can be characterized and shown to have normal root growth.

The effects of these constructs on suberin deposition can be assessed in these lines by Nile Red staining and confocal imaging. Using this process, one can find independent, homozygous lines and sibling lines in which more Nile Red signal is observed in the periderm as compared with a wild-type control. Thus, in this way we provided a highly reproducible means of increasing the levels of suberin by depositing more suberin in existing periderm cells as compared to wild-type plants.

Example 11: Use of Promoters to Drive Ectopic Expression of MYB41 Transcription Factor in Cotton The promoters of FACT, HORST, ASFT, GPAT5, RALPH and MYB84 derived or isolated from *Arabidopsis*, cotton or other plant species can each be used to drive ectopic expression of the MYB41 transcription factor in a root-layer specific manner. Using any one or more of proFACT:: MYB41, proHORST::MYB41, proASFT::MYB41, proGPAT5::MYB41, proRALPH::MYB41 and proMYB84:: MYB41 constructs (SEQ ID NO:7, SEQ ID NO:8, SEQ ID NO:9, SEQ ID NO: 10, SEQ ID NO:11 and SEQ ID NO: 12, respectively) and standard cotton transformation methods (see, Section V. Plant Transformation), independently generated cotton (genus *Gossypium*) lines can be characterized and shown to have normal root growth.

The effects of these constructs on suberin deposition can be assessed in these lines by Nile Red staining and confocal imaging. Using this process, one can find independent, homozygous lines and sibling lines in which more Nile Red signal is observed in the periderm as compared with a wild-type control. Thus, in this way we provided a highly reproducible means of increasing the levels of suberin by depositing more suberin in existing periderm cells as compared to wild-type plants.

Example 12: Use of Promoters to Drive Ectopic Expression of MYB41 Transcription Factor in Canola The promoters of FACT, HORST, ASFT, GPAT5, RALPH and MYB84 derived or isolated from *Arabidopsis*, canola or other plant species can each be used to drive ectopic expression of the MYB41 transcription factor in a root-layer specific manner. Using any one or more of proFACT:: MYB41, proHORST::MYB41, proASFT::MYB41, proGPAT5::MYB41, proRALPH::MYB41 and proMYB84:: MYB41 constructs (SEQ ID NO:7, SEQ ID NO:8, SEQ ID NO:9, SEQ ID NO: 10, SEQ ID NO:11 and SEQ ID NO: 12, respectively) and standard canola transformation methods (see, Section V. Plant Transformation), independently generated canola (genus *Brassica napus* L., spp. Oleifera, aka rapeseed) lines can be characterized and shown to have normal root growth.

The effects of these constructs on suberin deposition can be assessed in these lines by Nile Red staining and confocal imaging. Using this process, one can find independent, homozygous lines and sibling lines in which more Nile Red signal is observed in the periderm as compared with a wild-type control. Thus, in this way we provided a highly reproducible means of increasing the levels of suberin by depositing more suberin in existing periderm cells as compared to wild-type plants.

Example 13: Use of Promoters to Drive Ectopic Expression of MYB41 Transcription Factor in Radish The promoters of FACT, HORST, ASFT, GPAT5, RALPH and MYB84 derived or isolated from *Arabidopsis*, radish or other plant species can each be used to drive ectopic expression of the MYB41 transcription factor in a root-layer specific manner. Using any one or more of proFACT:: MYB41, proHORST::MYB41, proASFT::MYB41, proGPAT5::MYB41, proRALPH::MYB41 and proMYB84:: MYB41 constructs (SEQ ID NO:7, SEQ ID NO:8, SEQ ID NO:9, SEQ ID NO: 10, SEQ ID NO:11 and SEQ ID NO: 12, respectively) and standard radish transformation methods (see, Section V. Plant Transformation), independently generated radish (*Raphanus sativus*) lines can be characterized and shown to have normal root growth.

The effects of these constructs on suberin deposition can be assessed in these lines by Nile Red staining and confocal imaging. Using this process, one can find independent, homozygous lines and sibling lines in which more Nile Red signal is observed in the periderm as compared with a wild-type control. Thus, in this way we provided a highly reproducible means of increasing the levels of suberin by depositing more suberin in existing periderm cells as compared to wild-type plants.

Example 14: Use of Promoters to Drive Ectopic Expression of MYB41 Transcription Factor in Crimson Clover The promoters of FACT, HORST, ASFT, GPAT5, RALPH and MYB84 derived or isolated from *Arabidopsis*, crimson clover or other plant species can each be used to drive ectopic expression of the MYB41 transcription factor in a root-layer specific manner. Using any one or more of pro-FACT::MYB41, proHORST::MYB41, proASFT::MYB41, proGPAT5::MYB41, proRALPH::MYB41 and proMYB84:: MYB41 constructs (SEQ ID NO:7, SEQ ID NO:8, SEQ ID NO:9, SEQ ID NO:10, SEQ ID NO:11 and SEQ ID NO:12, respectively) and standard crimson clover transformation methods (see, Section V. Plant Transformation), independently generated crimson clover (*Trifolium incarnatum*) lines can be characterized and shown to have normal root growth.

The effects of these constructs on suberin deposition can be assessed in these lines by Nile Red staining and confocal imaging. Using this process, one can find independent, homozygous lines and sibling lines in which more Nile Red signal is observed in the periderm as compared with a wild-type control. Thus, in this way we provided a highly reproducible means of increasing the levels of suberin by depositing more suberin in existing periderm cells as compared to wild-type plants.

Example 15: Use of Promoters to Drive Ectopic Expression of MYB41 Transcription Factor in *Sorghum*

The promoters of FACT, HORST, ASFT, GPAT5, RALPH and MYB84 derived or isolated from *Arabidopsis, sorghum* or other plant species can each be used to drive ectopic expression of the MYB41 transcription factor in a root-layer specific manner. Using any one or more of proFACT:: MYB41, proHORST::MYB41, proASFT::MYB41, proGPAT5::MYB41, proRALPH::MYB41 and proMYB84:: MYB41 constructs (SEQ ID NO:7, SEQ ID NO:8, SEQ ID NO:9, SEQ ID NO: 10, SEQ ID NO:11 and SEQ ID NO:12, respectively) and standard *sorghum* transformation methods (see, Section V. Plant Transformation), independently generated *sorghum* (*Sorghum bicolor*) lines can be characterized and shown to have normal root growth.

The effects of these constructs on suberin deposition can be assessed in these lines by Nile Red staining and confocal imaging. Using this process, one can find independent, homozygous lines and sibling lines in which more Nile Red signal is observed in the periderm as compared with a wild-type control. Thus, in this way we provided a highly reproducible means of increasing the levels of suberin by depositing more suberin in existing periderm cells as compared to wild-type plants.

Example 16: Use of Promoters to Drive Ectopic Expression of MYB41 Transcription Factor in Field Pennycress/CoverCress The promoters of FACT, HORST, ASFT, GPAT5, RALPH and MYB84 derived or isolated from *Arabidopsis*, field pennycress or other plant species can each be used to drive ectopic expression of the MYB41 transcription factor in a root-layer specific manner. Using any one or more of pro-FACT::MYB41, proHORST::MYB41, proASFT::MYB41, proGPAT5::MYB41, proRALPH::MYB41 and proMYB84:: MYB41 constructs (SEQ ID NO:7, SEQ ID NO:8, SEQ ID NO:9, SEQ ID NO:10, SEQ ID NO:11 and SEQ ID NO:12, respectively) and standard pennycress and CoverCress transformation methods (see, Section V. Plant Transformation), independently generated field pennycress (*Thlaspi arvense*) or CoverCress lines can be characterized and shown to have normal root growth.

The effects of these constructs on suberin deposition can be assessed in these lines by Nile Red staining and confocal imaging. Using this process, one can find independent, homozygous lines and sibling lines in which more Nile Red signal is observed in the periderm as compared with a wild-type control. Thus, in this way we provided a highly reproducible means of increasing the levels of suberin by depositing more suberin in existing periderm cells as compared to wild-type plants.

Example 17: Use of Promoters to Drive Ectopic Expression of MYB41 Transcription Factor in Annual Ryegrass The promoters of FACT, HORST, ASFT, GPAT5, RALPH and MYB84 derived or isolated from *Arabidopsis*, annual ryegrass or other plant species can each be used to drive ectopic expression of the MYB41 transcription factor in a root-layer specific manner. Using any one or more of pro-FACT::MYB41, proHORST::MYB41, proASFT::MYB41, proGPAT5::MYB41, proRALPH::MYB41 and proMYB84:: MYB41 constructs (SEQ ID NO:7, SEQ ID NO:8, SEQ ID NO:9, SEQ ID NO: 10, SEQ ID NO:11 and SEQ ID NO:12, respectively) and standard ryegrass transformation methods (see, Section V. Plant Transformation), independently generated annual ryegrass (*Lolium perenne*) lines can be characterized and shown to have normal root growth.

The effects of these constructs on suberin deposition can be assessed in these lines by Nile Red staining and confocal imaging. Using this process, one can find independent, homozygous lines and sibling lines in which more Nile Red signal is observed in the periderm as compared with a wild-type control. Thus, in this way we provided a highly reproducible means of increasing the levels of suberin by depositing more suberin in existing periderm cells as compared to wild-type plants.

Further Numbered Embodiments of the Disclosure

Other subject matter contemplated by the present invention is set out in the following numbered embodiments:

1. An isolated nucleic acid molecule comprising a nucleic acid sequence encoding a MYB41 amino acid sequence with at least 80% sequence homology to SEQ ID NO:14 and/or a nucleic acid set forth in SEQ ID NO: 13 or SEQ ID NO: 15, operably linked to a nucleic acid sequence encoding a heterologous promoter, wherein expression of the isolated nucleic acid molecule in a plant results in increased levels of suberin as compared to wild-type check plants lacking the isolated nucleic acid molecule.

2. The isolated nucleic acid molecule of embodiment 1, wherein the increased levels of suberin occur by generating additional periderm cells and/or depositing more suberin in existing periderm cells.

3. The isolated nucleic acid molecule of embodiment 1 or embodiment 2, wherein the amino acid sequence homology is selected from the group consisting of at least 85% homology, at least 90% homology, at least 95% homology, at least 96% homology, at least 97% homology, at least 98% homology and at least 99% homology to SEQ ID NO: 14.

4. The isolated nucleic acid molecule of embodiment 1 or embodiment 2, wherein the amino acid sequence homology is 100% to SEQ ID NO:14.

5. The isolated nucleic acid molecule of embodiments 1-4, wherein the isolated nucleic acid molecule comprises an isolated nucleic acid sequence selected from the group comprising SEQ ID NO:7, SEQ ID NO: 8, SEQ ID NO:9, SEQ ID NO:10, SEQ ID NO:11 and SEQ ID NO: 12.

6. A transformation vector comprising one or more of the nucleic acid molecules of embodiments 1-5 and 22-28.

7. A method of transforming a plant cell comprising introducing the transformation vector of embodiment 6 into a plant cell, whereby the transformed plant cell produces increased levels of suberin as compared to an untransformed wild-type check plant cell.

8. The method of embodiment 7 further comprising producing transformed plant tissue from the transformed plant cell.

9. The method of embodiment 8 further comprising producing a transformed plantlet from the transformed plant tissue, wherein the transformed plantlet produces increased levels of suberin as compared to untransformed wild-type check plantlets lacking the isolated nucleic acid molecule.

10. The method of embodiment 9 further comprising producing a progeny of the transformed plantlet, wherein the progeny produces increased levels of suberin as compared to untransformed wild-type check plantlets lacking the isolated nucleic acid molecule.

11. The method of embodiment 9 or embodiment 10 further comprising growing the transformed plantlet or progeny of the transformed plantlet into a mature transformed plant, wherein the mature transformed plant produces increased levels of suberin as compared to mature untransformed wild-type checks lacking the isolated nucleic acid molecule.

12. The method of embodiments 9-11, wherein the increased levels of suberin occur by generating additional periderm cells and/or depositing more suberin in existing periderm cells.

13. The method of embodiments 9-12, wherein there is minimal or no expression of the nucleic acid molecule in cells that are not associated with normal suberin production.

14. The method of embodiments 9-13, wherein there is minimal or no expression of the nucleic acid molecule in rosette leaves.

15. The method of embodiments 11-14 further comprising using the mature transformed plant or clone of the mature transformed plant in a breeding method.

16. The method of embodiment 15, wherein the breeding method comprises selfing or crossing the mature transformed plant or clone of the mature transformed plant.

17. A plant breeding method comprising crossing a first plant comprising a nucleic acid molecule of embodiments 1-5 and 22-28 with a second plant of the same species and selecting resultant progeny of the cross based on increased levels of suberin as compared to wild-type check plants.

18. The plant breeding method of embodiment 17 further comprising producing clones of the resultant progeny of the cross wherein the clones are selected based on increased levels of suberin as compared to wild-type check plants.

19. The plant breeding method of embodiment 17 or embodiment 18, wherein the progeny of the cross that display increased levels of suberin as compared to wild-type check plants are selected using molecular markers that are designed based on the nucleic acid molecule of embodiments 1-5 and 22-28.

20. The method of embodiment 17 further comprising using the selected progeny in a breeding method.

21. The method of embodiments 11-14 further comprising growing the mature transformed plant or clone of the mature transformed plant in a greenhouse or outdoors.

22. The isolated nucleic acid molecule of embodiments 1-4, wherein the heterologous promoter comprises an isolated nucleic acid sequence selected from the group comprising SEQ ID NO:1, SEQ ID NO: 2, SEQ ID NO:3, SEQ ID NO:4, SEQ ID NO:5 and SEQ ID NO:6.

23. The isolated nucleic acid molecule of embodiments 1-4, wherein the heterologous promoter is a promoter of FACT gene.

24. The isolated nucleic acid molecule of embodiments 1-4, wherein the heterologous promoter is a promoter of HORST gene.

25. The isolated nucleic acid molecule of embodiments 1-4, wherein the heterologous promoter is a promoter of ASFT gene.

26. The isolated nucleic acid molecule of embodiments 1-4, wherein the heterologous promoter is a promoter of GPAT5 gene.

27. The isolated nucleic acid molecule of embodiments 1-4, wherein the heterologous promoter is a promoter of RALPH gene.

28. The isolated nucleic acid molecule of embodiments 1-4, wherein the heterologous promoter is a promoter of MYB84 gene.

INCORPORATION BY REFERENCE

All references, articles, publications, patents, patent publications, and patent applications cited herein within the above text and/or cited below are incorporated by reference in their entireties for all purposes. However, mention of any reference, article, publication, patent, patent publication, and patent application cited herein is not, and should not be taken as acknowledgment or any form of suggestion that they constitute valid prior art or form part of the common general knowledge in any country in the world.

REFERENCES

Vishwanath, S. J., Delude, C., Domergue, F. & Rowland, O. Suberin: biosynthesis, regulation, and polymer assembly of a protective extracellular barrier. *Plant cell reports* 34, 573-586 (2015).

Carrington, E. M., Hernes, P. J., Dyda, R. Y., Plante, A. F. & Six, J. Biochemical changes across a carbon saturation gradient: Lignin, cutin, and suberin decomposition and stabilization in fractionated carbon pools. *Soil Biology and Biochemistry* 47, 179-190 (2012).

Feng, X. & Simpson, M. J. Molecular-level methods for monitoring soil organic matter responses to global climate change. *Journal of environmental monitoring: JEM* 13, 1246-1254 (2011).

Preston, C. M., Trofymow, J. A., Niu, J. & Sayer, B. G. 13C nuclear magnetic resonance spectroscopy with cross-polarization and magic-angle spinning investigation of the proximate-analysis fractions used to assess litter quality in decomposition studies. *Canadian Journal of Botany* 75 (1997).

Winkler, A., Haumaier, L. & Zech, W. Insoluble alkyl carbon components in soils derive mainly from cutin and suberin. *Organic Geochemistry* 36, 519-529, (2005).

Mahmood, K. et al. Overexpression of ANAC046 Promotes Suberin Biosynthesis in Roots of *Arabidopsis thaliana*. *International journal of molecular sciences* 20 (2019).

Hofer, R. et al. The *Arabidopsis* cytochrome P450 CYP86A1 encodes a fatty acid omega-hydroxylase involved in suberin monomer biosynthesis. *Journal of experimental botany* 59, 2347-2360 (2008).

Wei, X. et al. Three Transcription Activators of ABA Signaling Positively Regulate Suberin Monomer Synthesis by Activating Cytochrome P450 CYP86A1 in Kiwifruit. *Frontiers in Plant Science* 10, 1650 (2020).

Kosma, D. K., Molina, I., Ohlrogge, J. B. & Pollard, M. Identification of an *Arabidopsis* Fatty Alcohol:Caffeoyl-Coenzyme A Acyltransferase Required for the Synthesis of Alkyl Hydroxycinnamates in Root Waxes. *Plant Physiology* 160, 237 (2012).

Molina, I., Li-Beisson, Y., Beisson, F., Ohlrogge, J. B. & Pollard, M. Identification of an *Arabidopsis* Feruloyl-Coenzyme A Transferase Required for Suberin Synthesis. *Plant Physiology* 151, 1317, (2009).

Kosma, D. K. et al. AtMYB41 activates ectopic suberin synthesis and assembly in multiple plant species and cell types. *Plant J* 80, 216-229, (2014).

What is claimed is:

1. An isolated nucleic acid molecule comprising a nucleic acid sequence: i) encoding a MYB41 amino acid sequence with at least 80% sequence identity to SEQ ID NO: 14 or ii) set forth in SEQ ID NO: 13 or SEQ ID NO: 15, wherein the nucleic acid sequence is operably linked to a nucleic acid sequence encoding a heterologous promoter, wherein expression of the isolated nucleic acid molecule in a plant results in increased levels of suberin as compared to wild-type check plants lacking the isolated nucleic acid molecule, wherein the heterologous promoter is a promoter of a FACT gene or a promoter of a HORST gene.

2. The isolated nucleic acid molecule of claim 1, wherein the increased levels of suberin occur by generating additional periderm cells or depositing more suberin in existing periderm cells.

3. The isolated nucleic acid molecule of claim 1, wherein the amino acid sequence identity is at least 85% identity, at least 90% identity, at least 95% identity, at least 96% identity, at least 97% identity, at least 98% identity, or at least 99% identity to SEQ ID NO: 14.

4. The isolated nucleic acid molecule of claim 1, wherein the amino acid sequence identity is 100% to SEQ ID NO: 14.

5. The isolated nucleic acid molecule of claim 1, wherein the heterologous promoter comprises a nucleic acid sequence comprising SEQ ID NO: 1 or SEQ ID NO: 2.

6. A transformation vector comprising one or more of the nucleic acid molecules of claim 1.

7. A method of transforming a plant cell comprising introducing the transformation vector of claim 6 into the plant cell, whereby the transformed cell produces increased levels of suberin as compared to an untransformed wild-type check plant cell.

8. The method of claim 7 further comprising producing transformed plant tissue from the transformed plant cell.

9. The method of claim 8 further comprising producing a transformed plantlet from the transformed plant tissue, wherein the transformed plantlet produces increased levels of suberin as compared to untransformed wild-type check plantlets lacking the isolated nucleic acid molecule.

10. The method of claim 9 further comprising producing a progeny of the transformed plantlet, wherein the progeny produces increased levels of suberin as compared to untransformed wild-type check plantlets lacking the isolated nucleic acid molecule.

11. The method of claim 10 further comprising growing the transformed plantlet or the progeny of the transformed plantlet into a mature transformed plant, wherein the mature transformed plant produces increased levels of suberin as compared to mature untransformed wild-type checks lacking the isolated nucleic acid molecule.

12. The method of claim 9, wherein there is minimal or no expression of the nucleic acid molecule in cells that are not associated with normal suberin production.

13. The method of claim 9, wherein there is minimal or no expression of the nucleic acid molecule in rosette leaves.

14. The method of claim 11 further comprising using the mature transformed plant or a clone of the mature transformed plant in a breeding method.

15. The method of claim 14, wherein the breeding method comprises selfing or crossing the mature transformed plant or the clone of the mature transformed plant.

16. A plant breeding method comprising crossing a first plant comprising the nucleic acid molecule of claim 1 with a second plant of the same species and selecting resultant progeny of the cross based on increased levels of suberin as compared to wild-type check plants.

17. The plant breeding method of claim 16 further comprising producing clones of the resultant progeny of the cross wherein the clones are selected based on increased levels of suberin as compared to wild-type check plants.

18. The plant breeding method of claim 16, wherein the progeny of the cross that display increased levels of suberin as compared to wild-type check plants are selected using molecular markers that are designed to detect and/or identify an isolated nucleic acid molecule comprising a nucleic acid sequence; i) encoding a MYB41 amino acid sequence with at least 80% sequence identity to SEQ ID NO: 14 or ii) set forth in SEQ ID NO: 13 or SEQ ID NO: 15, wherein the nucleic acid sequence is operably linked to a nucleic acid sequence encoding a heterologous promoter, wherein expression of the isolated nucleic acid molecule in a plant results in increased levels of suberin as compared to wild-type check plants lacking the isolated nucleic acid molecule, wherein the heterologous promoter is a promoter of a FACT gene or a promoter of a HORST gene.

19. The method of claim 16 further comprising using the selected progeny in a breeding method.

\* \* \* \* \*

SEQUENCE LISTING

<160> NUMBER OF SEQ ID NOS: 21

<210> SEQ ID NO 1
<211> LENGTH: 1582
<212> TYPE: DNA
<213> ORGANISM: Arabidopsis thaliana

<400> SEQUENCE: 1

```
ggttaagagt ttcgttttcc ttcgttcaaa atctaatgtg aaggaaagca aaactgacac      60
aacttttgtg tgaaccagag caagtgaaag tgtgtcgaat ctgtactttt gtactgtgta     120
atctctatag tctgactctc attatgtagt tttaagtgtc ttttacttgt gtagctgtta     180
cctgttacct gttaggtttt ctaatccttg ttttatttga tagccagata ctttagggaa     240
ttttacttct tcttttcttg ggtttaattt aagacatatt cgtatatttc atttaattct     300
gttatctgat ttgtgagatc atgaaaacga atgttgaact tgaaacttga gtgggttcag     360
aaaaactact ctgtattaaa aatcccagtg tcacatgata atgatccttc agtaaaggta     420
gacatagctt ttttgcagtg tgatatgcac aaatacaatc tatattttta tgtaaaagat     480
atatttcttt gaaagtactt ataaaaatat gtttttcata aaaaaaatta tatgtaattc     540
tgaaagtatg tgatatgcac aagcacaacc tatatttcct acattcaaat tcgggttttt     600
cttgacgcca agttacattc aattatcaat aatagggcta gttcaactaa tgctatttat     660
ttatacaatc cacccactac taaatctcaa tctccaagga tctttatata ttaataagaa     720
aagctactat ccaaatgcga ccttgttcgt gaagtgtttg gtttataatt tggtggctta     780
agactatagc ccaccattga cccaaaaaaa gaaaggaaaa ttaatagtag actatatagc     840
taccaactcc ctataattta ccttgaaatt aaaccagctt tgtatttttt taatagaagt     900
cagggctcta cagtttcatt ttaaactttt ttttttgtta tattacatcc tgcaggttag     960
ttgtaatttg taaacgtaat caacataata aaaccattta catagactga ttaaagttga    1020
```

-continued

```
ttccatttga taatatttag ctatttatat atcaatcaac caccagctct taaatatatg    1080
tattcaaatt gttttgttga ctcttttttgc tacactttaa atttgaatct agaatgttgt    1140
cctgaaacaa aaatctgtgg attgaacaaa attatacacc aggtaaaatt ttgaagtttt    1200
taaaagcagg atcacatact cctaatttta gattggatag atctagtata aaaatatgaa    1260
gtttttttcc caaaaaataa taataccatt tagctcttaa ttaaatgcat gcaaactaaa    1320
gataaaaaga ggaattattt taaccattct aactcgtcac aacatgccta atcattccag    1380
gttaatttta gagttttcaa atcgtcatat taacatgtga tcctgaagac tcttctcttc    1440
tttcttctac cattagctga aatctttact tgtaccacaa ttaacctcaa accctagccc    1500
ctaaatcccc ctagaaatca atccatcctc agttctccaa aaagatatct ttggtttttc    1560
ttcactgaca aaacccctaa aa                                             1582

<210> SEQ ID NO 2
<211> LENGTH: 2082
<212> TYPE: DNA
<213> ORGANISM: Arabidopsis thaliana

<400> SEQUENCE: 2
catctacaaa gcctataaaa tggaaagatg tatgcatcga tgatgattct gcctcactta      60
gaagaatcaa aaagctaaaa ggagctgcga atcctgggca acgatgactt agtatgtata     120
gaagaaaaaa aaagctttta cttggtatca aacagagcat gtgttgttgt atttgctacc     180 ttttctgca aagttattgg caattgtatt gttgttccac ttgtatatat acagagacca     240
tttatgttaa tatacaactt cgtatgggga aagatgattc catcaagtcc aaaatgccaa     300
aaccatgcac gatcttgtct gatcaagtat gataagatgt gagattttaa gaacgtgaag     360
cttttcatat tgtattctca atgaacgaag aattaataat tagagttaga aatgcagatt     420
acagagatta cacaatttga tctcatttct tggcaaagag gcccaggcca ccgaagccac     480
cgtccttctt tggattcctg tgtgttaatt ttcgtgtggc tttagttaca aagggattat     540
attgtcagcg aatctgagcc gttggatcgt tttgacatga gctttccata agtgtcttat     600
cctttgtttc tctcattttt cacatatgta tcagacattt aatcaagcac atatctacgt     660
gttgattatg ttgatgatgc tgagattatg ttgatttaga gaatgagtat tggtgatgat     720
ggtacacgtt agtaaacata tgaatttgga agtgccacgt gagagggagc agagttttgg     780
gctttctttt ggttatgtat ttgcattctt gttgtaacaa attctcttat taaaagcatt     840
gtgaaaaaaa ccaaatacca catagtctat gtttcaagat ttgttttta atactataat     900 tttctattac tttagtttgt gtaatttttg aaaagagaaa attggtattt tttaggattg     960
ggtgatctga aatttgacta caaaaatttt cttggacaca gacacacagt cacacaaata    1020
agctaattat tggaatttta tcttaagttg cattcacttt gcaaattaat attgaattat    1080
agactattag tgtatggcgt gatggcaaac aaaaaaatca gtgtgtgata ttgtggacta    1140
gccaaaaaaa ttttctgatg attttttttgc ctaaataatt tgaattgttg agaccgaaac    1200
tcttactaat atactaacaa tgtaacgcga caaataaaac attgttgaga ataaaatctg    1260
aaccatcata actatagtct atagtaaccg tccgaattca accacatatg tatgatcttt    1320 gccattttg atcatatttt ccgttgcgtt ttctttgaat tttctcaata tatttttagt    1380
gttttgattt gtacttttat ctaatttata taattgtttt tcaaatgttt cgcaattgtg    1440
cgtttaagta ttcgactcga agtaaaccca gtttcttaga atgggctaac tgccattgac    1500
```

-continued

```
caaatctttta tccgcgaaga aagatcttta gcagctaggc ttatttcata tcaacaaaag   1560
tatatattta tctctaacta aattcctaca attatttcaa aaacatagaa attaaaattt   1620
gaaatgccta ttcttttttg gttatacatt gcaaaggtta tgtatgtaat ttctgatctt   1680
gaaatttaag ttctttagcc catatctagt tgattttcac gaaatattgt cgtttactct   1740 cgttttata tataaagcat gtacatataa catataatca atgcttcaaa agaaaaaaat   1800
aatcataact aaattgaaac gggaaaacta atttgctttc gtgttctatt atgccaaact   1860
gtactcacaa tagtcttatc ctatcgaccc aaatttaatc ttcccaacta cttactccta   1920
attgaaacaa aatataacct ttcttactat agcctatatt taaaaaatat ctatgatttc   1980
tacatttata tatatacgca cacggcacat acctctcatt caccatatat gcctcttaac   2040
aatctctcca cagaacaaaa gcaaaaagcc taaaccggga ta                       2082
```

<210> SEQ ID NO 3
<211> LENGTH: 2010
<212> TYPE: DNA
<213> ORGANISM: Arabidopsis thaliana

<400> SEQUENCE: 3

```
agctcaaacc tttaaatggc ttttaattag atatatttag cgagaatgtg attgctagtg     60
aaatctcaaa cttgatagct tattcatagc ttattttact tcgatcagca agagaacaat    120
ggttcctaaa gctcaaacct tttttggcgt ttgctttaga ttgtgcatac ataaagtgag    180
aagatgaaat atggttttgc tgaaatctca atgtgctcat tcatagttta ttttgctcga    240
cctttcttta atcaatagct ttgatgtact gattacttta taaagttaag aagtaagttc    300
tgctctttaa actgtactga atggaggctt ctctgcataa ttaagcaaac actctgatga    360
ttgagtttcg ttgtacaaag gaaagttttt gccttagtta gaaattcatc ttgtttcttt    420
gcccagaagc tggcttgctg atagaatttg gactacgcta cgttttcttg ggtgaaaaac    480
aatccgcgtc cttccacgag aacagtgaaa ctgtacgatg ttcttattgt attgtgtcaa    540
cagcccataa tcaatgaaat gggcctcaat gacagtataa gccgaaaaat attcgaatgc    600
gatctagaac taatctgaaa ccaaacttct caaatcatta acatttgatt agggcctaaa    660
agtccatccg tattttaaaa aaagttgat aacaaatgca aaaatacaaa tatacattac     720
tattaaaact caatctttct gattatatgt ggatggagaa gctgttttgc agtgtggatt    780
tgaattttga agttcttgtt caaaaaagaa aagaaacttg gtcaagcttc aaaagaaaga    840
aagaaataaa gacaagtata caaatacgtt gacttcaatt aatatgaaga tagaagagaa    900
agatatagaa atgcgtttta aattggcggt gggagatatg tgattccctt ggtcccgctt    960
tctcgtttga ttcggtaacc taaaccttct ccatccaaga agacacaaac aaggaagaaa   1020
ttaacctacg tacgtacatc atttgaacta cttatatcta ttataaatgg aaaatctatt   1080
ttcttcttct ctctctttta accgaaaaag gaaaagtcct cgaaataact ctttaatata   1140
attcatgtgg aaaccttcta tatatttttt gcatgctttt ttgaaattaa gtaatggcat   1200
actaattaga agaagacgaa aaataatatg tctaagtaat tgagtttcgt ggtcaaggca   1260
aatcaagatt gcattcttta attaagtgta caaattatga tgtaagaacc gttatttggc   1320
ataacctaat atatattaaa aactgatttt tttttttttt aacttctgta agaaatggtt   1380
ttcttaatta ccaatcatga tctattattg taaaatgtgt aattttgtgt tgcgattgaa   1440
gtgttcttag ataagatat gtcatatgca tgatatcatc tatttgattt tgagaaaata    1500
aaaacataac atgagaacat cgtagagagt aagatacatg acaaagagaa agaataagct   1560
```

```
aagaagtcat ccaaaaattg ggaggcctac tctcaactac caaaaataca agtgtttgtt      1620
gtgttaggtc atttattcag tcacctaacc ctaactatat gaaatacgtt aaaattcata      1680
tatagaaaaa taaagaagaa atactattag tcaatataat ttttttttaac aaaataaaaa     1740 taaagaaaga aacactatta gtcaatgaat taaaaaaaaa aaaatccatc tttcgatcaa      1800
gaccgtccaa gtattctcct ttcacataac tcttacgttt tacactaaac aagacgagat      1860
ttttatgagc ttgtggctcc cacaacaatc ctcattgatt tctccatata tatcacatga      1920
gaatccaact cgacttcata ctaacattca tcccaaaagt tccattcttt ttcacaaagc      1980
cattgtgctg ttttctccat ttggatcaaa                                       2010

<210> SEQ ID NO 4
<211> LENGTH: 2146
<212> TYPE: DNA
<213> ORGANISM: Arabidopsis thaliana

<400> SEQUENCE: 4
tgatcgcaaa cgtcaatggt ctatatccat ctcttgggga tacaccattc agatatacac       60
ttacttcttg actgctacgg agctgactac gccgttgcag accttcaaaa cttggcggtc      120
ttccagcgat ggacctttcg tgtttaacac tcggcccttg aaacctgacc cctgtgagcg      180
tccggtcact tatttcatgg atggtgccga ggatgtacgg gatagtggga cgaaaacttg      240
gtatagcata ggggataaga actatggtca ttgcggaaag attgagcata ctcgattaac      300
taaagtgaag aggatattgg tgacttcaat gaagacggat cctgagtatt ggaacaaggt      360
acttagtgtt tgtatatttc tcatattgaa tttaacattt tgggtgagtt taggttacat      420
cttttttttt atttttttgct tttgttgata ggcaccgagg agacagtgtt gtgaggtgat      480
ggaaggaaaa gtaggaaaaa gaaaagagaa agaaatgttg ttaaggatta gaaaatgcag      540
atctttggag aagatataaa aaaagcgttt taattagaga gatttttgca catacagatt      600
tagattcgat cattagttat ttgtttctaa attcctcaat tcctagtacc aagagaatga      660
cgattttctc tagtaatact ggcactcttc gtttttcaac atgtaaacat tactttgtat      720
aattagtcta tatcaaataa atagttacaa catgaacgta actatttata cacgagggta      780
aatttttaac aaatttaaac cgaaccaaaa agatttcagt taatcatagt tttgttacaa      840
gcgaaatctg aaatattcac cctcaagttt gttacgtaat tgtctaatct gtgttttttt      900
gtgctagtgt tataattgtt tcctcgaatg ttaagcacca catagaagta tacacttttc      960
ttttattatt ttcgttcttc ttccatttag aaacttttat taattctact gttaaatcca     1020
acgttattag tttattttct ctgatgaagt tctaattttt tttgtttgtt ggaaaaaggg     1080 ttactttttct gatgaagttg ccgatttgtt tccaaccaaa cctcagctaa tatagttagg    1140
gagacggata agaaattgca taaagggaga ggctttgtaa acacgcaagt ttacgtcaac     1200
ttgacacata taaactcgta tataggaatt gtgtaaaatg ttaatcaata tatgtttatg     1260
aatatagtcc ttttatttcc ttaatctata gtcatgttat catcatatcg gcaagaaaat     1320
tactattaca acatatgttt ccgtgcttcg atttgtcgat caggtaggca accaaaccgg     1380
gccagattag tcacaaatga aattaggctc cactttggca agtttttttca caattaaaaa    1440 ttagaaagtc taaccaaact aatagaaact gaaccaaaca aaaatgttca cgcaattacg     1500
tagcacttct ctatgaaata ctgtggataa ttcgatttga gctaatctat ggtaagtcgt     1560
ttctctcaaa ctgaattaag ctaaaccaaa ccgaaaataa accgttgtag aacacccata     1620
```

-continued

```
ataaacatat atatgttctc tactcttatt tggctatttt tccatttgca gatacgtgtg   1680
acaacattcc aaatataggc acatgataca aattacaaag ccagaaatta taatttataa   1740
actatacata ataaggtcag tagcctaatt acatccatat atttagttgg gcataataag   1800
gatagcctaa ttttggtgca tcccgccaaa aattcggaca aatggtgaat ttcaaaccat   1860
gaatttcttt gttatacata cattacgtgc actattacat caaagaaaaa tagtgacgtg   1920
cataaacgta ttttcttcac ataatctata tataatatat acagccatgt acatttttca   1980
acatagaaaa atcatgtata caaatacggt aggtgcaata ctgataaact gccattccca   2040
ttgcattaga cgctagtcaa tccaaacctt ataacataaa aagttatagt ccatttcttt   2100
catatccaat cgagtcaaaa taatattcga gcaaaaaaca aaagaa               2146
```

<210> SEQ ID NO 5
<211> LENGTH: 1649
<212> TYPE: DNA
<213> ORGANISM: Arabidopsis thaliana

<400> SEQUENCE: 5

```
ctttcctctg aaacgattct ccacgctctt tgtttataag gattgcaaga aattactgaa     60
gaacatcagg aatcgcgaga gcttggggcg aatcaaaaac ctccattgat gaagaagact    120
gcatctagta ctttacttac tcggtagcac acctccatgg gcaggctcca gcaccatggt    180
tgggcccatt tcttattaat gggcctaaaa tagagcttct agggcctcta tatattttgt    240
cttttctctt ccgtttaggc gttttgctaa ctttcttacg tatatgaatg tgaattatag    300
ttagttaact ttagaactgt tgagcggcca atgccacgtc ctttgtacgt aaattatgtt    360
attcatgcta ttatttatgt accaattttc tattctaata tatattctaa gttttttttg    420
tatcaatact aagtatttat acaatttttg caaattttga cagaaagata gtacaaaaaa    480
tatgaaagac caaaaactac ataaaccacc aaaaattaca acacaaacag aaaacggaaa    540
gaaaactcaa tcgaaaactc tacaagtaga gaccttaaaa gaaacttaga ttccaaacca    600
caaagctcaa atatttgtgt ggtttcctca acttaaaaga tctcaaatac ttatagttgt    660
tgccactagc aatccaaacc taggccagtt ttcaaaatct ctaaaaaga gcttaccatt     720 ccaaacttag gacaatcctc ataatatttt aaattttatg acattttta gttttttctt     780 accgaacata gagatacaac gaataacaca aaataccaaa ttttactaaa caaacaatta    840
ctgcacaaat gaaaaagtaa tcaacaacat gagctcattt cacgaaaaaa gaagcgaaaa    900
agccaacggt cttgccacaa attagtatat tgcaaattac aaatgcttaa aaaaattcac    960
agatatattc atcaattata ccttttgatt atcttgcaaa taaatcttcc aattcatatt   1020
acctacgtca aaatttagcc atctaccctt attatcccat tatgaaaatt tcaaaatcga   1080
taagatgaca gacacccaac aacgaattat cattttatat actataggta ttagatacct   1140
acaatttatt tggtttattg ggaatatacg attcataaat tccctcataa aaatataaag   1200
caaatgtgga cggaagcaaa aaaactaaat atagaatgga gagaaattgt attattaact   1260
taggttaccc atcgccaaca acctctcatt tcctttccta aactatttca caattttggt   1320
caaaaacaca atctaacccc aaaaaagatt cgacctttga aattcccaaa accagaagca   1380
aaacccccaa aagaacccta cttatagtga aagaaaagta acataataat atatatacac   1440
gagaaccaag agccacttga atataaagtt cacagttttt gtctgctcac caaatcaaac   1500
caatttctcc tgatagccaa agtttttgtc cccaacaaga aactcatgca acattcttca   1560
cccactagct aactaacgac ttccattctt attaatctct ctcaattctt catttctgag   1620
```

-continued

```
attcatcgct ctctcttctc tttgtcaca                                      1649

<210> SEQ ID NO 6
<211> LENGTH: 2247
<212> TYPE: DNA
<213> ORGANISM: Arabidopsis thaliana

<400> SEQUENCE: 6
tctgagacat cattgatatc taacaatcaa aaactaaaaa gtgaagtatt aacattttaa      60
tcagattcaa accagaactt atcagtcatc aaaaatgttg gcaaataaca aatcaaactt     120 aagttttttgg atggagaaag caagctagat tcgaatctct aagaagcgtg gacttggact     180
tgtttacgac ctgaaaagat gtcatgatta tctcatgatt acgagataat aacatgtctt     240
atctactaaa ctaatctaaa aagtagtgag gatgacttga aacttaagtc ttatatgaat     300
tatctttaaa tatagaaaaa gaaaggagat agagaggtgt gtttttcatg tgaacaactt     360 tttttttacct ttagagtact tccagaagac ttattgggtc cttaataaaa gtagaccaaa     420
ttattgaaga gctaaaaaaa aatgcctact caaaatatcc aaacctcttc ttttagcctt     480 ttgtttttttt caatattcat actaatgtaa actacaatca ttgtatcatt ctataatcat     540 atgaatttttt tgtcaacacc atgcattatg ctagtttaaa tttaggtgat gatataaaga     600
tattttaagt acaaatcaat aggggcgatg ttcttatgtc tttatctaac tttatgaatt     660
tgtgttttat atattatgaa aaattggaaa agaagagatg gcctacgctc aagaccaatt     720
cctaccaatg ggcaatggtg ttgaaatctg aacaaaaaaa tttcctttct ttaacgttag     780
ctttaaagtt caaaaaactt tatttactttt ttcagtgata attctgtata aaataacata     840
taacaatgag gaaaaaactc aataatttga atcgcttatg actttatttc tccaagtgct     900 tgactttttaa aaccctaatg tccaatctca actaaagtca accttttttcg ttcgtctaga     960 agagtcagtc attaagtttc aattgaagta tacagtaaat tattagtact ttttatttta    1020
ttttaaccac agttcattgg ctgtatgaga tttctgttca agaaaacata taaatcgaaa    1080
ccaaagcaaa agacattatt tgcttcggtt tcttctactc aagctcattt ttagtaaaac    1140
taaattgtat tttcattttc ttaaaaagtt aattgttttt tttgtaaaat cagttttacc    1200
aaattggaca caataatgaa tatatgtcta tgtctagttt ttttttagctc agaatatatc    1260 ttatgtgaat agaatcgtct atcagatatt tttgtgatgc agatagaact taccgttata    1320
gaatcatttg tagattgttc atcgtgattg ttaagattag attcccatttt gtaatataac    1380 agaaactcga aaagtactta tattaagtat taacgatgta tcatgtgacc aaaatagaaa    1440
atactacgta atgatatgat tattaagcga gtgtgtaggt aattcaaata tttcaattaa    1500
tcaatctttg atatcactct ttagagtaat gtattatctt tcttattgtt ttaccctggg    1560
attaataagt ttaccggatc cggagtagaa tttcttcggt ttggcaattt tgttcaccta    1620
ccataacgaa cttttaccct tatacttagt ttcaatctac ttttggtgca tcctttcatt    1680
ttcaactgca aagaagtagt taaaagatcc aatacataat atatttaatt tatcataagt    1740
aacttagtgt aaagaaagac taaagtactt tttaaaatat gtatttgtat ttcccgatgt    1800
gaaagaaaag aaaattgaat ttgcacatat caataatatt agctaggaaa aaacttgtga    1860
gaaatttctt tgacgacttg cgtgtgcaat agtcttcctt atcttctcta ccatttctta    1920
attccactat tgtatagtat ttacttatgt tgaattaata aattaaaaca tttaaatttc    1980
cctaaagtta cttttttgatt tttgatttttc tattttttatt acaactttcc tactttttga    2040
```

```
catcttttct tacaaagact ttttgacatc tcccctcca gctattatat agtctccttt      2100
tttcttttct gcattcacat aatatttccc ctatatagtt tacacaacat catacccacc      2160
aacatatata atcttgatca tagagagata aacagaggcc gctatcaaga acaagactaa      2220
gaacaagact tcactaggag tacaagt                                        2247

<210> SEQ ID NO 7
<211> LENGTH: 11506
<212> TYPE: DNA
<213> ORGANISM: Artificial Sequence
<220> FEATURE:
<223> OTHER INFORMATION: pFACT::MYB41 construct

<400> SEQUENCE: 7
agctcgaatt atcatacatg agaattaagg gagtcacgtt atgacccccg ccgatgacgc        60
gggacaagcc gttttacgtt tggaactgac agaaccgcaa cgttgaagga gccactgagc       120
cgcgggtttc tggagtttaa tgagctaagc acatacgtca gaaaccatta ttgcgcgttc       180
aaaagtcgcc taaggtcact atcagctagc aaatatttct tgtcaaaaat gctccactga       240
cgttccataa attcccctcg gtatccaatt agagtctcat attcactctc aactcgatcg       300
aggggatcta ccatgagccc agaacgacgc ccggccgaca tccgccgtgc caccgaggcg       360
gacatgccgg cggtctgcac catcgtcaac cactacatcg agacaagcac ggtcaacttc       420
cgtaccgagc cgcaggaacc gcaggagtgg acggacgacc tcgtccgtct gcgggagcgc       480
tatccctggc tcgtcgccga ggtggacggc gaggtcgccg gcatcgccta cgcgggtccc       540
tggaaggcac gcaacgccta cgactggacg gccgagtcga ccgtgtacgt ctccccccgc       600
caccagcgga cgggactggg ctccacgctc tacacccacc tgctgaagtc cctggaggca       660
cagggcttca agagcgtggt cgctgtcatc gggctgccca cgacccgag cgtgcgcatg       720 cacgaggcgc tcggatatgc ccccgcggc atgctgcggg cggccggctt caagcacggg       780
aactggcatg acgtgggttt ctggcagctg gacttcagcc tgccggtgcc gccccgtccg       840
gtcctgcccg tcaccgaaat ctgatgaccc ctagagtcaa gcagatcgtt caaacatttg       900
gcaataaagt ttcttaagat tgaatcctgt tgccggtctt gcgatgatta tcatataatt       960
tctgttgaat tacgttaagc atgtaataat aacatgtaa tgcatgacgt tatttatgag      1020
atgggttttt atgattagag tcccgcaatt atacatttaa tacgcgatag aaaacaaaat      1080
atagcgcgca aactaggata aattatcgcg cgcggtgtca tctatatgtt actagatcga      1140
ccggcatgca agctgataat tcaattcggc gttaattcag tacattaaaa acgtccgcaa      1200
tgtgttatta agttgtctaa gcgtcaattt gtttacacca caatatatcc tgccaccagc      1260
cagccaacag ctccccgacc ggcagctcgg cacaaaatca ccactcgata caggcagccc      1320
atcagtccgg gacggcgtca gcgggagagc cgttgtaagg cggcagactt tgctcatgtt      1380
accgatgcta ttcggaagaa cggcaactaa gctgccgggt ttgaaacacg gatgatctcg      1440
cggagggtag catgttgatt gtaacgatga cagagcgttg ctgcctgtga tcaattcggg      1500
cacgaaccca gtggacataa gcctcgttcg gttcgtaagc tgtaatgcaa gtagcgtaac      1560
tgccgtcacg caactggtcc agaaccttga ccgaacgcag cggtggtaac ggcgcagtgg      1620
cggttttcat ggcttcttgt tatgacatgt ttttttgggg tacagtctat gcctcgggca      1680
tccaagcagc aagcgcgtta cgccgtgggt cgatgtttga tgttatggag cagcaacgat      1740
gttacgcagc agggcagtcg ccctaaaaca aagttaaaca tcatggggga agcggtgatc      1800
gccgaagtat cgactcaact atcagaggta gttggcgtca tcgagcgcca tctcgaaccg      1860
```

-continued

```
acgttgctgg ccgtacattt gtacggctcc gcagtggatg gcggcctgaa gccacacagt      1920
gatattgatt tgctggttac ggtgaccgta aggcttgatg aaacaacgcg gcgagctttg      1980
atcaacgacc tttttggaaac ttcggcttcc cctggagaga gcgagattct ccgcgctgta      2040
gaagtcacca ttgttgtgca cgacgacatc attccgtggc gttatccagc taagcgcgaa      2100
ctgcaatttg gagaatggca gcgcaatgac attcttgcag gtatcttcga gccagccacg      2160
atcgacattg atctggctat cttgctgaca aaagcaagag aacatagcgt tgccttggta      2220
ggtccagcgg cggaggaact cttttgatccg gttcctgaac aggatctatt tgaggcgcta      2280
aatgaaacct taacgctatg gaactcgccg cccgactggg ctggcgatga gcgaaatgta      2340
gtgcttacgt tgtcccgcat ttggtacagc gcagtaaccg gcaaaatcgc gccgaaggat      2400
gtcgctgccg actgggcaat ggagcgcctg ccggcccagt atcagcccgt catacttgaa      2460
gctagacagg cttatcttgg acaagaagaa gatcgcttgg cctcgcgcgc agatcagttg      2520
gaagaatttg tccactacgt gaaaggcgag atcaccaagg tagtcggcaa ataatgtcta      2580
gctagaaatt cgttcaagcc gacgccgctt cgccggcgtt aactcaagcg attagatgca      2640
ctaagcacat aattgctcac agccaaacta tcaggtcaag tctgctttta ttattttttaa      2700 gcgtgcataa taagccctac acaaattggg agatatatca tgcatgacca aaatcccctta     2760 acgtgagttt tcgttccact gagcgtcaga ccccgtagaa aagatcaaag gatcttcttg      2820
agatcctttt tttctgcgcg taatctgctg cttgcaaaca aaaaaaccac cgctaccagc      2880
ggtggtttgt ttgccggatc aagagctacc aactcttttt ccgaaggtaa ctggcttcag      2940
cagagcgcag ataccaaata ctgtccttct agtgtagccg tagttaggcc accacttcaa      3000
gaactctgta gcaccgccta catacctcgc tctgctaatc ctgttaccag tggctgctgc      3060
cagtggcgat aagtcgtgtc ttaccgggtt ggactcaaga cgatagttac cggataaggc      3120
gcagcggtcg ggctgaacgg ggggttcgtg cacacagccc agcttggagc gaacgaccta      3180
caccgaactg agatacctac agcgtgagct atgagaaagc gccacgcttc ccgaagggag      3240
aaaggcggac aggtatccgg taagcggcag ggtcggaaca ggagagcgca cgagggagct      3300
tccaggggga aacgcctggt atctttatag tcctgtcggg tttcgccacc tctgacttga      3360
gcgtcgattt ttgtgatgct cgtcaggggg gcggagccta tggaaaaacg ccagcaacgc      3420
ggccttttta cggttcctgg ccttttgctg gccttttgct cacatgttct ttcctgcgtt      3480 atccctgat tctgtggata accgtattac cgcctttgag tgagctgata ccgctcgccg      3540
cagccgaacg accgagcgca gcgagtcagt gagcgaggaa gcggaagagc gcctgatgcg      3600
gtattttctc cttacgcatc tgtgcggtat ttcacaccgc atatggtgca ctctcagtac      3660
aatctgctct gatgccgcat agttaagcca gtatacactc cgctatcgct acgtgactgg      3720
gtcatggctg cgccccgaca cccgccaaca cccgctgacg cgccctgacg ggcttgtctg      3780
ctcccggcat ccgcttacag acaagctgtg accgtctccg ggagctgcat gtgtcagagg      3840
ttttcaccgt catcaccgaa acgcgcgagg cagggtgcct tgatgtgggc gccggcggtc      3900
gagtggcgac ggcgcggctt gtccgcgccc tggtagattg cctggccgta ggccagccat      3960
ttttgagcgg ccagcggccg cgataggccg acgcgaagcg gcggggcgta gggagcgcag      4020
cgaccgaagg gtaggcgctt tttgcagctc ttcggctgtg cgctggccag acagttatgc      4080
acaggccagg cgggttttaa gagttttaat aagtttttaaa gagttttagg cggaaaaatc      4140 gcctttttttc tcttttatat cagtcactta catgtgtgac cggttcccaa tgtacggctt      4200
```

```
tgggttccca atgtacgggt tccggttccc aatgtacggc tttgggttcc caatgtacgt    4260
gctatccaca ggaaagagac cttttcgacc tttttcccct gctagggcaa tttgccctag    4320
catctgctcc gtacattagg aaccggcgga tgcttcgccc tcgatcaggt tgcggtagcg    4380
catgactagg atcgggccag cctgccccgc ctcctccttc aaatcgtact ccggcaggtc    4440
atttgacccg atcagcttgc gcacggtgaa acagaacttc ttgaactctc cggcgctgcc    4500
actgcgttcg tagatcgtct tgaacaacca tctggcttct gccttgcctg cggcgcggcg    4560
tgccaggcgg tagagaaaac ggccgatgcc gggatcgatc aaaaagtaat cggggtgaac    4620
cgtcagcacg tccgggttct tgccttctgt gatctcgcgg tacatccaat cagctagctc    4680
gatctcgatg tactccggcc gcccggtttc gctctttacg atcttgtagc ggctaatcaa    4740
ggcttcaccc tcggataccg tcaccaggcg gccgttcttg gccttcttcg tacgctgcat    4800
ggcaacgtgc gtggtgttta accgaatgca ggtttctacc aggtcgtctt tctgctttcc    4860
gccatcggct cgccggcaga acttgagtac gtccgcaacg tgtggacgga acacgcggcc    4920
gggcttgtct cccttccctt cccggtatcg gttcatggat tcggttagat gggaaaccgc    4980
catcagtacc aggtcgtaat cccacacact ggccatgccg gccggccctg cggaaacctc    5040
tacgtgcccg tctggaagct cgtagcggat cacctcgcca gctcgtcggt cacgcttcga    5100
cagacggaaa acggccacgt ccatgatgct gcgactatcg cgggtgccca cgtcatagag    5160
catcggaacg aaaaaatctg gttgctcgtc gcccttgggc ggcttcctaa tcgacggcgc    5220
accggctgcc ggcggttgcc gggattcttt gcggattcga tcagcggccg cttgccacga    5280
ttcaccgggg cgtgcttctg cctcgatgcg ttgccgctgg gcggcctgcg cggccttcaa    5340
cttctccacc aggtcatcac ccagcgccgc gccgatttgt accgggccgg atggtttgcg    5400
accgtcacgc cgattcctcg ggcttggggg ttccagtgcc attgcagggc cggcagacaa    5460
cccagccgct tacgcctggc caaccgcccg ttcctccaca catgggcat tccacggcgt    5520 cggtgcctgc ttgttcttga ttttccatgc cgcctccttt agccgctaaa attcatctac    5580
tcatttattc atttgctcat ttactctggt agctgcgcga tgtattcaga tagcagctcg    5640
gtaatggtct tgccttggcg taccgcgtac atcttcagct tggtgtgatc ctccgccggc    5700
aactgaaagt tgacccgctt catggctggc gtgtctgcca ggctggccaa cgttgcagcc    5760
ttgctgctgc gtgcgctcgg acggccggca cttagcgtgt ttgtgctttt gctcattttc    5820
tctttacctc attaactcaa atgagttttg atttaatttc agcggccagc gcctggacct    5880
cgcgggcagc gtcgccctcg ggttctgatt caagaacggt tgtgccggcg gcggcagtgc    5940
ctgggtagct cacgcgctgc gtgatacggg actcaagaat gggcagctcg tacccggcca    6000
gcgcctcggc aacctcaccg ccgatgcgcg tgcctttgat cgcccgcgac acgacaaagg    6060
ccgcttgtag ccttccatcc gtgacctcaa tgcgctgctt aaccagctcc accaggtcgg    6120
cggtggccca tatgtcgtaa gggcttggct gcaccggaat cagcacgaag tcggctgcct    6180
tgatcgcgga cacagccaag tccgccgcct ggggcgctcc gtcgatcact acgaagtcgc    6240
gccggccgat ggccttcacg tcgcggtcaa tcgtcgggcg gtcgatgccg acaacggtta    6300
gcggttgatc ttcccgcacg gccgcccaat cgcgggcact gccctgggga tcggaatcga    6360
ctaacagaac atcggccccg gcgagttgca gggcgcgggc tagatgggtt gcgatggtcg    6420
tcttgcctga cccgcctttc tggttaagta cagcgataac cttcatgcgt tccccttgcg    6480
tatttgttta tttactcatc gcatcatata cgcagcgacc gcatgacgca agctgtttta    6540
ctcaaataca catcaccttt ttagacggcg gcgctcggtt tcttcagcgg ccaagctggc    6600
```

-continued

```
cggccaggcc gccagcttgg catcagacaa accggccagg atttcatgca gccgcacggt    6660
tgagacgtgc gcgggcggct cgaacacgta cccggccgcg atcatctccg cctcgatctc    6720
ttcggtaatg aaaaacggtt cgtcctggcc gtcctggtgc ggtttcatgc ttgttcctct    6780
tggcgttcat tctcggcggc cgccagggcg tcggcctcgg tcaatgcgtc ctcacggaag    6840
gcaccgcgcc gcctggcctc ggtgggcgtc acttcctcgc tgcgctcaag tgcgcggtac    6900
agggtcgagc gatgcacgcc aagcagtgca gccgcctctt tcacggtgcg gccttcctgg    6960
tcgatcagct cgcgggcgtg cgcgatctgt gccggggtga gggtagggcg ggggccaaac    7020
ttcacgcctc gggccttggc ggcctcgcgc ccgctccggg tgcggtcgat gattagggaa    7080
cgctcgaact cggcaatgcc ggcgaacacg gtcaacacca tgcggccggc cggcgtggtg    7140
gtgtcggccc acggctctgc caggctacgc aggcccgcgc cggcctcctg gatgcgctcg    7200
gcaatgtcca gtaggtcgcg ggtgctgcgg gccaggcggt ctagcctggt cactgtcaca    7260
acgtcgccag ggcgtaggtg gtcaagcatc ctggccagct ccgggcggtc gcgcctggtg    7320
ccggtgatct tctcggaaaa cagcttggtg cagccggccg cgtgcagttc ggcccgttgg    7380
ttggtcaagt cctggtcgtc ggtgctgacg cgggcatagc ccagcaggcc agcggcggcg    7440
ctcttgttca tggcgtaatg tctccggttc tagtcgcaag tattctactt tatgcgacta    7500
aaacacgcga caagaaaacg ccaggaaaag ggcaggcgg cagcctgtcg cgtaacttag    7560
gacttgtgcg acatgtcgtt ttcagaagac ggctgcactg aacgtcagaa gccgactgca    7620
ctatagcagc ggaggggttg gatcaaagta ctttgatccc gaggggaacc ctgtggttgg    7680
catgcacata caaatggacg aacggataaa ccttttcacg ccctttaaa tatccgttat    7740 tctaataaac gctcttttct cttaggttta cccgccaata tatcctgtca aacactgata    7800
gtttaaactg aaggcgggaa acgacaatct gatccaagct caagctaagc ttgggcccga    7860
gcggataaca atttcacaca ggaaacagct atgaccatga ttacgccaag ctatcaactt    7920
tgtatagaaa agttgtaggt taagagtttc gttttccttc gttcaaaatc taatgtgaag    7980
gaaagcaaaa ctgacacaac ttttgtgtga accagagcaa gtgaaagtgt gtcgaatctg    8040
tacttttgta ctgtgtaatc tctatagtct gactctcatt atgtagtttt aagtgtcttt    8100
tacttgtgta gctgttacct gttacctgtt aggttttcta atccttgttt tatttgatag    8160
ccagatactt tagggaattt tacttcttct tttcttgggt ttaatttaag acatattcgt    8220
atatttcatt taattctgtt atctgatttg tgagatcatg aaaacgaatg ttgaacttga    8280
aacttgagtg ggttcagaaa aactactctg tattaaaaat cccagtgtca catgataatg    8340
atccttcagt aaaggtagac atagcttttt tgcagtgtga tatgcacaaa tacaatctat    8400 attttatgt aaaagatata tttctttgaa agtacttata aaaatatgtt tttcataaaa    8460
aaaattatat gtaattctga aagtatgtga tatgcacaag cacaacctat atttcctaca    8520
ttcaaattcg ggtttttctt gacgccaagt tacattcaat tatcaataat agggctagtt    8580
caactaatgc tatttattta tacaatccac ccactactaa atctcaatct ccaaggatct    8640
ttatatatta ataagaaaag ctactatcca aatgcgacct tgttcgtgaa gtgtttggtt    8700
tataatttgg tggcttaaga ctatagccca ccattgaccc aaaaaaagaa aggaaaatta    8760
atagtagact atatagctac caactcccta taatttacct tgaaattaaa ccagctttgt    8820 attttttaa tagaagtcag ggctctacag tttcatttta aacttttttt tttgttatat    8880
tacatcctgc aggttagttg taatttgtaa acgtaatcaa cataataaaa ccatttacat    8940
```

-continued

```
agactgatta aagttgattc catttgataa tatttagcta tttatatatc aatcaaccac    9000
cagctcttaa atatatgtat tcaaattgtt ttgttgactc tttttgctac actttaaatt    9060
tgaatctaga atgttgtcct gaaacaaaaa tctgtggatt gaacaaaatt atacaccagg    9120
taaaattttg aagtttttaa aagcaggatc acatactcct aattttagat tggatagatc    9180
tagtataaaa atatgaagtt tttttcccaa aaaataataa taccatttag ctcttaatta    9240
aatgcatgca aactaaagat aaaaagagga attattttaa ccattctaac tcgtcacaac    9300
atgcctaatc attccaggtt aattttagag ttttcaaatc gtcatattaa catgtgatcc    9360
tgaagactct tctcttcttt cttctaccat tagctgaaat ctttacttgt accacaatta    9420
acctcaaacc ctagcccta aatcccccta gaaatcaatc catcctcagt tctccaaaaa    9480
gatatctttg gttttttcttc actgacaaaa cccctaaaaa caagtttgta caaaaaagca    9540
ggctccatgg gaagatcacc ttgttgtgat aaaaatggag tgaagaaggg accatggact    9600
gctgaggagg atcagaaact catcgattat attcgatttc atggtcctgg caattggcgt    9660
acgctcccca aaaatgctgg tacgtataaa ctacacaccg ttccttatat tttgttctca    9720
tagattaata tatatgttct ctatttattg agtcacacac ttataagtcg tattgtacaa    9780
attaaaggac tccatagatg tggaaaaagc tgccgtcttc gatggaccaa ttatctaaga    9840
ccggacatca agagaggaag attctcgttc gaggaagaag aaactatcat tcagctacac    9900
agtgttatgg gaaacaagta agcctgatca ttcacaccat aattttttgtc tgaaattcat    9960 attcatcagc tacatgcttt tgtatgttaa ttaatgtaaa actcaaaaag ggagagtgta    10020
cgtttgcatg cgggggtaca tgtcaaatgt aggccatcaa ctccaataaa ctattattag    10080
tactttacta gtacgtattg acctatatta gaataataat aaaggagttt tgtattgatc    10140
atagattaat gtcactaata ttgaattgat gaatattagg tggtcagcaa tagccgctcg    10200
tctaccaggg aggaccgata acgaaataaa aaaccattgg aacactcaca tccgcaagag    10260
acttgtaagg agtggtatcg accctgttac tcattctcca cgccttgatc ttcttgattt    10320
gtcctcactt ttgagtgcac ttttcaacca gccaaacttt tcagcagttg caacacatgc    10380
gtcttctctt cttaatcctg atgtattgag gttggcctct ctactactgc cacttcaaaa    10440
ccctaatcca gtttacccat cgaacctcga ccaaaatctt caaactccaa atacatcatc    10500
agaatcgtct caaccacaag ctgagactag tacagtccca acaaactatg aaacttcatc    10560
attggagcct atgaacgcaa gactcgacga cgttggtctt gcagatgtat taccacctt    10620 gtcagagagt tttgacttag actcgctcat gtcaacgcca atgtcttctc cacgacaaaa    10680
tagcattgaa gcagaaacca actccagcac tttcttcgac tttggaattc cggaagattt    10740
catcttagat gactttatgt ttgacccagc tttcttgtac aaagtggcct aattttcaac    10800
atttgcatac acatgtcttg ctttcacaca tatgattctt tgttgcattc tttctttttgt    10860 ttgatgtata aatttcttgt ttttattctc tcaaaagata ttaagttatt agtctataaa    10920
attttcatga atgtttatgt attatctgct taggcgagat atctaaattc tgctccatta    10980
gtccatatac acagttgacg gaagcaaaca tagaattatt agcgtcaaac acatcacata    11040
ttcatattgc tttgttcgaa tcatcgtcaa tcaagttaat cagtttatgc gagttctatc    11100
atttaggccc aattcaaggc ccaattcaag ttcattttaa agccgttaat ttggccagca    11160
actttattat acatagttga taattcactg gccgtcgttt tacaacgtcg tgactgggaa    11220
aacgatctaa ctgactagcc gcggccatgg cggccgggag cggccatgct agagtccgca    11280
aaaatcacca gtctctctct acaaatctat ctctctctat ttttctccag aataatgtgt    11340
```

-continued

```
gagtagttcc cagataaggg aattagggtt cttatagggt ttcgctcatg tgttgagcat    11400
ataagaaacc cttagtatgt atttgtattt gtaaaatact tctatcaata aaatttctaa    11460
ttcctaaaac caaaatccag tgacctgcag gtcgaccata tgggag                   11506

<210> SEQ ID NO 8
<211> LENGTH: 12006
<212> TYPE: DNA
<213> ORGANISM: Artificial Sequence
<220> FEATURE:
<223> OTHER INFORMATION: proHORST::MYB41 construct

<400> SEQUENCE: 8
agctcgaatt atcatacatg agaattaagg gagtcacgtt atgaccccg ccgatgacgc        60 gggacaagcc gttttacgtt tggaactgac agaaccgcaa cgttgaagga gccactgagc      120
cgcgggtttc tggagtttaa tgagctaagc acatacgtca gaaaccatta ttgcgcgttc      180
aaaagtcgcc taaggtcact atcagctagc aaatatttct tgtcaaaaat gctccactga      240
cgttccataa attcccctcg gtatccaatt agagtctcat attcactctc aactcgatcg      300
aggggatcta ccatgagccc agaacgacgc ccggccgaca tccgccgtgc caccgaggcg      360
gacatgccgg cggtctgcac catcgtcaac cactacatcg agacaagcac ggtcaacttc      420
cgtaccgagc cgcaggaacc gcaggagtgg acggacgacc tcgtccgtct gcgggagcgc      480
tatccctggc tcgtcgccga ggtggacggc gaggtcgccg gcatcgccta cgcgggtccc      540
tggaaggcac gcaacgccta cgactggacg gccgagtcga ccgtgtacgt ctcccccgc       600 caccagcgga cgggactggg ctccacgctc tacacccacc tgctgaagtc cctggaggca      660
cagggcttca agagcgtggt cgctgtcatc gggctgccca cgacccgag cgtgcgcatg       720 cacgaggcgc tcggatatgc cccccgcggc atgctgcggg cggccggctt caagcacggg      780
aactggcatg acgtgggttt ctggcagctg gacttcagcc tgccggtgcc gccccgtccg      840
gtcctgcccg tcaccgaaat ctgatgaccc ctagagtcaa gcagatcgtt caaacatttg      900
gcaataaagt ttcttaagat tgaatcctgt tgccggtctt gcgatgatta tcatataatt      960
tctgttgaat tacgttaagc atgtaataat taacatgtaa tgcatgacgt tatttatgag     1020
atgggttttt atgattagag tcccgcaatt atacatttaa tacgcgatag aaaacaaaat     1080
atagcgcgca aactaggata aattatcgcg cgcggtgtca tctatatgtt actagatcga     1140
ccggcatgca agctgataat tcaattcggc gttaattcag tacattaaaa acgtccgcaa     1200
tgtgttatta agttgtctaa gcgtcaattt gtttacacca caatatatcc tgccaccagc     1260
cagccaacag ctccccgacc ggcagctcgg cacaaaatca ccactcgata caggcagccc     1320
atcagtccgg gacggcgtca gcgggagagc cgttgtaagg cggcagactt tgctcatgtt     1380
accgatgcta ttcggaagaa cggcaactaa gctgccgggt ttgaaacacg gatgatctcg     1440
cggagggtag catgttgatt gtaacgatga cagagcgttg ctgcctgtga tcaattcggg     1500
cacgaaccca gtggacataa gcctcgttcg gttcgtaagc tgtaatgcaa gtagcgtaac     1560
tgccgtcacg caactggtcc agaaccttga ccgaacgcag cggtggtaac ggcgcagtgg     1620
cggttttcat ggcttcttgt tatgacatgt ttttttgggg tacagtctat gcctcgggca     1680
tccaagcagc aagcgcgtta cgccgtgggt cgatgtttga tgttatggag cagcaacgat     1740
gttacgcagc agggcagtcg ccctaaaaca aagttaaaca tcatggggga agcggtgatc     1800
gccgaagtat cgactcaact atcagaggta gttggcgtca tcgagcgcca tctcgaaccg     1860
```

-continued

```
acgttgctgg ccgtacattt gtacggctcc gcagtggatg gcggcctgaa gccacacagt    1920
gatattgatt tgctggttac ggtgaccgta aggcttgatg aaacaacgcg gcgagctttg    1980
atcaacgacc ttttggaaac ttcggcttcc cctggagaga gcgagattct ccgcgctgta    2040
gaagtcacca ttgttgtgca cgacgacatc attccgtggc gttatccagc taagcgcgaa    2100
ctgcaatttg gagaatggca gcgcaatgac attcttgcag gtatcttcga gccagccacg    2160
atcgacattg atctggctat cttgctgaca aaagcaagag aacatagcgt tgccttggta    2220
ggtccagcgg cggaggaact cttttgatccg gttcctgaac aggatctatt tgaggcgcta    2280
aatgaaacct taacgctatg gaactcgccg cccgactggg ctggcgatga gcgaaatgta    2340
gtgcttacgt tgtcccgcat ttggtacagc gcagtaaccg gcaaaatcgc gccgaaggat    2400
gtcgctgccg actgggcaat ggagcgcctg ccggcccagt atcagcccgt catacttgaa    2460
gctagacagg cttatcttgg acaagaagaa gatcgcttgg cctcgcgcgc agatcagttg    2520
gaagaatttg tccactacgt gaaaggcgag atcaccaagg tagtcggcaa ataatgtcta    2580
gctagaaatt cgttcaagcc gacgccgctt cgccggcgtt aactcaagcg attagatgca    2640
ctaagcacat aattgctcac agccaaacta tcaggtcaag tctgctttta ttatttttaa    2700
gcgtgcataa taagccctac acaaattggg agatatatca tgcatgacca aaatccctta    2760
acgtgagttt tcgttccact gagcgtcaga ccccgtagaa aagatcaaag gatcttcttg    2820
agatcctttt tttctgcgcg taatctgctg cttgcaaaca aaaaaaccac cgctaccagc    2880
ggtggtttgt ttgccggatc aagagctacc aactcttttt ccgaaggtaa ctggcttcag    2940
cagagcgcag ataccaaata ctgtccttct agtgtagccg tagttaggcc accacttcaa    3000
gaactctgta gcaccgccta catacctcgc tctgctaatc ctgttaccag tggctgctgc    3060
cagtggcgat aagtcgtgtc ttaccgggtt ggactcaaga cgatagttac cggataaggc    3120
gcagcggtcg ggctgaacgg ggggttcgtg cacacagccc agcttggagc gaacgaccta    3180
caccgaactg agatacctac agcgtgagct atgagaaagc gccacgcttc ccgaagggag    3240
aaaggcggac aggtatccgg taagcggcag ggtcggaaca ggagagcgca cgagggagct    3300 tccagggggga aacgcctggt atctttatag tcctgtcggg tttcgccacc tctgacttga    3360
gcgtcgattt ttgtgatgct cgtcaggggg gcggagccta tggaaaaacg ccagcaacgc    3420
ggccttttta cggttcctgg ccttttgctg gccttttgct cacatgttct ttcctgcgtt    3480
atcccctgat tctgtggata accgtattac cgcctttgag tgagctgata ccgctcgccg    3540
cagccgaacg accgagcgca gcgagtcagt gagcgaggaa gcggaagagc gcctgatgcg    3600
gtattttctc cttacgcatc tgtgcggtat ttcacaccgc atatggtgca ctctcagtac    3660
aatctgctct gatgccgcat agttaagcca gtatacactc cgctatcgct acgtgactgg    3720
gtcatggctg cgccccgaca cccgccaaca cccgctgacg cgccctgacg gcttgtctg    3780 ctcccggcat ccgcttacag acaagctgtg accgtctccg ggagctgcat gtgtcagagg    3840
ttttcaccgt catcaccgaa acgcgcgagg caggggtgcct tgatgtgggc gccggcggtc    3900
gagtggcgac ggcgcggctt gtccgcgccc tggtagattg cctggccgta ggccagccat    3960
ttttgagcgg ccagcggccg cgataggccg acgcgaagcg gcggggcgta gggagcgcag    4020
cgaccgaagg gtaggcgctt tttgcagctc ttcggctgtg cgctggccag acagttatgc    4080
acaggccagg cgggttttaa gagttttaat aagtttttaaa gagttttagg cggaaaaatc    4140 gcctttttc tcttttatat cagtcactta catgtgtgac cggttcccaa tgtacgcatt    4200
tgggttccca atgtacgggt tccggttccc aatgtacggc tttgggttcc caatgtacgt    4260
```

```
gctatccaca ggaaagagac cttttcgacc tttttcccct gctagggcaa tttgccctag     4320
catctgctcc gtacattagg aaccggcgga tgcttcgccc tcgatcaggt tgcggtagcg     4380
catgactagg atcgggccag cctgccccgc ctcctccttc aaatcgtact ccggcaggtc     4440
atttgacccg atcagcttgc gcacggtgaa acagaacttc ttgaactctc cggcgctgcc     4500
actgcgttcg tagatcgtct tgaacaacca tctggcttct gccttgcctg cggcgcggcg     4560
tgccaggcgg tagagaaaac ggccgatgcc gggatcgatc aaaaagtaat cggggtgaac     4620
cgtcagcacg tccgggttct tgccttctgt gatctcgcgg tacatccaat cagctagctc     4680
gatctcgatg tactccggcc gcccggtttc gctctttacg atcttgtagc ggctaatcaa     4740
ggcttcaccc tcggataccg tcaccaggcg gccgttcttg gccttcttcg tacgctgcat     4800
ggcaacgtgc gtggtgttta accgaatgca ggtttctacc aggtcgtctt tctgctttcc     4860
gccatcggct cgccggcaga acttgagtac gtccgcaacg tgtggacgga acacgcggcc     4920
gggcttgtct cccttccctt cccggtatcg gttcatggat tcggttagat gggaaaccgc     4980
catcagtacc aggtcgtaat cccacacact ggccatgccg gccggccctg cggaaacctc     5040
tacgtgcccg tctggaagct cgtagcggat cacctcgcca gctcgtcggt cacgcttcga     5100
cagacggaaa acggccacgt ccatgatgct gcgactatcg cgggtgccca cgtcatagag     5160
catcggaacg aaaaaatctg gttgctcgtc gcccttgggc ggcttcctaa tcgacggcgc     5220
accggctgcc ggcggttgcc gggattcttt gcggattcga tcagcggccg cttgccacga     5280
ttcaccgggg cgtgcttctg cctcgatgcg ttgccgctgg gcggcctgcg cggccttcaa     5340
cttctccacc aggtcatcac ccagcgccgc gccgatttgt accgggccgg atggtttgcg     5400
accgtcacgc cgattcctcg ggcttggggg ttccagtgcc attgcagggc cggcagacaa     5460
cccagccgct tacgcctggc caaccgcccg ttcctccaca catggggcat tccacggcgt     5520
cggtgcctgg ttgttcttga ttttccatgc cgcctccttt agccgctaaa attcatctac     5580
tcatttattc atttgctcat ttactctggt agctgcgcga tgtattcaga tagcagctcg     5640
gtaatggtct tgccttggcg taccgcgtac atcttcagct tggtgtgatc ctccgccggc     5700
aactgaaagt tgacccgctt catggctggc gtgtctgcca ggctggccaa cgttgcagcc     5760
ttgctgctgc gtgcgctcgg acggccggca cttagcgtgt ttgtgctttt gctcattttc     5820
tctttacctc attaactcaa atgagttttg atttaatttc agcggccagc gcctggacct     5880
cgcgggcagc gtcgccctcg ggttctgatt caagaacggt tgtgccggcg gcggcagtgc     5940
ctgggtagct cacgcgctgc gtgatacggg actcaagaat gggcagctcg tacccggcca     6000
gcgcctcggc aacctcaccg ccgatgcgcg tgcctttgat cgcccgcgac acgacaaagg     6060
ccgcttgtag ccttccatcc gtgacctcaa tgcgctgctt aaccagctcc accaggtcgg     6120
cggtggccca tatgtcgtaa gggcttggct gcaccggaat cagcacgaag tcggctgcct     6180
tgatcgcgga cacagccaag tccgccgcct ggggcgctcc gtcgatcact acgaagtcgc     6240
gccggccgat ggccttcacg tcgcggtcaa tcgtcgggcg gtcgatgccg acaacggtta     6300
gcggttgatc ttcccgcacg gccgcccaat cgcgggcact gccctgggga tcggaatcga     6360
ctaacagaac atcggccccg gcgagttgca gggcgcgggc tagatgggtt gcgatggtcg     6420
tcttgcctga cccgcctttc tggttaagta cagcgataac cttcatgcgt tccccttgcg     6480
tatttgttta tttactcatc gcatcatata cgcagcgacc gcatgacgca agctgtttta     6540
ctcaaataca catcaccttt ttagacggcg gcgctcggtt tcttcagcgg ccaagctggc     6600
```

```
cggccaggcc gccagcttgg catcagacaa accggccagg atttcatgca gccgcacggt    6660
tgagacgtgc gcgggcggct cgaacacgta cccggccgcg atcatctccg cctcgatctc    6720
ttcggtaatg aaaaacggtt cgtcctggcc gtcctggtgc ggtttcatgc ttgttcctct    6780
tggcgttcat tctcggcggc cgccagggcg tcggcctcgg tcaatgcgtc ctcacggaag    6840
gcaccgcgcc gcctggcctc ggtgggcgtc acttcctcgc tgcgctcaag tgcgcggtac    6900
agggtcgagc gatgcacgcc aagcagtgca gccgcctctt tcacggtgcg gccttcctgg    6960
tcgatcagct cgcgggcgtg cgcgatctgt gccggggtga gggtagggcg ggggccaaac    7020
ttcacgcctc gggccttggc ggcctcgcgc ccgctccggg tgcggtcgat gattagggaa    7080
cgctcgaact cggcaatgcc ggcgaacacg gtcaacacca tgcggccggc cggcgtggtg    7140
gtgtcggccc acggctctgc caggctacgc aggcccgcgc cggcctcctg gatgcgctcg    7200
gcaatgtcca gtaggtcgcg ggtgctgcgg gccaggcggt ctagcctggt cactgtcaca    7260
acgtcgccag ggcgtaggtg gtcaagcatc ctggccagct ccgggcggtc gcgcctggtg    7320
ccggtgatct tctcggaaaa cagcttggtg cagccggccg cgtgcagttc ggcccgttgg    7380
ttggtcaagt cctggtcgtc ggtgctgacg cgggcatagc ccagcaggcc agcggcggcg    7440
ctcttgttca tggcgtaatg tctccggttc tagtcgcaag tattctactt tatgcgacta    7500
aaacacgcga caagaaaacg ccaggaaaag ggcagggcgg cagcctgtcg cgtaacttag    7560
gacttgtgcg acatgtcgtt ttcagaagac ggctgcactg aacgtcagaa gccgactgca    7620
ctatagcagc ggaggggttg gatcaaagta ctttgatccc gaggggaacc ctgtggttgg    7680
catgcacata caaatggacg aacgataaac cttttcacg cccttttaaa tatccgttat    7740
tctaataaac gctctttct cttaggttta cccgccaata tatcctgtca aacactgata    7800
gtttaaactg aaggcgggaa acgacaatct gatccaagct caagctaagc ttgggcccga    7860
gcggataaca atttcacaca ggaaacagct atgaccatga ttacgccaag ctatcaactt    7920
tgtatagaaa agttgcccat ctacaaagcc tataaaatgg aaagatgtat gcatcgatga    7980
tgattctgcc tcacttagaa gaatcaaaaa gctaaaagga gctgcgaatc ctgggcaacg    8040
atgacttagt atgtatagaa gaaaaaaaaa gcttttactt ggtatcaaac agagcatgtg    8100
ttgttgtatt tgctaccttt ttctgcaaag ttattggcaa ttgtattgtt gttccacttg    8160
tatatataca gagaccattt atgttaatat acaacttcgt atggggaaag atgattccat    8220
caagtccaaa atgccaaaac catgcacgat cttgtctgat caagtatgat aagatgtgag    8280
attttaagaa cgtgaagctt ttcatattgt attctcaatg aacgaagaat taataattag    8340
agttagaaat gcagattaca gagattacac aatttgatct catttcttgg caaagaggcc    8400
caggccaccg aagccaccgt ccttctttgg attcctgtgt gttaatttc gtgtggcttt    8460 agttacaaag ggattatatt gtcagcgaat ctgagccgtt ggatcgtttt gacatgagct    8520
ttccataagt gtcttatcct ttgtttctct cattttcac atatgtatca gacatttaat    8580
caagcacata tctacgtgtt gattatgttg atgatgctga gattatgttg atttagagaa    8640
tgagtattgg tgatgatggt acacgttagt aaacatatga atttggaagt gccacgtgag    8700
agggagcaga gttttgggct ttcttttggt tatgtatttg cattcttgtt gtaacaaatt    8760
ctcttattaa aagcattgtg aaaaaaacca aataccacat agtctatgtt tcaagatttg    8820
ttttttaata ctataatttt ctattacttt agtttgtgta atttttgaaa agagaaaatt    8880
ggtatttttt aggattgggt gatctgaaat ttgactacaa aaattttctt ggacacagac    8940
acacagtcac acaaataagc taattattgg aattttatct taagttgcat tcactttgca    9000
```

-continued

```
aattaatatt gaattataga ctattagtgt atggcgtgat ggcaaacaaa aaaatcagtg    9060
tgtgatattg tggactagcc aaaaaaattt tctgatgatt tttttgccta aataatttga    9120
attgttgaga ccgaaactct tactaatata ctaacaatgt aacgcgacaa ataaaacatt    9180
gttgagaata aaatctgaac catcataact atagtctata gtaaccgtcc gaattcaacc    9240
acatatgtat gatctttgcc atttttgatc atattttccg ttgcgttttc tttgaatttt    9300
ctcaatatat ttttagtgtt ttgatttgta cttttatcta atttatataa ttgttttttca   9360 aatgtttcgc aattgtgcgt ttaagtattc gactcgaagt aaacccagtt tcttagaatg    9420
ggctaactgc cattgaccaa atctttatcc gcgaagaaag atctttagca gctaggctta    9480
tttcatatca acaaaagtat atatttatct ctaactaaat tcctacaatt atttcaaaaa    9540
catagaaatt aaaatttgaa atgcctattc tttttttggtt atacattgca aaggttatgt    9600
atgtaatttc tgatcttgaa atttaagttc tttagcccat atctagttga ttttcacgaa    9660
atattgtcgt ttactctcgt ttttatatat aaagcatgta catataacat ataatcaatg    9720
cttcaaaaga aaaaataat cataactaaa ttgaaacggg aaaactaatt tgctttcgtg      9780
ttctattatg ccaaactgta ctcacaatag tcttatccta tcgacccaaa tttaatcttc    9840
ccaactactt actcctaatt gaaacaaaat ataacctttc ttactatagc ctatatttaa    9900
aaaatatcta tgatttctac atttatatat atacgcacac ggcacatacc tctcattcac    9960
catatatgcc tcttaacaat ctctccacag aacaaaagca aaaagcctaa accgggatag    10020
caagtttgta caaaaaagca ggctccatgg gaagatcacc ttgttgtgat aaaaatggag    10080
tgaagaaggg accatggact gctgaggagg atcagaaact catcgattat attcgatttc    10140
atggtcctgg caattggcgt acgctcccca aaaatgctgg tacgtataaa ctacacaccg    10200
ttccttatat tttgttctca tagattaata tatatgttct ctatttattg agtcacacac    10260
ttataagtcg tattgtacaa attaaaggac tccatagatg tggaaaaagc tgccgtcttc    10320
gatggaccaa ttatctaaga ccggacatca agagaggaag attctcgttc gaggaagaag    10380
aaactatcat tcagctacac agtgttatgg gaaacaagta agcctgatca ttcacaccat    10440 aattttttgtc tgaaattcat attcatcagc tacatgcttt tgtatgttaa ttaatgtaaa    10500
actcaaaaag ggagagtgta cgtttgcatg cgggggtaca tgtcaaatgt aggccatcaa    10560
ctccaataaa ctattattag tactttacta gtacgtattg acctatatta gaataataat    10620
aaaggagttt tgtattgatc atagattaat gtcactaata ttgaattgat gaatattagg    10680
tggtcagcaa tagccgctcg tctaccaggg aggaccgata acgaaataaa aaaccattgg    10740
aacactcaca tccgcaagag acttgtaagg agtggtatcg accctgttac tcattctcca    10800
cgccttgatc ttcttgattt gtcctcactt ttgagtgcac ttttcaacca gccaaacttt    10860
tcagcagttg caacacatgc gtcttctctt cttaatcctg atgtattgag gttggcctct    10920
ctactactgc cacttcaaaa ccctaatcca gtttacccat cgaacctcga ccaaaatctt    10980
caaactccaa atacatcatc agaatcgtct caaccacaag ctgagactag tacagtccca    11040
acaaactatg aaacttcatc attggagcct atgaacgcaa gactcgacga cgttggtctt    11100
gcagatgtat taccaccttt gtcagagagt tttgacttag actcgctcat gtcaacgcca    11160
atgtcttctc cacgacaaaa tagcattgaa gcagaaacca actccagcac tttcttcgac    11220
tttggaattc cggaagattt catcttagat gactttatgt ttgacccagc tttcttgtac    11280
aaagtggcct aattttcaac atttgcatac acatgtcttg ctttcacaca tatgattctt    11340
```

```
tgttgcattc tttcttttgt ttgatgtata aatttcttgt ttttattctc tcaaaagata   11400
ttaagttatt agtctataaa attttcatga atgtttatgt attatctgct taggcgagat   11460
atctaaattc tgctccatta gtccatatac acagttgacg gaagcaaaca tagaattatt   11520
agcgtcaaac acatcacata ttcatattgc tttgttcgaa tcatcgtcaa tcaagttaat   11580
cagtttatgc gagttctatc atttaggccc aattcaaggc ccaattcaag ttcattttaa   11640
agccgttaat ttggccagca actttattat acatagttga taattcactg gccgtcgttt   11700
tacaacgtcg tgactgggaa aacgatctaa ctgactagcc gcggccatgg cggccgggag   11760
cggccatgct agagtccgca aaaatcacca gtctctctct acaaatctat ctctctctat   11820
ttttctccag aataatgtgt gagtagttcc cagataaggg aattagggtt cttatagggt   11880
ttcgctcatg tgttgagcat ataagaaacc cttagtatgt atttgtattt gtaaaatact   11940
tctatcaata aaatttctaa ttcctaaaac caaaatccag tgacctgcag gtcgaccata   12000
tgggag                                                               12006
```

```
<210> SEQ ID NO 9
<211> LENGTH: 11934
<212> TYPE: DNA
<213> ORGANISM: Artificial Sequence
<220> FEATURE:
<223> OTHER INFORMATION: proASFT::MYB41 construct

<400> SEQUENCE: 9
```

```
agctcgaatt atcatacatg agaattaagg gagtcacgtt atgaccccg ccgatgacgc      60 gggacaagcc gttttacgtt tggaactgac agaaccgcaa cgttgaagga gccactgagc    120
cgcgggtttc tggagtttaa tgagctaagc acatacgtca gaaaccatta ttgcgcgttc    180
aaaagtcgcc taaggtcact atcagctagc aaatatttct tgtcaaaaat gctccactga    240
cgttccataa attcccctcg gtatccaatt agagtctcat attcactctc aactcgatcg    300
aggggatcta ccatgagccc agaacgacgc ccggccgaca tccgccgtgc caccgaggcg    360
gacatgccgg cggtctgcac catcgtcaac cactacatcg agacaagcac ggtcaacttc    420
cgtaccgagc gcaggaacc gcaggagtgg acggacgacc tcgtccgtct gcgggagcgc    480
tatccctggc tcgtcgccga ggtggacggc gaggtcgccg gcatcgccta cgcgggtccc    540
tggaaggcac gcaacgccta cgactggacg gccgagtcga ccgtgtacgt ctcccccgc    600 caccagcgga cgggactggg ctccacgctc tacacccacc tgctgaagtc cctggaggca    660
cagggcttca agagcgtggt cgctgtcatc gggctgccca acgacccgag cgtgcgcatg    720
cacgaggcgc tcggatatgc ccccgcggc atgctgcggg cggccggctt caagcacggg    780
aactggcatg acgtgggttt ctggcagctg gacttcagcc tgccggtgcc gccccgtccg    840
gtcctgcccg tcaccgaaat ctgatgaccc ctagagtcaa gcagatcgtt caaacatttg    900
gcaataaagt ttcttaagat tgaatcctgt tgccggtctt gcgatgatta tcatataatt    960
tctgttgaat tacgttaagc atgtaataat aacatgtaa tgcatgacgt tatttatgag   1020
atgggttttt atgattagag tcccgcaatt atacatttaa tacgcgatag aaaacaaaat   1080
atagcgcgca aactaggata aattatcgcg cgcggtgtca tctatatgtt actagatcga   1140
ccggcatgca agctgataat tcaattcggc gttaattcag tacattaaaa acgtccgcaa   1200
tgtgttatta agttgtctaa gcgtcaattt gtttacacca caatatatcc tgccaccagc   1260
cagccaacag ctccccgacc ggcagctcgg cacaaaatca ccactcgata caggcagccc   1320
atcagtccgg gacggcgtca gcgggagagc cgttgtaagg cggcagactt tgctcatgtt   1380
```

-continued

```
accgatgcta ttcggaagaa cggcaactaa gctgccgggt ttgaaacacg gatgatctcg      1440
cggagggtag catgttgatt gtaacgatga cagagcgttg ctgcctgtga tcaattcggg      1500
cacgaaccca gtggacataa gcctcgttcg gttcgtaagc tgtaatgcaa gtagcgtaac      1560
tgccgtcacg caactggtcc agaaccttga ccgaacgcag cggtggtaac ggcgcagtgg      1620 cggtttttcat ggcttcttgt tatgacatgt ttttttgggg tacagtctat gcctcgggca      1680
tccaagcagc aagcgcgtta cgccgtgggt cgatgtttga tgttatggag cagcaacgat      1740
gttacgcagc agggcagtcg ccctaaaaca aagttaaaca tcatggggga agcggtgatc      1800
gccgaagtat cgactcaact atcagaggta gttggcgtca tcgagcgcca tctcgaaccg      1860
acgttgctgg ccgtacattt gtacggctcc gcagtggatg gcggcctgaa gccacacagt      1920
gatattgatt tgctggttac ggtgaccgta aggcttgatg aaacaacgcg gcgagctttg      1980
atcaacgacc ttttggaaac ttcggcttcc cctggagaga gcgagattct ccgcgctgta      2040
gaagtcacca ttgttgtgca cgacgacatc attccgtggc gttatccagc taagcgcgaa      2100
ctgcaatttg gagaatggca gcgcaatgac attcttgcag gtatcttcga gccagccacg      2160
atcgacattg atctggctat cttgctgaca aaagcaagag aacatagcgt tgccttggta      2220
ggtccagcgg cggaggaact ctttgatccg gttcctgaac aggatctatt tgaggcgcta      2280
aatgaaacct taacgctatg gaactcgccg cccgactggg ctggcgatga gcgaaatgta      2340
gtgcttacgt tgtcccgcat ttggtacagc gcagtaaccg gcaaaatcgc gccgaaggat      2400
gtcgctgccg actgggcaat ggagcgcctg ccggcccagt atcagcccgt catacttgaa      2460
gctagacagg cttatcttgg acaagaagaa gatcgcttgg cctcgcgcgc agatcagttg      2520
gaagaatttg tccactacgt gaaaggcgag atcaccaagg tagtcggcaa ataatgtcta      2580
gctagaaatt cgttcaagcc gacgccgctt cgccggcgtt aactcaagcg attagatgca      2640
ctaagcacat aattgctcac agccaaacta tcaggtcaag tctgctttta ttatttttaa      2700
gcgtgcataa taagccctac acaaattggg agatatatca tgcatgacca aaatccctta      2760
acgtgagttt tcgttccact gagcgtcaga ccccgtagaa aagatcaaag gatcttcttg      2820
agatcctttt tttctgcgcg taatctgctg cttgcaaaca aaaaaaccac cgctaccagc      2880
ggtggtttgt ttgccggatc aagagctacc aactcttttt ccgaaggtaa ctggcttcag      2940
cagagcgcag ataccaaata ctgtccttct agtgtagccg tagttaggcc accacttcaa      3000
gaactctgta gcaccgccta catacctcgc tctgctaatc ctgttaccag tggctgctgc      3060
cagtggcgat aagtcgtgtc ttaccgggtt ggactcaaga cgatagttac cggataaggc      3120
gcagcggtcg ggctgaacgg ggggttcgtg cacacagccc agcttggagc gaacgaccta      3180
caccgaactg agatacctac agcgtgagct atgagaaagc gccacgcttc ccgaagggag      3240
aaaggcggac aggtatccgg taagcggcag ggtcggaaca ggagagcgca cgagggagct      3300 tccagggggga aacgcctggt atctttatag tcctgtcggg tttcgccacc tctgacttga      3360
gcgtcgattt ttgtgatgct cgtcaggggg gcggagccta tggaaaaacg ccagcaacgc      3420 ggcctttttta cggttcctgg ccttttgctg gccttttgct cacatgttct ttcctgcgtt      3480
atcccctgat tctgtggata accgtattac cgcctttgag tgagctgata ccgctcgccg      3540
cagccgaacg accgagcgca gcgagtcagt gagcgaggaa gcggaagagc gcctgatgcg      3600
gtattttctc cttacgcatc tgtgcggtat ttcacaccgc atatggtgca ctctcagtac      3660
aatctgctct gatgccgcat agttaagcca gtatacactc cgctatcgct acgtgactgg      3720
```

-continued

```
gtcatggctg cgccccgaca cccgccaaca cccgctgacg cgccctgacg ggcttgtctg      3780
ctcccggcat ccgcttacag acaagctgtg accgtctccg ggagctgcat gtgtcagagg      3840
ttttcaccgt catcaccgaa acgcgcgagg cagggtgcct tgatgtgggc gccggcggtc      3900
gagtggcgac ggcgcggctt gtccgcgccc tggtagattg cctggccgta ggccagccat      3960
ttttgagcgg ccagcggccg cgataggccg acgcgaagcg cgggggcgta gggagcgcag      4020
cgaccgaagg gtaggcgctt tttgcagctc ttcggctgtg cgctggccag acagttatgc      4080
acaggccagg cgggttttaa gagttttaat aagttttaaa gagtttttagg cggaaaaatc      4140 gcctttttc tcttttatat cagtcactta catgtgtgac cggttcccaa tgtacggctt      4200
tgggttccca atgtacgggt tccggttccc aatgtacggc tttgggttcc caatgtacgt      4260
gctatccaca ggaaagagac cttttcgacc ttttttcccct gctagggcaa tttgccctag      4320
catctgctcc gtacattagg aaccggcgga tgcttcgccc tcgatcaggt tgcggtagcg      4380
catgactagg atcgggccag cctgccccgc ctcctccttc aaatcgtact ccggcaggtc      4440
atttgacccg atcagcttgc gcacggtgaa acagaacttc ttgaactctc cggcgctgcc      4500
actgcgttcg tagatcgtct tgaacaacca tctggcttct gccttgcctg cggcgcggcg      4560
tgccaggcgg tagagaaaac ggccgatgcc gggatcgatc aaaaagtaat cggggtgaac      4620
cgtcagcacg tccgggttct tgccttctgt gatctcgcgg tacatccaat cagctagctc      4680
gatctcgatg tactccggcc gcccggtttc gctctttacg atcttgtagc ggctaatcaa      4740
ggcttcaccc tcggataccg tcaccaggcg gccgttcttg gccttcttcg tacgctgcat      4800
ggcaacgtgc gtggtgttta accgaatgca ggtttctacc aggtcgtctt tctgctttcc      4860
gccatcggct cgccggcaga acttgagtac gtccgcaacg tgtggacgga acacgcggcc      4920
gggcttgtct cccttcccttt cccggtatcg gttcatggat tcggttagat gggaaaccgc      4980
catcagtacc aggtcgtaat cccacacact ggccatgccg gccggccctg cggaaacctc      5040
tacgtgcccg tctggaagct cgtagcggat cacctcgcca gctcgtcggt cacgcttcga      5100
cagacggaaa acggccacgt ccatgatgct gcgactatcg cgggtgccca cgtcatagag      5160
catcggaacg aaaaaatctg gttgctcgtc gcccttgggc ggcttcctaa tcgacggcgc      5220
accggctgcc ggcggttgcc gggattcttt gcggattcga tcagcggccg cttgccacga      5280
ttcaccgggg cgtgcttctg cctcgatgcg ttgccgctgg gcggcctgcg cggccttcaa      5340
cttctccacc aggtcatcac ccagcgccgc gccgatttgt accgggccgg atggtttgcg      5400
accgtcacgc cgattcctcg ggcttggggg ttccagtgcc attgcagggc cggcagacaa      5460
cccagccgct tacgcctggc caaccgcccg ttcctccaca catggggcat tccacggcgt      5520
cggtgcctgg ttgttcttga ttttccatgc cgcctccttt agccgctaaa attcatctac      5580
tcatttattc atttgctcat ttactctggt agctgcgcga tgtattcaga tagcagctcg      5640
gtaatggtct tgccttggcg taccgcgtac atcttcagct tggtgtgatc ctccgccggc      5700
aactgaaagt tgacccgctt catggctggc gtgtctgcca ggctggccaa cgttgcagcc      5760
ttgctgctgc gtgcgctcgg acggccggca cttagcgtgt ttgtgctttt gctcattttc      5820
tctttacctc attaactcaa atgagttttg atttaatttc agcggccagc gcctggacct      5880
cgcgggcagc gtcgccctcg ggttctgatt caagaacggt tgtgccggcg cggcagtgc      5940 ctgggtagct cacgcgctgc gtgatacggg actcaagaat gggcagctcg tacccggcca      6000
gcgcctcggc aacctcaccg ccgatgcgcg tgcctttgat cgcccgcgac acgacaaagg      6060
ccgcttgtag ccttccatcc gtgacctcaa tgcgctgctt aaccagctcc accaggtcgg      6120
```

```
cggtggccca tatgtcgtaa gggcttggct gcaccggaat cagcacgaag tcggctgcct    6180
tgatcgcgga cacagccaag tccgccgcct ggggcgctcc gtcgatcact acgaagtcgc    6240
gccggccgat ggccttcacg tcgcggtcaa tcgtcgggcg gtcgatgccg acaacggtta    6300
gcggttgatc ttcccgcacg gccgcccaat cgcgggcact gccctgggga tcggaatcga    6360
ctaacagaac atcggccccg gcgagttgca gggcgcgggc tagatgggtt gcgatggtcg    6420
tcttgcctga cccgcctttc tggttaagta cagcgataac cttcatgcgt tccccttgcg    6480
tatttgttta tttactcatc gcatcatata cgcagcgacc gcatgacgca agctgtttta    6540
ctcaaataca catcaccttt ttagacggcg gcgctcggtt tcttcagcgg ccaagctggc    6600
cggccaggcc gccagcttgg catcagacaa accggccagg atttcatgca gccgcacggt    6660
tgagacgtgc gcgggcggct cgaacacgta cccggccgcg atcatctccg cctcgatctc    6720
ttcggtaatg aaaaacggtt cgtcctggcc gtcctggtgc ggtttcatgc ttgttcctct    6780
tggcgttcat tctcggcggc cgccaggcg tcggcctcgg tcaatgcgtc ctcacggaag    6840
gcaccgcgcc gcctggcctc ggtgggcgtc acttcctcgc tgcgctcaag tgcgcggtac    6900
agggtcgagc gatgcacgcc aagcagtgca gccgcctctt tcacggtgcg gccttcctgg    6960
tcgatcagct cgcgggcgtg cgcgatctgt gccggggtga gggtagggcg ggggccaaac    7020
ttcacgcctc gggccttggc ggcctcgcgc ccgctccggg tgcggtcgat gattagggaa    7080
cgctcgaact cggcaatgcc ggcgaacacg gtcaacacca tgcggccggc cggcgtggtg    7140
gtgtcggccc acggctctgc caggctacgc aggcccgcgc cggcctcctg gatgcgctcg    7200
gcaatgtcca gtaggtcgcg ggtgctgcgg gccaggcggt ctagcctggt cactgtcaca    7260
acgtcgccag ggcgtaggtg gtcaagcatc ctggccagct ccgggcggtc gcgcctggtg    7320
ccggtgatct tctcggaaaa cagcttggtg cagccggccg cgtgcagttc ggcccgttgg    7380
ttggtcaagt cctggtcgtc ggtgctgacg cgggcatagc ccagcaggcc agcggcggcg    7440
ctcttgttca tggcgtaatg tctccggttc tagtcgcaag tattctactt tatgcgacta    7500
aaacacgcga caagaaaacg ccaggaaaag ggcaggcgg cagcctgtcg cgtaacttag    7560
gacttgtgcg acatgtcgtt ttcagaagac ggctgcactg aacgtcagaa gccgactgca    7620
ctatagcagc ggagggggttg gatcaaagta ctttgatccc gaggggaacc ctgtggttgg    7680
catgcacata caaatggacg aacggataaa ccttttcacg cccttttaaa tatccgttat    7740
tctaataaac gctcttttct cttaggttta cccgccaata tatcctgtca aacactgata    7800
gtttaaactg aaggcgggaa acgacaatct gatccaagct caagctaagc ttgggcccga    7860
gcggataaca atttcacaca ggaaacagct atgaccatga ttacgccaag ctatcaactt    7920
tgtatagaaa agttgccagc tcaaaccttt aaatggcttt taattagata tatttagcga    7980
gaatgtgatt gctagtgaaa tctcaaactt gatagcttat tcatagctta ttttacttcg    8040
atcagcaaga gaacaatggt tcctaaagct caaacctttt ttggcgtttg ctttagattg    8100
tgcatacata aagtgagaag atgaaatatg gttttgctga aatctcaatg tgctcattca    8160
tagtttattt tgctcgacct ttctttaatc aatagctttg atgtactgat tactttataa    8220
agttaagaag taagttctgc tctttaaact gtactgaatg gaggcttctc tgcataatta    8280
agcaaacact ctgatgattg agtttcgttg tacaaaggaa agttttttgcc ttagttagaa    8340 attcatcttg tttctttgcc cagaagctgg cttgctgata gaatttggac tacgctacgt    8400
tttcttgggt gaaaaacaat ccgcgtcctt ccacgagaac agtgaaactg tacgatgttc    8460
```

-continued

```
ttattgtatt gtgtcaacag cccataatca atgaaatggg cctcaatgac agtataagcc    8520
gaaaaatatt cgaatgcgat ctagaactaa tctgaaacca aacttctcaa atcattaaca    8580
tttgattagg gcctaaaagt ccatccgtat tttaaaaaaa agttgataac aaatgcaaaa    8640
atacaaatat acattactat taaaactcaa tctttctgat tatatgtgga tggagaagct    8700
gttttgcagt gtggatttga attttgaagt tcttgttcaa aaaagaaaag aaacttggtc    8760
aagcttcaaa agaaagaaag aaataaagac aagtatacaa atacgttgac ttcaattaat    8820
atgaagatag aagagaaaga tatagaaatg cgttttaaat tggcggtggg agatatgtga    8880
ttcccttggt cccgctttct cgtttgattc ggtaacctaa accttctcca tccaagaaga    8940
cacaaacaag gaagaaatta acctacgtac gtacatcatt tgaactactt atatctatta    9000
taaatggaaa atctattttc ttcttctctc tcttttaacc gaaaaaggaa aagtcctcga    9060
aataactctt taatataatt catgtggaaa ccttctatat attttttgca tgcttttttg    9120
aaattaagta atggcatact aattagaaga agacgaaaaa taatatgtct aagtaattga    9180
gtttcgtggt caaggcaaat caagattgca ttctttaatt aagtgtacaa attatgatgt    9240
aagaaccgtt atttggcata acctaatata tattaaaaac tgattttttt ttttttttaac    9300 ttctgtaaga aatggttttc ttaattacca atcatgatct attattgtaa aatgtgtaat    9360
tttgtgttgc gattgaagtg ttcttagata aagatatgtc atatgcatga tatcatctat    9420
ttgattttga gaaaataaaa acataacatg agaacatcgt agagagtaag atacatgaca    9480
aagagaaaga ataagctaag aagtcatcca aaaattggga ggcctactct caactaccaa    9540
aaatacaagt gtttgttgtg ttaggtcatt tattcagtca cctaacccta actatatgaa    9600
atacgttaaa attcatatat agaaaaataa agaagaaata ctattagtca atataatttt    9660
ttttaacaaa ataaaaataa agaaagaaac actattagtc aatgaattaa aaaaaaaaaa    9720
atccatcttt cgatcaagac cgtccaagta ttctcctttc acataactct tacgttttac    9780
actaaacaag acgagatttt tatgagcttg tggctcccac aacaatcctc attgatttct    9840
ccatatatat cacatgagaa tccaactcga cttcatacta acattcatcc caaaagttcc    9900 attcttttc acaaagccat tgtgctgttt tctccatttg gatcaaagca agtttgtaca    9960
aaaaagcagg ctccatggga agatcacctt gttgtgataa aaatggagtg aagaagggac   10020
catggactgc tgaggaggat cagaaactca tcgattatat tcgatttcat ggtcctggca   10080
attggcgtac gctccccaaa aatgctggta cgtataaact acacaccgtt ccttatattt   10140
tgttctcata gattaatata tatgttctct atttattgag tcacacactt ataagtcgta   10200
ttgtacaaat taaaggactc catagatgtg gaaaaagctg ccgtcttcga tggaccaatt   10260
atctaagacc ggacatcaag agaggaagat tctcgttcga ggaagaagaa actatcattc   10320
agctacacag tgttatggga aacaagtaag cctgatcatt cacaccataa tttttgtctg   10380
aaattcatat tcatcagcta catgcttttg tatgttaatt aatgtaaaac tcaaaaaggg   10440
agagtgtacg tttgcatgcg ggggtacatg tcaaatgtag gccatcaact ccaataaact   10500
attattagta ctttactagt acgtattgac ctatattaga ataataataa aggagttttg   10560
tattgatcat agattaatgt cactaatatt gaattgatga atattaggtg gtcagcaata   10620
gccgctcgtc taccagggag gaccgataac gaaataaaaa accattggaa cactcacatc   10680
cgcaagagac ttgtaaggag tggtatcgac cctgttactc attctccacg ccttgatctt   10740
cttgatttgt cctcactttt gagtgcactt ttcaaccagc caaacttttc agcagttgca   10800
acacatgcgt cttctcttct taatcctgat gtattgaggt tggcctctct actactgcca   10860
```

-continued

```
cttcaaaacc ctaatccagt ttacccatcg aacctcgacc aaaatcttca aactccaaat    10920
acatcatcag aatcgtctca accacaagct gagactagta cagtcccaac aaactatgaa    10980
acttcatcat tggagcctat gaacgcaaga ctcgacgacg ttggtcttgc agatgtatta    11040
ccacctttgt cagagagttt tgacttagac tcgctcatgt caacgccaat gtcttctcca    11100
cgacaaaata gcattgaagc agaaaccaac tccagcactt tcttcgactt tggaattccg    11160
gaagatttca tcttagatga ctttatgttt gacccagctt tcttgtacaa agtggcctaa    11220
ttttcaacat ttgcatacac atgtcttgct ttcacacata tgattctttg ttgcattctt    11280 tctttttgttt gatgtataaa tttcttgttt ttattctctc aaaagatatt aagttattag    11340
tctataaaat tttcatgaat gtttatgtat tatctgctta ggcgagatat ctaaattctg    11400
ctccattagt ccatatacac agttgacgga agcaaacata gaattattag cgtcaaacac    11460
atcacatatt catattgctt tgttcgaatc atcgtcaatc aagttaatca gtttatgcga    11520
gttctatcat ttaggcccaa ttcaaggccc aattcaagtt cattttaaag ccgttaattt    11580
ggccagcaac tttattatac atagttgata attcactggc cgtcgtttta caacgtcgtg    11640
actgggaaaa cgatctaact gactagccgc ggccatggcg gccgggagcg gccatgctag    11700
agtccgcaaa aatcaccagt ctctctctac aaatctatct ctctcatttt ttctccagaa    11760
taatgtgtga gtagttccca gataagggaa ttagggttct tatagggttt cgctcatgtg    11820
ttgagcatat aagaaaccct tagtatgtat ttgtatttgt aaaatacttc tatcaataaa    11880
atttctaatt cctaaaacca aaatccagtg acctgcaggt cgaccatatg ggag          11934
```

```
<210> SEQ ID NO 10
<211> LENGTH: 12070
<212> TYPE: DNA
<213> ORGANISM: Artificial Sequence
<220> FEATURE:
<223> OTHER INFORMATION: proGPAT5::MYB41 construct

<400> SEQUENCE: 10
```

```
agctcgaatt atcatacatg agaattaagg gagtcacgtt atgacccccg ccgatgacgc     60
gggacaagcc gttttacgtt tggaactgac agaaccgcaa cgttgaagga gccactgagc    120
cgcgggtttc tggagtttaa tgagctaagc acatacgtca gaaaccatta ttgcgcgttc    180
aaaagtcgcc taaggtcact atcagctagc aaatatttct tgtcaaaaat gctccactga    240
cgttccataa attcccctcg gtatccaatt agagtctcat attcactctc aactcgatcg    300
aggggatcta ccatgagccc agaacgacgc ccggccgaca tccgccgtgc caccgaggcg    360
gacatgccgg cggtctgcac catcgtcaac cactacatcg agacaagcac ggtcaacttc    420
cgtaccgagc gcaggaacc gcaggagtgg acggacgacc tcgtccgtct gcgggagcgc    480
tatccctggc tcgtcgccga ggtggacggc gaggtcgccg gcatcgccta cgcgggtccc    540
tggaaggcac gcaacgccta cgactggacg gccgagtcga ccgtgtacgt ctcccccgc     600 caccagcgga cgggactggg ctccacgctc tacacccacc tgctgaagtc cctggaggca    660
cagggcttca agagcgtggt cgctgtcatc gggctgccca cgacccgag cgtgcgcatg    720 cacgaggcgc tcggatatgc cccccgcggc atgctgcggg cggccggctt caagcacggg    780
aactggcatg acgtgggttt ctggcagctg gacttcagcc tgccggtgcc gccccgtccg    840
gtcctgcccg tcaccgaaat ctgatgacc ctagagtcaa gcagatcgtt caaacatttg     900
gcaataaagt ttcttaagat tgaatcctgt tgccggtctt gcgatgatta tcatataatt    960
```

```
tctgttgaat tacgttaagc atgtaataat taacatgtaa tgcatgacgt tatttatgag    1020
atgggttttt atgattagag tcccgcaatt atacatttaa tacgcgatag aaaacaaaat    1080
atagcgcgca aactaggata aattatcgcg cgcggtgtca tctatatgtt actagatcga    1140
ccggcatgca agctgataat tcaattcggc gttaattcag tacattaaaa acgtccgcaa    1200
tgtgttatta agttgtctaa gcgtcaattt gtttacacca caatatatcc tgccaccagc    1260
cagccaacag ctccccgacc ggcagctcgg cacaaaatca ccactcgata caggcagccc    1320
atcagtccgg gacggcgtca gcgggagagc cgttgtaagg cggcagactt tgctcatgtt    1380
accgatgcta ttcggaagaa cggcaactaa gctgccgggt ttgaaacacg gatgatctcg    1440
cggagggtag catgttgatt gtaacgatga cagagcgttg ctgcctgtga tcaattcggg    1500
cacgaaccca gtggacataa gcctcgttcg gttcgtaagc tgtaatgcaa gtagcgtaac    1560
tgccgtcacg caactggtcc agaaccttga ccgaacgcag cggtggtaac ggcgcagtgg    1620 cggtttttcat ggcttcttgt tatgacatgt ttttttgggg tacagtctat gcctcgggca   1680
tccaagcagc aagcgcgtta cgccgtgggt cgatgtttga tgttatggag cagcaacgat    1740
gttacgcagc agggcagtcg ccctaaaaca aagttaaaca tcatgggggga agcggtgatc    1800 gccgaagtat cgactcaact atcagaggta gttggcgtca tcgagcgcca tctcgaaccg    1860
acgttgctgg ccgtacattt gtacggctcc gcagtggatg gcggcctgaa gccacacagt    1920
gatattgatt tgctggttac ggtgaccgta aggcttgatg aaacaacgcg gcgagctttg    1980
atcaacgacc ttttggaaac ttcggcttcc cctggagaga gcgagattct ccgcgctgta    2040
gaagtcacca ttgttgtgca cgacgacatc attccgtggc gttatccagc taagcgcgaa    2100
ctgcaatttg gagaatggca gcgcaatgac attcttgcag gtatcttcga gccagccacg    2160
atcgacattg atctggctat cttgctgaca aaagcaagag aacatagcgt tgccttggta    2220
ggtccagcgg cggaggaact ctttgatccg gttcctgaac aggatctatt tgaggcgcta    2280
aatgaaacct taacgctatg gaactcgccg cccgactggg ctggcgatga gcgaaatgta    2340
gtgcttacgt tgtcccgcat ttggtacagc gcagtaaccg gcaaaatcgc gccgaaggat    2400
gtcgctgccg actgggcaat ggagcgcctg ccggcccagt atcagcccgt catacttgaa    2460
gctagacagg cttatcttgg acaagaagaa gatcgcttgg cctcgcgcgc agatcagttg    2520
gaagaatttg tccactacgt gaaaggcgag atcaccaagg tagtcggcaa ataatgtcta    2580
gctagaaatt cgttcaagcc gacgccgctt cgccggcgtt aactcaagcg attagatgca    2640
ctaagcacat aattgctcac agccaaacta tcaggtcaag tctgctttta ttatttttaa    2700
gcgtgcataa taagccctac acaaattggg agatatatca tgcatgacca aaatccctta    2760
acgtgagttt tcgttccact gagcgtcaga ccccgtagaa aagatcaaag gatcttcttg    2820
agatcctttt tttctgcgcg taatctgctg cttgcaaaca aaaaaaccac cgctaccagc    2880
ggtggtttgt ttgccggatc aagagctacc aactcttttt ccgaaggtaa ctggcttcag    2940
cagagcgcag ataccaaata ctgtccttct agtgtagccg tagttaggcc accacttcaa    3000
gaactctgta gcaccgccta catacctcgc tctgctaatc ctgttaccag tggctgctgc    3060
cagtggcgat aagtcgtgtc ttaccgggtt ggactcaaga cgatagttac cggataaggc    3120
gcagcggtcg ggctgaacgg ggggttcgtg cacacagccc agcttggagc gaacgaccta    3180
caccgaactg agatacctac agcgtgagct atgagaaagc gccacgcttc ccgaagggag    3240
aaaggcggac aggtatccgg taagcggcag ggtcggaaca ggagagcgca cgagggagct    3300 tccagggggga aacgcctggt atctttatag tcctgtcggg tttcgccacc tctgacttga    3360
```

-continued

```
gcgtcgattt ttgtgatgct cgtcaggggg gcggagccta tggaaaaacg ccagcaacgc    3420 ggcctttta  cggttcctgg  cctttttgctg gcctttttgct cacatgttct ttcctgcgtt    3480
atcccctgat  tctgtggata accgtattac cgcctttgag tgagctgata ccgctcgccg    3540
cagccgaacg accgagcgca gcgagtcagt gagcgaggaa gcggaagagc gcctgatgcg    3600
gtattttctc cttacgcatc tgtgcggtat ttcacaccgc atatggtgca ctctcagtac    3660
aatctgctct gatgccgcat agttaagcca gtatacactc cgctatcgct acgtgactgg    3720
gtcatggctg cgccccgaca cccgccaaca cccgctgacg cgccctgacg ggcttgtctg    3780
ctcccggcat ccgcttacag acaagctgtg accgtctccg ggagctgcat gtgtcagagg    3840
ttttcaccgt catcaccgaa acgcgcgagg cagggtgcct tgatgtgggc gccggcggtc    3900
gagtggcgac ggcgcggctt gtccgcgccc tggtagattg cctggccgta ggccagccat    3960
ttttgagcgg ccagcggccg cgataggccg acgcgaagcg gcggggcgta gggagcgcag    4020
cgaccgaagg gtaggcgctt tttgcagctc ttcggctgtg cgctggccag acagttatgc    4080
acaggccagg cgggttttaa gagtttttaat aagtttttaaa gagtttttagg cggaaaaatc    4140 gcctttttttc tcttttatat cagtcactta catgtgtgac cggttcccaa tgtacggctt    4200
tgggttccca atgtacgggt tccggttccc aatgtacggc tttgggttcc caatgtacgt    4260
gctatccaca ggaaagagac cttttcgacc ttttttcccct gctagggcaa tttgccctag    4320
catctgctcc gtacattagg aaccggcgga tgcttcgccc tcgatcaggt tgcggtagcg    4380
catgactagg atcgggccag cctgccccgc ctcctccttc aaatcgtact ccggcaggtc    4440
atttgacccg atcagcttgc gcacggtgaa acagaacttc ttgaactctc cggcgctgcc    4500
actgcgttcg tagatcgtct tgaacaacca tctggcttct gccttgcctg cggcgcggcg    4560
tgccaggcgg tagagaaaac ggccgatgcc gggatcgatc aaaaagtaat cggggtgaac    4620
cgtcagcacg tccgggttct tgccttctgt gatctcgcgg tacatccaat cagctagctc    4680
gatctcgatg tactccggcc gcccggtttc gctctttacg atcttgtagc ggctaatcaa    4740 ggcttcacccc tcggataccg tcaccaggcg gccgttcttg gccttcttcg tacgctgcat    4800
ggcaacgtgc gtggtgttta accgaatgca ggtttctacc aggtcgtctt tctgctttcc    4860
gccatcggct cgccggcaga acttgagtac gtccgcaacg tgtggacgga acacgcggcc    4920
gggcttgtct cccttccctt cccggtatcg gttcatggat tcggttagat gggaaaccgc    4980
catcagtacc aggtcgtaat cccacacact ggccatgccg gccggccctg cggaaacctc    5040
tacgtgcccg tctggaagct cgtagcggat cacctcgcca gctcgtcggt cacgcttcga    5100
cagacggaaa acggccacgt ccatgatgct gcgactatcg cgggtgccca cgtcatagag    5160
catcggaacg aaaaaatctg gttgctcgtc gcccttgggc ggcttcctaa tcgacggcgc    5220
accggctgcc ggcggttgcc gggattcttt gcggattcga tcagcggccg cttgccacga    5280
ttcaccgggg cgtgcttctg cctcgatgcg ttgccgctgg gcggcctgcg cggccttcaa    5340
cttctccacc aggtcatcac ccagcgccgc gccgatttgt accgggccgg atggtttgcg    5400
accgtcacgc cgattcctcg ggcttggggg ttccagtgcc attgcagggc cggcagacaa    5460
cccagccgct tacgcctggc caaccgcccg ttcctccaca catggggcat tccacggcgt    5520
cggtgcctgg ttgttcttga ttttccatgc cgcctccttt agccgctaaa attcatctac    5580
tcatttattc atttgctcat ttactctggt agctgcgcga tgtattcaga tagcagctcg    5640
gtaatggtct tgccttggcg taccgcgtac atcttcagct tggtgtgatc ctccgccggc    5700
```

```
aactgaaagt tgacccgctt catggctggc gtgtctgcca ggctggccaa cgttgcagcc     5760
ttgctgctgc gtgcgctcgg acggccggca cttagcgtgt ttgtgctttt gctcattttc     5820
tctttacctc attaactcaa atgagttttg atttaatttc agcggccagc gcctggacct     5880
cgcgggcagc gtcgccctcg ggttctgatt caagaacggt tgtgccggcg gcggcagtgc     5940
ctgggtagct cacgcgctgc gtgatacggg actcaagaat gggcagctcg tacccggcca     6000
gcgcctcggc aacctcaccg ccgatgcgcg tgcctttgat cgcccgcgac acgacaaagg     6060
ccgcttgtag ccttccatcc gtgacctcaa tgcgctgctt aaccagctcc accaggtcgg     6120
cggtggccca tatgtcgtaa gggcttggct gcaccggaat cagcacgaag tcggctgcct     6180
tgatcgcgga cacagccaag tccgccgcct ggggcgctcc gtcgatcact acgaagtcgc     6240
gccggccgat ggccttcacg tcgcggtcaa tcgtcgggcg gtcgatgccg acaacggtta     6300
gcggttgatc ttcccgcacg gccgcccaat cgcgggcact gccctgggga tcggaatcga     6360
ctaacagaac atcggccccg gcgagttgca gggcgcgggc tagatgggtt gcgatggtcg     6420
tcttgcctga cccgcctttc tggttaagta cagcgataac cttcatgcgt tccccttgcg     6480
tatttgttta tttactcatc gcatcatata cgcagcgacc gcatgacgca agctgttttta    6540 ctcaaataca catcaccttt ttagacggcg gcgctcggtt tcttcagcgg ccaagctggc     6600
cggccaggcc gccagcttgg catcagacaa accggccagg atttcatgca gccgcacggt     6660
tgagacgtgc gcgggcggct cgaacacgta cccggccgcg atcatctccg cctcgatctc     6720
ttcggtaatg aaaaacggtt cgtcctggcc gtcctggtgc ggtttcatgc ttgttcctct     6780
tggcgttcat tctcggcggc cgccaggcg tcggcctcgg tcaatgcgtc ctcacggaag     6840
gcaccgcgcc gcctggcctc ggtgggcgtc acttcctcgc tgcgctcaag tgcgcggtac     6900
agggtcgagc gatgcacgcc aagcagtgca gccgcctctt tcacggtgcg gccttcctgg     6960
tcgatcagct cgcgggcgtg cgcgatctgt gccggggtga gggtagggcg ggggccaaac     7020
ttcacgcctc gggccttggc ggcctcgcgc ccgctccggg tgcggtcgat gattagggaa     7080
cgctcgaact cggcaatgcc ggcgaacacg gtcaacacca tgcggccggc cggcgtggtg     7140
gtgtcggccc acggctctgc caggctacgc aggcccgcgc cggcctcctg gatgcgctcg     7200
gcaatgtcca gtaggtcgcg ggtgctgcgg gccaggcggt ctagcctggt cactgtcaca     7260
acgtcgccag ggcgtaggtg gtcaagcatc ctggccagct ccgggcggtc gcgcctggtg     7320
ccggtgatct tctcggaaaa cagcttggtg cagccggccg cgtgcagttc ggcccgttgg     7380
ttggtcaagt cctggtcgtc ggtgctgacg cgggcatagc ccagcaggcc agcggcggcg     7440
ctcttgttca tggcgtaatg tctccggttc tagtcgcaag tattctactt tatgcgacta     7500
aaacacgcga caagaaaacg ccaggaaaag ggcaggcggg cagcctgtcg cgtaacttag     7560
gacttgtgcg acatgtcgtt ttcagaagac ggctgcactg aacgtcagaa gccgactgca     7620
ctatagcagc ggaggggttg gatcaaagta ctttgatccc gagggaacc ctgtggttgg     7680 catgcacata caaatggacg aacggataaa ccttttcacg cccttttaaa tatccgttat     7740
tctaataaac gctctttct cttaggttta cccgccaata tatcctgtca aacactgata     7800
gtttaaactg aaggcgggaa acgacaatct gatccaagct caagctaagc ttgggcccga     7860
gcggataaca atttcacaca ggaaacagct atgaccatga ttacgccaag ctatcaactt     7920
tgtatagaaa agttgcctga tcgcaaacgt caatggtcta tatccatctc ttggggatac     7980
accattcaga tatacactta cttcttgact gctacggagc tgactacgcc gttgcagacc     8040
ttcaaaactt ggcggtcttc cagcgatgga cctttcgtgt ttaacactcg gcccttgaaa     8100
```

-continued

```
cctgacccct gtgagcgtcc ggtcacttat ttcatggatg gtgccgagga tgtacgggat    8160
agtgggacga aaacttggta tagcataggg gataagaact atggtcattg cggaaagatt    8220
gagcatactc gattaactaa agtgaagagg atattggtga cttcaatgaa gacggatcct    8280
gagtattgga acaaggtact tagtgtttgt atatttctca tattgaattt aacattttgg    8340
gtgagtttag gttacatctt tttttttatt ttttgctttt gttgataggc accgaggaga    8400
cagtgttgtg aggtgatgga aggaaaagta ggaaaaagaa aagagaaaga aatgttgtta    8460
aggattagaa aatgcagatc tttggagaag atataaaaaa agcgttttaa ttagagagat    8520
ttttgcacat acagatttag attcgatcat tagttatttg tttctaaatt cctcaattcc    8580
tagtaccaag agaatgacga ttttctctag taatactggc actcttcgtt tttcaacatg    8640
taaacattac tttgtataat tagtctatat caaataaata gttacaacat gaacgtaact    8700
atttatacac gagggtaaat ttttaacaaa tttaaaccga accaaaaaga tttcagttaa    8760
tcatagtttt gttacaagcg aaatctgaaa tattcaccct caagtttgtt acgtaattgt    8820
ctaatctgtg ttttttttgtg ctagtgttat aattgtttcc tcgaatgtta agcaccacat    8880
agaagtatac acttttcttt tattattttc gttcttcttc catttagaaa cttttattaa    8940
ttctactgtt aaatccaacg ttattagttt attttctctg atgaagttct aattttttttt    9000 gtttgttgga aaaagggtta cttttctgat gaagttgccg atttgtttcc aaccaaacct    9060
cagctaatat agttagggag acggataaga aattgcataa agggagaggc tttgtaaaca    9120
cgcaagttta cgtcaacttg acacatataa actcgtatat aggaattgtg taaaatgtta    9180
atcaatatat gtttatgaat atagtccttt tatttcctta atctatagtc atgttatcat    9240
catatcggca agaaaattac tattacaaca tatgtttccg tgcttcgatt tgtcgatcag    9300
gtaggcaacc aaaccgggcc agattagtca caaatgaaat taggctccac tttggcaagt    9360
tttttcacaa ttaaaaatta gaaagtctaa ccaaactaat agaaactgaa ccaaacaaaa    9420
atgttcacgc aattacgtag cacttctcta tgaaatactg tggataattc gatttgagct    9480
aatctatggt aagtcgtttc tctcaaactg aattaagcta aaccaaaccg aaaataaacc    9540
gttgtagaac acccataata aacatatata tgttctctac tcttatttgg ctattttttcc    9600 atttgcagat acgtgtgaca acattccaaa tataggcaca tgatacaaat tacaaagcca    9660
gaaattataa tttataaact atacataata aggtcagtag cctaattaca tccatatatt    9720
tagttgggca taataaggat agcctaattt tggtgcatcc cgccaaaaat tcggacaaat    9780
ggtgaatttc aaaccatgaa tttctttgtt atacatacat tacgtgcact attacatcaa    9840
agaaaaatag tgacgtgcat aaacgtattt tcttcacata atctatatat aatatataca    9900
gccatgtaca tttttcaaca tagaaaaatc atgtatacaa atacggtagg tgcaatactg    9960
ataaactgcc attcccattg cattagacgc tagtcaatcc aaaccttata acataaaaag   10020
ttatagtcca tttctttcat atccaatcga gtcaaaataa tattcgagca aaaaacaaaa   10080
gaagcaagtt tgtacaaaaa agcaggctcc atgggaagat caccttgttg tgataaaaat   10140
ggagtgaaga agggaccatg gactgctgag gaggatcaga aactcatcga ttatattcga   10200
tttcatggtc ctggcaattg gcgtacgctc cccaaaaatg ctggtacgta taaactacac   10260
accgttcctt atattttgtt ctcatagatt aatatatatg ttctctattt attgagtcac   10320
acacttataa gtcgtattgt acaaattaaa ggactccata gatgtggaaa aagctgccgt   10380
cttcgatgga ccaattatct aagaccggac atcaagagag gaagattctc gttcgaggaa   10440
```

```
gaagaaacta tcattcagct acacagtgtt atgggaaaca agtaagcctg atcattcaca    10500
ccataatttt tgtctgaaat tcatattcat cagctacatg cttttgtatg ttaattaatg    10560
taaaactcaa aaagggagag tgtacgtttg catgcggggg tacatgtcaa atgtaggcca    10620
tcaactccaa taaactatta ttagtacttt actagtacgt attgacctat attagaataa    10680
taataaagga gttttgtatt gatcatagat taatgtcact aatattgaat tgatgaatat    10740
taggtggtca gcaatagccg ctcgtctacc agggaggacc gataacgaaa taaaaaacca    10800
ttggaacact cacatccgca agagacttgt aaggagtggt atcgaccctg ttactcattc    10860
tccacgcctt gatcttcttg atttgtcctc acttttgagt gcacttttca accagccaaa    10920
cttttcagca gttgcaacac atgcgtcttc tcttcttaat cctgatgtat tgaggttggc    10980
ctctctacta ctgccacttc aaaaccctaa tccagtttac ccatcgaacc tcgaccaaaa    11040
tcttcaaact ccaaatacat catcagaatc gtctcaacca caagctgaga ctagtacagt    11100
cccaacaaac tatgaaactt catcattgga gcctatgaac gcaagactcg acgacgttgg    11160
tcttgcagat gtattaccac ctttgtcaga gagttttgac ttagactcgc tcatgtcaac    11220
gccaatgtct tctccacgac aaaatagcat tgaagcagaa accaactcca gcactttctt    11280
cgactttgga attccggaag atttcatctt agatgacttt atgtttgacc cagctttctt    11340
gtacaaagtg gcctaatttt caacatttgc atacacatgt cttgctttca cacatatgat    11400
tctttgttgc attctttctt ttgtttgatg tataaatttc ttgtttttat tctctcaaaa    11460
gatattaagt tattagtcta taaaattttc atgaatgttt atgtattatc tgcttaggcg    11520
agatatctaa attctgctcc attagtccat atacacagtt gacggaagca aacatagaat    11580
tattagcgtc aaacacatca catattcata ttgctttgtt cgaatcatcg tcaatcaagt    11640
taatcagttt atgcgagttc tatcatttag gcccaattca aggcccaatt caagttcatt    11700
ttaaagccgt taatttggcc agcaacttta ttatacatag ttgataattc actggccgtc    11760
gttttacaac gtcgtgactg ggaaaacgat ctaactgact agccgcggcc atggcggccg    11820
ggagcggcca tgctagagtc cgcaaaaatc accagtctct ctctacaaat ctatctctct    11880
ctatttttct ccagaataat gtgtgagtag ttcccagata agggaattag ggttcttata    11940
gggtttcgct catgtgttga gcatataaga aacccttagt atgtatttgt atttgtaaaa    12000
tacttctatc aataaaattt ctaattccta aaaccaaaat ccagtgacct gcaggtcgac    12060
catatgggag                                                           12070
```

```
<210> SEQ ID NO 11
<211> LENGTH: 11573
<212> TYPE: DNA
<213> ORGANISM: Artificial Sequence
<220> FEATURE:
<223> OTHER INFORMATION: proRALPH::MYB41 construct

<400> SEQUENCE: 11
```

```
agctcgaatt atcatacatg agaattaagg gagtcacgtt atgacccccg ccgatgacgc      60
gggacaagcc gttttacgtt tggaactgac agaaccgcaa cgttgaagga gccactgagc     120
cgcgggtttc tggagtttaa tgagctaagc acatacgtca gaaaccatta ttgcgcgttc     180
aaaagtcgcc taaggtcact atcagctagc aaatatttct tgtcaaaaat gctccactga     240
cgttccataa attcccctcg gtatccaatt agagtctcat attcactctc aactcgatcg     300
aggggatcta ccatgagccc agaacgacgc ccggccgaca tccgccgtgc caccgaggcg     360
gacatgccgg cggtctgcac catcgtcaac cactacatcg agacaagcac ggtcaacttc     420
```

-continued

```
cgtaccgagc cgcaggaacc gcaggagtgg acggacgacc tcgtccgtct gcgggagcgc      480
tatccctggc tcgtcgccga ggtggacggc gaggtcgccg gcatcgccta cgcgggtccc      540
tggaaggcac gcaacgccta cgactggacg gccgagtcga ccgtgtacgt ctccccccgc      600
caccagcgga cgggactggg ctccacgctc tacacccacc tgctgaagtc cctggaggca      660
cagggcttca agagcgtggt cgctgtcatc gggctgccca acgacccgag cgtgcgcatg      720
cacgaggcgc tcggatatgc cccccgcggc atgctgcggg cggccggctt caagcacggg      780
aactggcatg acgtgggttt ctggcagctg gacttcagcc tgccggtgcc gccccgtccg      840
gtcctgcccg tcaccgaaat ctgatgaccc ctagagtcaa gcagatcgtt caaacatttg      900
gcaataaagt ttcttaagat tgaatcctgt tgccggtctt gcgatgatta tcatataatt      960
tctgttgaat tacgttaagc atgtaataat taacatgtaa tgcatgacgt tatttatgag     1020
atgggttttt atgattagag tcccgcaatt atacatttaa tacgcgatag aaaacaaaat     1080
atagcgcgca aactaggata aattatcgcg cgcggtgtca tctatatgtt actagatcga     1140
ccggcatgca agctgataat tcaattcggc gttaattcag tacattaaaa acgtccgcaa     1200
tgtgttatta agttgtctaa gcgtcaattt gtttacacca caatatatcc tgccaccagc     1260
cagccaacag ctccccgacc ggcagctcgg cacaaaatca ccactcgata caggcagccc     1320
atcagtccgg gacggcgtca gcgggagagc cgttgtaagg cggcagactt tgctcatgtt     1380
accgatgcta ttcggaagaa cggcaactaa gctgccgggt ttgaaacacg gatgatctcg     1440
cggagggtag catgttgatt gtaacgatga cagagcgttg ctgcctgtga tcaattcggg     1500
cacgaaccca gtggacataa gcctcgttcg gttcgtaagc tgtaatgcaa gtagcgtaac     1560
tgccgtcacg caactggtcc agaaccttga ccgaacgcag cggtggtaac ggcgcagtgg     1620
cggttttcat ggcttcttgt tatgacatgt ttttttgggg tacagtctat gcctcgggca     1680
tccaagcagc aagcgcgtta cgccgtgggt cgatgtttga tgttatggag cagcaacgat     1740
gttacgcagc agggcagtcg ccctaaaaca aagttaaaca tcatggggga agcggtgatc     1800
gccgaagtat cgactcaact atcagaggta gttggcgtca tcgagcgcca tctcgaaccg     1860
acgttgctgg ccgtacattt gtacggctcc gcagtggatg gcggcctgaa gccacacagt     1920
gatattgatt tgctggttac ggtgaccgta aggcttgatg aaacaacgcg gcgagctttg     1980
atcaacgacc ttttggaaac ttcggcttcc cctggagaga gcgagattct ccgcgctgta     2040
gaagtcacca ttgttgtgca cgacgacatc attccgtggc gttatccagc taagcgcgaa     2100
ctgcaatttg gagaatggca gcgcaatgac attcttgcag gtatcttcga gccagccacg     2160
atcgacattg atctggctat cttgctgaca aaagcaagag aacatagcgt tgccttggta     2220
ggtccagcgg cggaggaact ctttgatccg gttcctgaac aggatctatt tgaggcgcta     2280
aatgaaacct taacgctatg gaactcgccg cccgactggg ctggcgatga gcgaaatgta     2340
gtgcttacgt tgtcccgcat ttggtacagc gcagtaaccg gcaaaatcgc gccgaaggat     2400
gtcgctgccg actgggcaat ggagcgcctg ccggcccagt atcagcccgt catacttgaa     2460
gctagacagg cttatcttgg acaagaagaa gatcgcttgg cctcgcgcgc agatcagttg     2520
gaagaatttg tccactacgt gaaaggcgag atcaccaagg tagtcggcaa ataatgtcta     2580
gctagaaatt cgttcaagcc gacgccgctt cgccggcgtt aactcaagcg attagatgca     2640
ctaagcacat aattgctcac agccaaacta tcaggtcaag tctgctttta ttattttttaa     2700 gcgtgcataa taagccctac acaaattggg agatatatca tgcatgacca aaatccctta     2760
```

```
acgtgagttt tcgttccact gagcgtcaga ccccgtagaa aagatcaaag gatcttcttg    2820
agatcctttt tttctgcgcg taatctgctg cttgcaaaca aaaaaaccac cgctaccagc    2880
ggtggtttgt ttgccggatc aagagctacc aactcttttt ccgaaggtaa ctggcttcag    2940
cagagcgcag ataccaaata ctgtccttct agtgtagccg tagttaggcc accacttcaa    3000
gaactctgta gcaccgccta cataccctcgc tctgctaatc ctgttaccag tggctgctgc    3060
cagtggcgat aagtcgtgtc ttaccgggtt ggactcaaga cgatagttac cggataaggc    3120
gcagcggtcg ggctgaacgg ggggttcgtg cacacagccc agcttggagc gaacgaccta    3180
caccgaactg agatacctac agcgtgagct atgagaaagc gccacgcttc ccgaagggag    3240
aaaggcggac aggtatccgg taagcggcag ggtcggaaca ggagagcgca cgagggagct    3300 tccagggggga aacgcctggt atctttatag tcctgtcggg tttcgccacc tctgacttga    3360
gcgtcgattt ttgtgatgct cgtcaggggg gcggagccta tggaaaaacg ccagcaacgc    3420
ggccttttta cggttcctgg cctttttgctg gcctttttgct cacatgttct ttcctgcgtt    3480
atcccctgat tctgtggata accgtattac cgcctttgag tgagctgata ccgctcgccg    3540
cagccgaacg accgagcgca gcgagtcagt gagcgaggaa gcggaagagc gcctgatgcg    3600
gtattttctc cttacgcatc tgtgcggtat ttcacaccgc atatggtgca ctctcagtac    3660
aatctgctct gatgccgcat agttaagcca gtatacactc cgctatcgct acgtgactgg    3720
gtcatggctg cgccccgaca cccgccaaca cccgctgacg cgccctgacg ggcttgtctg    3780
ctcccggcat ccgcttacag acaagctgtg accgtctccg ggagctgcat gtgtcagagg    3840
ttttcaccgt catcaccgaa acgcgcgagg caggtgcct tgatgtgggc gccggcggtc    3900
gagtggcgac ggcgcggctt gtccgcgccc tggtagattg cctggccgta ggccagccat    3960
ttttgagcgg ccagcggccg cgataggccg acgcgaagcg gcggggcgta gggagcgcag    4020
cgaccgaagg gtaggcgctt tttgcagctc ttcggctgtg cgctggccag acagttatgc    4080
acaggccagg cgggttttaa gagtttttaat aagttttaaa gagtttttagg cggaaaaatc    4140 gccttttttc tcttttatat cagtcactta catgtgtgac cggttcccaa tgtacggctt    4200
tgggttccca atgtacgggt tccggttccc aatgtacggc tttgggttcc caatgtacgt    4260
gctatccaca ggaaagagac ctttttcgacc ttttttcccct gctagggcaa tttgccctag    4320
catctgctcc gtacattagg aaccggcgga tgcttcgccc tcgatcaggt tgcggtagcg    4380
catgactagg atcgggccag cctgccccgc ctcctccttc aaatcgtact ccggcaggtc    4440
atttgacccg atcagcttgc gcacggtgaa acagaacttc ttgaactctc cggcgctgcc    4500
actgcgttcg tagatcgtct tgaacaacca tctggcttct gccttgcctg cggcgcggcg    4560
tgccaggcgg tagagaaaac ggccgatgcc gggatcgatc aaaaagtaat cggggtgaac    4620
cgtcagcacg tccgggttct tgccttctgt gatctcgcgg tacatccaat cagctagctc    4680
gatctcgatg tactccggcc gcccggtttc gctctttacg atcttgtagc ggctaatcaa    4740
ggcttcaccc tcggataccg tcaccaggcg gccgttcttg gccttcttcg tacgctgcat    4800
ggcaacgtgc gtggtgttta accgaatgca ggtttctacc aggtcgtctt tctgctttcc    4860
gccatcggct cgccggcaga acttgagtac gtccgcaacg tgtggacgga acacgcggcc    4920
gggcttgtct cccttcccct cccggtatcg gttcatggat tcggttagat gggaaaccgc    4980
catcagtacc aggtcgtaat cccacacact ggccatgccg gccggccctg cggaaacctc    5040
tacgtgcccg tctggaagct cgtagcggat cacctcgcca gctcgtcggt cacgcttcga    5100
cagacggaaa acggccacgt ccatgatgct gcgactatcg cgggtgccca cgtcatagag    5160
```

-continued

```
catcggaacg aaaaaatctg gttgctcgtc gcccttgggc ggcttcctaa tcgacggcgc   5220
accggctgcc ggcggttgcc gggattcttt gcggattcga tcagcggccg cttgccacga   5280
ttcaccgggg cgtgcttctg cctcgatgcg ttgccgctgg gcggcctgcg cggccttcaa   5340
cttctccacc aggtcatcac ccagcgccgc gccgatttgt accgggccgg atggtttgcg   5400
accgtcacgc cgattcctcg ggcttggggg ttccagtgcc attgcagggc cggcagacaa   5460
cccagccgct tacgcctggc caaccgcccg ttcctccaca catggggcat tccacggcgt   5520
cggtgcctgg ttgttcttga ttttccatgc cgcctccttt agccgctaaa attcatctac   5580
tcatttattc atttgctcat ttactctggt agctgcgcga tgtattcaga tagcagctcg   5640
gtaatggtct tgccttggcg taccgcgtac atcttcagct tggtgtgatc ctccgccggc   5700
aactgaaagt tgacccgctt catggctggc gtgtctgcca ggctggccaa cgttgcagcc   5760
ttgctgctgc gtgcgctcgg acggccggca cttagcgtgt ttgtgctttt gctcattttc   5820
tctttacctc attaactcaa atgagttttg atttaatttc agcggccagc gcctggacct   5880
cgcgggcagc gtcgccctcg ggttctgatt caagaacggt tgtgccggcg gcggcagtgc   5940
ctgggtagct cacgcgctgc gtgatacggg actcaagaat gggcagctcg tacccggcca   6000
gcgcctcggc aacctcaccg ccgatgcgcg tgcctttgat cgcccgcgac acgacaaagg   6060
ccgcttgtag ccttccatcc gtgacctcaa tgcgctgctt aaccagctcc accaggtcgg   6120
cggtggccca tatgtcgtaa gggcttggct gcaccggaat cagcacgaag tcggctgcct   6180
tgatcgcgga cacagccaag tccgccgcct ggggcgctcc gtcgatcact acgaagtcgc   6240
gccggccgat ggccttcacg tcgcggtcaa tcgtcgggcg gtcgatgccg acaacggtta   6300
gcggttgatc ttcccgcacg gccgcccaat cgcgggcact gccctgggga tcggaatcga   6360
ctaacagaac atcggccccg gcgagttgca gggcgcgggc tagatgggtt gcgatggtcg   6420
tcttgcctga cccgcctttc tggttaagta cagcgataac cttcatgcgt tccccttgcg   6480
tatttgttta tttactcatc gcatcatata cgcagcgacc gcatgacgca agctgtttta   6540
ctcaaataca catcaccttt ttagacggcg gcgctcggtt tcttcagcgg ccaagctggc   6600
cggccaggcc gccagcttgg catcagacaa accggccagg atttcatgca gccgcacggt   6660
tgagacgtgc gcgggcggct cgaacacgta cccggccgcg atcatctccg cctcgatctc   6720
ttcggtaatg aaaaacggtt cgtcctggcc gtcctggtgc ggtttcatgc ttgttcctct   6780
tggcgttcat tctcggcggc cgccagggcg tcggcctcgg tcaatgcgtc ctcacggaag   6840
gcaccgcgcc gcctggcctc ggtgggcgtc acttcctcgc tgcgctcaag tgcgcggtac   6900
agggtcgagc gatgcacgcc aagcagtgca gccgcctctt tcacggtgcg gccttcctgg   6960
tcgatcagct cgcgggcgtg cgcgatctgt gccggggtga gggtagggcg ggggccaaac   7020
ttcacgcctc gggccttggc ggcctcgcgc ccgctccggg tgcggtcgat gattagggaa   7080
cgctcgaact cggcaatgcc ggcgaacacg gtcaacacca tgcggccggc cggcgtggtg   7140
gtgtcggccc acggctctgc caggctacgc aggcccgcgc cggcctcctg gatgcgctcg   7200
gcaatgtcca gtaggtcgcg ggtgctgcgg gccaggcggt ctagcctggt cactgtcaca   7260
acgtcgccag ggcgtaggtg gtcaagcatc ctggccagct ccgggcggtc gcgcctggtg   7320
ccggtgatct tctcggaaaa cagcttggtg cagccggccg cgtgcagttc ggcccgttgg   7380
ttggtcaagt cctggtcgtc ggtgctgacg cgggcatagc ccagcaggcc agcggcggcg   7440
ctcttgttca tggcgtaatg tctccggttc tagtcgcaag tattctactt tatgcgacta   7500
```

-continued

```
aaacacgcga caagaaaacg ccaggaaaag ggcagggcgg cagcctgtcg cgtaacttag   7560
gacttgtgcg acatgtcgtt ttcagaagac ggctgcactg aacgtcagaa gccgactgca   7620
ctatagcagc ggaggggttg gatcaaagta ctttgatccc gaggggaacc ctgtggttgg   7680
catgcacata caaatggacg aacggataaa ccttttcacg cccttttaaa tatccgttat   7740
tctaataaac gctcttttct cttaggttta cccgccaata tatcctgtca aacactgata   7800
gtttaaactg aaggcgggaa acgacaatct gatccaagct caagctaagc ttgggcccga   7860
gcggataaca atttcacaca ggaaacagct atgaccatga ttacgccaag ctatcaactt   7920
tgtatagaaa agttgccctt tcctctgaaa cgattctcca cgctctttgt ttataaggat   7980
tgcaagaaat tactgaagaa catcaggaat cgcgagagct tggggcgaat caaaaacctc   8040
cattgatgaa gaagactgca tctagtactt tacttactcg gtagcacacc tccatgggca   8100
ggctccagca ccatggttgg gcccatttct tattaatggg cctaaaatag agcttctagg   8160
gcctctatat attttgtctt ttctcttccg tttaggcgtt ttgctaactt tcttacgtat   8220
atgaatgtga attatagtta gttaacttta gaactgttga gcggccaatg ccacgtcctt   8280
tgtacgtaaa ttatgttatt catgctatta tttatgtacc aattttctat tctaatatat   8340
attctaagtt tttttttgtat caatactaag tatttataca atttttgcaa attttgacag   8400
aaagatagta caaaaaatat gaaagaccaa aaactacata aaccaccaaa aattacaaca   8460
caaacagaaa acggaaagaa aactcaatcg aaaactctac aagtagagac cttaaaagaa   8520
acttagattc caaaccacaa agctcaaata tttgtgtggt ttcctcaact taaaagatct   8580
caaatactta tagttgttgc cactagcaat ccaaacctag gccagttttc aaaatctcta   8640
aaaaagagct taccattcca aacttaggac aatcctcata atattttaaa ttttatgaca   8700
ttttttagtt ttttcttacc gaacatagag atacaacgaa taacacaaaa taccaaattt   8760
tactaaacaa acaattactg cacaaatgaa aaagtaatca acaacatgag ctcatttcac   8820
gaaaaaagaa gcgaaaaagc caacggtctt gccacaaatt agtatattgc aaaattacaaa   8880 tgcttaaaaa aattcacaga tatattcatc aattatacct tttgattatc ttgcaaataa   8940
atcttccaat tcatattacc tacgtcaaaa tttagccatc tacccttatt atcccattat   9000
gaaaatttca aaatcgataa gatgacagac acccaacaac gaattatcat tttatatact   9060
ataggtatta gatacctaca atttatttgg tttattggga atatacgatt cataaattcc   9120
ctcataaaaa tataaagcaa atgtggacgg aagcaaaaaa actaaatata gaatggagag   9180
aaattgtatt attaacttag gttacccatc gccaacaacc tctcatttcc tttcctaaac   9240
tatttcacaa ttttggtcaa aaacacaatc taaccccaaa aaagattcga cctttgaaat   9300
tcccaaaacc agaagcaaaa cccccaaaag aaccctactt atagtgaaag aaaagtaaca   9360
taataatata tatacacgag aaccaagagc cacttgaata taaagttcac agttttgtc    9420 tgctcaccaa atcaaaccaa tttctcctga tagccaagt ttttgtcccc aacaagaaac    9480
tcatgcaaca ttcttcaccc actagctaac taacgacttc cattcttatt aatctctctc   9540
aattcttcat ttctgagatt catcgctctc tcttctcttt gtcacagcaa gtttgtacaa   9600
aaaagcaggc tccatgggaa gatcaccttg ttgtgataaa aatggagtga agaagggacc   9660
atggactgct gaggaggatc agaaactcat cgattatatt cgatttcatg gtcctggcaa   9720
ttggcgtacg ctccccaaaa atgctggtac gtataaacta cacaccgttc cttatatttt   9780
gttctcatag attaatatat atgttctcta tttattgagt cacacactta taagtcgtat   9840
tgtacaaatt aaaggactcc atagatgtgg aaaaagctgc cgtcttcgat ggaccaatta   9900
```

-continued

```
tctaagaccg gacatcaaga gaggaagatt ctcgttcgag gaagaagaaa ctatcattca      9960
gctacacagt gttatgggaa acaagtaagc ctgatcattc acaccataat ttttgtctga     10020
aattcatatt catcagctac atgcttttgt atgttaatta atgtaaaact caaaaaggga     10080
gagtgtacgt ttgcatgcgg gggtacatgt caaatgtagg ccatcaactc caataaacta     10140
ttattagtac tttactagta cgtattgacc tatattagaa taataataaa ggagttttgt     10200
attgatcata gattaatgtc actaatattg aattgatgaa tattaggtgg tcagcaatag     10260
ccgctcgtct accagggagg accgataacg aaataaaaaa ccattggaac actcacatcc     10320
gcaagagact tgtaaggagt ggtatcgacc ctgttactca ttctccacgc cttgatcttc     10380
ttgatttgtc ctcacttttg agtgcacttt tcaaccagcc aaacttttca gcagttgcaa     10440
cacatgcgtc ttctcttctt aatcctgatg tattgaggtt ggcctctcta ctactgccac     10500
ttcaaaaccc taatccagtt tacccatcga acctcgacca aaatcttcaa actccaaata     10560
catcatcaga atcgtctcaa ccacaagctg agactagtac agtcccaaca aactatgaaa     10620
cttcatcatt ggagcctatg aacgcaagac tcgacgacgt tggtcttgca gatgtattac     10680
cacctttgtc agagagtttt gacttagact cgctcatgtc aacgccaatg tcttctccac     10740
gacaaaatag cattgaagca gaaaccaact ccagcacttt cttcgacttt ggaattccgg     10800
aagatttcat cttagatgac tttatgtttg acccagcttt cttgtacaaa gtggcctaat     10860
tttcaacatt tgcatacaca tgtcttgctt tcacacatat gattctttgt tgcattcttt     10920
cttttgtttg atgtataaat ttcttgtttt tattctctca aaagatatta agttattagt     10980
ctataaaatt ttcatgaatg tttatgtatt atctgcttag gcgagatatc taaattctgc     11040
tccattagtc catatacaca gttgacggaa gcaaacatag aattattagc gtcaaacaca     11100
tcacatattc atattgcttt gttcgaatca tcgtcaatca agttaatcag tttatgcgag     11160
ttctatcatt taggcccaat tcaaggccca attcaagttc attttaaagc cgttaatttg     11220
gccagcaact ttattataca tagttgataa ttcactggcc gtcgttttac aacgtcgtga     11280
ctgggaaaac gatctaactg actagccgcg gccatggcgg ccgggagcgg ccatgctaga     11340
gtccgcaaaa atcaccagtc tctctctaca aatctatctc tctctatttt tctccagaat     11400
aatgtgtgag tagttcccag ataagggaat tagggttctt atagggtttc gctcatgtgt     11460
tgagcatata agaaaccctt agtatgtatt tgtatttgta aaatacttct atcaataaaa     11520
tttctaattc ctaaaaccaa aatccagtga cctgcaggtc gaccatatgg gag           11573
```

<210> SEQ ID NO 12
<211> LENGTH: 12171
<212> TYPE: DNA
<213> ORGANISM: Artificial Sequence
<220> FEATURE:
<223> OTHER INFORMATION: proMYB84::MYB41 construct

<400> SEQUENCE: 12

```
agctcgaatt atcatacatg agaattaagg gagtcacgtt atgacccccg ccgatgacgc       60
gggacaagcc gttttacgtt tggaactgac agaaccgcaa cgttgaagga gccactgagc      120
cgcgggtttc tggagtttaa tgagctaagc acatacgtca gaaaccatta ttgcgcgttc      180
aaaagtcgcc taaggtcact atcagctagc aaatatttct tgtcaaaaat gctccactga      240
cgttccataa attcccctcg gtatccaatt agagtctcat attcactctc aactcgatcg      300
aggggatcta ccatgagccc agaacgacgc ccggccgaca tccgccgtgc caccgaggcg      360
```

```
gacatgccgg cggtctgcac catcgtcaac cactacatcg agacaagcac ggtcaacttc    420
cgtaccgagc cgcaggaacc gcaggagtgg acggacgacc tcgtccgtct gcgggagcgc    480
tatccctggc tcgtcgccga ggtggacggc gaggtcgccg gcatcgccta cgcgggtccc    540
tggaaggcac gcaacgccta cgactggacg gccgagtcga ccgtgtacgt ctcccccgc     600 caccagcgga cgggactggg ctccacgctc tacacccacc tgctgaagtc cctggaggca    660
cagggcttca agagcgtggt cgctgtcatc gggctgccca acgacccgag cgtgcgcatg    720
cacgaggcgc tcggatatgc cccccgcggc atgctgcggg cggccggctt caagcacggg    780
aactggcatg acgtgggttt ctggcagctg gacttcagcc tgccggtgcc gccccgtccg    840
gtcctgcccg tcaccgaaat ctgatgaccc ctagagtcaa gcagatcgtt caaacatttg    900
gcaataaagt ttcttaagat tgaatcctgt tgccggtctt gcgatgatta tcatataatt    960
tctgttgaat tacgttaagc atgtaataat taacatgtaa tgcatgacgt tatttatgag   1020
atgggttttt atgattagag tcccgcaatt atacatttaa tacgcgatag aaaacaaaat   1080
atagcgcgca aactaggata aattatcgcg cgcggtgtca tctatatgtt actagatcga   1140
ccggcatgca agctgataat tcaattcggc gttaattcag tacattaaaa acgtccgcaa   1200
tgtgttatta agttgtctaa gcgtcaattt gtttacacca caatatatcc tgccaccagc   1260
cagccaacag ctccccgacc ggcagctcgg cacaaaatca ccactcgata caggcagccc   1320
atcagtccgg gacggcgtca gcgggagagc cgttgtaagg cggcagactt tgctcatgtt   1380
accgatgcta ttcggaagaa cggcaactaa gctgccgggt ttgaaacacg gatgatctcg   1440
cggagggtag catgttgatt gtaacgatga cagagcgttg ctgcctgtga tcaattcggg   1500
cacgaaccca gtggacataa gcctcgttcg gttcgtaagc tgtaatgcaa gtagcgtaac   1560
tgccgtcacg caactggtcc agaaccttga ccgaacgcag cggtggtaac ggcgcagtgg   1620
cggttttcat ggcttcttgt tatgacatgt tttttgggg tacagtctat gcctcgggca    1680
tccaagcagc aagcgcgtta cgccgtgggt cgatgtttga tgttatggag cagcaacgat   1740
gttacgcagc agggcagtcg ccctaaaaca aagttaaaca tcatggggga agcggtgatc   1800
gccgaagtat cgactcaact atcagaggta gttggcgtca tcgagcgcca tctcgaaccg   1860
acgttgctgg ccgtacattt gtacggctcc gcagtggatg cggcctgaa  gccacacagt   1920 gatattgatt tgctggttac ggtgaccgta aggcttgatg aaacaacgcg gcgagctttg   1980
atcaacgacc ttttggaaac ttcggcttcc cctggagaga gcgagattct ccgcgctgta   2040
gaagtcacca ttgttgtgca cgacgacatc attccgtggc gttatccagc taagcgcgaa   2100
ctgcaatttg gagaatggca gcgcaatgac attcttgcag gtatcttcga gccagccacg   2160
atcgacattg atctggctat cttgctgaca aaagcaagag aacatagcgt tgccttggta   2220
ggtccagcgg cggaggaact ctttgatccg gttcctgaac aggatctatt tgaggcgcta   2280
aatgaaacct taacgctatg gaactcgccg cccgactggg ctggcgatga gcgaaatgta   2340
gtgcttacgt tgtcccgcat ttggtacagc gcagtaaccg gcaaaatcgc gccgaaggat   2400
gtcgctgccg actgggcaat ggagcgcctg ccggcccagt atcagcccgt catacttgaa   2460
gctagacagc cttatcttgg acaagaagaa gatcgcttgg cctcgcgcgc agatcagttg   2520
gaagaatttg tccactacgt gaaaggcgag atcaccaagg tagtcggcaa ataatgtcta   2580
gctagaaatt cgttcaagcc gacgccgctt cgccggcgtt aactcaagcg attagatgca   2640
ctaagcacat aattgctcac agccaaacta tcaggtcaag tctgctttta ttatttttaa   2700
gcgtgcataa taagccctac acaaattggg agatatatca tgcatgacca aaatccctta   2760
```

-continued

```
acgtgagttt tcgttccact gagcgtcaga ccccgtagaa aagatcaaag gatcttcttg    2820
agatcctttt tttctgcgcg taatctgctg cttgcaaaca aaaaaaccac cgctaccagc    2880
ggtggtttgt ttgccggatc aagagctacc aactcttttt ccgaaggtaa ctggcttcag    2940
cagagcgcag ataccaaata ctgtccttct agtgtagccg tagttaggcc accacttcaa    3000
gaactctgta gcaccgccta catacctcgc tctgctaatc ctgttaccag tggctgctgc    3060
cagtggcgat aagtcgtgtc ttaccgggtt ggactcaaga cgatagttac cggataaggc    3120
gcagcggtcg ggctgaacgg ggggttcgtg cacacagccc agcttggagc gaacgaccta    3180
caccgaactg agatacctac agcgtgagct atgagaaagc gccacgcttc ccgaagggag    3240
aaaggcggac aggtatccgg taagcggcag ggtcggaaca ggagagcgca cgagggagct    3300
tccaggggga aacgcctggt atctttatag tcctgtcggg tttcgccacc tctgacttga    3360
gcgtcgattt ttgtgatgct cgtcaggggg gcggagccta tggaaaaacg ccagcaacgc    3420
ggccttttta cggttcctgg ccttttgctg gccttttgct cacatgttct ttcctgcgtt    3480
atcccctgat tctgtggata accgtattac cgcctttgag tgagctgata ccgctcgccg    3540
cagccgaacg accgagcgca gcgagtcagt gagcgaggaa gcggaagagc gcctgatgcg    3600
gtattttctc cttacgcatc tgtgcggtat ttcacaccgc atatggtgca ctctcagtac    3660
aatctgctct gatgccgcat agttaagcca gtatacactc cgctatcgct acgtgactgg    3720
gtcatggctg cgccccgaca cccgccaaca cccgctgacg cgccctgacg ggcttgtctg    3780
ctcccggcat ccgcttacag acaagctgtg accgtctccg ggagctgcat gtgtcagagg    3840
ttttcaccgt catcaccgaa acgcgcgagg cagggtgcct tgatgtgggc gccggcggtc    3900
gagtggcgac ggcgcggctt gtccgcgccc tggtagattg cctggccgta ggccagccat    3960
ttttgagcgg ccagcggccg cgataggccg acgcgaagcg gcggggcgta gggagcgcag    4020
cgaccgaagg gtaggcgctt tttgcagctc ttcggctgtg cgctggccag acagttatgc    4080
acaggccagg cgggttttaa gagtttttaat aagttttaaa gagtttttagg cggaaaaatc    4140 gcctttttttc tctttatat cagtcactta catgtgtgac cggttcccaa tgtacggctt    4200
tgggttccca atgtacgggt tccggttccc aatgtacggc tttgggttcc caatgtacgt    4260
gctatccaca ggaaagagac cttttcgacc ttttttcccct gctagggcaa tttgccctag    4320
catctgctcc gtacattagg aaccggcgga tgcttcgccc tcgatcaggt tgcggtagcg    4380
catgactagg atcgggccag cctgccccgc ctcctccttc aaatcgtact ccggcaggtc    4440
atttgacccg atcagcttgc gcacggtgaa acagaacttc ttgaactctc cggcgctgcc    4500
actgcgttcg tagatcgtct tgaacaacca tctggcttct gccttgcctg cggcgcggcg    4560
tgccaggcgg tagagaaaac ggccgatgcc gggatcgatc aaaaagtaat cggggtgaac    4620
cgtcagcacg tccgggttct tgccttctgt gatctcgcgg tacatccaat cagctagctc    4680
gatctcgatg tactccggcc gcccggtttc gctctttacg atcttgtagc ggctaatcaa    4740
ggcttcaccc tcggataccg tcaccaggcg gccgttcttg gccttcttcg tacgctgcat    4800
ggcaacgtgc gtggtgttta accgaatgca ggtttctacc aggtcgtctt tctgctttcc    4860
gccatcggct cgccggcaga acttgagtac gtccgcaacg tgtggacgga acacgcggcc    4920
gggcttgtct cccttccctt cccggtatcg gttcatggat tcggttagat gggaaaccgc    4980
catcagtacc aggtcgtaat cccacacact ggccatgccg gccggccctg cggaaacctc    5040
tacgtgcccg tctggaagct cgtagcggat cacctcgcca gctcgtcggt cacgcttcga    5100
```

-continued

```
cagacggaaa acggccacgt ccatgatgct gcgactatcg cgggtgccca cgtcatagag    5160
catcggaacg aaaaaatctg gttgctcgtc gcccttgggc ggcttcctaa tcgacggcgc    5220
accggctgcc ggcggttgcc gggattcttt gcggattcga tcagcggccg cttgccacga    5280
ttcaccgggg cgtgcttctg cctcgatgcg ttgccgctgg gcggcctgcg cggccttcaa    5340
cttctccacc aggtcatcac ccagcgccgc gccgatttgt accgggccgg atggtttgcg    5400
accgtcacgc cgattcctcg ggcttggggg ttccagtgcc attgcagggc cggcagacaa    5460
cccagccgct tacgcctggc caaccgcccg ttcctccaca catggggcat tccacggcgt    5520
cggtgcctgg ttgttcttga ttttccatgc cgcctccttt agccgctaaa attcatctac    5580
tcatttattc atttgctcat ttactctggt agctgcgcga tgtattcaga tagcagctcg    5640
gtaatggtct tgccttggcg taccgcgtac atcttcagct tggtgtgatc ctccgccggc    5700
aactgaaagt tgacccgctt catggctggc gtgtctgcca ggctgccaa cgttgcagcc    5760 ttgctgctgc gtgcgctcgg acggccggca cttagcgtgt ttgtgctttt gctcattttc    5820
tctttacctc attaactcaa atgagttttg atttaatttc agcggccagc gcctggacct    5880
cgcgggcagc gtcgccctcg ggttctgatt caagaacggt tgtgccggcg gcggcagtgc    5940
ctgggtagct cacgcgctgc gtgatacggg actcaagaat gggcagctcg tacccggcca    6000
gcgcctcggc aacctcaccg ccgatgcgcg tgcctttgat cgcccgcgac acgacaaagg    6060
ccgcttgtag ccttccatcc gtgacctcaa tgcgctgctt aaccagctcc accaggtcgg    6120
cggtggccca tatgtcgtaa gggcttggct gcaccggaat cagcacgaag tcggctgcct    6180
tgatcgcgga cacagccaag tccgccgcct ggggcgctcc gtcgatcact acgaagtcgc    6240
gccggccgat ggccttcacg tcgcggtcaa tcgtcgggcg gtcgatgccg acaacggtta    6300
gcggttgatc ttcccgcacg gccgcccaat cgcgggcact gccctgggga tcggaatcga    6360
ctaacagaac atcggccccg gcgagttgca gggcgcgggc tagatgggtt gcgatggtcg    6420
tcttgcctga cccgcctttc tggttaagta cagcgataac cttcatgcgt tccccttgcg    6480
tatttgttta tttactcatc gcatcatata cgcagcgacc gcatgacgca agctgtttta    6540
ctcaaataca catcaccttt ttagacggcg gcgctcggtt tcttcagcgg ccaagctggc    6600
cggccaggcc gccagcttgg catcagacaa accggccagg atttcatgca gccgcacggt    6660
tgagacgtgc gcgggcggct cgaacacgta cccggccgcg atcatctccg cctcgatctc    6720
ttcggtaatg aaaaacggtt cgtcctggcc gtcctggtgc ggtttcatgc ttgttcctct    6780
tggcgttcat tctcggcggc cgccaggcg tcggcctcgg tcaatgcgtc ctcacggaag    6840
gcaccgcgcc gcctggcctc ggtgggcgtc acttcctcgc tgcgctcaag tgcgcggtac    6900
agggtcgagc gatgcacgcc aagcagtgca gccgcctctt tcacggtgcg gccttcctgg    6960
tcgatcagct cgcgggcgtg cgcgatctgt gccggggtga gggtagggcg ggggccaaac    7020
ttcacgcctc gggccttggc ggcctcgcgc ccgctccggg tgcggtcgat gattagggaa    7080
cgctcgaact cggcaatgcc ggcgaacacg gtcaacacca tgcggccggc cggcgtggtg    7140
gtgtcggccc acggctctgc caggctacgc aggcccgcgc cggcctcctg gatgcgctcg    7200
gcaatgtcca gtaggtcgcg ggtgctgcgg gccaggcggt ctagcctggt cactgtcaca    7260
acgtcgccag ggcgtaggtg gtcaagcatc ctggccagct ccgggcggtc gcgcctggtg    7320
ccggtgatct tctcggaaaa cagcttggtg cagccggccg cgtgcagttc ggcccgttgg    7380
ttggtcaagt cctggtcgtc ggtgctgacg cgggcatagc ccagcaggcc agcggcggcg    7440
ctcttgttca tggcgtaatg tctccggttc tagtcgcaag tattctactt tatgcgacta    7500
```

```
aaacacgcga caagaaaacg ccaggaaaag ggcagggcgg cagcctgtcg cgtaacttag    7560
gacttgtgcg acatgtcgtt ttcagaagac ggctgcactg aacgtcagaa gccgactgca    7620
ctatagcagc ggaggggttg gatcaaagta ctttgatccc gaggggaacc ctgtggttgg    7680
catgcacata caaatggacg aacgatataa cctttttcacg cccttttaaa tatccgttat    7740
tctaataaac gctcttttct cttaggttta cccgccaata tatcctgtca aacactgata    7800
gtttaaactg aaggcgggaa acgacaatct gatccaagct caagctaagc ttgggcccga    7860
gcggataaca atttcacaca ggaaacagct atgaccatga ttacgccaag ctatcaactt    7920
tgtatagaaa agttgcctct gagacatcat tgatatctaa caatcaaaaa ctaaaaagtg    7980
aagtattaac attttaatca gattcaaacc agaacttatc agtcatcaaa aatgttggca    8040
aataacaaat caaacttaag tttttggatg gagaaagcaa gctagattcg aatctctaag    8100
aagcgtggac ttggacttgt ttacgacctg aaaagatgtc atgattatct catgattacg    8160
agataataac atgtcttatc tactaaacta atctaaaaag tagtgaggat gacttgaaac    8220
ttaagtctta tatgaattat ctttaaatat agaaaaagaa aggagataga gaggtgtgtt    8280
tttcatgtga acaacttttt tttaccttta gagtacttcc agaagactta ttgggtcctt    8340
aataaaagta gaccaaatta ttgaagagct aaaaaaaaat gcctactcaa aatatccaaa    8400
cctcttcttt tagccttttg ttttttttcaa tattcatact aatgtaaact acaatcattg    8460
tatcattcta taatcatatg aattttttgt caacaccatg cattatgcta gtttaaattt    8520
aggtgatgat ataaagatat tttaagtaca aatcaatagg ggcgatgttc ttatgtcttt    8580
atctaacttt atgaatttgt gttttatata ttatgaaaaa ttggaaaaga agagatggcc    8640
tacgctcaag accaattcct accaatgggc aatggtgttg aaatctgaac aaaaaaattt    8700 cctttctta acgttagctt taaagttcaa aaaactttat ttacttttc agtgataatt    8760 ctgtataaaa taacatataa caatgaggaa aaaactcaat aatttgaatc gcttatgact    8820
ttatttctcc aagtgcttga cttttaaaac cctaatgtcc aatctcaact aaagtcaacc    8880 ttttcgttc gtctagaaga gtcagtcatt aagtttcaat tgaagtatac agtaaattat    8940
tagtactttt tatttatttt taaccacagt tcattggctg tatgagattt ctgttcaaga    9000
aaacatataa atcgaaacca aagcaaaaga cattatttgc ttcggtttct tctactcaag    9060
ctcattttta gtaaaactaa attgtatttt cattttctta aaaagttaat tgttttttt    9120 gtaaaatcag ttttaccaaa ttggacacaa taatgaatat atgtctatgt ctagtttttt    9180
ttagctcaga atatatctta tgtgaataga atcgtctatc agatattttt gtgatgcaga    9240
tagaacttac cgttatagaa tcatttgtag attgttcatc gtgattgtta agattagatt    9300
cccatttgta atataacaga aactcgaaaa gtacttatat taagtattaa cgatgtatca    9360
tgtgaccaaa atagaaaata ctacgtaatg atatgattat taagcgagtg tgtaggtaat    9420
tcaaatattt caattaatca atctttgata tcactcttta gagtaatgta ttatctttct    9480
tattgtttta ccctgggatt aataagttta ccggatccgg agtagaattt cttcggtttg    9540 gcaatttttgt tcacctacca taacgaactt ttacccttat acttagtttc aatctacttt    9600
tggtgcatcc tttcattttc aactgcaaag aagtagttaa aagatccaat acataatata    9660
tttaatttat cataagtaac ttagtgtaaa gaaagactaa agtacttttt aaaatatgta    9720
tttgtatttc ccgatgtgaa agaaaagaaa attgaatttg cacatatcaa taatattagc    9780
taggaaaaaa cttgtgagaa atttctttga cgacttgcgt gtgcaatagt cttccttatc    9840
```

-continued

```
ttctctacca tttcttaatt ccactattgt atagtattta cttatgttga attaataaat    9900
taaaacattt aaatttccct aaagttactt tttgatttttt gattttctat ttttattaca    9960
actttcctac tttttgacat cttttcttac aaagactttt tgacatctcc ccctccagct   10020
attatatagt ctccttttt cttttctgca ttcacataat atttcccta tatagtttac     10080 acaacatcat acccaccaac atatataatc ttgatcatag agagataaac agaggccgct   10140
atcaagaaca agactaagaa caagacttca ctaggagtac aagtgcaagt ttgtacaaaa   10200
aagcaggctc catgggaaga tcaccttgtt gtgataaaaa tggagtgaag aagggaccat   10260
ggactgctga ggaggatcag aaactcatcg attatattcg atttcatggt cctggcaatt   10320
ggcgtacgct ccccaaaaat gctggtacgt ataaactaca caccgttcct tatattttgt   10380
tctcatagat taatatatat gttctctatt tattgagtca cacacttata agtcgtattg   10440
tacaaattaa aggactccat agatgtggaa aaagctgccg tcttcgatgg accaattatc   10500
taagaccgga catcaagaga ggaagattct cgttcgagga agaagaaact atcattcagc   10560
tacacagtgt tatgggaaac aagtaagcct gatcattcac accataattt ttgtctgaaa   10620
ttcatattca tcagctacat gcttttgtat gttaattaat gtaaaactca aaaagggaga   10680
gtgtacgttt gcatgcgggg gtacatgtca aatgtaggcc atcaactcca ataaactatt   10740
attagtactt tactagtacg tattgaccta tattagaata ataataaagg agttttgtat   10800
tgatcataga ttaatgtcac taatattgaa ttgatgaata ttaggtggtc agcaatagcc   10860
gctcgtctac cagggaggac cgataacgaa ataaaaaacc attggaacac tcacatccgc   10920
aagagacttg taaggagtgg tatcgaccct gttactcatt ctccacgcct tgatcttctt   10980
gatttgtcct cacttttgag tgcactttc aaccagccaa acttttcagc agttgcaaca   11040
catgcgtctt ctcttcttaa tcctgatgta ttgaggttgg cctctctact actgccactt   11100
caaaacccta atccagttta cccatcgaac ctcgaccaaa atcttcaaac tccaaataca   11160
tcatcagaat cgtctcaacc acaagctgag actagtacag tcccaacaaa ctatgaaact   11220
tcatcattgg agcctatgaa cgcaagactc gacgacgttg gtcttgcaga tgtattacca   11280
cctttgtcag agagttttga cttagactcg ctcatgtcaa cgccaatgtc ttctccacga   11340
caaaatagca ttgaagcaga aaccaactcc agcactttct tcgactttgg aattccggaa   11400
gatttcatct tagatgactt tatgtttgac ccagctttct tgtacaaagt ggcctaattt   11460
tcaacatttg catacacatg tcttgctttc acacatatga ttctttgttg cattcttct    11520 tttgtttgat gtataaattt cttgtttta ttctctcaaa agatattaag ttattagtct   11580
ataaaatttt catgaatgtt tatgtattat ctgcttaggc gagatatcta aattctgctc   11640
cattagtcca tatacacagt tgacggaagc aaacatagaa ttattagcgt caaacacatc   11700
acatattcat attgctttgt tcgaatcatc gtcaatcaag ttaatcagtt tatgcgagtt   11760
ctatcattta ggcccaattc aaggcccaat tcaagttcat tttaaagccg ttaatttggc   11820
cagcaacttt attatacata gttgataatt cactggccgt cgttttacaa cgtcgtgact   11880
gggaaaacga tctaactgac tagccgcggc catggcggcc gggagcggcc atgctagagt   11940
ccgcaaaaat caccagtctc tctctacaaa tctatctctc tcatttttc tccagaataa   12000 tgtgtgagta gttcccagat aagggaatta gggttcttat agggtttcgc tcatgtgttg   12060
agcatataag aaacccttag tatgtatttg tatttgtaaa atacttctat caataaaatt   12120
tctaattcct aaaaccaaaa tccagtgacc tgcaggtcga ccatatggga g             12171
```

```
<210> SEQ ID NO 13
<211> LENGTH: 1216
<212> TYPE: DNA
<213> ORGANISM: Arabidopsis thaliana

<400> SEQUENCE: 13
atgggaagat caccttgttg tgataaaaat ggagtgaaga agggaccatg gactgctgag      60
gaggatcaga aactcatcga ttatattcga tttcatggtc ctggcaattg gcgtacgctc     120
cccaaaaatg ctggtacgta taaactacac accgttcctt atattttgtt ctcatagatt     180
aatatatatg ttctctattt attgagtcac acacttataa gtcgtattgt acaaattaaa     240
ggactccata gatgtggaaa aagctgccgt cttcgatgga ccaattatct aagaccggac     300
atcaagagag gaagattctc gttcgaggaa gaagaaacta tcattcagct cacagtgtt      360 atgggaaaca gtaagcctg atcattcaca ccataatttt tgtctgaaat tcatattcat      420
cagctacatg ctttttgtatg ttaattaatg taaaactcaa aaagggagag tgtacgtttg     480
catgcggggg tacatgtcaa atgtaggcca tcaactccaa taaactatta ttagtacttt     540
actagtacgt attgacctat attagaataa taataaagga gttttgtatt gatcatagat     600
taatgtcact aatattgaat tgatgaatat taggtggtca gcaatagccg ctcgtctacc     660
agggaggacc gataacgaaa taaaaaacca ttggaacact cacatccgca agagacttgt     720
aaggagtggt atcgaccctg ttactcattc tccacgcctt gatcttcttg atttgtcctc     780
acttttgagt gcacttttca accagccaaa ctttttcagca gttgcaacac atgcgtcttc     840
tcttcttaat cctgatgtat tgaggttggc ctctctacta ctgccacttc aaaaccctaa     900
tccagtttac ccatcgaacc tcgaccaaaa tcttcaaact ccaaatacat catcagaatc     960
gtctcaacca caagctgaga ctagtacagt cccaacaaac tatgaaactt catcattgga    1020
gcctatgaac gcaagactcg acgacgttgg tcttgcagat gtattaccac ctttgtcaga    1080
gagttttgac ttagactcgc tcatgtcaac gccaatgtct tctccacgac aaaatagcat    1140
tgaagcagaa accaactcca gcactttctt cgactttgga attccggaag atttcatctt    1200
agatgacttt atgttt                                                    1216

<210> SEQ ID NO 14
<211> LENGTH: 282
<212> TYPE: PRT
<213> ORGANISM: Arabidopsis thaliana

<400> SEQUENCE: 14

Met Gly Arg Ser Pro Cys Cys Asp Lys Asn Gly Val Lys Lys Gly Pro
1               5                   10                  15

Trp Thr Ala Glu Glu Asp Gln Lys Leu Ile Asp Tyr Ile Arg Phe His
                20                  25                  30

Gly Pro Gly Asn Trp Arg Thr Leu Pro Lys Asn Ala Gly Leu His Arg
            35                  40                  45

Cys Gly Lys Ser Cys Arg Leu Arg Trp Thr Asn Tyr Leu Arg Pro Asp
        50                  55                  60

Ile Lys Arg Gly Arg Phe Ser Phe Glu Glu Glu Glu Thr Ile Ile Gln
65                  70                  75                  80

Leu His Ser Val Met Gly Asn Lys Trp Ser Ala Ile Ala Ala Arg Leu
                85                  90                  95

Pro Gly Arg Thr Asp Asn Glu Ile Lys Asn His Trp Asn Thr His Ile
                100                 105                 110

Arg Lys Arg Leu Val Arg Ser Gly Ile Asp Pro Val Thr His Ser Pro
```

-continued

```
              115                 120                 125

Arg Leu Asp Leu Leu Asp Leu Ser Ser Leu Leu Ser Ala Leu Phe Asn
    130                 135                 140

Gln Pro Asn Phe Ser Ala Val Ala Thr His Ala Ser Ser Leu Leu Asn
145                 150                 155                 160

Pro Asp Val Leu Arg Leu Ala Ser Leu Leu Leu Pro Leu Gln Asn Pro
                165                 170                 175

Asn Pro Val Tyr Pro Ser Asn Leu Asp Gln Asn Leu Gln Thr Pro Asn
                180                 185                 190

Thr Ser Ser Glu Ser Ser Gln Pro Gln Ala Glu Thr Ser Thr Val Pro
                195                 200                 205

Thr Asn Tyr Glu Thr Ser Ser Leu Glu Pro Met Asn Ala Arg Leu Asp
    210                 215                 220

Asp Val Gly Leu Ala Asp Val Leu Pro Pro Leu Ser Glu Ser Phe Asp
225                 230                 235                 240

Leu Asp Ser Leu Met Ser Thr Pro Met Ser Ser Pro Arg Gln Asn Ser
                245                 250                 255

Ile Glu Ala Glu Thr Asn Ser Ser Thr Phe Phe Asp Phe Gly Ile Pro
                260                 265                 270

Glu Asp Phe Ile Leu Asp Asp Phe Met Phe
                275                 280
```

```
<210> SEQ ID NO 15
<211> LENGTH: 849
<212> TYPE: DNA
<213> ORGANISM: Arabidopsis thaliana

<400> SEQUENCE: 15
atgggaagat caccttgttg tgataaaaat ggagtgaaga agggaccatg gactgctgag      60
gaggatcaga aactcatcga ttatattcga tttcatggtc ctggcaattg gcgtacgctc     120
cccaaaaatg ctggactcca tagatgtgga aaaagctgcc gtcttcgatg gaccaattat     180
ctaagaccgg acatcaagag aggaagattc tcgttcgagg aagaagaaac tatcattcag     240
ctacacagtg ttatgggaaa caagtggtca gcaatagccg ctcgtctacc agggaggacc     300
gataacgaaa taaaaaacca ttggaacact cacatccgca agagacttgt aaggagtggt     360
atcgaccctg ttactcattc tccacgcctt gatcttcttg atttgtcctc acttttgagt     420
gcacttttca accagccaaa cttttcagca gttgcaacac atgcgtcttc tcttcttaat     480
cctgatgtat tgaggttggc ctctctacta ctgccacttc aaaaccctaa tccagtttac     540
ccatcgaacc tcgaccaaaa tcttcaaact ccaaatacat catcagaatc gtctcaacca     600
caagctgaga ctagtacagt cccaacaaac tatgaaactt catcattgga gcctatgaac     660
gcaagactcg acgacgttgg tcttgcagat gtattaccac ctttgtcaga gagttttgac     720
ttagactcgc tcatgtcaac gccaatgtct tctccacgac aaaatagcat tgaagcagaa     780
accaactcca gcactttctt cgactttgga attccggaag atttcatctt agatgacttt     840
atgttttaa                                                              849
```

```
<210> SEQ ID NO 16
<211> LENGTH: 3220
<212> TYPE: DNA
<213> ORGANISM: Artificial Sequence
<220> FEATURE:
<223> OTHER INFORMATION: proFACT::MYB41 expression cassette

<400> SEQUENCE: 16
```

```
ggttaagagt ttcgttttcc ttcgttcaaa atctaatgtg aaggaaagca aaactgacac      60
aacttttgtg tgaaccagag caagtgaaag tgtgtcgaat ctgtactttt gtactgtgta     120
atctctatag tctgactctc attatgtagt tttaagtgtc ttttacttgt gtagctgtta     180
cctgttacct gttaggtttt ctaatccttg ttttatttga tagccagata ctttagggaa     240
ttttacttct tcttttcttg ggtttaattt aagacatatt cgtatatttc atttaattct     300
gttatctgat ttgtgagatc atgaaaacga atgttgaact tgaaacttga gtgggttcag     360
aaaaactact ctgtattaaa aatcccagtg tcacatgata atgatccttc agtaaaggta     420
gacatagctt ttttgcagtg tgatatgcac aaatacaatc tatatttta  tgtaaaagat     480 atatttcttt gaaagtactt ataaaaatat gttttcata  aaaaaaatta tatgtaattc     540
tgaaagtatg tgatatgcac aagcacaacc tatatttcct acattcaaat tcggtttttt     600
cttgacgcca agttacattc aattatcaat aatagggcta gttcaactaa tgctatttat     660
ttatacaatc cacccactac taaatctcaa tctccaagga tctttatata ttaataagaa     720
aagctactat ccaaatgcga ccttgttcgt gaagtgtttg gtttataatt tggtggctta     780
agactatagc ccaccattga cccaaaaaaa gaaaggaaaa ttaatagtag actatatagc     840
taccaactcc ctataattta ccttgaaatt aaaccagctt tgtattttt  taatagaagt     900 cagggctcta cagtttcatt ttaaactttt tttttgtta  tattacatcc tgcaggttag     960
ttgtaatttg taaacgtaat caacataata aaaccattta catagactga ttaaagttga    1020
ttccatttga taatatttag ctatttatat atcaatcaac caccagctct taaatatatg    1080
tattcaaatt gttttgttga ctcttttgc  tacactttaa atttgaatct agaatgttgt    1140
cctgaaacaa aaatctgtgg attgaacaaa attatacacc aggtaaaatt ttgaagtttt    1200
taaaagcagg atcacatact cctaattta  gattggatag atctagtata aaaatatgaa    1260 gttttttcc  caaaaaataa taataccatt tagctcttaa ttaaatgcat gcaaactaaa    1320
gataaaaaga ggaattattt taaccattct aactcgtcac aacatgccta atcattccag    1380
gttaatttta gagttttcaa atcgtcatat taacatgtga tcctgaagac tcttctcttc    1440
tttcttctac cattagctga aatctttact tgtaccacaa ttaacctcaa accctagccc    1500
ctaaatcccc ctagaaatca atccatcctc agttctccaa aaagatatct ttggtttttc    1560
ttcactgaca aaacccctaa aaacaagttt gtacaaaaaa gcaggctcca tgggaagatc    1620
accttgttgt gataaaaatg gagtgaagaa gggaccatgg actgctgagg aggatcagaa    1680
actcatcgat tatattcgat ttcatggtcc tggcaattgg cgtacgctcc ccaaaaatgc    1740
tggtacgtat aaactacaca ccgttcctta tattttgttc tcatagatta atatatatgt    1800
tctctattta ttgagtcaca cacttataag tcgtattgta caaattaaag gactccatag    1860
atgtggaaaa agctgccgtc ttcgatggac caattatcta agaccggaca tcaagagagg    1920
aagattctcg ttcgaggaag aagaaactat cattcagcta cacagtgtta tgggaaacaa    1980
gtaagcctga tcattcacac cataattttt gtctgaaatt catattcatc agctacatgc    2040
ttttgtatgt taattaatgt aaaactcaaa aagggagagt gtacgtttgc atgcgggggt    2100
acatgtcaaa tgtaggccat caactccaat aaactattat tagtactta  ctagtacgta    2160 ttgacctata ttagaataat aataaaggag ttttgtattg atcatagatt aatgtcacta    2220
atattgaatt gatgaatatt aggtggtcag caatagccgc tcgtctacca gggaggaccg    2280
ataacgaaat aaaaaaccat tggaacactc acatccgcaa gagacttgta aggagtggta    2340
```

-continued

```
tcgaccctgt tactcattct ccacgccttg atcttcttga tttgtcctca cttttgagtg      2400 cactttcaa  ccagccaaac tttcagcag  ttgcaacaca tgcgtcttct cttcttaatc      2460
ctgatgtatt gaggttggcc tctctactac tgccacttca aaaccctaat ccagtttacc      2520
catcgaacct cgaccaaaat cttcaaactc caaatacatc atcagaatcg tctcaaccac      2580
aagctgagac tagtacagtc ccaacaaact atgaaacttc atcattggag cctatgaacg      2640
caagactcga cgacgttggt cttgcagatg tattaccacc tttgtcagag agttttgact      2700
tagactcgct catgtcaacg ccaatgtctt ctccacgaca aaatagcatt gaagcagaaa      2760
ccaactccag cactttcttc gactttggaa ttccggaaga tttcatctta gatgacttta      2820
tgtttgaccc agctttcttg tacaaagtgg cctaattttc aacatttgca tacacatgtc      2880
ttgctttcac acatatgatt ctttgttgca ttctttcttt tgtttgatgt ataaatttct      2940
tgtttttatt ctctcaaaag atattaagtt attagtctat aaaattttca tgaatgttta      3000
tgtattatct gcttaggcga gatatctaaa ttctgctcca ttagtccata tacacagttg      3060
acggaagcaa acatagaatt attagcgtca aacacatcac atattcatat tgctttgttc      3120
gaatcatcgt caatcaagtt aatcagttta tgcgagttct atcatttagg cccaattcaa      3180
ggcccaattc aagttcattt taaagccgtt aatttggcca                            3220
```

```
<210> SEQ ID NO 17
<211> LENGTH: 3720
<212> TYPE: DNA
<213> ORGANISM: Artificial Sequence
<220> FEATURE:
<223> OTHER INFORMATION: proHORST::MYB41 expression cassette

<400> SEQUENCE: 17
catctacaaa gcctataaaa tggaaagatg tatgcatcga tgatgattct gcctcactta        60
gaagaatcaa aaagctaaaa ggagctgcga atcctgggca acgatgactt agtatgtata       120
gaagaaaaaa aaagcttta  cttggtatca aacagagcat gtgttgttgt atttgctacc       180 ttttttctgca aagttattgg caattgtatt gttgttccac ttgtatatat acagagacca      240
tttatgttaa tatacaactt cgtatgggga aagatgattc catcaagtcc aaaatgccaa       300
aaccatgcac gatcttgtct gatcaagtat gataagatgt gagattttaa gaacgtgaag       360
cttttcatat tgtattctca atgaacgaag aattaataat tagagttaga aatgcagatt       420
acagagatta cacaatttga tctcatttct tggcaaagag gcccaggcca ccgaagccac       480
cgtccttctt tggattcctg tgtgttaatt ttcgtgtggc tttagttaca aagggattat       540
attgtcagcg aatctgagcc gttggatcgt tttgacatga gctttccata agtgtcttat       600
cctttgtttc tctcattttt cacatatgta tcagacattt aatcaagcac atatctacgt       660
gttgattatg ttgatgatgc tgagattatg ttgatttaga gaatgagtat tggtgatgat       720
ggtacacgtt agtaaacata tgaatttgga agtgccacgt gagagggagc agagttttgg       780
gctttctttt ggttatgtat ttgcattctt gttgtaacaa attctcttat taaaagcatt       840
gtgaaaaaaa ccaaatacca catagtctat gtttcaagat ttgttttta atactataat        900 tttctattac tttagtttgt gtaatttttg aaaagagaaa attggtattt tttaggattg       960
ggtgatctga aatttgacta caaaaatttt cttggacaca gacacacagt cacacaaata      1020
agctaattat tggaattta  tcttaagttg cattcacttt gcaaattaat attgaattat      1080
agactattag tgtatggcgt gatggcaaac aaaaaaatca gtgtgtgata ttgtggacta      1140
gccaaaaaaa ttttctgatg atttttttgc ctaaataatt tgaattgttg agaccgaaac      1200
```

-continued

```
tcttactaat atactaacaa tgtaacgcga caaataaaac attgttgaga ataaaatctg    1260
aaccatcata actatagtct atagtaaccg tccgaattca accacatatg tatgatcttt    1320
gccatttttg atcatatttt ccgttgcgtt ttctttgaat tttctcaata tatttttagt    1380
gttttgattt gtacttttat ctaatttata taattgtttt tcaaatgttt cgcaattgtg    1440
cgtttaagta ttcgactcga agtaaaccca gtttcttaga atgggctaac tgccattgac    1500
caaatcttta tccgcgaaga aagatcttta gcagctaggc ttatttcata tcaacaaaag    1560
tatatattta tctctaacta aattcctaca attatttcaa aaacatagaa attaaaattt    1620
gaaatgccta ttcttttttg gttatacatt gcaaaggtta tgtatgtaat ttctgatctt    1680
gaaatttaag ttctttagcc catatctagt tgattttcac gaaatattgt cgtttactct    1740 cgttttata tataaagcat gtacatataa catataatca atgcttcaaa agaaaaaaat    1800
aatcataact aaattgaaac gggaaaacta atttgctttc gtgttctatt atgccaaact    1860
gtactcacaa tagtcttatc ctatcgaccc aaatttaatc ttcccaacta cttactccta    1920
attgaaacaa aatataacct ttcttactat agcctatatt taaaaaatat ctatgatttc    1980
tacatttata tatatacgca cacggcacat acctctcatt caccatatat gcctcttaac    2040
aatctctcca cagaacaaaa gcaaaaagcc taaaccggga tagcaagttt gtacaaaaaa    2100
gcaggctcca tgggaagatc accttgttgt gataaaaatg gagtgaagaa gggaccatgg    2160
actgctgagg aggatcagaa actcatcgat tatattcgat ttcatggtcc tggcaattgg    2220
cgtacgctcc ccaaaaatgc tggtacgtat aaactacaca ccgttcctta tattttgttc    2280
tcatagatta atatatatgt tctctattta ttgagtcaca cacttataag tcgtattgta    2340
caaattaaag gactccatag atgtggaaaa agctgccgtc ttcgatggac caattatcta    2400
agaccggaca tcaagagagg aagattctcg ttcgaggaag aagaaactat cattcagcta    2460
cacagtgtta tgggaaacaa gtaagcctga tcattcacac cataattttt gtctgaaatt    2520
catattcatc agctacatgc ttttgtatgt taattaatgt aaaactcaaa aagggagagt    2580
gtacgtttgc atgcggggt acatgtcaaa tgtaggccat caactccaat aaactattat    2640
tagtacttta ctagtacgta ttgacctata ttagaataat aataaaggag ttttgtattg    2700
atcatagatt aatgtcacta atattgaatt gatgaatatt aggtggtcag caatagccgc    2760
tcgtctacca gggaggaccg ataacgaaat aaaaaaccat tggaacactc acatccgcaa    2820
gagacttgta aggagtggta tcgaccctgt tactcattct ccacgccttg atcttcttga    2880
tttgtcctca ctttttgagtg cacttttcaa ccagccaaac ttttcagcag ttgcaacaca    2940
tgcgtcttct cttcttaatc ctgatgtatt gaggttggcc tctctactac tgccacttca    3000
aaaccctaat ccagtttacc catcgaacct cgaccaaaat cttcaaactc caaatacatc    3060
atcagaatcg tctcaaccac aagctgagac tagtacagtc ccaacaaact atgaaacttc    3120
atcattggag cctatgaacg caagactcga cgacgttggt cttgcagatg tattaccacc    3180
tttgtcagag agttttgact tagactcgct catgtcaacg ccaatgtctt ctccacgaca    3240
aaatagcatt gaagcagaaa ccaactccag cactttcttc gactttggaa ttccggaaga    3300
tttcatctta gatgacttta tgtttgaccc agctttcttg tacaaagtgg cctaattttc    3360
aacatttgca tacacatgtc ttgctttcac acatatgatt ctttgttgca ttctttcttt    3420
tgtttgatgt ataaatttct tgttttttatt ctctcaaaag atattaagtt attagtctat    3480
aaaattttca tgaatgttta tgtattatct gcttaggcga gatatctaaa ttctgctcca    3540
```

```
ttagtccata tacacagttg acggaagcaa acatagaatt attagcgtca aacacatcac    3600
atattcatat tgctttgttc gaatcatcgt caatcaagtt aatcagttta tgcgagttct    3660
atcatttagg cccaattcaa ggcccaattc aagttcattt taaagccgtt aatttggcca    3720

<210> SEQ ID NO 18
<211> LENGTH: 3648
<212> TYPE: DNA
<213> ORGANISM: Artificial Sequence
<220> FEATURE:
<223> OTHER INFORMATION: proASFT::MYB41 expression cassette

<400> SEQUENCE: 18
agctcaaacc tttaaatggc ttttaattag atatatttag cgagaatgtg attgctagtg      60
aaatctcaaa cttgatagct tattcatagc ttattttact tcgatcagca agagaacaat     120
ggttcctaaa gctcaaacct tttttggcgt ttgctttaga ttgtgcatac ataaagtgag     180
aagatgaaat atggttttgc tgaaatctca atgtgctcat tcatagttta ttttgctcga     240
cctttcttta atcaatagct ttgatgtact gattactttta taaagttaag aagtaagttc     300
tgctctttaa actgtactga atggaggctt ctctgcataa ttaagcaaac actctgatga     360
ttgagtttcg ttgtacaaag gaaagttttt gccttagtta gaaattcatc ttgtttcttt     420
gcccagaagc tggcttgctg atagaatttg gactacgcta cgttttcttg ggtgaaaaac     480
aatccgcgtc cttccacgag aacagtgaaa ctgtacgatg ttcttattgt attgtgtcaa     540
cagcccataa tcaatgaaat gggcctcaat gacagtataa gccgaaaaat attcgaatgc     600
gatctagaac taatctgaaa ccaaacttct caaatcatta acatttgatt agggcctaaa     660
agtccatccg tattttaaaa aaagttgat aacaaatgca aaaatacaaa tatacattac     720
tattaaaact caatctttct gattatatgt ggatggagaa gctgtttttgc agtgtggatt     780 tgaattttga agttcttgtt caaaaaagaa aagaaacttg gtcaagcttc aaaagaaaga     840
aagaaataaa gacaagtata caaatacgtt gacttcaatt aatatgaaga tagaagagaa     900
agatatagaa atgcgtttta aattggcggt gggagatatg tgattccctt ggtcccgctt     960
tctcgtttga ttcggtaacc taaaccttct ccatccaaga agacacaaac aaggaagaaa    1020
ttaacctacg tacgtacatc atttgaacta cttatatcta ttataaatgg aaaatctatt    1080
ttcttcttct ctctctttta accgaaaaag gaaaagtcct cgaaataact ctttaatata    1140
attcatgtgg aaaccttcta tatattttt gcatgctttt ttgaaattaa gtaatggcat    1200
actaattaga agaagacgaa aaataatatg tctaagtaat tgagtttcgt ggtcaaggca    1260
aatcaagatt gcattcttta attaagtgta caaattatga tgtaagaacc gttatttggc    1320
ataacctaat atatattaaa aactgatttt tttttttttt aacttctgta agaaatggtt    1380
ttcttaatta ccaatcatga tctattattg taaaatgtgt aattttgtgt tgcgattgaa    1440
gtgttcttag ataaagatat gtcatatgca tgatatcatc tatttgattt tgagaaaata    1500
aaaacataac atgagaacat cgtagagagt aagtacatg acaaagagaa agaataagct    1560
aagaagtcat ccaaaaattg ggaggcctac tctcaactac caaaaataca agtgtttgtt    1620
gtgttaggtc atttattcag tcacctaacc ctaactatat gaaatacgtt aaaattcata    1680
tatagaaaaa taagaagaa atactattag tcaatataat ttttttttaac aaaataaaaa    1740 taaagaaaga aacactatta gtcaatgaat taaaaaaaaa aaaatccatc tttcgatcaa    1800
gaccgtccaa gtattctcct ttcacataac tcttacgttt tacactaaac aagacgagat    1860
ttttatgagc ttgtggctcc cacaacaatc ctcattgatt tctccatata tatcacatga    1920
```

```
gaatccaact cgacttcata ctaacattca tcccaaaagt tccattcttt ttcacaaagc    1980
cattgtgctg ttttctccat ttggatcaaa gcaagtttgt acaaaaaagc aggctccatg    2040
ggaagatcac cttgttgtga taaaaatgga gtgaagaagg gaccatggac tgctgaggag    2100
gatcagaaac tcatcgatta tattcgattt catggtcctg gcaattggcg tacgctcccc    2160
aaaaatgctg gtacgtataa actacacacc gttccttata ttttgttctc atagattaat    2220
atatatgttc tctatttatt gagtcacaca cttataagtc gtattgtaca aattaaagga    2280
ctccatagat gtggaaaaag ctgccgtctt cgatggacca attatctaag accggacatc    2340
aagagaggaa gattctcgtt cgaggaagaa gaaactatca ttcagctaca cagtgttatg    2400
ggaaacaagt aagcctgatc attcacacca taatttttgt ctgaaattca tattcatcag    2460
ctacatgctt ttgtatgtta attaatgtaa aactcaaaaa gggagagtgt acgtttgcat    2520
gcgggggtac atgtcaaatg taggccatca actccaataa actattatta gtactttact    2580
agtacgtatt gacctatatt agaataataa taaaggagtt ttgtattgat catagattaa    2640
tgtcactaat attgaattga tgaatattag gtggtcagca atagccgctc gtctaccagg    2700
gaggaccgat aacgaaataa aaaaccattg gaacactcac atccgcaaga gacttgtaag    2760
gagtggtatc gaccctgtta ctcattctcc acgccttgat cttcttgatt tgtcctcact    2820
tttgagtgca cttttcaacc agccaaactt ttcagcagtt gcaacacatg cgtcttctct    2880
tcttaatcct gatgtattga ggttggcctc tctactactg ccacttcaaa accctaatcc    2940
agtttaccca tcgaacctcg accaaaatct tcaaactcca aatacatcat cagaatcgtc    3000
tcaaccacaa gctgagacta gtacagtccc aacaaactat gaaacttcat cattggagcc    3060
tatgaacgca agactcgacg acgttggtct tgcagatgta ttaccacctt tgtcagagag    3120
ttttgactta gactcgctca tgtcaacgcc aatgtcttct ccacgacaaa atagcattga    3180
agcagaaacc aactccagca ctttcttcga ctttggaatt ccggaagatt tcatcttaga    3240
tgactttatg tttgacccag ctttcttgta caaagtggcc taattttcaa catttgcata    3300
cacatgtctt gctttcacac atatgattct ttgttgcatt ctttcttttg tttgatgtat    3360
aaatttcttg tttttattct ctcaaaagat attaagttat tagtctataa aattttcatg    3420
aatgtttatg tattatctgc ttaggcgaga tatctaaatt ctgctccatt agtccatata    3480
cacagttgac ggaagcaaac atagaattat tagcgtcaaa cacatcacat attcatattg    3540
ctttgttcga atcatcgtca atcaagttaa tcagtttatg cgagttctat catttaggcc    3600
caattcaagg cccaattcaa gttcatttta aagccgttaa tttggcca              3648
```

```
<210> SEQ ID NO 19
<211> LENGTH: 3784
<212> TYPE: DNA
<213> ORGANISM: Artificial Sequence
<220> FEATURE:
<223> OTHER INFORMATION: proGPAT5::MYB41 expression cassette

<400> SEQUENCE: 19
tgatcgcaaa cgtcaatggt ctatatccat ctcttgggga tacaccattc agatatacac     60
ttacttcttg actgctacgg agctgactac gccgttgcag accttcaaaa cttggcggtc    120
ttccagcgat ggacctttcg tgtttaacac tcggcccttg aaacctgacc cctgtgagcg    180
tccggtcact tatttcatgg atggtgccga ggatgtacgg gatagtggga cgaaaacttg    240
gtatagcata ggggataaga actatggtca ttgcggaaag attgagcata ctcgattaac    300
```

-continued

```
taaagtgaag aggatattgg tgacttcaat gaagacggat cctgagtatt ggaacaaggt     360
acttagtgtt tgtatatttc tcatattgaa tttaacattt tgggtgagtt taggttacat     420
cttttttttt attttttgct tttgttgata ggcaccgagg agacagtgtt gtgaggtgat     480
ggaaggaaaa gtaggaaaaa gaaaagagaa agaaatgttg ttaaggatta gaaaatgcag     540
atctttggag aagatataaa aaaagcgttt taattagaga gattttttgca catacagatt    600 tagattcgat cattagttat ttgtttctaa attcctcaat tcctagtacc aagagaatga     660
cgattttctc tagtaatact ggcactcttc gttttcaac atgtaaacat tactttgtat      720
aattagtcta tatcaaataa atagttacaa catgaacgta actatttata cacgagggta     780
aatttttaac aaatttaaac cgaaccaaaa agatttcagt taatcatagt tttgttacaa     840
gcgaaatctg aaatattcac cctcaagttt gttacgtaat tgtctaatct gtgttttttt     900
gtgctagtgt tataattgtt tcctcgaatg ttaagcacca catagaagta tacacttttc     960
ttttattatt ttcgttcttc ttccatttag aaacttttat taattctact gttaaatcca    1020
acgttattag tttattttct ctgatgaagt tctaattttt tttgtttgtt ggaaaaaggg    1080
ttacttttct gatgaagttg ccgatttgtt tccaaccaaa cctcagctaa tatagttagg    1140
gagacggata agaaattgca taaagggaga ggctttgtaa acacgcaagt ttacgtcaac    1200
ttgacacata taaactcgta tataggaatt gtgtaaaatg ttaatcaata tatgtttatg    1260
aatatagtcc ttttatttcc ttaatctata gtcatgttat catcatatcg gcaagaaaat    1320
tactattaca acatatgttt ccgtgcttcg atttgtcgat caggtaggca accaaaccgg    1380
gccagattag tcacaaatga aattaggctc cactttggca agtttttttca caattaaaaa   1440 ttagaaagtc taaccaaact aatagaaact gaaccaaaca aaaatgttca cgcaattacg    1500
tagcacttct ctatgaaata ctgtggataa ttcgatttga gctaatctat ggtaagtcgt    1560
ttctctcaaa ctgaattaag ctaaaccaaa ccgaaaataa accgttgtag aacacccata    1620
ataaacatat atatgttctc tactcttatt tggctatttt tccatttgca gatacgtgtg    1680
acaacattcc aaatataggc acatgataca aattacaaag ccagaaatta taatttataa    1740
actatacata ataaggtcag tagcctaatt acatccatat atttagttgg gcataataag    1800
gatagcctaa ttttggtgca tcccgccaaa aattcggaca aatggtgaat ttcaaaccat    1860
gaatttcttt gttatacata cattacgtgc actattacat caaagaaaaa tagtgacgtg    1920
cataaacgta ttttcttcac ataatctata tataatatat acagccatgt acatttttca    1980
acatagaaaa atcatgtata caaatacggt aggtgcaata ctgataaact gccattccca    2040
ttgcattaga cgctagtcaa tccaaacctt ataacataaa aagttatagt ccatttcttt    2100
catatccaat cgagtcaaaa taatattcga gcaaaaaaca aaagaagcaa gtttgtacaa    2160
aaaagcaggc tccatgggaa gatcaccttg ttgtgataaa aatggagtga agaagggacc    2220
atggactgct gaggaggatc agaaactcat cgattatatt cgatttcatg gtcctggcaa    2280
ttggcgtacg ctccccaaaa atgctggtac gtataaacta cacaccgttc cttatatttt    2340
gttctcatag attaatatat atgttctcta tttattgagt cacacactta taagtcgtat    2400
tgtacaaatt aaaggactcc atagatgtgg aaaaagctgc cgtcttcgat ggaccaatta    2460
tctaagaccg gacatcaaga gaggaagatt ctcgttcgag gaagaagaaa ctatcattca    2520
gctacacagt gttatgggaa acaagtaagc ctgatcattc acaccataat ttttgtctga    2580
aattcatatt catcagctac atgctttgt atgttaatta atgtaaaact caaaaaggga     2640
gagtgtacgt ttgcatgcgg gggtacatgt caaatgtagg ccatcaactc caataaacta   2700
```

-continued

```
ttattagtac tttactagta cgtattgacc tatattagaa taataataaa ggagttttgt     2760
attgatcata gattaatgtc actaatattg aattgatgaa tattaggtgg tcagcaatag     2820
ccgctcgtct accagggagg accgataacg aaataaaaaa ccattggaac actcacatcc     2880
gcaagagact tgtaaggagt ggtatcgacc ctgttactca ttctccacgc cttgatcttc     2940
ttgatttgtc ctcacttttg agtgcacttt tcaaccagcc aaacttttca gcagttgcaa     3000
cacatgcgtc ttctcttctt aatcctgatg tattgaggtt ggcctctcta ctactgccac     3060
ttcaaaaccc taatccagtt tacccatcga acctcgacca aaatcttcaa actccaaata     3120
catcatcaga atcgtctcaa ccacaagctg agactagtac agtcccaaca aactatgaaa     3180
cttcatcatt ggagcctatg aacgcaagac tcgacgacgt tggtcttgca gatgtattac     3240
cacctttgtc agagagtttt gacttagact cgctcatgtc aacgccaatg tcttctccac     3300
gacaaaatag cattgaagca gaaaccaact ccagcacttt cttcgacttt ggaattccgg     3360
aagatttcat cttagatgac tttatgtttg acccagcttt cttgtacaaa gtggcctaat     3420
tttcaacatt tgcatacaca tgtcttgctt tcacacatat gattctttgt tgcattcttt     3480
cttttgtttg atgtataaat ttcttgtttt tattctctca aaagatatta agttattagt     3540
ctataaaatt ttcatgaatg tttatgtatt atctgcttag gcgagatatc taaattctgc     3600
tccattagtc catatacaca gttgacggaa gcaaacatag aattattagc gtcaaacaca     3660
tcacatattc atattgcttt gttcgaatca tcgtcaatca agttaatcag tttatgcgag     3720
ttctatcatt taggcccaat tcaaggccca attcaagttc attttaaagc cgttaatttg     3780
gcca                                                                  3784
```

<210> SEQ ID NO 20
<211> LENGTH: 3287
<212> TYPE: DNA
<213> ORGANISM: Artificial Sequence
<220> FEATURE:
<223> OTHER INFORMATION: proRALPH::MYB41 expression cassette

<400> SEQUENCE: 20

```
ctttcctctg aaacgattct ccacgctctt tgtttataag gattgcaaga aattactgaa       60
gaacatcagg aatcgcgaga gcttggggcg aatcaaaaac ctccattgat gaagaagact      120
gcatctagta ctttacttac tcggtagcac acctccatgg gcaggctcca gcaccatggt      180
tgggcccatt tcttattaat gggcctaaaa tagagcttct agggcctcta tatattttgt      240
cttttctctt ccgtttaggc gttttgctaa cttttcttacg tatatgaatg tgaattatag      300
ttagttaact ttagaactgt tgagcggcca atgccacgtc ctttgtacgt aaattatgtt      360
attcatgcta ttatttatgt accaattttc tattctaata tatattctaa gttttttttg      420
tatcaatact aagtatttat acaatttttg caaattttga cagaaagata gtacaaaaaa      480
tatgaaagac caaaaactac ataaaccacc aaaaattaca acacaaacag aaaacgaaaa      540
gaaaactcaa tcgaaaactc tacaagtaga gaccttaaaa gaaacttaga ttccaaacca      600
caaagctcaa atatttgtgt ggtttcctca acttaaaaga tctcaaatac ttatagttgt      660
tgccactagc aatccaaacc taggccagtt ttcaaaatct ctaaaaaga gcttaccatt      720 ccaaacttag gacaatcctc ataatatttt aaatttatg acattttta gtttttttctt      780 accgaacata gagatacaac gaataacaca aaataccaaa ttttactaaa caaacaatta      840
ctgcacaaat gaaaaagtaa tcaacaacat gagctcattt cacgaaaaaa gaagcgaaaa      900
```

```
agccaacggt cttgccacaa attagtatat tgcaaattac aaatgcttaa aaaaattcac      960
agatatattc atcaattata ccttttgatt atcttgcaaa taaatcttcc aattcatatt     1020
acctacgtca aaatttagcc atctaccctt attatcccat tatgaaaatt tcaaaatcga     1080
taagatgaca gacacccaac aacgaattat cattttatat actataggta ttagatacct     1140
acaatttatt tggtttattg ggaatatacg attcataaat tccctcataa aaatataaag     1200
caaatgtgga cggaagcaaa aaaactaaat atagaatgga gagaaattgt attattaact     1260
taggttaccc atcgccaaca acctctcatt tcctttccta aactatttca caattttggt     1320
caaaaacaca atctaacccc aaaaaagatt cgacctttga aattcccaaa accagaagca     1380 aaaccccaa aagaaccta cttatagtga aagaaaagta acataataat atatatacac        1440
gagaaccaag agccacttga atataaagtt cacagttttt gtctgctcac caaatcaaac     1500
caatttctcc tgatagccaa agttttttgtc cccaacaaga aactcatgca acattcttca    1560
cccactagct aactaacgac ttccattctt attaatctct ctcaattctt catttctgag     1620
attcatcgct ctctcttctc tttgtcacag caagtttgta caaaaaagca ggctccatgg     1680
gaagatcacc ttgttgtgat aaaaatggag tgaagaaggg accatggact gctgaggagg      1740
atcagaaact catcgattat attcgatttc atggtcctgg caattggcgt acgctcccca      1800
aaaatgctgg tacgtataaa ctacacaccg ttccttatat tttgttctca tagattaata     1860
tatatgttct ctatttattg agtcacacac ttataagtcg tattgtacaa attaaaggac     1920
tccatagatg tggaaaaagc tgccgtcttc gatggaccaa ttatctaaga ccggacatca     1980
agagaggaag attctcgttc gaggaagaag aaactatcat tcagctacac agtgttatgg     2040
gaaacaagta agcctgatca ttcacaccat aattttttgtc tgaaattcat attcatcagc    2100
tacatgcttt tgtatgttaa ttaatgtaaa actcaaaaag ggagagtgta cgtttgcatg     2160 cggggggtaca tgtcaaatgt aggccatcaa ctccaataaa ctattattag tactttacta    2220
gtacgtattg accctatatta gaataataat aaaggagttt tgtattgatc atagattaat    2280
gtcactaata ttgaattgat gaatattagg tggtcagcaa tagccgctcg tctaccaggg     2340
aggaccgata acgaaataaa aaaccattgg aacactcaca tccgcaagag acttgtaagg     2400
agtggtatcg accctgttac tcattctcca cgccttgatc ttcttgattt gtcctcactt     2460
ttgagtgcac ttttcaacca gccaaacttt tcagcagttg caacacatgc gtcttctctt     2520
cttaatcctg atgtattgag gttggcctct ctactactgc cacttcaaaa ccctaatcca     2580 gtttaccccat cgaacctcga ccaaaatctt caaactccaa atacatcatc agaatcgtct    2640
caaccacaag ctgagactag tacagtccca acaaactatg aaacttcatc attggagcct     2700
atgaacgcaa gactcgacga cgttggtctt gcagatgtat taccaccttt gtcagagagt     2760
tttgacttag actcgctcat gtcaacgcca atgtcttctc cacgacaaaa tagcattgaa     2820
gcagaaacca actccagcac tttcttcgac tttggaattc cggaagattt catcttagat     2880
gactttatgt ttgacccagc tttcttgtac aaagtggcct aattttcaac atttgcatac     2940
acatgtcttg ctttcacaca tatgattctt tgttgcattc tttcttttgt ttgatgtata     3000
aatttcttgt ttttattctc tcaaaagata ttaagttatt agtctataaa attttcatga     3060
atgtttatgt attatctgct taggcgagat atctaaattc tgctccatta gtccatatac     3120
acagttgacg gaagcaaaca tagaattatt agcgtcaaac acatcacata ttcatattgc     3180
tttgttcgaa tcatcgtcaa tcaagttaat cagtttatgc gagttctatc atttaggccc     3240
aattcaaggc ccaattcaag ttcattttaa agccgttaat ttggcca                   3287
```

```
<210> SEQ ID NO 21
<211> LENGTH: 3885
<212> TYPE: DNA
<213> ORGANISM: Artificial Sequence
<220> FEATURE:
<223> OTHER INFORMATION: proMYB84::MYB41 expression cassette

<400> SEQUENCE: 21
tctgagacat cattgatatc taacaatcaa aaactaaaaa gtgaagtatt aacattttaa      60
tcagattcaa accagaactt atcagtcatc aaaaatgttg gcaaataaca aatcaaactt     120 aagttttttgg atggagaaag caagctagat tcgaatctct aagaagcgtg gacttggact    180
tgtttacgac ctgaaaagat gtcatgatta tctcatgatt acgagataat aacatgtctt     240
atctactaaa ctaatctaaa aagtagtgag gatgacttga aacttaagtc ttatatgaat     300
tatctttaaa tatagaaaaa gaaaggagat agagaggtgt gtttttcatg tgaacaactt     360 tttttttacct ttagagtact tccagaagac ttattgggtc cttaataaaa gtagaccaaa    420
ttattgaaga gctaaaaaaa aatgcctact caaaatatcc aaacctcttc ttttagcctt     480 ttgtttttttt caatattcat actaatgtaa actacaatca ttgtatcatt ctataatcat    540
atgaattttt tgtcaacacc atgcattatg ctagtttaaa tttaggtgat gatataaaga     600
tattttaagt acaaatcaat aggggcgatg ttcttatgtc tttatctaac tttatgaatt     660
tgtgttttat atattatgaa aaattggaaa agaagagatg gcctacgctc aagaccaatt     720
cctaccaatg ggcaatggtg ttgaaatctg aacaaaaaaa tttcctttct ttaacgttag     780
ctttaaagtt caaaaaactt tatttacttt ttcagtgata attctgtata aaataacata    840
taacaatgag gaaaaaactc aataatttga atcgcttatg actttatttc tccaagtgct    900 tgactttttaa aaccctaatg tccaatctca actaaagtca acctttttcg ttcgtctaga    960
agagtcagtc attaagtttc aattgaagta tacagtaaat tattagtact tttttatttta   1020 ttttaaccac agttcattgg ctgtatgaga tttctgttca agaaaacata taaatcgaaa    1080
ccaaagcaaa agacattatt tgcttcggtt tcttctactc aagctcattt ttagtaaaac   1140
taaattgtat tttcattttc ttaaaaagtt aattgttttt tttgtaaaat cagttttacc   1200
aaattggaca caataatgaa tatatgtcta tgtctagttt tttttagctc agaatatatc    1260
ttatgtgaat agaatcgtct atcagatatt tttgtgatgc agatagaact taccgttata   1320
gaatcatttg tagattgttc atcgtgattg ttaagattag attcccattt gtaatataac    1380
agaaactcga aaagtactta tattaagtat taacgatgta tcatgtgacc aaaatagaaa    1440
atactacgta atgatatgat tattaagcga gtgtgtaggt aattcaaata tttcaattaa   1500
tcaatctttg atatcactct ttagagtaat gtattatctt tcttattgtt ttaccctggg    1560
attaataagt ttaccggatc cggagtagaa tttcttcggt ttggcaattt tgttcaccta   1620
ccataacgaa cttttacccct tatacttagt ttcaatctac ttttggtgca tcctttcatt   1680
ttcaactgca aagaagtagt taaaagatcc aatacataat atatttaatt tatcataagt   1740
aacttagtgt aaagaaagac taaagtactt tttaaaatat gtatttgtat ttcccgatgt    1800
gaaagaaaag aaaattgaat ttgcacatat caataatatt agctaggaaa aaacttgtga   1860
gaaatttctt tgacgacttg cgtgtgcaat agtcttcctt atcttctcta ccatttctta   1920
attccactat tgtatagtat ttacttatgt tgaattaata aattaaaaca tttaaatttc   1980
cctaaagtta cttttttgatt tttgattttc tattttttatt acaactttcc tactttttga   2040
```

-continued

```
catcttttct  tacaaagact  ttttgacatc  tccccctcca  gctattatat  agtctccttt  2100 tttctttttct gcattcacat  aatatttccc  ctatatagtt  tacacaacat  catacccacc  2160
aacatatata  atcttgatca  tagagagata  aacagaggcc  gctatcaaga  acaagactaa  2220
gaacaagact  tcactaggag  tacaagtgca  agtttgtaca  aaaaagcagg  ctccatggga  2280
agatcacctt  gttgtgataa  aaatggagtg  aagaagggac  catggactgc  tgaggaggat  2340
cagaaactca  tcgattatat  tcgatttcat  ggtcctggca  attggcgtac  gctccccaaa  2400
aatgctggta  cgtataaact  acacaccgtt  ccttatattt  tgttctcata  gattaatata  2460
tatgttctct  atttattgag  tcacacactt  ataagtcgta  ttgtacaaat  taaaggactc  2520
catagatgtg  gaaaaagctg  ccgtcttcga  tggaccaatt  atctaagacc  ggacatcaag  2580
agaggaagat  tctcgttcga  ggaagaagaa  actatcattc  agctacacag  tgttatggga  2640
aacaagtaag  cctgatcatt  cacaccataa  tttttgtctg  aaattcatat  tcatcagcta  2700
catgcttttg  tatgttaatt  aatgtaaaac  tcaaaaaggg  agagtgtacg  tttgcatgcg  2760
ggggtacatg  tcaaatgtag  gccatcaact  ccaataaact  attattagta  ctttactagt  2820
acgtattgac  ctatattaga  ataataataa  aggagttttg  tattgatcat  agattaatgt  2880
cactaatatt  gaattgatga  atattaggtg  gtcagcaata  gccgctcgtc  taccagggag  2940
gaccgataac  gaaataaaaa  accattggaa  cactcacatc  cgcaagagac  ttgtaaggag  3000
tggtatcgac  cctgttactc  attctccacg  ccttgatctt  cttgatttgt  cctcactttt  3060
gagtgcactt  ttcaaccagc  caaacttttc  agcagttgca  acacatgcgt  cttctcttct  3120
taatcctgat  gtattgaggt  tggcctctct  actactgcca  cttcaaaacc  ctaatccagt  3180
ttacccatcg  aacctcgacc  aaaatcttca  aactccaaat  acatcatcag  aatcgtctca  3240
accacaagct  gagactagta  cagtcccaac  aaactatgaa  acttcatcat  tggagcctat  3300
gaacgcaaga  ctcgacgacg  ttggtcttgc  agatgtatta  ccacctttgt  cagagagttt  3360
tgacttagac  tcgctcatgt  caacgccaat  gtcttctcca  cgacaaaata  gcattgaagc  3420
agaaaccaac  tccagcactt  tcttcgactt  tggaattccg  gaagatttca  tcttagatga  3480
ctttatgttt  gacccagctt  tcttgtacaa  agtggcctaa  ttttcaacat  ttgcatacac  3540
atgtcttgct  ttcacacata  tgattctttg  ttgcattctt  tcttttgttt  gatgtataaa  3600
tttcttgttt  ttattctctc  aaaagatatt  aagttattag  tctataaaat  tttcatgaat  3660
gtttatgtat  tatctgctta  ggcgagatat  ctaaattctg  ctccattagt  ccatatacac  3720
agttgacgga  agcaaacata  gaattattag  cgtcaaacac  atcacatatt  catattgctt  3780
tgttcgaatc  atcgtcaatc  aagttaatca  gtttatgcga  gttctatcat  ttaggcccaa  3840
ttcaaggccc  aattcaagtt  cattttaaag  ccgttaattt  ggcca                   3885
```